US009655956B2

(12) United States Patent
Florkiewicz

(10) Patent No.: US 9,655,956 B2
(45) Date of Patent: May 23, 2017

(54) CHIMERIC NUCLEIC ACID MOLECULES WITH NON-AUG TRANSLATION INITIATION SEQUENCES AND USES THEREOF

(71) Applicant: TapImmune Inc., Jacksonville, FL (US)

(72) Inventor: Robert Z. Florkiewicz, Seattle, WA (US)

(73) Assignee: TapImmune Inc., Jacksonville, FL (US)

( * ) Notice: Subject to any disclaimer, the term of this patent is extended or adjusted under 35 U.S.C. 154(b) by 0 days.

(21) Appl. No.: 15/222,619

(22) Filed: Jul. 28, 2016

(65) Prior Publication Data

US 2016/0367652 A1 Dec. 22, 2016

Related U.S. Application Data

(60) Continuation of application No. 15/180,852, filed on Jun. 13, 2016, which is a division of application No. 14/660,924, filed on Mar. 17, 2015, now Pat. No. 9,364,523.

(60) Provisional application No. 61/954,588, filed on Mar. 17, 2014.

(51) Int. Cl.

| | |
|---|---|
| ***A61K 39/00*** | (2006.01) |
| ***A61K 45/06*** | (2006.01) |
| ***C07K 14/705*** | (2006.01) |
| ***C12N 15/67*** | (2006.01) |
| ***C12N 15/85*** | (2006.01) |
| ***C07K 14/50*** | (2006.01) |
| ***C07K 14/82*** | (2006.01) |

(52) U.S. Cl.

CPC .......... *A61K 39/0011* (2013.01); *A61K 45/06* (2013.01); *C07K 14/503* (2013.01); *C07K 14/705* (2013.01); *C07K 14/82* (2013.01); *C12N 15/67* (2013.01); *C12N 15/85* (2013.01); *A61K 2039/53* (2013.01); *A61K 2039/645* (2013.01); *C07K 2319/00* (2013.01); *C07K 2319/40* (2013.01); *C12N 2840/203* (2013.01); *C12N 2840/50* (2013.01)

(58) Field of Classification Search

None

See application file for complete search history.

(56) References Cited

U.S. PATENT DOCUMENTS

| | | | | |
|---|---|---|---|---|
| 7,888,472 | B2 * | 2/2011 | Sette | A61K 39/292 424/184.1 |
| 9,402,901 | B2 * | 8/2016 | Binder | A61K 31/404 |
| 2003/0092001 | A1 | 5/2003 | Schnable et al. | |
| 2010/0310640 | A1 | 12/2010 | Knutson et al. | |
| 2013/0011424 | A1 * | 1/2013 | Maksyutov | A61K 39/0011 424/185.1 |

FOREIGN PATENT DOCUMENTS

| | | | |
|---|---|---|---|
| WO | 2008/064451 A1 | | 6/2008 |
| WO | WO2011110953 | * | 9/2011 |

OTHER PUBLICATIONS

Spevak et al (Biochemical and Biophysical Research, Communications, 2006, 350:834-841).*
Koh et al (PLos ONE, Dec. 2013, 8:e82100, internet pp. 1-9).*
Scardoni et al (Cancer Research, 2007, 67:7028-7036).*
Alexandrov et al., "Signatures of mutational processes in human cancer," *Nature 500*(7463):415-421, 2013.
Anandasabapathy et al., "Classical Flt3L-dependent dendritic cells control immunity to protein vaccine," *Journal of Experimental Medicine 211*(9):1875-1891, 2014.
Apostolopoulos et al., "Targeting Antigens to Dendritic Cell Receptors for Vaccine Development," *Journal of Drug Delivery 2013*:869718, 2013, 22 pages.
Ayyavoo et al., "Immunogenicity of a novel DNA vaccine cassette expressing multiple human immunodeficiency virus (HIV-1) accessory genes," *AIDS 14*:1-9, 2000.
Banerji et al., "Sequence analysis of mutations and translocations across breast cancer subtypes," *Nature 486*(7403):405-409, 2012.
Basal et al., "Functional Folate Receptor Alpha is Elevated in the Blood of Ovarian Cancer Patients," *PLoS ONE 4*(7):e6292, 2009, 7 pages.
Bedford et al., "Assembly, Structure and Function of the 26S proteasome," *Trends Cell Biol. 20*(7):391-401, Jul. 2010.
Benencia et al., "Perspectives on reprogamming cancer-associated dendritic cells for anti-tumor therapies," *Frontiers in Oncology 4*:72, Apr. 2014, 5 pages.
Birkholz et al., "Targeting of DEC-205 on human dendritic cells results in efficient MHC class II-restricted antigen presentation," *Blood 116*(13):2277-2285, Sep. 30, 2010.
Bonnal et al., "A Single Internal Ribosome Entry Site Contain a G Quartet RNA Structure Drives Fibroblast Growth Factor 2 Gene Expression at Four Alternative Translation Initiation Codons," *The Journal of Biological Chemistry 278*(41):39330-39336, Oct. 10, 2003.
Brastianos et al., "Exome sequencing identifies BRAF mutations in papillary craniopharyngiomas," *Nat. Genet. 46*(2):161-165, 2014.
Crown et al., "Emerging targeted therapies in triple-negative breast cancer," *Annals of Oncology 23*(Supplement 6):vi56-vi65, 2012.
Diebold et al., "MHC class II presentation of endogenously expressed antigens by transfected dendritic cells," *Gene Therapy 8*:487-493, 2001.
Douin et al., "Use and comparison of different internal ribosomal entry sites (IRES) in tricistronic retroviral vectors," *BMC Biotechnology 4*:16, Jul. 27, 2004, 12 pages.

(Continued)

*Primary Examiner* — Laura B Goddard
(74) *Attorney, Agent, or Firm* — Seed IP Law Group LLP

(57) ABSTRACT

The present disclosure relates to nucleic acid vaccine compositions and methods for preventing or treating pathological conditions, such as cancer or infectious disease. Further, the disclosure provides methods for more efficient production of antigens via mRNA containing one or more non-conventional start codons to promote multiplex initiation of translation in eukaryotic cells.

53 Claims, 7 Drawing Sheets

(56) References Cited

OTHER PUBLICATIONS

Erskine et al., "MHC class II epitope nesting modulates dendritic cell function and improves generation of antigen-specific CD4 helper T cells," *J. Immunol. 187*(1):316-324, Jul. 1, 2011.
Fioretti et al., "Recent Advances in Design of Immunogenic and Effective Naked DNA Vaccines Against Cancer," *Recent Patents on Anti-Cancer Drug Discovery 9*:66-82, 2014.
Flingai et al., "Synthetic DNA vaccines: improved vaccine potency by electroporation and co-delivered genetic adjuvants," *Frontiers in Immunology 4*:354, Nov. 2013, 10 pages.
Florkiewicz et al., "Human basic fibroblast growth factor gene encodes four polypeptides: Three initiate translation from non-AUG codons," *Proc. Natl. Acad. Sci. USA 86*:3978-3981, Jun. 1989.
Florkiewicz et al., "Multiple Forms of bFGF: Differential Nuclear and Cell Surface Localization," *Growth Factors 4*:265-275, 1991.
Gieseler et al., "DC-SIGN-Specific Liposomal Targeting and Selective Intracellular Compound Delivery to Human Myeloid Dendritic Cells: Implications for HIV Disease," *Scandinavian Journal of Immunology 59*:415-424, 2004.
Glénisson et al., "Identification of New Candidate Therapeutic Target Genes in Triple-Negative Breast Cancer," *Genes & Cancer 3*(1):63-70, 2012.
Graham et al., "DNA Vaccine Delivered by a Needle-Free Injection Device Improves Potency of Priming for Antibody and CD8+ T-Cell Responses after rAd5 Boost in a Randomized Clinical Trial," *PLoS One 8*(4):e59340, Apr. 2013, 11 pages.
Ivanov et al., "Identification of evolutionarily conserved non-AUG-initiated N-terminal extensions in human coding sequences," *Nucleic Acids Research 39*(10):4220-4234, 2011.
Kim et al., "Potential functional role of plasmacytoid dendritic cells in cancer immunity," *Immunology 121*:149-157 (2007).
Kim et al., "Regulation of dendritic cell activation by microRNA let-7c and BLIMP1," *The Journal of Clinical Investigation 123*(2):823-833 (Feb. 1, 2013).
Kloetzel, "The proteasome and MHC class I antigen processing," *Biochimica et Biophysica Acta 1695*:217-225 (2004).
Kuipers et al., "Dicer-Dependent MicroRNAs Control Maturation, Function, and Maintenance of Langerhans Cells in Vivo," *J Immunol 185*:400-409 (2010).
Leung et al., "Folate-receptor 1 (FOLR1) protein is elevated in the serum of ovarian cancer patients," *Clin. Biochem. 46*(15):1462-1468 (Oct. 2013).
Lewis et al., "Microparticle Surface Modifications Targeting Dendritic Cells for Non-Activating Applications," *Biomaterials 33*(29):7221-7232 (Oct. 2012).
Machamer et al., "A Single N-Linked Oligosaccharide at Either of the Two Normal Sites Is Sufficient for Transport of Vesicular Stomatitis Virus G Protein to the Cell Surface," *Molecular and Cellular Biology 5*(11):3074-3083 (Nov. 1985).
Mir et al., "A Multicistronic DNA Vaccine Induces Significant Protection against Tuberculosis in Mice and Offers Flexibility in the Expressed Antigen Repertoire," *Clinical and Vaccine Immunology 16*(10):1467-1475 (Oct. 2009).
Mishra et al., "Dendritic Cell-Mediated, DNA-Based Vaccination against Hepatitis C Induces the Multi-Epitope-Specific Response of Humanized, HLA Transgenic Mice," *PLoS One 9*(8):e104606 (8 pages) (Aug. 2014).
Norell et al., "Vaccination with a plasmid DNA encoding HER-2/neu together with low doses of GM-CSF and IL-2 in patients with metastatic breast carcinoma: a pilot clinical trial," *Journal of Translational Medicine 8*:53 (11 pages) (2010).
Overwijk et al., "Mining the mutanome: developing highly personalized Immunotherapies based on mutational analysis of tumors," *Journal for ImmunoTherapy of Cancer 1*:11 (4 pages) (2013).
Peabody, "Translation Initiation at Non-AUG Triplets in Mammalian Cells," *The Journal of Biological Chemistry 264*(9):5031-5035 (Mar. 25, 1989).
Pintucci et al., "Methylation of High Molecular Weight Fibroblast Growth Factor-2 Determines Post-translational Increases in Molecular Weight and Affects its Intracellular Distribution," *Molecular Biology of the Cell 7*:1249-1258 (Aug. 1996).
Quarto et al., "The $NH_2$-Terminal Extension of High Molecular Weight bFGF is a Nuclear Targeting Signal," *Journal of Cellular Physiology 147*:311-318 (1991).
Rock et al., "Post-proteasomal antigen processing for major histocompatibility complex class I presentation," *Nature Immunology 5*(7):670-677 (Jul. 2004).
Rose et al., "Nucleotide Sequences of the mRNA's Encoding the Vesicular Stomatitis Virus G and M Proteins Determined from cDNA Clones Containing the Complete Coding Regions," *Journal of Virology 39*(2):519-528 (Aug. 1981).
Rottier et al., "An Internalized Amino-terminal Signal Sequence Retains Full Activity in Vivo but not in Vitro," *The Journal of Biological Chemistry 262*(18):8889-8895 (Jun. 25, 1987).
Saade et al., "Technologies for enhanced efficacy of DNA vaccines," *Expert Reviews Vaccines 11*(2):189-209 (Feb. 2012).
Santambrogio et al., "Abundant empty class II MHC molecules on the surface of immature dendritic cells," *PNAS 96*(26):15050-15055 (Dec. 21, 1999).
Sardesai et al., "Electroporation Delivery of DNA Vaccines: Prospects for Success," *Curr. Opin. Immunol. 23*(3):421-429 (Jun. 2011).
Segal et al., "Epitope Landscape in Breast and Colorectal Cancer," *Cancer Res. 68*(3):889-892 (Feb. 1, 2008).
Shedlock et al., "DNA vaccination: antigen presentation and the induction of immunity," *Journal of Leukocyte Biology 68*:793-806 (Dec. 2000).
Sheng et al., "Nuclear and Nucleolar Localization of 18-kDa Fibroblast Growth Factor-2 Is Controlled by C-terminal Signals," *Journal of Biological Chemistry 279*(38):40153-40160 (Sep. 17, 2004).
Sijts et al., "The role of the proteasome in the generation of MHC class I ligands and immune responses," *Cell. Mol. Life Sci. 68*:1491-1502 (2011).
Stoitzner et al., "Human skin dendritic cells can be targeted in situ by intradermal injection of antibodies against lectin receptors," *Experimental Dermatology 23*:909-915 (2014).
Tel et al., "Human plasmacytoid dendritic cells efficiently cross-present exogenous Ags to $CD8^+$ T cells despite lower Ag uptake than myeloid dendritic cell subsets," *Blood 121*(3):459-467 (Jan. 17, 2013).
Teng et al., "Mutations in the epidermal growth factor receptor (EGFR) gene in triple negative breast cancer: possible implications for targeted therapy," *Breast Cancer Research 13*:R35 (9 pages) (2011).
Vacchelli et al., "Dendritic cell-based interventions for cancer therapy," *Oncoimmunology 2*(10):e25771 (15 pages) (Oct. 2013).
Vasaturo et al., "Clinical implications of co-inhibitory molecule expression in the tumor microenvironment for DC vaccination : a game of stop and go," *Frontiers in Immunology 4*:417 (14 pages) (Dec. 2013).
Vogelstein et al., "Cancer Genome Landscapes," *Science 339*(6127):1546-1558 (Mar. 29, 2013).
Wang et al., "Targeting of the non-mutated tumor antigen HER2/neu to mature dendritic cells induces an integrated immune response that protects against breast cancer in mice," *Breast Cancer Research 14*:R39 (17 pages) (2012).
Wilk et al., "Properties of the Nuclear Proteasome Activator PA28γ (REGγ)," *Archives of Biochemistry and Biophysics 383*(2): 265-271 (Nov. 15, 2000).
Xie, "Structure, Assembly and Homeostatic Regulation of the 26S Proteasome," *Journal of Molecular Cell Biology 2*:308-317 (2010).
You et al., "Targeting Dendritic Cells to Enhance DNA Vaccine Potency," *Cancer Research 61*:3704-3711 (May 1, 2011).
Zhang et al., "Folate Receptor a Associated With Triple-Negative Breast Cancer and Poor Prognosis," *Arch Pathol Lab Med 138*:890-895 (Jul. 2014).

* cited by examiner

| PAA translation products | |
|---|---|
| Amino Acids | MW (kDa) |
| 194 | 22.3 |
| 185 | 21.3 |
| 180 | 20.7 |
| 135 | 155 |

CHIMERIC NUCLEIC ACID MOLECULES WITH NON-AUG TRANSLATION INITIATION SEQUENCES AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 890079_401C2_SEQUENCE_LISTING.txt. The text file is 210 KB, was created on Sep. 1, 2016, and is being submitted electronically via EFS-Web.

BACKGROUND

The immune system can be categorized into innate immunity, which involves numerous cellular and soluble factors that respond to all foreign challenges, and adaptive immunity, which responds specifically to precise epitopes from foreign or abnormal agents. The adaptive immune response includes a humoral arm, which involves the production of antibodies by B lymphocytes, and a cellular arm, which involves the killer activity of cytotoxic T lymphocytes (CTLs). A key mechanism for detecting and eliminating abnormal cells by the adaptive immune response is surveillance by CTLs. Abnormal cells may be those infected with a virus, parasite or bacteria, or those that have undergone a tumorigenic transformation.

Cells naturally produce a repertoire of peptides from essentially any cellular translation product that has been marked for elimination (e.g., ubiquitination), which results in presentation of peptide/major histocompatibility complex (MHC; in humans known as human leukocyte antigen or HLA) class I complexes on their surface. A ubiquitinated protein is targeted to the proteasome for proteolysis, producing smaller peptides that may be recognized by transporter associated with antigen presentation (TAP) proteins that are localized in the endoplasmic reticulum. TAP is a heterodimer that moves small peptides from the cytosol into the endoplasmic reticulum where they bind to HLA/MHC molecules to form a peptide/HLA complex. The peptide/HLA complex is then trafficked to the cell surface.

T cell receptors (TCRs) on the surface of circulating CTLs probe the peptide/MHC complexes for the presence of foreign peptides, such as viral proteins or tumor specific proteins, which will trigger a T cell directed immune response. Cells can present tens of thousands of distinct peptides in the context of WIC molecules as potential ligands for the TCR, although the quantity of each peptide will be very low. Nonetheless, CTLs are very sensitive probes for peptides displayed by WIC class I. By some estimates, only three copies of an antigenic peptide are sufficient to target cells for lysis (Purbhoo et al., *Nat. Immunol.* 5:524, 2004).

Vaccines have had a profound and long lasting effect on world health. Smallpox has been eradicated, polio is near elimination, and diseases such as diphtheria, measles, mumps, pertussis, and tetanus are contained. Gene therapy and nucleic acid immunization are promising approaches for the treatment and prevention of both acquired and inherited diseases (Li et al., *J. Biotechnol.* 162:171, 2012). These techniques involve the administration of a desired nucleic acid vaccine directly into a subject in vivo, or by transfecting a subject's cells or tissues ex vivo and reintroducing the transformed material into the subject. Each of these techniques requires efficient expression of a nucleic acid molecule in the transfected cell, which may be affected by several factors, to provide a sufficient amount of a therapeutic or antigenic gene product. Alternatively, antigenic peptides that are defined T cell epitopes may be administered directly to form productive peptide/MHC complexes and stimulate a T cell response.

Current vaccines, however, address only a handful of the infections or cancers suffered by people and domesticated animals. Common infectious diseases for which there are no vaccines cost the United States alone about $120 billion per year (Robinson et al., *American Acad. Microbiol.,* 1996). In first world countries, emerging infections such as immunodeficiency viruses, as well as reemerging diseases like drug resistant forms of tuberculosis, pose new threats and challenges for vaccine development. The need for both new and improved vaccines is even more pronounced in third world countries where effective vaccines are often unavailable or cost-prohibitive.

In view of the limitations associated with current vaccines, there is a need in the art for alternative compositions and methods useful for more efficient and manageable vaccines and vaccinations. The present disclosure meets such needs, and further provides other related advantages.

BRIEF SUMMARY

In some embodiments, the present disclosure provides a chimeric nucleic acid molecule, comprising a multiplex translation initiation (MTI) sequence and a nucleic acid molecule encoding an antigen, an antigenic epitope, or a combination thereof, wherein the MTI comprises at least one non-AUG translation initiation site that mediates translation initiation of the antigen, antigenic epitope, or combination thereof.

In certain embodiments, the present disclosure provides a vector, comprising a multiplex translation initiation (MTI) sequence and a nucleic acid molecule encoding an antigen, an antigenic epitope, or a combination thereof, wherein the MTI comprises at least one non-AUG translation initiation site that mediates translation initiation of the antigen, antigenic epitope, or combination thereof.

In some embodiments, the present disclosure provides a cell, comprising a chimeric nucleic comprising a multiplex translation initiation (MTI) sequence and a nucleic acid molecule encoding an antigen, an antigenic epitope, or a combination thereof, wherein the MTI comprises at least one non-AUG translation initiation site that mediates translation initiation of the antigen, antigenic epitope, or combination thereof.

In further embodiments, the present disclosure provides a cell comprising a vector, comprising a chimeric nucleic comprising a multiplex translation initiation (MTI) sequence and a nucleic acid molecule encoding an antigen, an antigenic epitope, or a combination thereof, wherein the MTI comprises at least one non-AUG translation initiation site that mediates translation initiation of the antigen, antigenic epitope, or combination thereof.

In some embodiments, the present disclosure provides a method of eliciting a cellular immune response, comprising administering to a subject an effective amount of an immunization composition comprising a nucleic acid molecule according as described in embodiments herein, an antigen encoded by a nucleic acid molecule as described in embodiments herein, or both, thereby eliciting a cellular immune response.

In some embodiments, the present disclosure provides a method of eliciting a cellular immune response, comprising administering to a subject an effective amount of a cell comprising a nucleic acid molecule as described in embodiments herein, or a vector as described in embodiments herein, thereby eliciting a cellular immune response, thereby eliciting a cellular immune response.

In further embodiments, the present disclosure provides a method of eliciting a cellular immune response, comprising (a) administering to a subject an effective amount of an antigen immunization composition comprising one or more antigens encoded by any one of the nucleic acid molecules as described in embodiments herein, and (b) administering to the subject an effective amount of a nucleic acid molecule immunization composition comprising a nucleic acid molecule as described in embodiments herein or a vector as described in embodiments herein.

In in yet further embodiments, the present disclosure provides a method of eliciting an cellular immune response, comprising (a) administering to a subject an effective amount of a nucleic acid molecule immunization composition comprising a nucleic acid molecule as described in embodiments herein, (b) allowing a time sufficient to generate an initial immune response, and (c) administering to the subject a second effective amount of a nucleic acid molecule immunization composition comprising a nucleic acid molecule as described in embodiments herein, or an effective amount of an antigen immunization composition.

In some embodiments, the present disclosure provides a method of treating breast cancer, comprising administering to a subject an effective amount of nucleic acid molecule immunization composition comprising a comprising a multiplex translation initiation (MTI) sequence and a nucleic acid molecule encoding an antigen, an antigenic epitope, or a combination thereof, wherein the MTI comprises at least one non-AUG translation initiation site that mediates translation initiation of the antigen, antigenic epitope, or combination thereof, and the antigenic epitope comprises a peptide from folate receptor alpha, HER2/neu, or any combination thereof.

In some embodiments, the present disclosure provides a method of treating cancer, comprising administering to a subject an effective amount of a nucleic acid immunization composition comprising a nucleic acid molecule as described in embodiments herein, wherein the one or more antigens encoded the nucleic acid molecule comprise an antigen having an oncogenic mutation identified in the subject.

DETAILED DESCRIPTION

Figure 1:
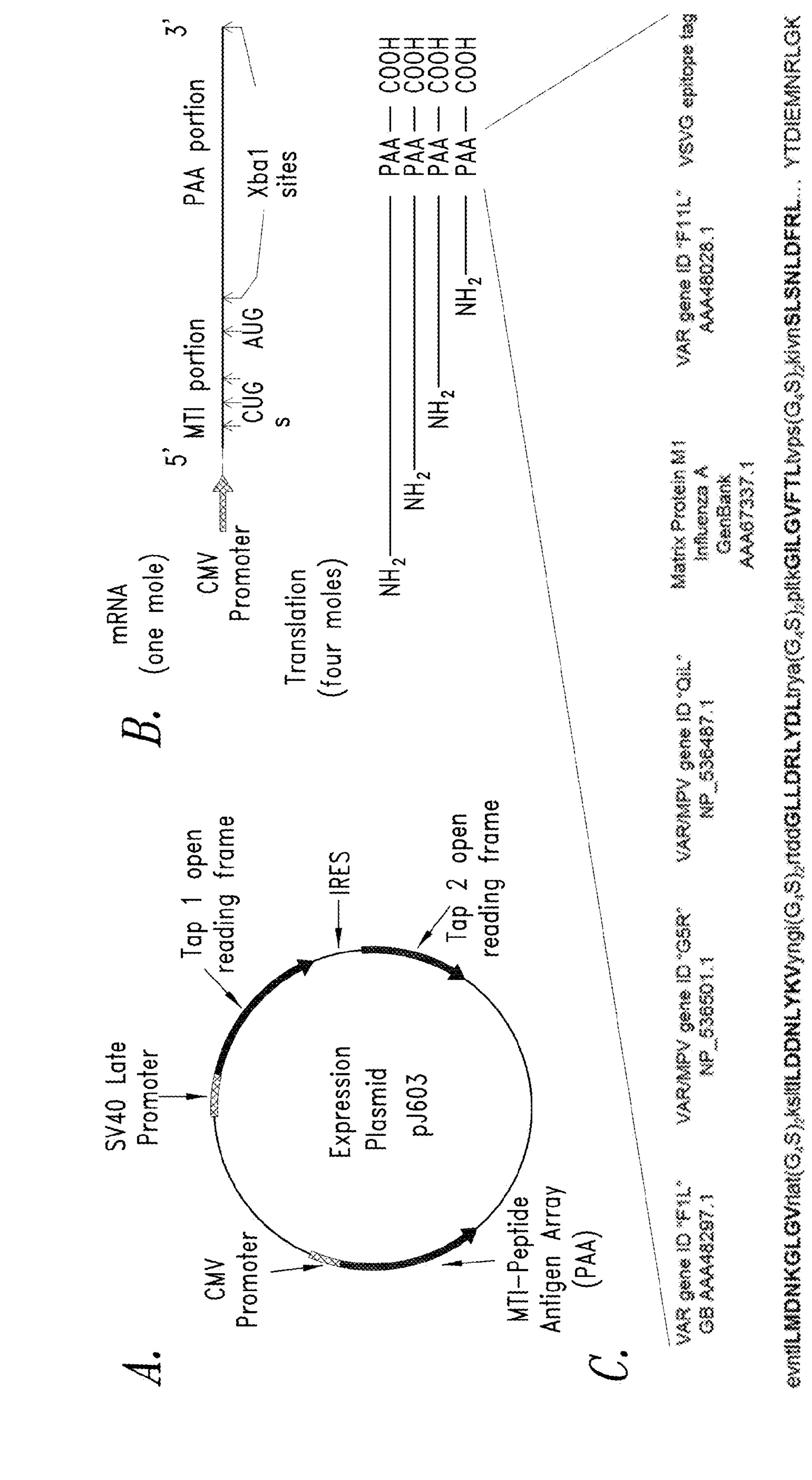
FIG. 1 depicts an exemplary DNA vaccine expression vector. A) The vaccine vector contains full-length, codon-optimized TAP 1 and TAP 2 driven by an SV40 promoter and the MTI-peptide antigen array (PAA) under the control of the CMV promoter. B) Overexpression of the PAA is achieved through the application of three non-classical translation initiation sites (CUG) that can be found in the MTI. These CUG and AUG sites mediate nuclear and cytosolic expression respectively, and can be altered as needed. The PAA is flanked by Xba1 sites facilitating insertion and excision of various PAAs. C) Peptide sequences in the A*0201 PAA are depicted (SEQ ID NO.: 204). A2 binding peptides are presented in bold font. Each peptide is flanked by 3-4 amino acid residues at the NH2 and COOH ends to retain the natural proteasome processing sites for each peptide. Each peptide is also separated by the $(G_4S)_2$ spacer. This specific PAA also includes an Influenza M1 protein as a control, and a C-terminal VSVG protein epitope tag (SEQ ID NO.: 14) for evaluating epitope expression.

In some aspects, the present disclosure provides a chimeric nucleic acid molecule comprising a multiplex translation initiation (MTI) sequence and a nucleic acid molecule encoding one or more antigens, antigenic epitopes, or a combination thereof (e.g., polyantigen array or PAA), wherein the multiplex translation sequence comprises at least one non-AUG translation initiation site that mediates translation initiation of the one or more antigens, antigenic epitopes, or a combination thereof.

In certain embodiments, the present disclosure provides a method for prime and boost or multiple antigenic challenges to elicit a robust immune response that results in the production memory T cells. For example, an immune response is elicited against a cancer or infectious disease by (a) contacting a subject with an antigenic peptide immunization composition, (b) optionally allowing a time sufficient to generate an initial immune response, (c) contacting the subject with a nucleic acid molecule immunization composition as described herein, wherein the nucleic acid molecule of the nucleic acid molecule immunization composition encode one or more of the same antigenic peptides as used in step (a).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range includes the value of any integer within the recited range and, when appropriate, fractions thereof (such as one tenth or one hundredth of an integer), unless otherwise indicated. Also, any number range recited herein relating to any physical feature (such as polymer subunits, size or thickness) include any integer within the recited range, unless otherwise indicated. As used herein, the term "about" means (1) ±20% of the indicated range, value or structure; (2) a value that includes the inherent variation of error for the method being employed to determine the value; or (3) a value that includes the variation that exists among replicate experiments, unless otherwise indicated. As used herein, the terms "a" and "an" refer to "one or more" of the enumerated components. The use of the alternative (e.g., "or") means either one, both, or any combination thereof of the alternatives or enumerated components. As used herein, the terms "include," "have" and "comprise" are used synonymously, which terms and variants thereof are intended to be construed as non-limiting.

The term "multiplex translation leader sequence," "multiplex translation initiation sequence," or "MTI" refers to a nucleic acid molecule comprising at least one non-conventional CUG start codon in addition to the one standard ATG start codon. In some embodiments, an MTI allows the production of more than one mole of protein per mole of mRNA. In certain embodiments, an MTI nucleic acid molecule corresponds to a 5'-portion of an FGF2 gene (e.g., a human FGF2 gene as set forth in GenBank Accession No. NM_002006.4) containing (a) the ATG start codon of FGF2 and (b) a sequence comprising about 123 nucleotides to about 385 nucleotides upstream (5') of the ATG start codon of FGF2, wherein this portion upstream of the ATG start codon comprises from one to three translationally active non-conventional (e.g., CUG) start codons. In certain embodiments, an MTI further comprises (c) about 15 nucleotides (encoding about 5 amino acids) to about 45 nucleotides (encoding about 15 amino acids) downstream (3') of the ATG start codon of FGF2. In some embodiments, an MTI comprises (d) at least one to two nuclear localization domains located upstream of the AUG start codon and downstream of at least one non-conventional CUG start codon.

For example, a multiplex translation initiation sequence comprising four FGF2 translation initiation sites (three non-conventional CUG start codons and one standard ATG start codon) linked upstream of a nucleic acid molecule encoding a fusion protein (e.g., a plurality of antigen peptides linked in a linear array) can yield four moles of a multi-peptide fusion protein translation product for every one mole of transcribed mRNA. In certain embodiments, a nucleic acid molecule encoding a fusion protein is introduced into a host cell and expressed, wherein the nucleic acid molecule contains a multiplex translation leader sequence comprising at least one non-AUG (e.g., CUG) translation initiation site that mediates translation initiation at the non-AUG (e.g., CUG) translation initiation site. In some embodiments, the MTI comprises at least five translation initiation sites (four non-conventional CUG start codons and one standard ATG start codon).

Non-canonical translation initiation start site have been described by Florkiewicz et al., *BBRC* 409 (3):494-499, 2011; Ivanov et al., *Nucleic Acids Res* 39 (10), 2011; Peabody D S, *J Biological Chem* 264 (9):5031-5035, 1989; Starck et al., *Science* 336 (6089):1719-23, 2012; Hann et al., *Genes and Dev* 6:1229-1240, 1992; Touriol et al., *Biol Cell* 95 (3-4):169-78, 2003; Schwab et al., *Science* 301 (5638): 1367-71, 2003; Malarkannan et al., *Immunity* 10 (6):681-90, 1999, all of which are incorporated by reference in entirety. In certain situations, classical AUG mediated translation may be inhibited while translation initiation from non-AUG initiation codons may continue or may even be enhanced.

As used herein, "tumor associated antigen" or "TAA" refers to a protein, peptide, or variant thereof that is preferentially expressed on cancer cells or pre-cancer cells that exhibit deregulated growth. "Preferentially expressed" refers to expression of detectable levels of the protein or peptide in a cell or on the surface of a cell, wherein the protein or peptide is not expressed on normal cells of the same type. Preferably, the TAA is not expressed on non-cancer cells. Exemplary, TAAs include human epidermal growth factor receptor 2 (also known as ERBB2, EGFR2, Neu (neuro/glioblastoma derived oncogene homolog), HER2, or HER2/neu), BRAF, BRCA1/2, folate receptor-α, WT1, PI3K, NY-ES01, GNRH1, CTAG1A, CEA, IGFBP2, Cyclin D1, and MIF. The terms "tumor associated antigen," "TAA," "biomarker," "cancer marker," and "marker" are used interchangeably throughout.

A "fusion protein" or "chimeric protein," as used herein, refers to a linear single chain protein that includes polypeptide components based on one or more parental proteins, polypeptides, or fragments thereof (e.g., antigenic peptides) and does not naturally occur in a host cell. A fusion protein can contain two or more naturally-arising amino acid sequences that are linked together in a way that does not occur naturally. For example, a fusion protein may have two or more portions from the same protein or a fragment thereof (e.g., antigenic fragment) linked in a way not normally found in a cell or a protein, or a fusion protein may have portions (e.g., antigenic portions) from two, three, four, five or more different proteins linked in a way not normally found in a cell. Also, a fusion protein may have two or more copies of the same portion of a protein or a fragment thereof (e.g., antigenic fragment). A fusion protein can be encoded by a nucleic acid molecule wherein a polynucleotide sequence encoding one protein or a portion thereof (e.g., antigen) is appended in frame with a nucleic acid molecule that encodes one or more proteins or a portion thereof (e.g., same or different antigens), which two or more proteins or portions thereof are optionally separated by nucleotides that encode a linker, spacer, cleavage site, junction amino acids, or a combination thereof. The valency of any one or more antigenic peptide epitope of the compositions herein, for example of a fusion protein comprising antigenic peptides, may be increased by duplicating, tripling, quadrupling, or further expanding the number of individual antigenic peptide epitopes contained therein.

A "spacer" refers to an amino acid sequence that connects two proteins, polypeptides, peptides, or domains and may provide a spacer function compatible with cleavage of a linear antigen array into individual antigenic peptides capable of associating with an MHC (HLA) molecule. A spacer can promote proteolytic processing into antigenic peptides by enhancing or promoting a disordered conformation of a primary translation product and thereby promoting its ubiquitin modification.

"Junction amino acids" or "junction amino acid residues" refer to one or more (e.g., about 2-10) amino acid residues between two adjacent motifs, regions or domains of a polypeptide, such as between a antigenic peptides or between an antigenic peptide and an adjacent peptide encoded by a multiplex translation leader sequence or between an antigenic peptide and a spacer or cleavage site. Junction amino acids may result from the construct design of a fusion protein (e.g., amino acid residues resulting from the use of a restriction enzyme site during the construction of a nucleic acid molecule encoding a fusion protein). Junction amino acids may be derived from a sequence authentic or native to a T-cell antigenic epitope sequence by extending the NH2 and/or COOH-terminus of a HLA Class 1 or HLA Class II peptide identified by computer algorithm or other means such as mass spectrometry analysis of peptides eluted from HLA Class I or HLA Class II restricted protein complexes.

As used herein, a molecule or compound "consists essentially of" one or more domains or encodes one or more domains "consisting essentially of" (e.g., an antigen, a linker or spacer, a proteolytic cleavage site, a nuclear localization signal, a multiplex translation initiation sequence) when the portions outside of the one or more domains (e.g., amino acids at the amino- or carboxy-terminus or between domains), in combination, contribute to no more than 20% (e.g., no more than 15%, 10%, 8%, 6%, 5%, 4%, 3%, 2% or 1%) of the length of the molecule or compound and do not substantially affect (i.e., do not alter the activity by more than 50% (e.g., no more than 40%, 30%, 25%, 20%, 15%, 10%, 5%, 4%, 3%, 2%, 1%) of the activities of one or more of the various domains (e.g., the immunogenicity of an antigen or antigenic epitope, the capability of localizing to the nucleus, the capability of forming a polypeptide complex (such as an HLA-peptide complex), the capability of promoting translation initiation from non-AUG codons). In certain embodiments, a nucleic acid molecule consists essentially of a multiplex translation leader sequence and a sequence encoding one or more antigens, antigenic epitopes or combination thereof, wherein an encoded antigen may comprise junction amino acids at the amino- and/or carboxy-terminus or between antigens. In certain embodiments, such junction amino acids between antigens or antigenic epitopes form proteolytic cleavage sites such that the antigens or antigenic epitopes are separated in vivo and can associate, for example, with a corresponding mammalian class I or class II HLA or MHC molecule.

As used herein, "nucleic acid" or "nucleic acid molecule" refers to any of deoxyribonucleic acid (DNA), ribonucleic acid (RNA), oligonucleotides, fragments generated, for example, by the polymerase chain reaction (PCR) or by in vitro translation, and fragments generated by any one or more of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination thereof. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, morpholino, or the like. The term "nucleic acid molecule" also includes "peptide nucleic acids" (PNAs), which comprise naturally occurring or modified nucleic acid bases attached to a polyamide backbone. Nucleic acid molecules can be either single stranded or double stranded.

The term "construct" refers to any polynucleotide that contains a recombinant nucleic acid. A construct may be present in a vector (e.g., a bacterial vector, a viral vector) or may be integrated into a genome. A "vector" is a nucleic acid molecule that is capable of transporting another nucleic acid. Vectors may be, for example, plasmids, cosmids, viruses, a RNA vector, or a linear or circular DNA or RNA molecule that may include chromosomal, non-chromosomal, semi-synthetic or synthetic nucleic acids. Exemplary vectors are those capable of autonomous replication (episomal vector) and/or expression of nucleic acids to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

"Lentiviral vector," as used herein, means HIV-based lentiviral vectors that are useful for gene delivery because of their relatively large packaging capacity, reduced immunogenicity and their ability to stably transduce with high efficiency a large range of different cell types. Lentiviral vectors are usually generated following transient transfection of three or more plasmids (e.g., packaging, envelope, and transfer) into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. A viral vector may be DNA (e.g., an Adenovirus or Vaccinia virus) or RNA-based including an oncolytic virus vector (e.g., VSV), replication competent or incompetent. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression," as used herein, refers to the process by which a polypeptide is produced based on the nucleic acid sequence of a gene. The process includes both transcription and translation. Translation may initiate from a non-conventional start codon, such as a CUG codon, or translation may initiate from several start codons (standard AUG and non-conventional) to produce more protein (on a per mole amount) than mRNA produced.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, "contacting," "contacting a cell," "contacting a subject" or variants thereof, in the context of contacting with a nucleic acid molecule or composition refers to introducing the nucleic acid into the cell such that the at least some of the encoded content of the nucleic acid molecule is expressed in the cell. By "introduced" is meant transformation, transfection, transduction, or other methods known in the art for the introduction of nucleic acid molecules such as by a gene gun or nanoparticles.

Expression of recombinant proteins may be inefficient outside their original host since codon usage bias has been observed across different species of bacteria (Sharp et al., *Nucl. Acids Res.* 33:1141, 2005). Even over-expression of recombinant proteins within their native host may be difficult. In certain embodiments, nucleic acid molecules (e.g., nucleic acids encoding antigenic peptides) to be introduced into a host as described herein may be subjected to codon optimization prior to introduction into the host to ensure protein expression is enhanced. "Codon optimization" refers to the alteration of codons in genes or coding regions of nucleic acids before transformation to reflect the typical codon usage of the host without altering the polypeptide encoded by the DNA molecule. Codon optimization methods for optimum gene expression in heterologous hosts have been previously described (see, e.g., Welch et al., *PLoS One* 4:e7002, 2009; Gustafsson et al., *Trends Biotechnol.* 22:346, 2004; Wu et al., *Nucl. Acids Res.* 35:D76, 2007; Villalobos et al., *BMC Bioinformatics* 7:285, 2006; U.S. Patent Publication Nos. 2011/0111413 and 2008/0292918; disclosure of which are incorporated herein by reference, in their entirety). In certain embodiments, the multiplex translation leader sequence of this disclosure is human and is not codon optimized. Codon optimized recombinant nucleic acids may be distinguished from corresponding endogenous genes based on the use of PCR primers designed to recognize a codon optimized portion that is consequently distinct from a non-codon optimized portion of a nucleic acid.

The terms "identical" or "percent identity," in the context of two or more polypeptide or nucleic acid molecule sequences, means two or more sequences or subsequences that are the same or have a specified percentage of amino acid residues or nucleotides that are the same over a specified region (e.g., 60%, 65%, 70%, 75%, 80%, 85%, 90%, 91%, 92%, 93%, 94%, 95%, 96%, 97%, 98%, 99%, or 100% identity), when compared and aligned for maximum correspondence over a comparison window, or designated region, as measured using methods known in the art, such as a sequence comparison algorithm, by manual alignment, or by visual inspection. For example, a preferred algorithm suitable for determining percent sequence identity and sequence similarity is the BLAST 2.0 algorithm, which is described in Altschul et al., *J. Mol. Biol.* 215:403, 1990, with the parameters set to default values.

As used herein, TAP (Transporter Associated with Antigen Processing), refers to a heterodimer comprising a TAP1 and a TAP2 protein. Heterodimers of TAP are located in the endoplasmic reticulum (ER) where it functions to move selected peptides from the cytosol into the lumen of the ER where the peptide binds to a HLA Class I protein. Another intracellular TAP protein is TAPL (transporter associated with antigen processing like protein) localized to intracellular vesicular compartments such as the endosome and lysosome. TAP1, TAP2, and TAPL are members of the ATP binding cassette (ABC) transporter family. However, unlike ER localized TAP1/2 heterodimers, TAPL functions as a homodimer. Examples of TAP include TAP1 (GenBank No. NM_000593.5), TAP2 (GenBank No. NM_000544.3), and TAPL (GenBank No. NM_019624.3).

As used herein, "mutation" refers to a change in the sequence of a nucleic acid molecule or polypeptide molecule as compared to a reference or wild-type nucleic acid molecule or polypeptide molecule, respectively. A mutation can result in several different types of changes in sequence, including substitution, insertion or deletion of nucleotide(s) or amino acid(s). In other embodiments, a mutation is a substitution of one or more nucleotides or residues. In certain embodiments, an altered or mutated protein or polypeptide only contains conservative amino acid substitutions as compared to the reference molecule. In certain other embodiments, an altered or mutated protein or polypeptide only contains non-conservative amino acid substitutions as compared to the reference molecule. In yet other embodiments, an altered or mutated protein or polypeptide contains both conservative and non-conservative amino acid substitutions. In any of these embodiments, an alteration or mutation does not alter or eliminate an antigenic epitope of a protein or peptide and the altered or mutated peptide is still recognized by its cognate MHC (HLA) molecule.

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY: N.Y. (1975), pp. 71-77; Lewin, Genes IV, Oxford University Press, NY and Cell Press, Cambridge, Mass. (1990), p. 8). In certain embodiments, a conservative substitution includes, for example, a leucine to serine substitution.

As used herein, "recombinant" or "non-natural" refers to an organism, microorganism, cell, nucleic acid molecule, or vector that has at least one engineered genetic alteration or has been modified by the introduction of a heterologous nucleic acid molecule, or refers to a cell that has been altered such that the expression of an endogenous nucleic acid molecule or gene can be controlled. Recombinant also refers to a cell that is derived from a non-natural cell or is progeny of a non-natural cell having one or more such modifications. Genetic alterations include, for example, modifications introducing expressible nucleic acid molecules encoding proteins, or other nucleic acid molecule additions, deletions, substitutions or other functional alteration of a cell's genetic material. For example, recombinant cells may express genes or other nucleic acid molecules that are not found in identical or homologous form within a native (wild-type) cell (e.g., a fusion or chimeric protein), or may provide an altered expression pattern of endogenous genes, such as being over-expressed, under-expressed, minimally expressed, or not expressed at all.

Recombinant methods for expression of exogenous or heterologous nucleic acids in cells are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Exemplary exogenous proteins or enzymes to be expressed include TAP1, TAP2, antigens, cytokines, or any combination thereof. Genetic modifications to nucleic acid molecules encoding fusion proteins can confer a biochemical or metabolic capability to a recombinant or non-natural cell that is altered from its naturally occurring state.

As used herein, the term "endogenous" or "native" refers to a gene, protein, compound or activity that is normally present in a host cell. The term "homologous" or "homolog" refers to a molecule or activity from an exogenous (non-native) source that is the same or similar molecule or activity as that found in or derived from a host or host cell.

As used herein, "heterologous" nucleic acid molecule, construct or sequence refers to a nucleic acid molecule or portion of a nucleic acid molecule sequence that is not native to a cell in which it is expressed, a nucleic acid molecule or portion of a nucleic acid molecule native to a host cell that has been altered or mutated, or a nucleic acid molecule with an altered expression as compared to the native expression levels under similar conditions. For example, a heterologous control sequence (e.g., promoter, enhancer) may be used to regulate expression of a gene or a nucleic acid molecule in a way that is different than the gene or a nucleic acid molecule that is normally expressed in nature or culture. In certain embodiments, a heterologous nucleic acid molecule may be homologous to a native host cell gene, but may have an altered expression level or have a different sequence or both. In other embodiments, heterologous or exogenous nucleic acid molecules may not be endogenous to a host cell or host genome (e.g., fusion protein), but instead may have been introduced into a host cell by transformation (e.g., transfection, electroporation), wherein the added molecule may integrate into the host genome or can exist as extra-chromosomal genetic material either transiently (e.g., mRNA) or semi-stably for more than one generation (e.g., episomal viral vector, plasmid or other self-replicating vector).

In certain embodiments, more than one heterologous or exogenous nucleic acid molecule can be introduced into a host cell as separate nucleic acid molecules, as a polycistronic nucleic acid molecule, as a single nucleic acid molecule encoding a fusion protein, or any combination thereof, and still be considered as more than one heterologous or exogenous nucleic acid. When two or more exogenous nucleic acid molecules are introduced into a host cell, it is understood that the two more exogenous nucleic acid molecules can be introduced as a single nucleic acid molecule (e.g., on a single vector), on separate vectors, as single or multiple mRNA molecules, integrated into the host chromosome at a single site or multiple sites, and each of these embodiments is still to be considered two or more exogenous nucleic acid molecules. Thus, the number of referenced heterologous nucleic acid molecules or protein activities refers to the number of encoding nucleic acid molecules or the number of protein activities, not the number of separate nucleic acid molecules introduced into a host cell.

For example, a cell can be modified to express two or more heterologous or exogenous nucleic acid molecules, which may be the same or different, that encode one or more fusion proteins, as disclosed herein. In certain embodiments, a host cell will contain a first nucleic acid molecule encoding a first fusion protein and a separate second nucleic acid molecule encoding a second fusion protein, or a host cell will contain a single polycistronic nucleic acid molecule that encodes a first fusion protein and second fusion protein, or single nucleic acid molecule that encodes a first fusion protein, a cleavable amino acid sequence (e.g., trypsin, pepsin, proteasome site) or a self-cleaving amino acid sequence (e.g., 2A protein), and a second fusion protein.

"T cell receptor" (TCR) is a molecule found on the surface of T cells that, along with CD3, is generally responsible for recognizing antigens bound to major histocompatibility complex (MHC) molecules. A TCR consists of a disulfide-linked heterodimer of the highly variable $\alpha$ and $\beta$ chains in most T cells. In other T cells, an alternative receptor made up of variable $\gamma$ and $\delta$ chains is expressed. Each chain of the TCR is a member of the immunoglobulin superfamily and possesses one amino-terminal immunoglobulin variable domain, one immunoglobulin constant domain, a transmembrane region, and a short cytoplasmic tail at the C-terminal end (see, Abbas and Lichtman, *Cellular and Molecular Immunology* (5th Ed.), Editor: Saunders, Philadelphia, 2003; Janeway et al., *Immunobiology: The Immune System in Health and Disease,* $4^{th}$ Ed., Current Biology Publications, p 148, 149, and 172, 1999).

HLA Class I binding CD8+ T-cell are T-cells that kill tumor cells or virally infected cells through interactions between an antigenic peptide bound cell surface localized HLA (also known as MHC). Cells that present HLA class I antigenic peptide epitopes are referred to as antigen presenting cells.

HLA Class II presentation is different than HLA Class I in that peptide antigens are bound to HLA class II complexes that are already on the cell surface or that are present in certain intracellular vesicles, such as endosomes or lysosomes. Class II antigen presentation thus does not a priori require the activity of TAP. However, the protein referred to as TAPL, which is found localized to certain intracellular vesicles such as an endosome or lysosome, may function to recognize cytosol localized class II peptides and consequently transfer a 12-18 amino acid peptide from the cytosol into a intracellular vesicle containing a Class II HLA that then traffics back onto the cell surface where it can then interact with and consequently expand a population of CD4+ T-cells. A host's T-cells that recognized cell surface localized HLA class II peptide complexes are called CD4+ T-cells, which are principally responsible for preserving the function of CD8+ killer T-cells mediated by the release of a set of CD8+ cytokines.

The term "antigen specific T-cell response" refers to an immune response mediated by T-cells directed at a cell expressing a specific antigen. In some embodiments, the T-cell response is a CD8+ T-cell response, a CD4+ T-cell response, or a combination thereof.

The term "antigen, "antigenic peptide" or variants thereof refers to a polypeptide that can stimulate a cellular immune response. In some embodiments, an antigen is an HLA Class I, an HLA Class II peptide, or HLA Class II peptide having an embedded HLA Class I peptide.

The term "immunization composition" refers to a composition that can stimulate or elicit an immune response. Preferably, the immune response is a cellular immune response, such as an adaptive immune response mediated by T-cells (e.g., CD8+ T-cells or CD4+ T-cells). In some embodiments, an immunization composition is a pharmaceutical formulation. In further embodiments, an immunization composition is an antigenic peptide immunization composition, a nucleic acid immunization composition, a cell immunization composition, or a combination thereof.

The term "antigen immunization composition" or "peptide immunization composition" refers to an immunization composition that includes one or more antigens that are capable of promoting or stimulating a cellular immune response. In some embodiments, an antigen immunization composition comprises an HLA Class I peptide, HLA Class II peptide, HLA Class II peptide having an embedded HLA Class I peptide, or combinations thereof.

The term "nucleic acid immunization composition" refers to an immunization composition that includes a nucleic acid molecule that encodes one or more antigens or antigenic epitopes, and that can be contained in a vector (e.g., plasmid, virus). A nucleic acid immunization composition can be introduced into a host cell ex vivo, or in vivo for expression of the one or more antigenic peptides in a subject. In certain embodiments, a nucleic acid immunization composition encodes an HLA Class I peptide, HLA Class II peptide, HLA Class II peptide having an embedded HLA Class I peptide, or combinations thereof.

The term "nucleic acid molecule immunization" or "DNA immunization" as used herein refers to a nucleic acid molecule encoding one or more antigens introduced into a host or host cell in order to express the one or more antigens in vivo. A nucleic acid molecule immunization can be by direct administration into a host, such as by standard injection (e.g., intramuscular, intradermal), transdermal particle delivery, inhalation, topically, orally, intranasally, or mucosally. Alternatively, a nucleic acid molecule can be introduced ex vivo into host cells (e.g., host cells or cells from a donor HLA matched to the host) and the transfected host cells can be administered into the host such that an immune response can be mounted against the one or more antigens encoded by the nucleic acid molecule.

The term "nucleic acid molecule vaccine" or "DNA vaccine" as used herein refers to a nucleic acid molecule encoding one or more antigens or antigenic epitopes that is used in a nucleic acid molecule immunization as defined herein.

"Treatment," "treating" or "ameliorating" refers to medical management of a disease, disorder, or condition of a subject (e.g., patient), which may be therapeutic, prophylactic/preventative, or a combination treatment thereof. A treatment may improve or decrease the severity at least one symptom of a disease, delay worsening or progression of a disease, or delay or prevent onset of additional associated diseases. "Reducing the risk of developing a disease" refers to preventing or delaying onset of a disease (e.g., cancer) or reoccurrence of one or more symptoms of the disease.

A "therapeutically effective amount (or dose)" or "effective amount (or dose)" of a compound or composition refers to that amount of compound sufficient to result in amelioration of one or more symptoms of the disease being treated in a statistically significant manner. The precise amount will depend upon numerous factors, e.g., the activity of the composition, the method of delivery employed, the immune stimulating ability of the composition, the intended patient and patient considerations, or the like, and can readily be determined by one of ordinary skill in the art.

A therapeutic effect may include, directly or indirectly, the reduction of one or more symptoms of a disease (e.g., reduction in tumor burden or reduction in pathogen load). A therapeutic effect may also include, directly or indirectly, the stimulation of a cellular immune response.

A "matched" vaccination strategy is one in which a peptide vaccine and a DNA vaccine are administered to a subject wherein the peptides of the peptide vaccine and peptides encoded by the DNA vaccine are derived from the same protein (e.g., same cancer related TAA or pathogen derived antigen). In some embodiments, the peptide vaccine peptides are HLA class II antigens. In some embodiments, the peptides encoded by the DNA vaccine are HLA class I peptides. A matched vaccination strategy can include administering respective compositions as a prime-and-boost.

As used herein, "prime-and-boost" or "immunogenic challenge" refers to sequentially or simultaneously delivering one or more of a series of peptide vaccines followed by one or more in a series of DNA vaccines, or, in the alternative, sequentially or simultaneously delivering one or more of a series of DNA vaccines followed by one or more in a series of peptide vaccines.

Cancer cells may aberrantly express certain polypeptides, either by inappropriate expression or overexpression. As such, inappropriately expressed polypeptides have been identified as tumor associated antigens (TAAs). Tumor-associated antigens however may be functionally non-immunogenic or are ineffectively or weakly immunogenic. This may be referred to immune tolerance. Compositions and methods of the instant disclosure are designed to enhance or further stimulate a patient's immune system so that it is capable of functioning more effectively to kill cancer cells or to kill pathogen infected cells.

As used herein, a "subject," may be any organism capable of developing a cellular immune response, such as humans, pets, livestock, show animals, zoo specimens, or other animals. For example, a subject may be a human, a non-human primate, dog, cat, rabbit, rat, mouse, guinea pig, horse, cow, sheep, goat, pig, or the like. Subjects in need of administration of therapeutic agents as described herein include subjects at high risk for developing a cancer or infectious disease as well as subjects presenting with an existing cancer or infectious disease. A subject may be at high risk for developing a cancer if the subject has experienced an injury, such as exposure to carcinogens or radiation, or has a genetic predisposition, such as a mutation in the BRCA1/2, folate receptor-α, or p53 genes. Subjects suffering from or suspected of having an infectious disease or a cancer can be identified using methods as described herein and known in the art.

A "subject in need" refers to a subject at high risk of, or suffering from, a disease, disorder or condition that is amenable to treatment or amelioration with a compound or a composition thereof provided herein. In certain embodiments, a subject in need is a human.

Accordingly, in some embodiments the composition of the instant disclosure provides a chimeric nucleic acid molecule, comprising a multiplex translation initiation (MTI) sequence and a nucleic acid molecule encoding an antigen, an antigenic epitope, or a combination thereof, wherein the MTI comprises at least one non-AUG translation initiation site that mediates translation initiation of the antigen, antigenic epitope, or combination thereof.

A nucleic acid based plasmid or virus delivery system as described herein provides a transcribed mRNA that is recognized by eukaryotic cell translation components, which is translated into a protein following the initiation of translation that occurs at the first or appropriate translation initiation codon. The canonical mechanism of translation initiation starts at an AUG codon. However, as used herein, translation initiation can also begin at a non-AUG codon, such as a CUG codon. The human gene encoding FGF2 is an example of a gene with translation that is mediated via three CUG start codons, in addition to one AUG codon. In some embodiments, the MTI nucleic acid molecule set forth herein comprises a portion of the FGF2 multiple translation initiation domain of the gene/mRNA.

In some embodiments, an MTI of the chimeric nucleic acid molecule corresponds to a 5'-portion of an FGF2 gene (e.g., a human FGF2 gene as set forth in GenBank Accession No. NM_002006.4) containing the ATG start codon of FGF2 and a sequence comprising about 123 nucleotides to about 385 nucleotides upstream (5') of the ATG start codon of FGF2, wherein this portion upstream of the ATG start codon comprises from one to three translationally active non-conventional (e.g., CUG) start codons. In certain embodiments, the MTI further comprises about 15 nucleotides (encoding about 5 amino acids) to about 45 nucleotides (encoding about 15 amino acids) downstream (3') of the ATG start codon of FGF2. In some embodiments, the MTI comprises at least one to two nuclear localization domains located upstream of the AUG start codon and downstream of at least one non-conventional CUG start codon. In certain embodiments, an MTI sequence comprising four FGF2 translation initiation sites (three non-conventional CUG start codons and one standard ATG start codon) linked upstream of a nucleic acid molecule encoding a fusion protein (e.g., a plurality of antigen peptides linked in a linear array) can yield four moles of a multi-peptide fusion protein translation product for every one mole of transcribed mRNA. In certain embodiments, a nucleic acid molecule encoding a fusion protein is introduced into a host cell and expressed, wherein the nucleic acid molecule contains a multiplex translation leader sequence comprising at least one non-AUG (e.g., CUG) translation initiation site that mediates translation initiation at the non-AUG (e.g., CUG) translation initiation site. In some embodiments, an MTI sequence is a nucleic acid molecule having a sequence as set forth in any one of SEQ ID NOS.: 1-6, 95, or 96. In certain embodiments, an MTI sequence is nucleic acid molecule having at least about 80%, 85%, 90%, 91%, 92%, 93%, 94%, 95%, 96%, 97%, 98%, or 99% sequence identity to the sequence set forth in any one of SEQ ID NOS.:1-6.

In certain embodiments, a nucleic acid molecule encoding a fusion protein comprises a plurality of class I MHC (HLA) antigenic peptides, a plurality of class II MHC (HLA) antigenic peptides, or a combination thereof. In further embodiments, a plurality of MHC (HLA) class I antigenic peptides, class II antigenic peptides, or a combination thereof are expressed as a linear single-chain polypeptide antigen array, wherein each antigen is separated from the adjacent antigen by a spacer, a cleavable site (e.g., enzyme recognition site or self-cleaving), or both, and wherein the polypeptide antigen array is processed by the cellular machinery (e.g., proteasome or nuclear proteasome) into individual antigen peptides capable of forming a complex with their cognate MHC molecules.

In accordance with the disclosure set forth herein, a translated polypeptide or protein comprises, for example, a linear peptide antigen array (PAA) that is or may then be modified intracellularly by the addition of a ubiquitin moiety. The ubiquitin-modified PAA is recognized by and proteolytically processed through the actions of the proteasome. The results of proteolytic processing are small peptides approximately 8-12 amino acids in length that are then recognized by the intracellular ER localized protein termed TAP.

Accordingly, in some embodiments, the chimeric nucleic acid molecule includes a nucleic acid molecule that encodes one or more antigens, antigenic epitopes, or a combination thereof (referred to collectively as antigens), which is referred to herein as a polyantigen array (PAA). In some embodiments, a PAA encodes one or more antigens from the same protein. In other embodiments, a PAA encodes one or more antigens from more than one protein (i.e., comprises a chimeric polypeptide). For example, a PAA can encode one or more antigens from folate receptor-α and one or more antigens from Her2/neu. In some embodiments, a nucleic acid molecule encodes a plurality of antigens ranging from about 2 to about 20, from about 2 to about 15, from about 2 to about 10, from about 2 to about 9, from about 2 to about 8, or a nucleic acid molecule encodes 2, 4, 5, 6, 7, or 8 antigens.

In some embodiments, a PAA encodes a plurality of antigens wherein two or more of the plurality of antigens are separated by a spacer. In certain embodiments, a spacer is comprised of about 2 to about 35 amino acids, or about 5 to about 25 amino acids or about 8 to about 20 amino acids or about 10 to about 15 amino acids. In some embodiments, a spacer may have a particular sequence, such as a $(G_4S)_n$ repeat, wherein n is an integer from 1-20, from 1-15, from 1-10, from 1-5, from 1-3, or the like. In particular embodiments, a spacer is a $(G_4S)_2$ peptide.

In some embodiments, a chimeric nucleic acid encodes a PAA wherein two or more of the plurality of antigens are separated by a cleavage site. In certain embodiments, a cleavage site comprises from about 2 to about 20 amino acids amino-terminal to the antigenic peptide as found in the reference protein, from about 2 to about 20 amino acids carboxy-terminal to the antigenic peptide as found in the reference protein, a self-cleaving amino acid sequence, or a combination thereof. In certain embodiments, the cleavage site comprises from about 2 to about 15, about 2 to about 10, or about 2 to about 5 amino acids at the amino-terminal or the carboxy-terminal end of the antigen. In some embodiments, the cleavage site is a self-cleaving amino acid sequence comprising a 2A peptide from porcine teschovirus-1 (P2A), equine rhinitis A virus (E2A), *Thosea asigna* virus (T2A), foot-and-mouth disease virus (F2A), or any combination thereof (see, e.g., Kim et al., *PLOS One* 6:e18556, 2011, which 2A nucleic acid and amino acid sequences are incorporated herein by reference in their entirety).

In some embodiments, an antigen or antigenic epitope is an HLA Class I antigenic peptide, an HLA Class II antigenic peptide, an HLA class II antigenic peptide with an embedded HLA Class I antigenic peptide, or any combination thereof. In certain embodiments, an antigen or antigenic epitope is an HLA class II antigenic peptide comprising an embedded HLA Class I antigenic peptide. An "embedded antigen" is an antigenic sequence or epitope that is contained within a larger antigenic sequence or epitope. For example, a sequence corresponding to an antigenic HLA Class II peptide antigen may contain within it a sequence representative of an HLA Class I antigenic peptide. In some embodiments, an extended antigenic peptide sequence may contain multiple overlapping (i.e., embedded) antigens.

Cancer cells may be distinguished from normal cells by the de novo expression of one or more marker proteins or tumor-associated antigens (TAA). A marker protein or a TAA may comprise one or more antigenic peptides. For example, antigenic peptides may represent either HLA Class I or HLA Class II restricted antigenic peptide epitopes. A TAA or cancer marker protein or antigenic peptides thereof may be used in a vaccine composition capable of eliciting an immune response (e.g., a cellular immune response, such as an antigen-specific T cell response) targeting the unwanted cancer cell for destruction by the patients' immune system.

In some embodiments, an antigen or antigenic epitope is a tumor-associated antigen (TAA). An antigenic peptide of a PAA disclosed herein may be derived from one or more TAAs. A TAA can be an antigen associated with breast cancer, triple negative breast cancer, inflammatory breast cancer, ovarian cancer, uterine cancer, colorectal cancer, colon cancer, primary peritoneal cancer, testicular cancer, renal cancer, melanoma, glioblastoma, lung cancer, or prostate cancer. In certain embodiments, a TAA derived antigenic T-cell epitope (either Class I or Class II) is from a HER2/neu, folate receptor alpha, Cyclin D1, IGFBP2, macrophage migration inhibitory factor (MIF), human carcinoembryonic antigen (CEA), gonadotropin releasing hormone (GnRH), melanoma related gp100 as well as MAGE-2 and MAGE-3, a testis cancer antigen (e.g., NY-ESO-1), cancer/testis antigen 1A (CTAG1A), Wilms tumor protein 1 (WT1), p53, BRCA1, BRCA2, PI3K, BRAF, insulin-like growth factor binding protein 2, or PD-1 antagonists. In some embodiments, a PAA as used herein is a combination of T-cell antigenic epitopes from more than one TAA (e.g., a combination of a HER2/neu and folate receptor alpha antigenic T-cell epitopes). In certain embodiments, a TAA comprises a HER2/neu antigen, a folate receptor-α antigen, or a combination thereof. Exemplary folate receptor-α antigenic peptides are presented in U.S. Pat. No. 8,486,412, which peptides are herein incorporated by reference. Exemplary HER2/neu, Cyclin D1, IGFBP2, and CEA antigenic peptides are described in Table I and II of U.S. Application Publication No. US 2010/0310640, which antigenic peptides are herein incorporated by reference in their entirety.

In certain embodiments, a TAA has an amino acid sequence derived from HER2 as set forth in SEQ ID NOS.:117-135, or any combination thereof. In some embodiments, the TAA has an amino acid sequence derived from folate receptor-α as set forth in SEQ ID NOS.:69-93, or any combination thereof. Accordingly, in some embodiments, the TAA has an amino acid sequence as set forth in any one of SEQ ID NOS.:69-93 or 117-135, or any combination thereof. In certain embodiments, the nucleic acid molecule has at least 80%, 85%, 90%, 91%, 92%, 93%, 94%, 95%, 96%, 97%, 98%, or 99% sequence identity to any one of SEQ ID NOS.:97, 98, 136, or any combination thereof. In certain embodiments, the nucleic acid molecule encodes an antigen having an amino acid sequence as set forth in any one of SEQ ID NOS.:67, 68, 115, 116, or any combination thereof. In some embodiments, the acid molecule has at least 80%, 85%, 90%, 91%, 92%, 93%, 94%, 95%, 96%, 97%, 98%, or 99% sequence identity to SEQ ID NOS.:52, 57, 58, 100, 137, 139, 141, 145, or 149. In some embodiments, the TAA has an amino acid sequence derived from IGFB2 as set forth in SEQ ID NOS.:103-112, or any combination thereof. In some embodiments, the TAA has an amino acid sequence derived from CEA as set forth in SEQ ID NOS.:186-202, or any combination thereof. In some embodiments, the TAA has an amino acid sequence derived from Cyclin D1 as set forth in SEQ ID NOS.:152-183, or any combination thereof. In certain embodiments, the TAA has an amino acid sequence having at least 80%, 85%, 90%, 91%, 92%, 93%, 94%, 95%, 96%, 97%, 98%, or 99% sequence identity to the sequence set forth in any one of SEQ ID NOS.:69-93, 103-112, 117-135, 152-183, 186-202, or any combination thereof. As noted herein, an antigenic T-cell epitope may be identified using a patient's sample.

In certain embodiments, the instant disclosure provides a chimeric nucleic acid molecule, comprising a multiplex translation initiation (MTI) sequence and a nucleic acid molecule encoding a fusion protein comprising from two to about ten human folate receptor-alpha (FRα) antigenic peptides, wherein the MTI comprises at least one non-AUG translation initiation site that mediates translation initiation of the fusion protein and allows the production of more than one mole of fusion protein per mole of mRNA. In some embodiments, the MTI sequence has at least 90% sequence identity to a nucleotide sequence as set forth in any one of SEQ ID NOS.:1-6, 95, or 96. In further embodiments, the fusion protein comprises from two to about five antigenic peptides or comprises five antigenic peptides. In further embodiments, two or more of the FRα antigenic peptides of the fusion protein are separated by a spacer comprising a $(G_4S)_n$, wherein n is an integer from 1 to 5. In further embodiments, two or more of the FRα antigenic peptides of the fusion protein are separated by a natural cleavage site comprising from about two to about ten amino acids, a self-cleaving amino acid sequence, or combinations thereof. In further embodiments, each FRα antigenic peptide of the fusion protein has at least 90% sequence identity to any one of SEQ ID NOS.:69-93. In further embodiments, the encoded fusion protein comprises a polypeptide having at least 90% sequence identity with any one of the polypeptides set forth in SEQ ID NOS.:49, 67, or 68. In further embodiments, the encoded fusion protein comprises a polypeptide having at least 90% sequence identity with any one of the polypeptides set forth in SEQ ID NOS.:53-55 or 59-61. In further embodiments, one or more of the FRα antigenic peptides are an HLA Class I antigenic peptide, an HLA Class II antigenic peptide, an HLA Class II antigenic peptide comprising an embedded HLA Class I antigenic peptide, or any combination thereof.

In certain aspects, this disclosure provides a method of eliciting a cellular immune response, comprising administering to a human subject a therapeutically effective amount of a chimeric nucleic acid molecule, wherein the chimeric nucleic acid molecule comprises a multiplex translation initiation (MTI) sequence and a nucleic acid molecule encoding a fusion protein comprising from two to about ten human folate receptor-alpha (FRα) antigenic peptides, wherein the MTI comprises at least one non-AUG translation initiation site that mediates translation initiation of the fusion protein and allows the production of more than one mole of fusion protein per mole of mRNA, thereby eliciting a cellular immune response. In further embodiments, the MTI sequence has at least 90% sequence identity to a nucleotide sequence as set forth in any one of SEQ ID NOS.:1-6, 95, or 96. In further embodiments, each FRα antigenic peptide of the fusion protein has at least 90% sequence identity to any one of SEQ ID NOS.: 69-93. In further embodiments, the encoded fusion protein comprises a polypeptide having at least 90% sequence identity with any one of the polypeptides set forth in SEQ ID NOS.:49, 67, or 68. In further embodiments, the encoded fusion protein comprises a polypeptide having at least 90% sequence identity with any one of the polypeptides set forth in SEQ ID NOS.:53-55 or 59-61. In further embodiments, the chimeric nucleic acid molecule is formulated as a composition comprising a therapeutically acceptable carrier or excipient. In further embodiments, the method comprises contacting the chimeric nucleic acid molecule with an immune cell ex vivo before administration, and administering to the human subject a population of immune cells containing the chimeric nucleic acid molecule. In further embodiments, the elicited immune response treats FRα-associated cancer.

In other aspects, this disclosure provides a method of eliciting a cellular immune response, comprising (a) administering to a human subject an effective amount of an antigenic peptide immunization composition comprising at least one FRα antigenic peptide, and (b) administering to the human subject an effective amount of a chimeric nucleic acid molecule, wherein the chimeric nucleic acid molecule comprises a multiplex translation initiation (MTI) sequence and a nucleic acid molecule encoding a fusion protein comprising from two to about ten human folate receptor-alpha (FRα) antigenic peptides, wherein the MTI comprises at least one non-AUG translation initiation site that mediates translation initiation of the fusion protein and allows the production of more than one mole of fusion protein per mole of mRNA, thereby eliciting a cellular immune response. In further embodiments, the chimeric nucleic acid molecule encodes one or more of the same antigenic peptides as used in step (a). In further embodiments, step (b) is performed simultaneously with step (a), or step (b) is performed from 1 hour to 8 weeks after step (a), or wherein step (a) is performed from 1 hour to 8 weeks after step (b). In further embodiments, the method further comprises (c) administering to the human subject an effective amount of a second antigenic peptide immunization composition, wherein the second antigenic peptide immunization composition comprises the same antigenic peptide immunization composition as used in (a). In further embodiments, the method further comprises administering an adjunctive therapy selected from surgery, chemotherapy, radiation therapy, antibody therapy, immunosuppressive therapy, or any combination thereof, such as cyclophosphamide, trastuzumab, anti-PD1, anti-PDL1, anti-CTLA4, or any combination thereof. In further embodiments, the the elicited immune response treats FRα-associated cancer.

Accordingly, cancers that may be treated using the compositions and methods disclosed herein include breast cancer, triple negative breast cancer, inflammatory breast cancer, ovarian cancer, uterine cancer, colorectal cancer, colon cancer, primary peritoneal cancer, testicular cancer, renal cancer, melanoma, glioblastoma, lung cancer, or prostate cancer.

Effective countermeasures to biological pathogens are a critical component of biodefense and national security (Altmann, *Expert Rev Vaccines* 4, 275-279, 2005), and additional products are needed to meet biodefense needs (Matheny, J., Mair, M. & Smith, B. *Nat Biotechnol* 26, 981-983, 2008; Cohen, J. *Science* 333, 1216-1218, 2011; Artenstein, A. W. & Grabenstein, J. D. *Expert Rev Vaccines* 7, 1225-1237, 2008). Vaccines provide not only preventive or therapeutic countermeasures, but can also serve as actual deterrents (Poland et al., *Vaccine* 27, D23-D27, 2009) in that they can be rapidly deployed to negate the primary outcomes of biological terrorism and thereby removing the motivation to use a bioweapon.

For a vaccine composition incorporating nucleic acid molecules as described herein, the desired end result is a safe product capable of inducing long-lasting, protective immunity with minimal side effects, and as compared to other strategies (e.g., whole live or attenuated pathogens), is inexpensive to produce, will minimize or eliminate contraindications that have otherwise (typically) been associated with the use of whole or attenuated virus vaccine compositions, and have an extended shelf-life because it is nucleic acid and/or synthetic peptide-based. The ability to rapidly respond to infectious disease emergencies (natural outbreaks, pandemics, or bioterrorism) is a benefit of an effective use of the embodiments disclosed herein, whether in context of biodefense or cancer immunotherapies or technologies. The instant disclosure sets forth the rapid identification and selection of relevant pathogen-related or cancer-related antigenic epitopes for peptide-based vaccines and nucleic acid-based vaccines and is easily adaptable to multiple Category A-C agents, as well as new and emerging pathogens.

In other embodiments, a chimeric nucleic acid molecule encodes an antigen or antigenic epitope from a pathogen. In certain embodiments, the pathogen is a virus, parasite, or bacteria. In further embodiments, a chimeric nucleic acid molecule encodes a PAA from one or more pathogens.

In certain embodiments, a PAA comprises an antigen from a virus, wherein the virus is a small pox virus and other related pox viruses, lentiviruses such as HIV, influenza virus, Arenaviruses such as Junin, Machupo, Guanarito, Chapare, Lassa, and Lujo, Bunyaviruses such as Hantaviruses, Rift Valley Fever virus, and Crimean Congo Hemorrhagic Fever virus, Flaviruses such as Dengue fever virus, Filoviruses such as Ebola and Marburg virus, retrovirus, adenovirus, parvovirus, coronavirus, rhabdovirus, paramyxovirus, picornavirus, alphavirus, adenovirus, herpesvirus, Norwalk virus, togavirus, reovirus, papovarius, hepadnavirus, hepatitis virus, avian leucosis-sarcoma, mammalian C-type viruses, B-type viruses, D-type viruses, HTLV-BLV group viruses, or spumavirus. In some embodiments, the influenza virus is influenza strain H7N9 (bird flu), H5N1, H3N8, H2N2, H3N2, H3N3, H9N2, H7N7, H1N1, or a combination thereof.

In other embodiments, a PAA comprises an antigen from a bacteria. In certain embodiments, the bacteria is a *Myco-*

*bacterium tuberculosis*, pathogenic *Escherichia coli, Yersinia pestis, Listeria monocytogenes, Clostridium botulinum, Bacillus anthracis, Staphylococcus aureus, Streptococcus pyogenes, Streptococcus pneumoniae*, or *Salmonella enterica*. The pathogenic *E. coli* can be *E. coli* strain 0157:H7, ETEC, EPEC, EIEC, EHEC, EAEC, or a combination thereof.

In certain embodiments, a PAA comprises an antigen from a parasite. In some embodiments, the parasite is a Protozoa such as *Plasmodium* sp., *Entamoeba, Giardia Trypanosoma brucei, Toxoplasma gondii, Acanthamoeba, Leishmania, Babesia, Balamuthia mandrillaris, Cryptosporidium, Cyclospora*, or *Naegleria fowleri*, a Parasitic worms such as Guinea worm (*Dracunculus*), *Ascaris lumbricoides*, Pinworm, *Strongyloides stercoralis, Toxocara*, Guinea Worm, Hookworm, Tapeworm, or Whipworm, or a Parasitic fluke such as *Schistosoma, Gnathostoma, Paragonimus, Fasciola hepatica*, or *Trichobilharzia* regent.

In any of the embodiments disclosed herein, a nucleic acid sequence encoding the antigen can be codon optimized for expression in the appropriate subject (e.g., human). In certain embodiments, a smallpox nucleic acid sequence comprises a smallpox MTI-PAA encoding an antigen set forth in SEQ ID NOS.:24-30, or any combination thereof. In some embodiments, a nucleic acid sequence encoding a smallpox MTI-PAA corresponds to the sequence set forth in SEQ ID NO.:7. In further embodiments, a nucleic acid sequence encoding a smallpox MTI-PAA corresponds to a sequence having at least 80%, 85%, 90%, 91%, 92%, 93%, 94%, 95%, 96%, 97%, 98%, or 99% sequence identity to the sequence set forth in SEQ ID NO.: 7.

In certain embodiments, a nucleic acid vector containing a multiplex translation leader sequence portion (or PolyStart™) may also contain a nucleic acid sequence encoding a TAP protein. An encoded TAP may be as a heterodimer (TAP1 plus TAP2) or only TAP1 or only TAP2. A TAP may be codon optimized so that it can be distinguished from an endogenous TAP. In addition, a TAP translation product may incorporate a peptide tag detection moiety/portion such as a VSV G protein epitope tag, an HA epitope tag, a Myc epitope tag or any other detection portion.

Accordingly, in addition to the MTI-PAA, the chimeric nucleic acid molecule disclosed herein can further include a nucleic acid molecule encoding a TAP protein. In some embodiments the TAP protein is TAP1, TAP2, TAPL, or any combination thereof. In certain embodiments, the TAP protein is a heterodimer of TAP1 and TAP2. In some embodiments, the nucleic acid molecule encoding the TAP protein has a polynucleotide sequence as set forth in any one of SEQ ID NOS.:206-210, or any combination thereof.

In some embodiments, the chimeric nucleic acid disclosed herein is included in a nucleic acid vector. In some embodiments, the vector is an expression vector. Examples of an expression vector include a plasmid, a cosmid, a viral vector, an RNA vector, or a linear or circular DNA or RNA molecule. In some embodiments, the vector is a plasmid and comprises pcDNA3, pSG5, pJ603, or pCMV. In some embodiments, the vector is a viral vector selected from a retrovirus, adenovirus, parvovirus, coronavirus, influenza virus, rhabdovirus, paramyxovirus, picornavirus, alphavirus, adenovirus, herpesvirus, poxvirus, Norwalk virus, togavirus, flavivirus, reovirus, papovarius, hepadnavirus, hepatitis virus, avian leucosis-sarcoma, mammalian C-type viruses, B-type viruses, D-type viruses, HTLV-BLV group viruses, lentivirus, or spumavirus. In the case of a viral vector incorporating a nucleic acid molecule of this disclosure, a virus may be a DNA virus (e.g., vaccinia, adenovirus) or an RNA virus (e.g., vesicular stomatitis virus). In certain embodiments, a virus is oncolytic.

In certain embodiments, a multiplex vector of the instant disclosure has a nucleic acid molecule that encodes an MTI-PAA fusion operably linked to a CMV promoter and the fusion protein contains a carboxy-terminal VSV-g epitope tag (SEQ ID NO.:13). In further embodiments, a multiplex vector of the instant disclosure includes a Tap1 gene expressed by an SV40 promoter and the TAP1 includes an amino-terminal V5 epitope tag (SEQ ID NO.:14), while a nucleic acid encoding an MTI-PAA is operably linked to a CMV promoter and a carboxy-terminal VSV-g epitope tag (SEQ ID NO.:13). In still further embodiments, a multiplex vector of the instant disclosure includes a Tap2 gene expressed by an SV40 promoter and the TAP2 includes an amino-terminal AU5 epitope tag (SEQ ID NO.:15), while a nucleic acid molecule encoding an MTI-PAA is operably linked to a CMV promoter and the PAA included a carboxy-terminal VSV-g epitope tag (SEQ ID NO.:13). In yet further embodiments, a multiplex vector of the instant disclosure includes a Tap1 and Tap2 gene separated by an IRES and operably linked to an SV40 promoter, wherein the TAP1 includes an amino-terminal V5 epitope tag (SEQ ID NO.:14) and the TAP2 includes an amino-terminal AU5 epitope tag (SEQ ID NO.:15), while a nucleic acid molecule encoding an MTI-PAA is operably linked to a CMV promoter and the PAA included a carboxy-terminal VSV-g epitope tag (SEQ ID NO.:13).

A class I peptide vaccines incorporated into a nucleic acid-based immunization composition can elicit protective immunity, and the inclusion of HLA class II peptides and the generation of T helper responses is expected to stimulate optimal cellular immunity and augment the protection provided by CTL alone. In some embodiments, a nucleic acid of the instant disclosure encoding one or more Class II 'reporter epitope' PAA and class II epitope-containing PAAs may be represented as a MTI-VSVG-PAA, wherein the MTI portion is mutated to remain cytosolic. As designed, a MTI-VSVG-PAA results in a primary translation product containing what is referred to herein as an internalized VSVG signal sequence (e.g., SEQ ID NO.: 42). The internalized signal sequence is processed and the chimeric protein secreted or membrane localized, thereby facilitating entry of the PAA into the endocytic compartment and class II processing pathway. VSVG processing and signaling sequences are discussed in greater detail in Rose et al, *J. Virol.* 39: 519-528, 1981; Gallione et al. *J. Virol.* 54:374-382, 1985; Machamer et al., *Mol. Cell. Biol.* 5:3074-3083, 1985; Rottier et al. *J. Biol. Chem.* 262:8889-8895, 1987, all of which are herein incorporated by reference in their entirety.

Accordingly, in some embodiments is a chimeric nucleic acid disclosed in any of the embodiments herein further comprises an internalization VSVG signal sequence, a VSVG secretion signal sequence, a trafficking sequence, a dendritic cell targeting sequence, a membrane localization sequence, or any combination thereof. In some embodiments, the chimeric nucleic acid comprises an internalization VSVG signal sequence as set for in SEQ ID NO.: 43. In some embodiments, the nucleic acid comprises a VSVG secretion signal sequence as set for SEQ ID NOS.:47 or 48. The VSVG secretion signal sequence promotes trafficking through ER/Golgi to the cell surface (i.e., plasma membrane). In some embodiments, the nucleic acid comprises a dendritic cell targeting sequence as set for in SEQ ID NO 45. The DC targeting sequence is optional, and may be placed at the COOH terminus. In some embodiments, the nucleic acid comprises a VSVG membrane localization sequence as set for in SEQ ID NO.:57. In some embodiments, the nucleic acid comprises a PAA including sequences encoding folate receptor-α Class II antigens and is a secreted chimera. In some embodiments, the nucleic acid comprises a sequence as set forth in SEQ ID NO.:52. In some embodiments, the nucleic acid comprises a PAA including sequences encoding folate receptor-α Class II antigens and is a membrane localized polypeptide. In some embodiments, nucleic acid comprises a PAA including sequences encoding folate receptor-α Class II antigens and is a membrane localized polypeptide such as the fusion protein encoded by the nucleic acid sequence as set forth in SEQ ID NO.:58.

The chimeric nucleic acid and vectors described herein can be introduced into a cell. Methods of introducing nucleic acid molecules are well known in the art and include transformation and transduction. Accordingly, some embodiments comprise a cell that includes a nucleic acid molecule as described herein. In addition, certain embodiments comprise a cell that includes a vector according to any of the embodiments described herein. In some embodiments, the cell is an autologous cell obtained from a first subject or an allogeneic cell from a subject different from the first subject. The cell can be located in vitro or in vivo. In some embodiments, the cell is an antigen presenting cell, such as a professional or non-professional antigen presenting cell. The antigen presenting cell can be a professional antigen presenting cell such as a dendritic cell or a macrophage. In a preferred embodiment, the antigen presenting cell is a dendritic cell.

The term dendritic cells (DCs) was described by Steinman et al in 1973 (Steinman R M and Cohn Z A J Exp Med 137:1142-62, 1973). Dendritic cells are derived from myeloid bone marrow progenitor cells and have the potential to be used as a viable cell-based anti-cancer therapy (Vacchelli et al., *OncoImmunology* 2:10, 2013; Slingluff et al., *Clin Cancer Res* 12 (7 Suppl):2342s-2345s, 2006; Steinman, *Immunity* 29: 319-324, 2008). DCs localize to lymphoid tissues, skin (e.g., epidermal Langerhans cells) and various mucosae. When mature, DCs are potent professional antigen presenting cells for both HLA Class II as well as HLA Class I restricted systems (Santambrogio et al., *PNAS* 96 (26): 15050-55, 1999). Mature DCs express elevated levels of HLA Class II proteins on the cell surface, migrate to lymph nodes and secrete high levels of cytokines/chemokines. T-cell activating antigenic peptides bound to MHC Class II proteins presented on the cell surface of an activated DC stimulate (activate) both cognate $CD4^+$ helper T-cells and $CD8^+$ cytotoxic T-cells, while at the same time secreting a number of cytokines and other growth promoting factors. Subdermal administration (a site rich in DCs) of a peptide or nucleic acid-based composition set forth herein results the uptake and immune system presentation of antigenic T-cell peptides (including naturally processed antigenic peptides) in context with DC expressed HLA Class I or Class II proteins.

The affinity of a TAA-derived peptide or nucleic acid-based antigenic T-cell peptide composition, as disclosed herein, for a DC may be enhanced by inclusion of one or more DC targeting motif such as a polypeptide, small molecule, or antibody-based technology such as taught in Diebold et al., *Gene Therapy* 8:487-493, 2001; Bonifaz et al., *J Exp Med* 196 (12):1627-1638, 2002; Birkholz et al., *Blood* 116 (13):2277-2284, 2010; Apostolopoulos et al., *J. Drug Delivery, p* 1-22, 2013; Lewis et al., *Biomaterials* 33 (29):7221-7232, 2012; Gieseler et al., *Scandinavian J Immunol.* 59: 415-424, 2004, all of which are herein incorporated by reference in their entirety. For example, DC affinity may be enhanced by including one or more antibodies or other molecules with affinity to DC surface markers such as DEC-205, DC-SIGN, CLEC4A, and may also include a maturation signal, e.g., IL-15.

In contrast to conventional polypeptide based vaccines, DNA vaccines may comprise a nucleic acid in the form of a plasmid (Li et al., *J. Biotechnol.* 162:171, 2012) but may also be incorporated in the form of RNA or incorporated into the nucleic acid of a virus vector for delivery. The plasmid DNA includes a promoter driving expression of one or more transcription units set forth herein, as would be appreciated by one of ordinary skill in the art. A nucleic acid based vaccine can be administered by, for example, intramuscular injection, subcutaneously, intranasally, via mucosal presentation, intravenously or by intradermal or subcutaneous administration.

A nucleic acid based vaccine is administered to a patient (either using a DNA plasmid, a RNA, or a viral vector) whereby the nucleic acid is taken up into a cell's cytoplasm and/or nucleus where it is transcribed into mRNA and then translated into a polypeptide or protein. Vaccine modalities set forth herein may be administered individually or sequentially as a prime-and-boost platform. The priming vaccine composition may be peptide-based followed by a vaccine boost comprising a nucleic acid delivered, for example, as a plasmid DNA or as a viral delivery system. Alternately, the priming vaccine composition may be nucleic acid delivered followed by a peptide-based vaccine. Either the vaccine prime or boost, or both the prime and boost, may be administered once or multiple times to a patient in need thereof.

Accordingly, in some embodiments are methods of eliciting a cellular immune response, comprising administering to a subject an effective amount of an immunization composition comprising a nucleic acid molecules including an MTI-PAA as described in any of the embodiments herein, an antigen encoded by a nucleic acid molecule according to any of the embodiments herein, or both, thereby eliciting a cellular immune response. In some embodiments, the immunization composition comprises a nucleic acid immunization composition. In some embodiments, the immunization composition comprises an antigen or polyantigen immunization composition. In some embodiments, the nucleic acid immunization composition and the antigen immunization composition are both administered. In certain embodiments, the antigen immunization composition is administered first and the nucleic acid immunization composition is administered second. In other embodiments, the nucleic acid immunization composition is administered first and the antigen immunization composition is administered second. In yet further embodiments, the nucleic acid immunization composition and the antigen immunization composition are administered concurrently. In some embodiments, the immunization composition comprises a cell comprising a nucleic acid according to the embodiments disclosed herein. In some embodiments, the cellular immune response is an antigen-specific T-cell response. In some embodiments, the subject is human. In certain embodiments, the nucleic acid immunization composition is taken up by an antigen presenting cell. The antigen presenting cell can be a professional or non-professional antigen presenting cell. In some embodiments, the antigen presenting cell is a dendritic cell. In certain embodiments, the method comprises administering a nucleic acid immunization composition to a subject wherein the nucleic acid immunization composition comprises a chimeric nucleic acid molecule including an MTI as described herein (e.g., any of SEQ ID NOS.:1-6, 95, or 96) and including a PAA wherein the PAA comprises antigens from folate receptor-α (e.g., any of SEQ ID NOS.:69-93), Her2/neu (e.g., any of SEQ ID NOS.:117-135), or any combination thereof. Exemplary folate receptor-α PAA and MTI-PAA sequences are provided in SEQ ID NOS.:49, 50, 52, 53-55, 58-64, 66-68, and 97-100. Exemplary HER2/neu PAA and MTI-PAA sequences are provided in 115, 116, 136-150.

The MTI technology described herein may also be used to modify a patient's cells ex vivo. For example, isolated or enriched preparations of a patient's T-cells, dendritic cells, or other antigen presenting cell population may be transfected with a nucleic acid molecule as disclosed herein. Transfected cells may be expanded and then reintroduced into the patient as effector T-cells.

Therefore, in certain embodiments, the method of eliciting a cellular immune response includes contacting a cell with a nucleic acid immunization composition comprising the chimeric nucleic acid molecule as described in any of the embodiments herein, wherein the cell is contacted ex vivo and then administered to a subject. Methods of isolating cells from a subject and introducing nucleic acid molecules are known in the art. In some embodiments, the cell is autologous or allogeneic. In certain embodiments, the cell is an antigen presenting cell. In some embodiments, the cell is a dendritic cell. In some embodiments, the subject is a human.

In certain embodiments, the instant disclosure provides a method of eliciting a cellular immune response, comprising administering to a subject an effective amount of a cell comprising a nucleic acid molecule or a vector of any one of the embodiments disclosed herein, thereby eliciting a cellular immune response. In some embodiments, a cell is autologous or allogeneic. In some embodiments, a cell is an antigen presenting cell. In certain embodiments, the antigen presenting cell is a dendritic cell. In some embodiments, the subject is a human.

In some embodiments, the present disclosure provides a method for prime and boost to elicit a robust immune response that results in the production of memory T cells. For example, an immune response is elicited against a cancer or infectious disease by (a) contacting the subject with a nucleic acid molecule immunization composition as described herein, wherein the nucleic acid molecule of the nucleic acid molecule immunization composition encodes one or more antigenic peptides, (b) optionally allowing a time sufficient to generate an initial immune response, (c) contacting a subject with an antigenic peptide immunization composition. The peptide immunization composition and the nucleic acid immunization composition can correspond to the same one or more HLA Class I peptide antigen(s). Alternatively, the peptide immunization composition and the nucleic acid immunization composition can correspond to the same cancer marker protein or TAA.

In certain embodiments, provided herein is a method of eliciting a cellular immune response, comprising (a) administering to a subject an effective amount of an antigen immunization composition comprising one or more antigens encoded by any one of the nucleic acid molecules disclosed herein, and (b) administering to the subject an effective amount of a nucleic acid molecule immunization composition comprising a nucleic acid molecule or vector of any one of the embodiments described herein. In some embodiments, the nucleic acid molecule immunization composition of step (b) encodes a plurality of antigens. In some embodiments, the antigen immunization composition of step (a) comprises a plurality of antigens. In certain embodiments, the nucleic acid molecule encodes one or more antigens from the same protein as the one or more antigens used in step (a). In some embodiments, the nucleic acid molecule of the nucleic acid molecule immunization composition encodes one or more of the same antigens as the one or more antigens used in step (a). In certain embodiments, step (b) is performed simultaneously with step (a). In other embodiments, step (b) is performed sequentially to step (a). In some embodiments, step (b) is performed from 1 hour to 5 months, from 1 hour to 4 months, from 1 hour to 3 months, from 1 hour to 8 weeks, from 1 hour to 6 weeks, from 1 hour to 4 weeks, from 1 hour to 3 weeks, from 1 hour to 2 weeks, from 1 hour to 1 week, from 1 hour to 72 hours, from 1 hour to 48 hours, or from 1 hour to 24 hours after step (a). In other embodiments, step (a) is performed 1 hour to 5 months, from 1 hour to 4 months, from 1 hour to 3 months, from 1 hour to 8 weeks, from 1 hour to 6 weeks, from 1 hour to 4 weeks, from 1 hour to 3 weeks, from 1 hour to 2 weeks, from 1 hour to 1 week, from 1 hour to 72 hours, from 1 hour to 48 hours, or from 1 hour to 24 hours after step (b). In some embodiments, the method further comprising (c) administering to the subject a second effective amount of an antigen immunization composition, wherein the antigen immunization composition comprises a peptide that is derived from the same protein as the antigenic peptide used in (a). For example, in some embodiments the antigen immunization composition of step (c) is the same as the antigen immunization composition used in (a).

In other embodiments, provided herein is a method of eliciting an cellular immune response, comprising (a) administering to a subject an effective amount of a nucleic acid molecule immunization composition comprising the nucleic acid molecule of any of the embodiments described herein, (b) allowing a time sufficient to generate an initial immune response, and (c) administering to the subject a second effective amount of a nucleic acid molecule immunization composition comprising a nucleic acid molecule according to any of the embodiments described herein, or an effective amount of an antigenic peptide immunization composition. In some embodiments, the antigen immunization composition comprises one or more antigens that are from the same protein as the antigen encoded by the nucleic acid molecule of step (a). In some embodiments, the nucleic acid molecule of the nucleic acid molecule immunization composition encodes one or more of the same antigenic peptides as used in (c). In certain embodiments, the time sufficient to generate an initial immune response is from 1 hour to 5 months, from 1 hour to 4 months, from 1 hour to 3 months, from 1 hour to 8 weeks, from 1 hour to 6 weeks, from 1 hour to 4 weeks, from 1 hour to 3 weeks, from 1 hour to 2 weeks, from 1 hour to 1 week, from 1 hour to 72 hours, from 1 hour to 48 hours, or from 1 hour to 24 hours after step (a). In certain embodiments, the method further comprising (d) administering to a subject an effective amount of an antigen immunization composition, wherein the antigen immunization composition comprises one or more antigens that are from the same protein as the antigen used in (c). In some embodiments, the antigen immunization composition of step (d) comprises the same antigen used in (c).

In certain embodiments, a nucleic acid molecule immunization composition and a antigen immunization composition encode a different peptide antigen class, for example peptide(s) of a peptide immunization complex may comprise one or more HLA Class II antigenic peptide epitopes derived from a cancer marker protein, while the nucleic acid molecule may encode one or more HLA Class I antigenic peptides derived from the same cancer marker protein (e.g., Her2/neu or folate receptor alpha).

Antigenic peptide epitopes contained within a nucleic acid immunization composition and antigenic peptide epitopes contained within a peptide immunization composition may be derived from more than one cancer marker protein (e.g., Her2/neu and folate receptor alpha).

Typically, a patient having cancer is incapable of eliciting a strong enough immune response that can destroy sufficient numbers of cancer cells to either eliminate the tumor entirely or sufficient to reduce tumor burden to a manageable level and thereby provide an improved standard of living, with a long time to recurrence. The health care options to patients with cancer have historically focused on surgical resection of the tumor mass, chemotherapy or radiation therapy. In each of these historical options, the treatment is particularly invasive or particularly indiscreet in that chemotherapies also kill a patient's good cell as well as unwanted cancer cells.

An advantage of stimulating a patient's own immune system to destroy cancer cells is that, in general accordance with the embodiments set forth herein, such immune stimulation is long lived and consequently should prevent or extend the time to recurrence. In contrast, radiation therapy or chemotherapy requires continued repetitive treatment in order to keep killing unwanted cancer cells. Stimulating a patient's own immune system cells may be mediated in vivo or ex vivo. For an ex vivo administration, a patient's cells (e.g., dendritic cells and/or T-cells) are removed from the patient then contacted with a peptide, nucleic acid or viral composition of the instant invention. After contacting, the patient's cells are administered back to the patient.

A vaccine approach as described herein is designed to stimulate a patient's immune cells to function for a long time and therefore if a new cancer cell comes into existence it will be destroyed. In one embodiment, long term immune function is accomplished using a multi-antigenic peptide composition capable of stimulating both cytotoxic $CD8^+$ T-cells (HLA Class I restricted) and helper $CD4^+$ T-cells (HLA Class II restricted). Thereby, the patient does not need to repeatedly go to their health care provider (doctor, hospital) for another round of chemotherapy or radiation therapy. In many situations in which the treatment with chemotherapy, radiation therapy or surgery, the treatment can be an obstacle to success, indeed, often the patient feels worse as a consequence of treatment rather than the disease (cancer) itself.

In some embodiments, the methods of eliciting a cellular immune response described above are to elicit an immune response against a TAA as described herein. In other embodiments, the methods of eliciting a cellular immune response described above are to elicit an immune response against a pathogen as described herein. In any of the methods of eliciting a cellular immune response described above, the subject can be a human.

In any of the methods of eliciting a cellular immune response described above, the method can further comprise administering an adjunctive therapy. In some embodiments, the adjunctive therapy is surgery, chemotherapy, radiation therapy, antibody therapy, or a combination thereof. In some embodiments, the adjunctive therapy is cyclophosphamide.

Cancer, for example breast cancer, is diagnosed in approximately 210,000 women each year. Conventional standards of care such as surgery, chemotherapy and radiation therapy are successful treatments at least initially however recurrence is a common problem and is frequently the main source of morbidity and mortality. Monoclonal antibodies have been advanced in the treatment of some cancers, for example trastuzumab for HER2/neu+ breast cancer. Although the combination of trastuzumab extends survival time for women with advanced HER2/neu+ cancer, a majority of women develop resistance within one year of the beginning of treatment. The development of additional or alternative strategies may provide patients with new treatment options and improve the current standard of care. A vaccine that delays the time to disease recurrence or prevents disease recurrence has significant clinical and commercial potential. In addition, a cancer vaccine described herein may be used to boost immunity against tumor antigenic T-cell epitopes that are known or expected to generate pre-existent immunity towards a TAA detected in a cancer patient.

In other embodiments, provided herein is a method of treating breast cancer, comprising administering an effective amount of nucleic acid molecule immunization composition comprising a nucleic acid molecule immunization composition comprising a breast cancer TAA. In some embodiments, the breast cancer TAA is HER2/neu, folate receptor-$\alpha$, or a combination thereof. In some embodiments, the nucleic acid immunization composition comprises a nucleic acid sequence corresponding SEQ ID NOS.:49, 50, 52-55, 58-64, 66-93, 97-100, 115-150, or any combination thereof. In certain embodiments, the method of treating breast cancer further comprises administering an adjunctive therapy. The adjunctive therapy can be surgery, chemotherapy, radiation therapy, antibody therapy, or any combination thereof. In some embodiments, an antibody therapy comprises trastuzumab, pertuzumab, anti-CTLA4, anti-PD1, anti-PDL1, anti-VEGF (e.g., bevacizumab), anti-Folate Receptor alpha (e.g., farletuzumab); as well as small molecule inhibitors of kinase domain function (e.g., laptinib, gefitinib, erlotinib, or the like). In some embodiments, the adjunctive therapy is cyclophosphamide. In some embodiment, the adjunctive therapy is therapy that inhibits immunosuppression. In certain embodiments, the therapy that inhibits immunosuppression, is an inhibitor of an immunosuppression signal is an antibody, fusion protein, or siRNA specific for PD-1, PD-L1, PD-L2, CTLA4, HVEM, BTLA, KIR, LAG3, GAL9, TIM3, TGF$\beta$, IL-10, IL-35, or any combination thereof. In some embodiments, the anti-CTL4 antibody is an CTLA4 specific antibody or binding fragment thereof, such as ipilimumab, tremelimumab, CTLA4-Ig fusion proteins (e.g., abatacept, belatacept), or any combination thereof. In some embodiments, the anti-PD-1 antibody is a PD-1 specific antibody or binding fragment thereof, such as pidilizumab, nivolumab, pembrolizumab, MK-3475, AMP-224, or any combination thereof. In some embodiments, the anti-PD-L1 antibody is a PD-L1 specific antibody or binding fragment thereof, such as MDX-1105, BMS-936559, MEDI4736, MPDL3280A, MSB0010718C, or any combination thereof.

In some embodiments, the methods of eliciting a cellular immune response as described herein further comprise identifying patient specific TAA antigens. Accordingly a population of a patient's T-cells can be screened against a collection of Class I and/or Class II T-cell peptides in order to identify antigenic epitopes to which the patient already has a detectable T-cell immune response. A patient's cells are isolated, incubated with peptides displayed using a multi-well plate and cytokine responses are measured, such as gamma interferon. One or more of the antigenic peptides so identified can then be formulated into a peptide-based vaccine composition. The detected antigenic peptides may be Class I or Class II restricted. In addition, the same Class I and/or Class II peptides may be incorporated into a nucleic acid-based delivery system disclosed herein. A patient may then be administered the tailored peptide or corresponding nucleic acid based compositions as standalone medicines or in sequential combination as a prime-and-boost modality as described in embodiments above. In this regard, the prime may be nucleic acid based and the boost peptides-based, or vice versa. Accordingly, in some embodiments is a method of treating cancer, comprising administering to a subject an effective amount of a nucleic acid immunization composition comprising a nucleic acid molecule of any of the embodiments described herein, wherein the one or more antigens encoded by the nucleic acid molecule comprise an antigen having an oncogenic mutation identified in the subject.

Supporting of the instant disclosure, compositions and methods described herein combine mass spectrometry to aid in the identification of novel peptide epitopes presented by HLA class I and HLA class II alleles. After administration, one of ordinary skill in the art can follow and characterize immune responses using cell culture and small animal or non-human primate model systems. Peptide sequences are converted into a nucleic acid sequence (which may be fully or partially codon optimized) and designed for inclusion into nucleic acid-based expression/delivery vaccine systems. Exemplary peptides may be from cancer (e.g., HER2/neu peptides such as those disclosed in US Patent Pub. No. 2010/0310640, which peptides are incorporated herein by reference; folate receptor-α peptides; NY-ES01 testes specific antigens; WT1 peptides, or the like) or other infectious diseases (e.g., other viruses, parasites, bacteria).

The compositions and methods of the instant disclosure may include a molecular adjuvant mechanism (TAP1/TAP2) that is suited to enhance HLA class I peptide presentation and subsequent CD8 T cell responses and combines it with a vaccine vector designed to maximize antigen expression (FIG. 1) incorporating features that enhance translation efficiency; induces production of an array of antigenic peptides; and marks peptides for proteasome targeting/trafficking and proteolytic processing. The compositions and methods of the instant disclosure may incorporate multiple translation initiation sites for increased expression (for example, one mRNA initiates and synthesizes four translation products); incorporate cytosolic and/or nuclear targeting and subsequent processing; distinguish between endogenous and recombinant protein; distinguish between endogenous and recombinant nucleic acid encoding a TAP1 and/or a TAP2; and allow for nuclear and cytosolic antigen targeting. The vectors may also be constructed such that each feature can be independently manipulated for characterization and testing.

Additional immune stimulatory or modulating agents, including negative immune modulators such as regulatory T-cells and related check point inhibitors (anti-PD1, Yervoy®, cyclophosphamide), may be included in any composition or method described herein. For example, granulocyte-macrophage colony-stimulating factor (GM-CSF) may function as a vaccine adjuvant as previously described (see Mohebtash et al., *Clin. Cancer Res.* 17:7164, 2011). Other adjuvants such as alum, MF59, CpG, R848 and the like may be included in the compositions or methods described herein.

As an example, one infectious disease treatable by administering the instant invention is smallpox as this disease has claimed hundreds of millions of lives in the last two centuries alone (Dixon, C. W. *Smallpox*. (J. & A. Churchill, 1962); Fenner et al., *Smallpox and its Eradication*, Vol. 6, World Health Organization, 1988), and although considered eradicated since 1980 (Fenner, 1988), biodefense research into poxviruses remains vitally important because of the following: (1) concerns about the use of smallpox as a biological weapon (Henderson et al., Working Group on Civilian Biodefense. *JAMA* 281:2127-2137, 1999; Kennedy et al., *Vaccine* 27 (Suppl 4):D73-79, 2009; Whitley, *Antiviral Res* 57:7-12, 2003; Bossi et al., *Cell Mol Life Sci* 63:2196-2212, 2006; Mayr, *Comp. Immunol. Microbiol. Infect. Dis.* 26:423-430, 2003; Wiser et al., *Vaccine* 25:976-984, 2007); (2) emerging zoonotic poxviruses, such as monkeypox in the US and Africa (Hutson et al., *Am. J. Trop. Med. Hyg.* 76:757-768, 2007; Kile et al., *Arch. Ped. Adolesc. Med.* 159:1022-1025, 2005; Di Giulio and Eckburg, *The Lancet Infect. Dis.* 4:15-25, 2004; Edghill-Smith et al., *J. Infect. Dis.* 191:372-381, 2005; Larkin, *The Lancet Infect. Dis.* 3:461, 2003; Jezek et al., *Am. J. Epidemiol.* 123:1004, 1986), vaccinia-like viruses in South America (Leite et al., *Emerging Infect. Dis.* 11:1935-1938, 2005; Silva-Fernandes et al., *J. Clin. Virol.* 44:308-313, 2009; Trindade et al., *Clin. Infect. Dis.* 48:e37-40, 2009), and buffalopox in India (Singh et al., *Animal Health Res. Rev./Conference of Research Workers in Animal Diseases* 8:105-114, 2007); (3) numerous vaccine contraindications (Neff et al., *Clin. Infect. Dis.* 46 (Suppl 3):S258-270, 2008; Poland et al., *Vaccine* 23:2078-2081, 2005; Bonilla-Guerrero & Poland, *J. Lab. Clin. Med.* 142:252-257, 2003); (4) concerns with VACV transmission (Fulginiti et al., *Clin. Infect. Dis.* 37:241-250, 2003; Wharton et al., *MMWR Recomm. Rep.* 52:1-16, 2003; Redfield et al., *N. Engl. J. Med.* 316:673-676, 1987); and (5) safety issues inherent to live virus smallpox vaccines resulting in rare but serious adverse events (Fulginiti et al., *Clin. Infect. Dis.* 37:251-271, 2003; Fulginiti, *JAMA* 290:1452; author reply 1452, 2003; Lane et al., *JAMA* 212:441-444, 1970; Lane et al., *N. Engl. J. Med.* 281:1201-1208, 1969; Morgan et al., *Clin. Infect. Dis.* 46 (Suppl 3):S242-250, 2008; Vellozzi et al., *Clin. Infect. Dis.* 39:1660-1666, 2004; Halsell et al., *JAMA* 289:3283-3289, 2003; Poland and Neff, *Immunol. Allergy Clin. North Am.* 23:731-743, 2003; Chapman et al., *Clin. Infect. Dis.* 46 (Suppl 3):S271-293, 2008). Recently introduced second-generation (live) tissue culture-based vaccines (ACAM2000) have replaced Dryvax®, but retain nearly all of the drawbacks of the first-generation vaccines (Kennedy et al., *Curr. Opin. Immunol.* 21:314-320, 2009; Artenstein et al., *Vaccine* 23:3301-3309, 2005; Greenberg and Kennedy, *Expert Opin. Investig. Drugs* 17:555-564, 2008; Poland, *Lancet* 365:362-363, 2005; Greenberg et al., *Lancet* 365:398-409, 2005). Attenuated vaccines based on MVA (IMVAMUNE) may have improved safety profiles (Kennedy and Greenberg, *Expert Rev Vaccines* 8:13-24, 2009; Frey et al., *Vaccine* 25:8562-8573, 2007; Vollmar et al., *Vaccine* 24:2065-2070, 2006; Edghill-Smith et al., *J. Infect. Dis.* 188:1181, 2003), but remain live viral vaccines and there are some concerns regarding both safety and immunogenicity.

The preparation and characterization of expression vectors (plasmid and vaccinia virus based) encoding peptide antigen arrays (PAAs) consisting of multiple HLA Class I and Class II-derived peptides together with TAP1 and/or TAP2 is set forth herein. As one example of the instant disclosure, a plasmid expression vector encoding various combinations of the features outlined in FIG. 1: (1) a vaccinia-peptide antigen array and (2) an expression cassette containing TAP1 and/or TAP2. These expression vectors direct the synthesis of a chimeric protein containing an amino-terminal portion of FGF2 (MTI) followed by an interchangeable peptide antigen array containing a selection of peptides associated with infectious disease or cancer.

In order to promote efficient proteasome processing of the encoded peptide sequences and thereby preserve complete protease processing sites, the $NH_2$ and COOH ends can be extended by three or four or more native/naturally occurring amino acids (FIG. 1, lower case). Each antigenic peptide portion may be further separated from the next antigenic peptide by a spacer (e.g., $G_4S$). The four MTI translation initiation sites will yield four moles of a multi-peptide PAA translation product for every one mole of transcribed mRNA (FIG. 1) (Florkiewicz and Sommer, *PNAS* 86:3978-3981, 1989; Florkiewicz et al., *Growth Factors* 4:265-275, 1991).

In accordance with the instant disclosure, nucleic acid molecule-based expression vectors have been designed so that a PAA portion of a MTI-PAA is a cassette that is easily excised and replaced. This enables one of ordinary skill to rapidly incorporate additional VACV/VARV epitopes, create a 'reporter epitope' PAA, or design PAAs specific to other pathogens or cancer targets, consistent with a modular recombinant strategy.

The COOH-terminal VSVG epitope-tag can be used for detection by immunoprecipitation, immunoblotting and indirect immunofluorescence (and can also be used to design PCR primer pairs for detection of transcribed mRNA). In order to enhance expression of antigenic peptides/proteins along with TAP1 and/or TAP2, nucleic acid molecule encoding TAP1, TAP2, and PAA (not MTI) are prepared synthetically and in context with a preferred codon utilization algorithm, thereby providing enhanced translation efficiency consistent with the preferred codon bias of *Homo sapiens*, while at the same time minimizing potential cis-acting mRNA sequences that could negatively impact translation efficiency.

Furthermore, nucleic acids of this disclosure may incorporate common epitope tags for the differential immune detection of vector-encoded, as opposed to endogenous Tap1 and/or Tap2, protein. The $NH_2$-terminal Tap1 tag is V5 and the $NH_2$-terminal tag for Tap2 is AU5.

It is appreciated that proteasomes differ in composition and processing ability (Bedford et al., *Trends Cell Biol.* 20:391, 2010; de Graaf et al., *Eur J Immunol* 41:926-935, 2011; Khan et al., *J Immunol* 167:6859, 2001; Sijts & Kloetzel, *Cellular and Molecular Life Sciences: CMLS* 68, 1491-1502, 2011; Wilk et al., *Arch Biochem Biophys* 383, 265, 2000; Xie, Y. *J Mol Cell Biol* 2, 308-317, 2010). Furthermore, it is recognized, although not well characterized, that nuclear proteasomes appear different from cytosolic proteasomes. In accordance with the invention, MTI translation products initiated with CUG codons are targeted to the nucleus while the translation product initiated at the AUG codon remain cytosolic. By adjusting the MTI sequence (site specific or deletion mutagenesis remove multiple GR repeats), the invention disclosed can exclusively express either cytosolic or nuclear localized MTI-PAA.

The invention disclosed herein may include a molecular adjuvant, such as the proteins termed Tap1 and/or Tap2, and can be used to demonstrate that inclusion of TAP1 can further enhance presentation of a PAA derived peptide.

In some embodiments, a 'reporter epitope' PAA consisting of epitopes for which there are peptide/MHC complex-specific antibodies may be incorporated into a PAA. Such a reporter epitope may allow one of ordinary skill to use these antibodies to directly measure surface expression of the presented peptides in the context of their restricting MHC/HLA allele.

Immunogenicity testing includes a series of dose-ranging and vaccination-schedule-testing experiments designed to characterize vaccine-induced immune responses. Different HLA class I and HLA class II transgenic animal strains with matching HLA restriction to the antigenic epitopes may be used within the context of the disclosed invention.

Vaccine efficacy testing includes evaluation of the PAA/TAP vector vaccination dose/schedule followed by survival studies using, for example, the intranasal infection model. Intranasal inoculation of Vaccinia Western Reserve (WR) into mice results in a lethal infection characterized by weight loss, ruffled fur, lethargy, and death by day six or seven post infection (Turner, *J Gen Virol* 1:399, 1967; Reading & Smith *J. Gen. Virol.* 84:1973, 2003; Williamson et al., *J. Gen. Virol.* 71:2761, 1990).

Prior to the vaccine efficacy experiments, the VACV-WR $LD_{50}$ for each transgenic strain may be determined experimentally as per the Reed-Muench method, and 5-10 $LD_{50}$ will be used for survival experiments, and to develop correlates of protection/immunity to derive levels of protection in a human vaccinated population (Reed & Muench, *Am. J. Epidemiol.* 27:493, 1938).

CTL function: as appreciated by one of ordinary skill in the relevant art, percent specific lysis is calculated for each effector:target ratio according to established protocols (Latchman, Y. E. et al. PNAS 101, 10691-10696, 2004) and compared between groups using ANOVA.

T helper function: Antigen-specific T cell activity is calculated by subtracting the median IFNγ ELISPOT response value of the unstimulated wells from that of the stimulated wells. Values may be calculated for individual mice and differences between immunized and control groups will be compared using Student's t test. CFSE a tracking reagent used in flow cytometry is used to determine proliferation rate differences between groups and compared using established models (Banks et al., *J. Immunol. Methods* 373:143-160, 2011; Banks et al. *Bull. Math Biol.* 73:116-150, 2011).

Survival studies: Power calculations (assuming a type I error rate of 0.05 and a two-sided test of hypothesis) indicate that, with 20 mice/group, about an 80% power of detection for a difference in survival will be measurable if the true survival rates at seven days are 50% for the immunized group and 10% for the unimmunized group. For all survival experiments, Kaplan-Meier survival curves will be plotted and compared using standard statistical tests for survival, such as the log rank test.

Proteasome processing of a PAA modified to include a consensus protein ubiquitination motif (e.g., KEEE (SEQ ID NO.: 203) or EKE) (Catic et al., *Bioinformatics* 20:3302-3307, 2004; Chen, Z. et al. *PLoS One* 6, e22930, 2011; Jadhav, T. & Wooten, M. W. *J Proteomics Bioinform* 2, 316, 2009; Sadowski, M. & Sarcevic, B. *Cell Div* 5, 19, 2010) may be included in the embodiments listed herein along with fluorescently-labeled antibodies specific for peptide/MHC complexes in order to directly measure epitope presentation.

In certain embodiments, TAP is selected as a molecular adjuvant to enhance class I antigen presentation. By way of background, there is considerable cross-talk between the HLA class I and class II processing and presentation pathways (Chicz, R. M. et al. *The Journal of experimental medicine* 178, 27-47, 1993; Lechler, R., Aichinger, G. & Lightstone, L. *Immunological reviews* 151, 51-79, 1996; Rudensky, A., et al., *Nature* 353, 622-627, 1991). In addition, intracellular peptides can be loaded onto HLA class II peptides through multiple mechanisms (Dengjel et al., *PNAS* 102:7922-7927, 2005; Dongre, A. R. et al. *Eur J Immunol* 31, 1485-1494, 2001; Nedjic, J., et al., *Curr Opin Immunol* 21, 92-97, 2009). There is also increasing evidence that the class I antigen processing machinery affects this endogenous pathway for class II processing and presentation (Jaraquemada et al., *J. Exp. Med.* 172:947-954, 1990; Loss et al., *J. Exp. Med.* 178:73-85, 1993; Oxenius, A. et al., *Euro. J. Immunol.* 25:3402-3411, 1995). Tewari et al. have identified two I-$E^d$ restricted epitopes from the influenza HA and NA proteins that are processed by TAP and the proteasomal machinery and loaded onto recycling MHC class II molecules (*Nature Immunol.* 6:287-294, 2005).

Plasmid expression vectors: Detection of overexpressed TAPs or MTI-PAA is determined by PCR, immunoprecipitation, Western blot, immunofluorescence and/or IHC. Immuno-detection makes use of commercially available antibodies (see Examples). Intracellular localization is evaluated by indirect immunofluorescence and subcellular fractionation using commercially available methodologies (e.g., NE-PER, Pierce, Inc.). Preparation of VACV vectors may be accomplished by the ordinary skill artisan in accordance with standard methodologies.

Levels of antigen presentation are assessed by several methods: flow cytometry using purified p/MHC specific antibodies isolated from hybridomas and conjugated to PE or APC (Molecular Probes Antibody Staining Kits); co-incubation of transfected APCs with peptide-specific T cells and assessing immune recognition by IFNγ ELISPOT assay or intracellular cytokine staining.

One or more epitope tags may be used to aid in the detection of a fusion polypeptide encoded by a nucleic acid molecule of this disclosure when contained in a plasmid or viral vector, wherein the nucleic acid molecule is operably linked to an expression control sequence.

Antigenic peptides (Class I or II restricted) arise when proteins or fragments thereof undergo proteasomal processing. The peptides generated can then bind to MHC (HLA) molecules and can elicit protective immunity if various additional parameters are met (Gilchuk et al., *J. Clin. Investig.* 123:1976-1987, 2013), such as (1) HLA binding affinity; (2) peptide/HLA stability; (3) interactions with molecular chaperones (TAP/HLA-DM) (Yin et al., *J. Immunol.* 189:3983-3994, 2012); (4) strength of the TCR:peptide: MHC complex interaction; (5) antigen expression level and kinetics; (6) cellular localization; and (7) T cell recognition/peptide immunogenicity. In certain embodiments, peptides elicit multi-functional T cell responses and generate long-lived memory cells that protect the host from infectious disease or from developing cancer.

EXAMPLES

Example 1

Nucleic Acid Molecules Comprising a Multiplex Translation Initiation Sequence FIG. 1 depicts an exemplary construction of a nucleic acid-based expression vector incorporating the MTI (based on FGF2 upstream multiplex translation initiation from CUG start codons) technology as disclosed herein. Expression vectors may comprise a plasmid vector or may comprise a nucleic acid molecule encoding peptide antigenic epitopes incorporated into one or more viral delivery systems. A first series of plasmid expression vectors encoding (a) MTI-PAA (PAA=Peptide Antigen Array; see FIG. 1C), (b) codon-optimized and epitope tagged TAP1, and (c) codon-optimized TAP2. These MTI-PAA nucleic acid molecule-based systems may further include combinations of TAP1 and/or TAP2. The vector design allows the PAA portion to be easily excised as a cassette and replaced with the sequence corresponding to any series of T-cell epitopes, enabling incorporation of additional epitopes from other pathogens, cancer genes or HLA supertypes into the expression vector—enhancing its utility as a "plug-and-play" platform.

In the context of MHC Class I peptides, expression vectors direct the synthesis of a chimeric protein containing an $NH_2$ portion of hFGF2 (MTI) followed by a specific peptide antigen array (PAA) representative of the aforementioned antigenic peptides. We assembled a selection of peptides into a linear peptide antigen Array (PAA) and converted the same into a nucleic acid expression vector. However, we hypothesized that protease processing requires the presentation of a complete protease processing site. Therefore, in order to encourage or otherwise recapitulate efficient proteasome processing of the peptide sequences, we extended the amino acid sequence at their $NH_2$ and COOH ends by three or four or more native/naturally occurring amino acids.

The expression vectors incorporate features that will enhance the amount of selected PAA/peptides (T cell epitopes) synthesized. Particular features include (1) codon optimized DNAs, and (2) the ability to synthesize four moles of MTI-PAA for every one mole of mRNA transcribed. Codon optimization of the PAA portion of the expression vectors used herein will increase the translational efficiency of transcribed mRNAs. In some cases, codon optimization also provides a means by which to molecularly distinguish (e.g., by PCR) vector encoded genes (e.g., TAP1 and TAP2) from corresponding endogenous genes in preclinical as well as clinical evaluation.

Regarding above mentioned ability to synthesize four moles of MTI-PAA for every one mole of mRNA transcribed, expression system takes advantage of the fact the human FGF2 gene is capable of directing the synthesis of four polypeptides from one mRNA via the recognition of three unconventional CUG translation initiation codons and one classical AUG codon. The three CUG codons initiate translation of three co-linear amino terminally extended versions of 18 kDa FGF2 that initiates translation at a downstream AUG codon. The portion of FGF2 included in the vector described above retains the three CUG codons as well as the one AUG codon. Therefore, the vector provides four moles of a particular PAA for every one mole of mRNA.

An additional feature of the FGF2 portion of the expression vectors is the ability to evaluate the efficiency of cytosolic versus nuclear proteasome processing. It is well established that proteasome processing provides peptide substrates for MHC Class I mediated cell surface presentation. It is also appreciated that proteasomes differ in composition, where, for example, immune proteasomes are distinct from non-immune (normal) proteasomes. Further, it is recognized, although not well characterized, that nuclear proteasomes appear different from cytosolic proteasomes.

FGF2 translation products initiated with CUG codons are targeted to the nucleus while the translation product initiated at the AUG codon is cytosolic (Data not shown). Accordingly, FGF2 sequences are modified (site specific or deletion mutagenesis) to exclusively express either cytosolic or nuclear localized MTI-PAA chimera.

Example 2

Expression of Poly-Antigen Array Epitopes

TAP1, TAP2, and PolyStart™ MTI-PAA gene expression in transfected COS-1 cells have been observed by PCR (data not shown). The pJ603 expression plasmid was selected for these experiments. The CMV and/or SV40 late promoter contained in the plasmid drives transcription of downstream coding sequence and (in some cases) sequence deemed important for maintaining mRNA structure and appropriate recognition of CUG/AUG translation initiation codons. Accordingly, we have designed/prepared a first series of plasmid expression vectors encoding (a) MTI-PAA (smallpox peptides), (b) Tap1 only, (c) Tap2 only, (d) Tap1-IRES-Tap2, (e) Tap1 plus MTI-PAA, and (f) Tap2 plus MTI-PAA. A VSVG peptide-tag epitope tag was included at the COOH-terminal end of the MTI-PAA.

The expression vectors have been designed so that the PAA portion of the MTI-PAA can be easily excised and replaced with any codon-optimized DNA sequence encoding any PAA corresponding to any series of T-cell peptide epitopes (or full length/truncated protein), enabling us to rapidly incorporate additional peptide epitopes such as VEEV E3 or E2, cancer epitopes such as breast cancer related epitopes (e.g., Her2/neu, folate receptor alpha, NY-ESO-1, MIF, GnRh or GnRHR), or peptide epitopes specific to any pathogen(s) or targeted cancer cell protein into our expression vector.

In addition, the nucleic acid sequences encoding TAP1, TAP2, and PAA, were prepared synthetically and in context with a preferred codon utilization algorithm. Codon optimization provides enhanced translation efficiency consistent with the preferred codon bias of *Homo sapiens* while simultaneously minimizing potential cis-acting mRNA sequences that could also negatively impact translation efficiency. In this example, the FGF2 (MTI) portion was not codon optimized to preserve sequence dependent mRNA structure that may be needed to mediate translation from unconventional (i.e., CUG) translation initiation codons in a manner mechanistically consistent with internal ribosome entry. This strategy will support higher levels of expression and thereby provide a higher level of corresponding antigenic polypeptide. This in turn is expected to result in higher proteasome mediated peptide processing and consequently higher TAP mediated peptide presentation to MHC and subsequent cell surface presentation.

The unique aspects of the codon-refined synthetic DNAs encoding TAP1 and TAP2 have been utilized to design PCR primer pairs that distinguish cDNAs derived from endogenous mRNA transcripts from cDNA derived from vector transcribed mRNA. The primer pairs were then used in PCR reactions using template DNA obtained from three sources: codon refined plasmid DNA for TAP1 and TAP2; cDNA template from non-transfected COS-7 and PANC-1 cells; and cDNA template from COS-7 cells transfected with TAP1 and TAP2 plasmid DNA.

COS-1 cells (70% confluent) were transfected in 60 mm plates using the Fugene HD reagent (Promega, Inc.). Approximately 40 hours post-transfection, total RNA was prepared. The total RNA was treated with DNase free RNase and cDNA was generated using M-MLV reverse transcriptase. HotStart Polymerase (Qiagen, Inc.) was used in the PCR reaction as follows: 95° hold, 95° 15', [95° 30", 54/57° 30", 72° 1'30"]$_{40x}$ 72° 5', 12° hold; +/−Q solution.

The results demonstrated that the PCR primers designed to detect endogenous TAP1 and TAP2 do not recognize plasmid DNAs containing codon refined TAP1 or TAP2 (data not shown). In comparison, PCR primer pairs that are specific to the synthetic codon refined DNAs do prime. In addition, TAP1 primers do not cross-prime with TAP2 templates. Similarly, using total RNA prepared from non-transfected COS-7 and PANC-1 cells, PCR primer pairs recognizing endogenous TAP1 and TAP2 do not recognize cDNA derived from vector encoded mRNA but do recognize cDNA templates derived from endogenous TAP1 and TAP2 mRNA (data not shown). Finally, cDNA prepared from mRNA derived from COS-7 cells transfected with plasmid expression vectors containing codon preferred TAP1 and TAP2 sequences distinguished endogenous from transfected mRNAs (data not shown). These PCR conditions were used in order to follow/confirm TAP1 and TAP2 expression following presentation of therapeutic plasmid DNAs or following infection with recombinant vaccinia virus.

Further, since both TAP1 and TAP2 contain internalized non-cleaved signal sequences, leaving an exposed cytosolic NH2 portion of TAP1 and an exposed ER-lumen localized NH2 portion of TAP2, our synthetic constructs incorporate commonly used NH2-terminal epitope tags for the differential detection of vector encoded, as opposed to endogenous, TAP1 and/or TAP2. The NH2-terminal TAP1 tag is V5 and the NH2-terminally tag for TAP2 is AU5. Commercially available antibodies were used to detect expression and intracellular localization by immunoprecipitation, immunoblotting, and immunofluorescence.

Figure 2:
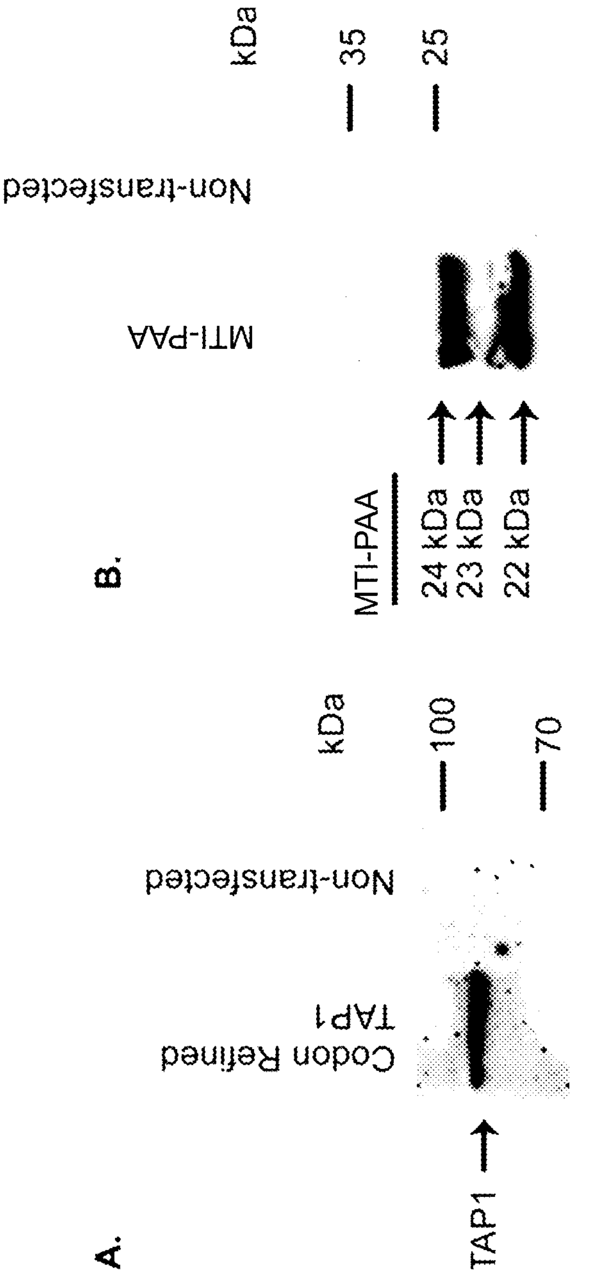
FIG. 2 depicts immunoprecipitation detection of TAP1 and MTI-PAA. A) Cell extracts from TAP1-transfected COS cells were immunoprecipitated with goat anti-V5 antibody (the NH2-terminal tag on recombinant TAP1) and protein G agarose, separated by 12% SDS-PAGE, transferred to PVDF, and immunoblotted with rabbit anti-V5 antibody. B) Cell extracts from MTI-PAA transfected COS cell were heparin sepharose (HS) purified, separated by 12% PAGE, transferred, and immunoblotted with goat anti-FGF2 antibodies.
Figure 3:
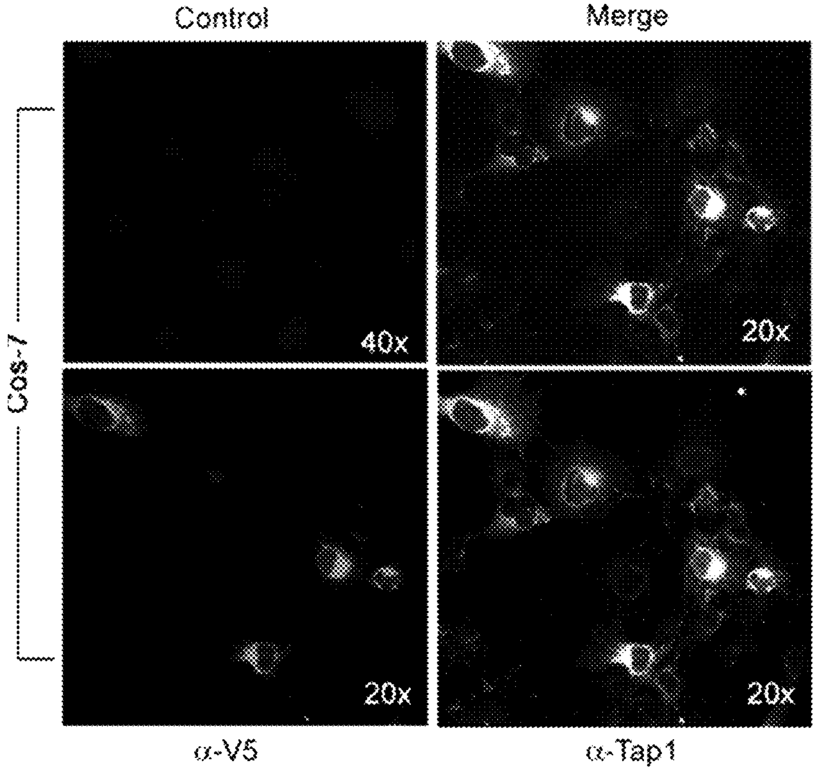
FIG. 3 depicts immunofluorescence micrographs of expression of TAP1 in COS cells using anti-V5 and anti-TAP1 antibodies.
Figure 4:
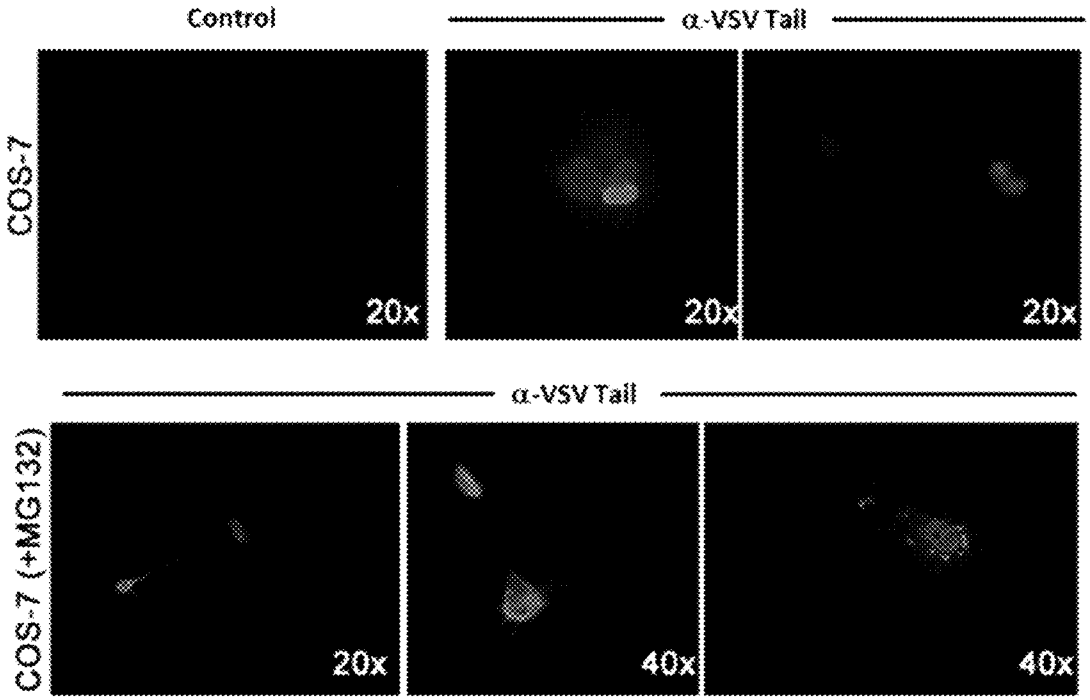
FIG. 4 depicts immunofluorescence micrographs of expression of MTI-PAA. Staining was performed using an anti-VSV antibody directed against the C-terminal portion of the MTI-PAA.
Figure 5:
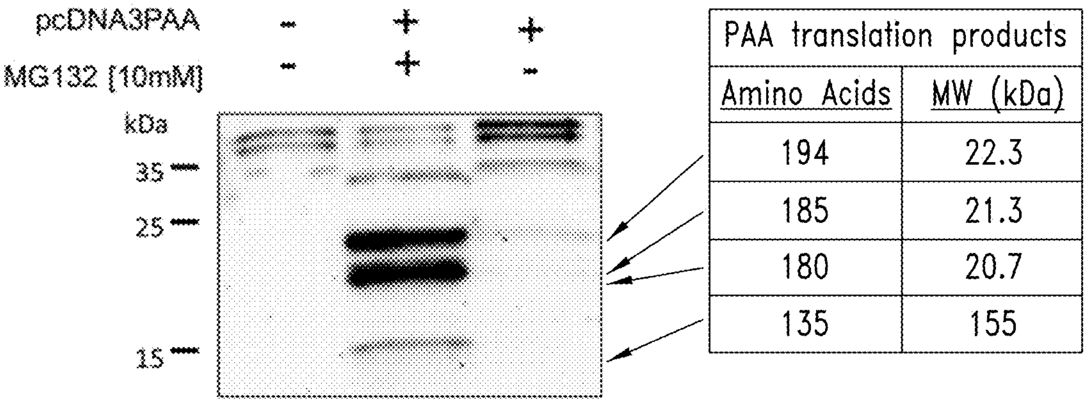
FIG. 5 depicts the immunoprecipitation detection of PAA products in the presence or absence of proteasome activity. HEK cells were transfected with pcDNA3PAA or control. Immunoprecipitation of expression products in the presence of the proteasome inhibitor MG132 showed the expression of the predicted translation products of MTI-PAA.

Protein expression of both TAP1 and MTI-PAA was confirmed by immunoprecipitation (FIG. 2). Codon-optimized TAP2 protein expression was problematic and we are recreating the vectors using native human TAP2 sequence. Immunofluorescence data demonstrate the cytosolic expression of TAP1 using both anti-V5 and anti-TAP1 antibodies (FIG. 3). Control experiments characterizing full length expression of MTI-PAA was also confirmed by immunofluorescence staining of transfected COS cells using an anti-FGF2 Ab targeting the amino-terminus (data not shown) and an anti-VSV Ab directed against the C-terminal portion of MTI-PAA (FIG. 4). These data also demonstrate that MTI-PAA is predominantly localized to the nucleus. FIG. 2 also illustrates that MTI-PAA expression is enhanced in the presence of the proteosomal inhibitor MG132 (10 nM). IP data from transfected HEK cells also indicates increased levels of MTI-PAA in the presence of MG132 (FIG. 5) as well as detection of all four predicted translation products of the MTI-PAA (FIG. 5).

Example 3

Expression and Immune Recognition of Poly-Antigen Array Epitopes

Figure 6:
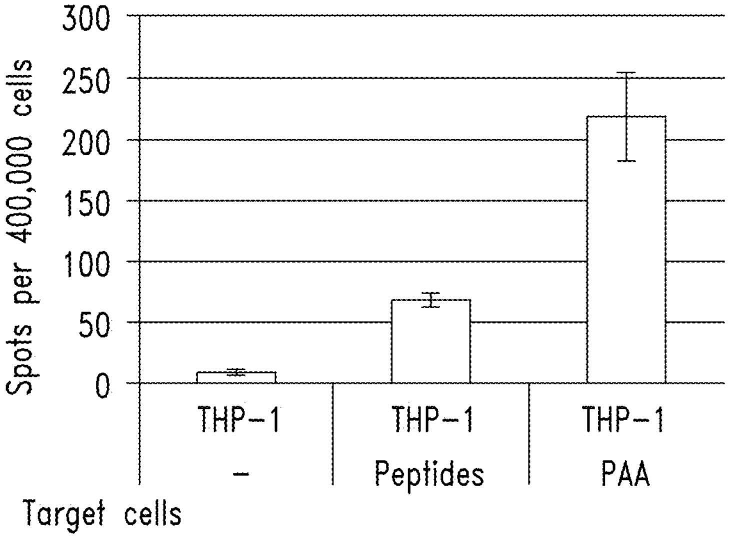
FIG. 6 depicts T cell recognition of PAA-expressing targets. Splenocytes from peptide-vaccinated (#22, #25, #28, #30, HBV core Ag: emulsified in incomplete Freund's adjuvant (IFA)) mice were incubated with THP-1 cells (column 1), THP-1 cells pulsed with 1 ug/ml of each peptide (p22, p25, p28, p30) (column 2), or were transfected with MTI-PAA expression vector for 18 hours (column 3).
Figure 7:
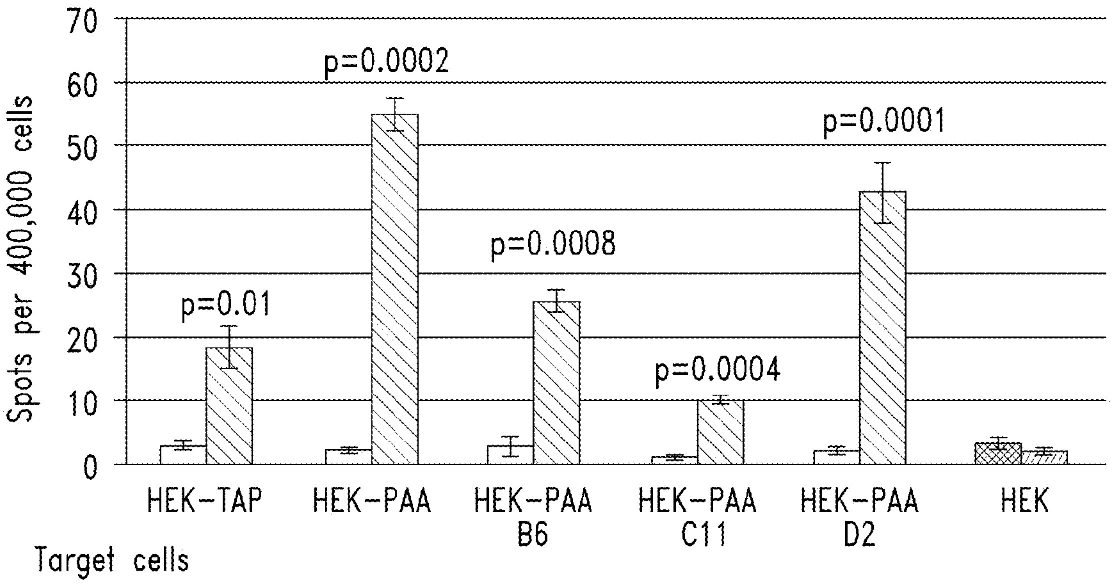
FIG. 7 depicts T cell reactivity, measured by ELISPOT, against a series of stably transfected HEK cell lines. The cell lines were super-transfected as described. The first pair of bars correspond to HEK cells stably transfected with a clone expressing Tap1 (white/clear bar). These cells were super-transfected with an expression vector encoding a small pox PAA (diagonal line bar). Moving left to right, the next four pairs of bars represent four independent stably transfected HEK cell lines expressing Tap1. Each Tap1 transfected cell line was super-transfected with a PolyStart™-PAA encoding small pox antigenic peptides. The diagonal lined bars show elevated T-cell reactivity, indicating proteasome processing of a small pox PAA. The two right most bars are negative controls (clear/white is non-transfected normal HEK cells and HEK cells pulsed with small pox peptides only).

FIG. 6 demonstrates that peptide-specific T cells (from peptide vaccinated mice) recognize THP-1 cells transfected (Lipofectamine LTX, Invitrogen) with PolyStart™ MTI-PAA, confirming PAA-driven expression, processing, and presentation of immunogenic peptides. Furthermore, as illustrated in FIG. 7, co-expression of TAP1 in HEK PAA-transfected cells influences antigen recognition by T cells.

Example 4

Murine Peptide Reactivity

Peptide-specific T cell responses from HLA-A2 transgenic mice intradermally vaccinated with Dryvax® were detected using IFNα ELISPOT. Positive responses are defined as ≥2 fold increase in spot count over background with $p<0.05$ and peptides exhibiting consistent reactivity in multiple mice are shown in Table 1. These same seven peptides were recognized by T cells from two different strains of HLA-A2 mice (chimeric A2/$K^b$ on a BL/6×Balb/c F1 background and chimeric A2/$D^d$ on a BL/6×CBA F1 background), increasing confidence in the immunologic relevance of these peptides following smallpox immunization

TABLE 1

Positive Peptides From HLA-A2 Mice

| Peptide No. | Sequence | Protein Source | Description | SEQ ID NO. |
|---|---|---|---|---|
| 16 | VLSLELPEV | D13L (127) | Virion Coat Protein | 24 |
| 19 | KIDYYIPYV | E2L (068) | Hypothetical Protein | 25 |
| 22 | SLSNLDFRL | F11L (058) | Unknown Function | 26 |
| 25 | ILMDNKGLGV | F1L (048) | Apoptosis Inhibitor | 27 |
| 28 | ILDDNLYKV | G5R (091) | Viral Morphogenesis | 28 |
| 30 | KLLLGELFFL | J3R (104) | Poly(A) Polymerase | 29 |
| 33 | GLLDRLYDL | O1L (079) | Unknown Function | 30 |

Example 5

Peptide Immunogenicity Testing

Figure 8:
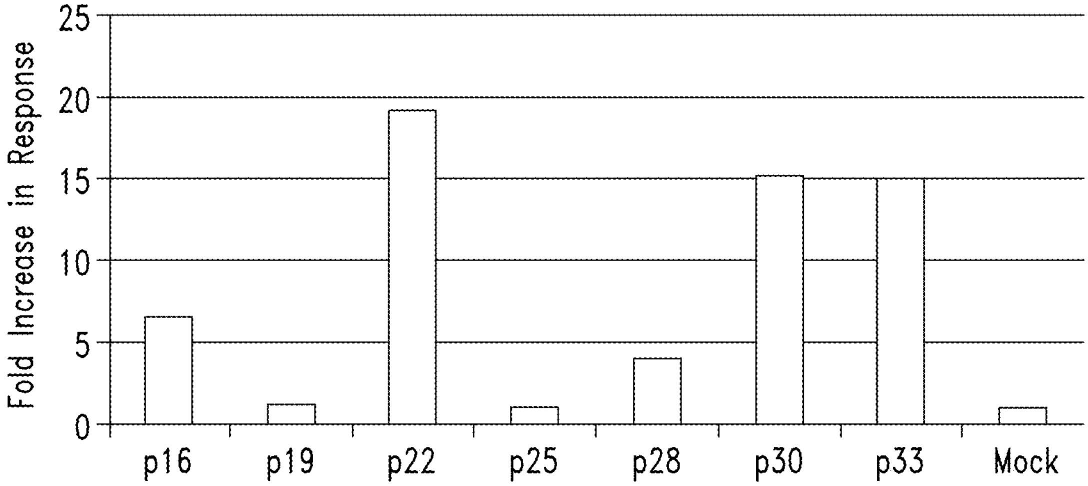
FIG. 8 depicts results from IFNγ ELISPOT assays measuring the immune response in HLA-A2 mice after a two-dose vaccination regimen. Peptide responses are reported as the fold increase (in IFNγ spot forming units) in response to target cells expressing peptide immunogen over response to target cells expressing an unrelated peptide. All responses shown are significant ($p<0.05$) except p19 and p25.
Figure 9:
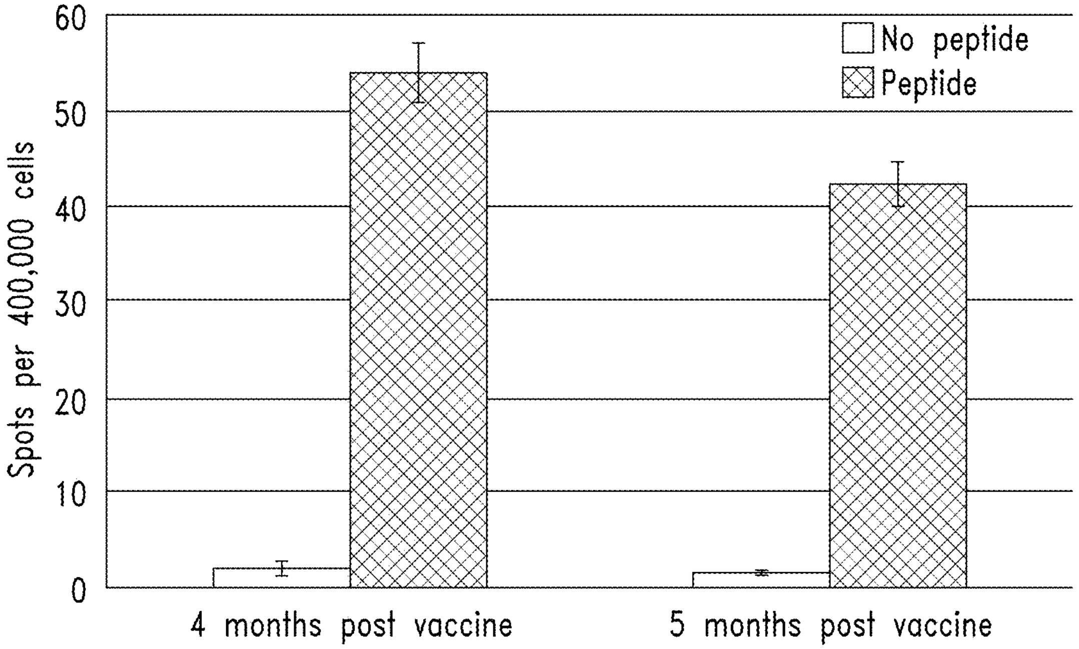
FIG. 9 depicts an immune response after peptide vaccination. HLA-A2 mice were vaccinated twice with peptides #22, #25, #28 emulsified in IFA. Immune responses were measured against syngeneic splenocytes pulsed with pooled peptide cocktail (peptides #22, #25, #28: 1 uM each) (cross-hatched bars) or unpulsed (white bars).

HLA-A2 transgenic mice (n=3/group) were immunized twice with 10 μg of the individual peptides listed in Table 1. A2 peptides were emulsified in IFA along with 100 μg CpG1826 and 140 μg HBV core antigen (SEQ ID NO.: 31; TPPAYRPPNAPIL). Immune responses against peptide-pulsed target cells were readily detectable four weeks after the second vaccination (FIG. 8). Mice immunized with a combination of peptides had detectable responses 4-5 months (FIG. 9) after the second immunization. IFN-γ ELISPOT responses to individual peptides range from 2 to 19-fold increase over background with each peptide exhibiting a consistent magnitude of response (data not shown). These results demonstrate successfully elicited A2-restricted murine T cell responses to epitopes identified from infected human cell lines, thus the model system recapitulates the antigen processing and presentation of a natural human infection.

Example 6

Verification of Murine Model Epitopes in Human Vaccines

Immune responses against a peptide pool (all 7 peptides from Table 1) were tested in 83 HLA-A2 supertype positive, human subjects who had received the smallpox vaccine 1-4 years previously. 42.2% of the subjects (35/83) had positive IFNγ ELISPOT responses to the peptide pool (Spot count≥1.5 times that of background wells with t-test $p<0.05$). Responses ranged from 1.5 to 6.2-fold increase over background. Furthermore, 20.4% of an additional 54 HLA-A2 supertype positive subjects had detectable immune responses against one or more of the individual. Some peptides were not recognized by any of the subjects, while other peptides were recognized by multiple subjects (data not shown). These results support the use of the HLA transgenic mice to identify relevant peptides recognized by human vaccine recipients.

Example 7

Efficacy of Identified Peptides

Mice (n=5) were vaccinated subcutaneously on the right flank with four CTL peptides (#22, #25, #28, #30 from Table 1) 140 μg of the HBV T helper epitope, and 100 μg of CpG 1826 emulsified in IFA. Unvaccinated mice (n=5) served as controls. Three weeks after immunization, mice were challenged intranasally with $1\times10^6$ pfu Vaccinia Western Reserve. Survival, weight loss, and clinical symptoms of illness were monitored daily. Mice losing 25% of their body weight were euthanized.

Figure 10:
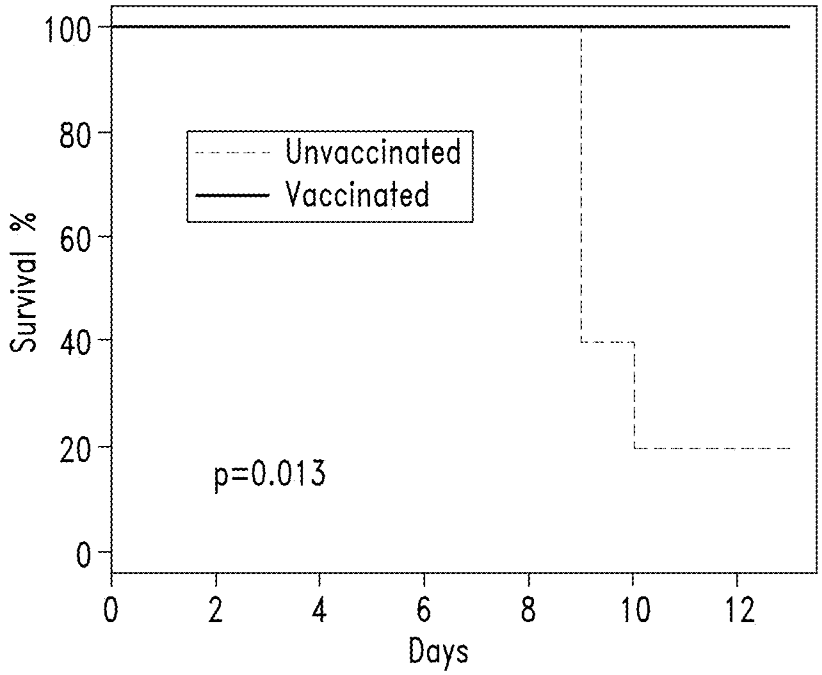
FIG. 10 depicts the effect of peptide-vaccine on survival after lethal intranasal challenge with VACV-WR. Kaplan-Meier survival curve for unvaccinated mice (broken line) and peptide-vaccinated (#22, #25, #28, #30) mice (solid line) following lethal intranasal challenge with VACV-WR ($1\times10^6$ pfu). Significance was assessed using the log-rank test.

Survival data are presented in FIG. 10. Peptide-vaccinated mice were completely protected from lethal challenge. In contrast, all of the unvaccinated mice developed severe clinical symptoms (ruffled fur, hunched posture, loss of mobility) and 80% of them succumbed to the infectious challenge.

Example 8

Epitope Identification in Additional Pathogens

Methods of this disclosure can be used to create a nucleic acid molecule vaccine that encodes antigenic peptide epitopes from seven HLA class I supertypes (A1, A2, A11, A24, B7, B27, B44) and three HLA-C alleles (Cw*0401, Cw*0602, Cw*0702), which would protect across a world-wide populations on average of >96% and is obtainable even without considering peptide binding promiscuity. Frequencies and resources for determine HLA class haplotypes are described in Robinson et al. Nucleic Acids Res. 41:D1222, 2012.

Example 9

HER2/Neu+ Cancer Vaccine Compositions

The following example illustrates a peptide-based and a nucleic acid-based immunization composition for treating cancers that overexpress a HER2/neu marker protein such as HER2/neu overexpressing breast cancer.

Compositions are prepared containing one or more HLA Class I and/or Class II antigenic T-cell peptide sequence generated by computer algorithms or identified by testing human patient samples. For example, computer-based predictions identified a panel of 84 Class II HLA-DR binding epitopes (Kalli et al., Cancer Res 68:4893, 2008; Karyampudi et al., Cancer Immunol Immunother 59:161, 2010). A pool containing four HLA-DR epitopes are immunogenic, naturally processed, and cover about 84% of Caucasians, African Americans and Asians (Hardy-Weinberg equilibrium analysis). The amino acid sequence of four individual peptide epitopes includes NLELTYLPTNASLSF (SEQ ID NO.: 32), HNQVRQVPLQRLRIV (SEQ ID NO.: 33), LSVFQNLQVIRGRIL (SEQ ID NO.: 34), and PIKWMALESILRRRF (SEQ ID NO.: 35). Compositions containing these four HLA-DR peptides are described in the Phase I Clinical Trial entitled "A Phase I Trial of a Multi-Epitope HER2/neu Peptide Vaccine for Previously Treated HER-2 Positive Breast Cancer". In the trial, 500 μg of each peptide generate an immune response in up to about 90% of breast and ovarian cancer patients (Knutson et al., *J. Clin. Invest.* 107:477, 2001; Disis et al., *J. Clin. Oncol.* 20:2624, 2002).

The peptide or nucleic acid vaccine compositions may also contain one or more HLA Class I antigenic $CD8^+$ T-cell antigenic epitope in combination with one or more HLA Class II epitopes. For example, the composition can include the epitopes as described in U.S. Provisional Application No. 61/600,480 entitled "Methods and materials for generating $CD8^+$ T-cells having the ability to recognize cancer cells expressing a Her2/neu polypeptide." An exemplary amino acid sequence is SLAFLPESFD (SEQ ID NO.:36) (amino acids 373-382).

An HLA Class I antigenic epitope may be modified by extending at its NH2 and/or COOH end by one or more naturally occurring amino acid. Such an extension may recapitulate an endogenously recognized naturally processed polypeptide sequence involved in proteolytic processing through a cells proteasome mediated degradation pathway, which may include sequences that promote ubiqutination. Accordingly, a plasmid-based nucleic acid immunization composition can incorporate the corresponding DNA coding sequences, which may include nucleic acid sequences reflecting natural NH2 and/or COOH terminal extensions, and which may incorporate linker regions positioned between the coding sequences of each peptide.

An exemplary vaccination strategy is to administer as a prime-and-boost, i.e., sequentially delivering one or more in a series of peptide vaccine composition(s), followed by one or more in a series of nucleic-acid (e.g., plasmid or viral) vaccine compositions, or vice versa. In one aspect, a peptide immunization composition is administered prior to administration of a nucleic acid immunization composition. In another aspect, the nucleic acid immunization composition is administered prior to administration of the peptide immunization composition.

In addition, some patients may have a better outcome if prior to administering a vaccine composition, the patient receives cyclophosphamide, or a similar composition, orally for 1 week followed by a 1 week rest, and then another week of cyclophosphamide treatment. About 7-10 days following cyclophosphamide treatment, patients are vaccinated intradermally, intramuscularly, or ex vivo using isolated cells. The peptides may be HLA-DR related and the nucleic acid may encode one or more HLA-Class I antigenic cytotoxic T-cell epitopes.

Compositions are prepared containing one or more HLA Class I and/or Class II antigenic T-cell peptide sequences from computer algorithms or testing human patient samples. The vaccine compositions may contain an adjuvant, such as GM-CSF (e.g., 125 μg/injection).

Example 10

Folate Receptor Alpha and Cancer Vaccine Compositions

This Example illustrates a combined or sequentially administered nucleic acid-based composition and peptide-based composition for treating a folate receptor alpha expressing cancer. Folate receptor alpha is overexpressed in a number of cancers such as ovarian, primary peritoneal, lung, uterine, testicular, colon, renal, $HER2/neu^+$ breast, and triple negative breast cancer (Zhang et al., Arch. Pathol. Lab. Med. p 1-6, 2013; Weitman et al., *Cancer Res.* 52:3396, 1992; O'Shannesst et al., SpringerPlus 1:1, 2012; Kelemen, *Int. J. Cancer* 119:243, 2006; U.S. Pat. No. 8,486,412).

In one aspect, the vaccine composition contains one or more antigenic folate receptor alpha HLA Class II and/or HLA Class I antigenic peptide epitopes as described in a Phase I Clinical Trial entitled "A Phase I Trial of the Safety and Immunogenicity of a Multi-epitope Folate Receptor Alpha Peptide Vaccine in Combination with Cyclophosphamide in Subjects Previously Treated for Breast or Ovarian Cancer." A vaccine composition comprising one or more HLA Class II folate receptor alpha antigenic T-cell peptides comprising for example peptides FR30 (amino acid sequence RTELLNVCMNAKHHKEK (SEQ ID NO.: 37)), peptide FR56 (amino acid sequence QCRPWRKNACCSTNT (SEQ ID NO.: 38)), peptide FR76 (amino acid sequence KDVSYLYRFNWNHCGEMA (SEQ ID NO.: 39)); peptide FR113 (amino acid sequence LGPWIQQVDQSWRKERV (SEQ ID NO.: 40)), and peptide FR238 (amino acid sequence PWAAWPPLLSLALMLLWL (SEQ ID NO.: 41)), and may optionally be formulated with one or more similarly identified HLA Class I folate receptor alpha antigenic T-cell peptides. It is of note that one or more Class I antigenic T-cell epitopes may be contained within the sequence of a HLA Class II epitope. For example, the Class II peptide FR56 and the peptide sequence of FR238 containing the HLA Class I epitope of folate receptor alpha peptides 245-253. Composition may also be formulated with an adjuvant such as GM-CSF and/or combined with prior treatment with an immune-regulatory substance such as cyclophosphamide or denileukin diftitox (Ontak).

The plasmid-based nucleic acid immunization composition incorporates the corresponding DNA coding sequences for a folate receptor alpha HLA Class II and/or HLA Class I antigenic T-cell peptide. The DNA may include nucleic acid sequences reflecting natural NH2 and/or COOH terminal extensions which are thought to recapitulate the naturally occurring protease processing site for proteasome mediated degradation. Further, the DNA may incorporate linker regions positioned between the coding sequences of each peptide.

A matched vaccination strategy is one in which the peptides and nucleic acid encoded sequences are derived from the same cancer related TAA. The matched vaccination strategy includes administering respective compositions as a prime-and-boost, i.e., sequentially delivering one or more of a series of folate receptor alpha antigenic T-cell peptide vaccine composition(s), followed by one or more in a series of folate receptor alpha peptide derived nucleic-acid vaccine compositions (e.g., plasmid or viral). In one aspect, the peptide immunization composition is administered prior to administration of a nucleic acid immunization composition. In another aspect, the nucleic acid immunization composition is administered prior to administration of the peptide immunization composition. The peptides may be HLA-DR related and the nucleic acid may encode one or more HLA-Class I antigenic cytotoxic T-cell epitopes.

Additional cancer TAAs may be included in the vaccine compositions, including antigenic T cell peptides from insulin-like growth factor binding protein 2 (Kalli et al., *Cancer Res.* 68:4893, 2008), carcinoembryonic antigen (Karyampudi et al., *Cancer Immunol. Immunother.* 59:161, 2010), and PD-1 antagonists (Krempski et al., *J. Immunol.* 186: 6905, 2011).

Compositions are prepared containing one or more HLA Class I and/or Class II antigenic T-cell peptide sequences from computer algorithms or testing human patient samples. The vaccine compositions may contain an adjuvant such as GM-CSF (e.g., 125 μg/injection). In addition, some patients may have a better outcome if prior to administering a vaccine composition, the patient receives cyclophosphamide, or a similar composition, orally for 1 week followed by a 1 week rest, and then another week of cyclophosphamide treatment. About 7-10 days following cyclophosphamide treatment, patients are vaccinated intradermally, intramuscularly, or ex vivo using isolated cells.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Patent Application No. 61/954,588, filed Mar. 17, 2014, are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A chimeric nucleic acid molecule, comprising a multiplex translation initiation (MTI) sequence comprising from two to about five translation initiation sites operatively linked in frame to a nucleic acid molecule encoding a fusion protein comprising from two to about ten human epidermal growth factor receptor 2 (HER2) antigenic peptides, wherein at least one of the MTI translation initiation sites is a non-AUG translation initiation site and the MTI allows the production of more than one mole of fusion protein per mole of mRNA.

2. The chimeric nucleic acid molecule of claim 1, wherein the MTI comprises one, two, three, or four non-AUG translation initiation sites.

3. The chimeric nucleic acid molecule of claim 2, wherein the non-AUG translation initiation sites are CUG translation initiation sites.

4. The chimeric nucleic acid molecule of claim 3, wherein the MTI comprises an AUG translation initiation site downstream of the CUG translation initiation sites.

5. The chimeric nucleic acid molecule of claim 1, wherein the MTI comprises (a) a nucleic acid molecule encoding one or two nuclear localization domains located downstream of two or three CUG translation initiation sites and upstream of an AUG translation initiation site, or (b) two or three CUG translation initiation sites upstream of a nucleic acid molecule encoding one or two nuclear localization domains and no AUG translation initiation site.

6. The chimeric nucleic acid molecule of claim 1, wherein the MTI comprises a 5'-portion of a human FGF2 gene, wherein the 5'-portion of the human FGF2 gene contains an AUG translation initiation site and about 123 nucleotides to about 385 nucleotides upstream of the AUG translation initiation site that is in frame with the nucleic acid molecule encoding the fusion protein.

7. The chimeric nucleic acid molecule of claim 6, wherein the MTI further comprises from about 15 nucleotides to about 45 nucleotides downstream of the AUG translation initiation site.

8. The chimeric nucleic acid molecule of claim 6, wherein the 5'-portion of the human FGF2 gene encodes a polypeptide having at least 90% sequence identity to any one of the amino acid sequences set forth in SEQ ID NOS.:8-12, or encodes a polypeptide as set forth in any one of SEQ ID NOS.:8-12.

9. The chimeric nucleic acid molecule of claim 1, wherein the MTI sequence has at least 90% sequence identity to a nucleotide sequence as set forth in any one of SEQ ID NOS.:1-6, 95, or 96.

10. The chimeric nucleic acid molecule of claim 1, wherein the encoded fusion protein comprises from two to about five different or same antigenic HER2 peptides, or the encoded fusion protein comprises five different antigenic HER2 peptides.

11. The chimeric nucleic acid molecule of claim 1, wherein one or more of the antigenic peptides are an HLA Class I antigenic HER2 peptide, an HLA Class II antigenic HER2 peptide, an HLA Class II antigenic HER2 peptide comprising an embedded HLA Class I antigenic HER2 peptide, or any combination thereof.

12. The chimeric nucleic acid molecule of claim 1, wherein one or more of the encoded HER2 antigenic peptides of the fusion protein comprise on the N-terminus and/or C-terminus: (a) from one to about ten junction amino acids; (b) a spacer comprising from two to about 35 amino acids; (c) a spacer comprising a $(Gly_4Ser)_n$ wherein n is an integer from 1 to 5; (d) a natural cleavage site comprising from one to about ten amino acids; (e) a self-cleaving amino acid sequence; (f) an intracellular trafficking sequence; or (g) any combination thereof.

13. The chimeric nucleic acid molecule of claim 1, wherein two or more of the HER2 antigenic peptides of the fusion protein are separated by a spacer comprising a $(Gly_4Ser)_n$, wherein n is an integer from 1 to 5.

14. The chimeric nucleic acid molecule of claim 1, wherein the encoded fusion protein comprises an amino acid cleavage sequence amino-terminal to one or more of the encoded polypeptide components of the fusion protein, wherein the amino acid cleavage sequence comprises a 2A peptide from porcine teschovirus-1 (P2A), equine rhinitis A virus (E2A), *Thosea asigna* virus (T2A), or foot-and-mouth disease virus (F2A).

15. The chimeric nucleic acid molecule of claim 1, wherein the encoded fusion protein comprises a secretion signal amino acid sequence, a membrane localization amino acid sequence, an endosome targeting sequence, a dendritic cell targeting amino acid sequence, or any combination thereof.

16. The chimeric nucleic acid molecule of claim 1, wherein each encoded HER2 antigenic peptide of the fusion protein has:

(a) at least 90% amino acid sequence identity to any one of SEQ ID NOS.:121-135;
(b) an amino acid sequence of SEQ ID NOS.:121-135;
(c) at least 90% amino acid sequence identity to any one of SEQ ID NOS.:117-120;
(d) an amino acid sequence of SEQ ID NOS.:117-120;
(e) at least 90% amino acid sequence identity to any one of SEQ ID NOS.:117-135;
(f) an amino acid sequence of SEQ ID NOS.:117-135; or
(g) any one of (a)-(f) further comprising from one to about five spacer amino acids on the N-terminus, C-terminus or both of one or more of each HER2 antigenic peptide of the fusion protein.

17. The chimeric nucleic acid molecule of claim 16, wherein the encoded fusion protein encoding any one or more of SEQ ID NOS.:117-135 further comprises a secretion signal amino acid sequence, a membrane localization amino acid sequence, an endosome targeting sequence, a dendritic cell targeting amino acid sequence, or any combination thereof.

18. The chimeric nucleic acid molecule of claim 16, wherein the encoded fusion protein encoding any one or more of SEQ ID NOS.:117-120 comprises:

(a) a VSVG signal amino acid sequence as encoded by the polynucleotide of SEQ ID NO.:43 that is operably linked in frame to and disposed between the MTI sequence and the nucleic acid molecule encoding the fusion protein, optionally comprising a nucleic acid molecule encoding an amino acid cleavage sequence operably linked in frame to and disposed between the MTI sequence and the nucleic acid molecule encoding the VSVG signal amino acid sequence;
(b) a VSVG trafficking amino acid sequence as encoded by the polynucleotide of SEQ ID NO.:47 or 48 that is operably linked in frame to the MTI sequence;
(c) a VSVG membrane localization amino acid sequence as encoded by nucleotides 457 to 516 of SEQ ID NO.:57 that is operably linked in frame to the MTI sequence;
(d) a VSVG trafficking amino acid sequence and membrane localization amino acid sequence as encoded by the polynucleotide of SEQ ID NO.:57 that is operably linked in frame to the MTI sequence; or
(e) any one of (a)-(d) further comprising a dendritic cell targeting amino acid sequence as encoded by the polynucleotide of SEQ ID NO.:45;
(f) any one of (a) or (c)-(e) further comprising an intracellular trafficking sequence.

19. The chimeric nucleic acid molecule of claim 1, wherein the encoded fusion protein comprises a polypeptide having at least 90% sequence identity with any one of the polypeptides set forth in SEQ ID NOS.:115 or 116; or wherein the encoded fusion protein comprises a polypeptide having at least 90% sequence identity with any one of the polypeptides set forth in SEQ ID NOS.:138, 140, 142-144, 146-148 or 150.

20. The chimeric nucleic acid molecule of claim 1, wherein the chimeric nucleic acid molecule comprises:

(a) an mRNA molecule;
(b) a DNA molecule; or
(c) a DNA or RNA molecule contained in a vector and operably linked to an expression control sequence.

21. The chimeric nucleic acid molecule of claim 20, wherein the vector of subpart (c) comprises a plasmid vector or a viral vector.

22. The chimeric nucleic acid molecule of claim 21, wherein the vector comprises a viral vector selected from a rhabdoviral, adenoviral, herpesviral, poxviral, or retroviral vector.

23. A composition, comprising a chimeric nucleic acid molecule of claim 1 and a therapeutically acceptable carrier or excipient.

24. A method of eliciting an immune response, comprising administering to a human subject a therapeutically effective amount of a chimeric nucleic acid molecule, wherein the chimeric nucleic acid molecule comprises a multiplex translation initiation (MTI) sequence comprising from two to about five translation initiation sites operatively linked in frame to a nucleic acid molecule encoding a fusion protein comprising from two to about ten human epidermal growth factor receptor 2 (HER2) antigenic peptides, wherein at least one of the MTI translation initiation sites is a non-AUG translation initiation site and the MTI allows the production of more than one mole of fusion protein per mole of mRNA, thereby eliciting an immune response against one or more of the HER2 antigenic peptides.

25. The method of claim 24, wherein the elicited immune response comprises a cellular immune response that treats a HER2-associated cancer.

26. The method of claim 24, further comprising administering an effective amount of an antigenic peptide immunization composition comprising at least one HER2 antigenic peptide.

27. The method of claim 26, wherein:

(a) the chimeric nucleic acid molecule and the antigenic peptide immunization compositions are administered simultaneously;

(b) the chimeric nucleic acid molecule and the antigenic peptide immunization compositions are administered sequentially;

(c) the chimeric nucleic acid molecule is administered from 1 hour to 8 weeks after the antigenic peptide immunization composition;

(d) the antigenic peptide immunization composition is administered from 1 hour to 8 weeks after the chimeric nucleic acid molecule; or (e) any one of subparts (a) to (d) wherein the chimeric nucleic acid molecule encodes one or more of the same HER2 antigenic peptides of the antigenic peptide composition.

28. The method of claim 27, further comprising one or more additional administrations of an effective amount of the antigenic peptide immunization composition and/or the chimeric nucleic acid molecule after the first administration of the antigenic peptide immunization composition and/or the chimeric nucleic acid molecule.

29. The method of claim 24, further comprising administering an adjunctive therapy selected from the group consisting of surgery, chemotherapy, radiation therapy, antibody therapy, immunosuppressive therapy, and any combination thereof.

30. The method of claim 24, further comprising administering an adjunctive therapy selected from the group consisting of cyclophosphamide, trastuzumab, anti-PD1, anti-PDL1, anti-CTLA4, and any combination thereof.

31. The method of claim 24, wherein the MTI comprises one, two, three, or four non-AUG translation initiation sites.

32. The method of claim 31, wherein the non-AUG translation initiation sites are CUG translation initiation sites.

33. The method of claim 32, wherein the MTI comprises an AUG translation initiation site downstream of the CUG translation initiation sites.

34. The method of claim 24, wherein the MTI comprises (a) a nucleic acid molecule encoding one or two nuclear localization domains located downstream of two or three CUG translation initiation sites and upstream of an AUG translation initiation site, or (b) two or three CUG translation initiation sites upstream of a nucleic acid molecule encoding one or two nuclear localization domains and no AUG translation initiation site.

35. The method of claim 24, wherein the MTI comprises a 5'-portion of a human FGF2 gene, wherein the 5'-portion of the human FGF2 gene contains an AUG translation initiation site and about 123 nucleotides to about 385 nucleotides upstream of the AUG translation initiation site that is in frame with the nucleic acid molecule encoding the fusion protein.

36. The method of claim 35, wherein the MTI further comprises from about 15 nucleotides to about 45 nucleotides downstream of the AUG translation initiation site.

37. The method of claim 35, wherein the 5'-portion of the human FGF2 gene encodes a polypeptide having at least 90% sequence identity to any one of the amino acid sequences set forth in SEQ ID NOS.:8-12, or encodes a polypeptide as set forth in any one of SEQ ID NOS.:8-12.

38. The method of claim 24, wherein the MTI sequence has at least 90% sequence identity to a nucleotide sequence as set forth in any one of SEQ ID NOS.:1-6, 95, or 96.

39. The method of claim 24, wherein the encoded fusion protein comprises from two to about five different or same antigenic HER2 peptides, or the encoded fusion protein comprises five different antigenic HER2 peptides.

40. The method of claim 24, wherein one or more of the antigenic peptides are an HLA Class I antigenic HER2 peptide, an HLA Class II antigenic HER2 peptide, an HLA Class II antigenic HER2 peptide comprising an embedded HLA Class I antigenic HER2 peptide, or any combination thereof.

41. The method of claim 24, wherein one or more of the encoded HER2 antigenic peptides of the fusion protein comprise on the N-terminus and/or C-terminus: (a) from one to about ten junction amino acids; (b) a spacer comprising from two to about 35 amino acids; (c) a spacer comprising a $(Gly_4Ser)_n$ wherein n is an integer from 1 to 5; (d) a natural cleavage site comprising from one to about ten amino acids; (e) a self-cleaving amino acid sequence; (f) an intracellular trafficking sequence; or (g) any combination thereof.

42. The method of claim 24, wherein two or more of the HER2 antigenic peptides of the fusion protein are separated by a spacer comprising a $(Gly_4Ser)_n$, wherein n is an integer from 1 to 5.

43. The method of claim 24, wherein the encoded fusion protein comprises an amino acid cleavage sequence amino-terminal to one or more of the encoded polypeptide components of the fusion protein, wherein the amino acid cleavage sequence comprises a 2A peptide from porcine teschovirus-1 (P2A), equine rhinitis A virus (E2A), *Thosea asigna* virus (T2A), or foot-and-mouth disease virus (F2A).

44. The method of claim 24, wherein the encoded fusion protein comprises a secretion signal amino acid sequence, a membrane localization amino acid sequence, an endosome targeting sequence, a dendritic cell targeting amino acid sequence, or any combination thereof.

45. The method of claim 24, wherein each encoded HER2 antigenic peptide of the fusion protein has:

(a) at least 90% amino acid sequence identity to any one of SEQ ID NOS.:121-135;

(b) an amino acid sequence of SEQ ID NOS.:121-135;

(c) at least 90% amino acid sequence identity to any one of SEQ ID NOS.:117-120;

(d) an amino acid sequence of SEQ ID NOS.:117-120;

(e) at least 90% amino acid sequence identity to any one of SEQ ID NOS.:117-135;

(f) an amino acid sequence of SEQ ID NOS.:117-135; or (g) any one of (a)-(f) further comprising from one to about five spacer amino acids on the N-terminus, C-terminus or both of one or more of each HER2 antigenic peptide of the fusion protein.

46. The method of claim 45, wherein the encoded fusion protein encoding any one or more of SEQ ID NOS.:117-135 further comprises a secretion signal amino acid sequence, a membrane localization amino acid sequence, a dendritic cell targeting amino acid sequence, or any combination thereof.

47. The method of claim 45, wherein the encoded fusion protein encoding any one or more of SEQ ID NOS.:117-120 comprises:

(a) a VSVG signal amino acid sequence as encoded by the polynucleotide of SEQ ID NO.:43 that is operably linked in frame to and disposed between the MTI sequence and the nucleic acid molecule encoding the fusion protein, optionally comprising a nucleic acid molecule encoding an amino acid cleavage sequence operably linked in frame to and disposed between the MTI sequence and the nucleic acid molecule encoding the VSVG signal amino acid sequence;

(b) a VSVG trafficking amino acid sequence as encoded by the polynucleotide of SEQ ID NO.:47 or 48 that is operably linked in frame to the MTI sequence;

(c) a VSVG membrane localization amino acid sequence as encoded by nucleotides 457 to 516 of SEQ ID NO.:57 that is operably linked in frame to the MTI sequence;

(d) a VSVG trafficking amino acid sequence and membrane localization amino acid sequence as encoded by the polynucleotide of SEQ ID NO.:57 that is operably linked in frame to the MTI sequence; or (e) any one of (a)-(d) further comprising a dendritic cell targeting amino acid sequence as encoded by the polynucleotide of SEQ ID NO.:45;

(f) any one of (a) or (c)-(e) further comprising an intracellular trafficking sequence.

48. The method of claim 24, wherein the encoded fusion protein comprises a polypeptide having at least 90% sequence identity with any one of the polypeptides set forth in SEQ ID NOS.:115 or 116; or wherein the encoded fusion protein comprises a polypeptide having at least 90% sequence identity with any one of the polypeptides set forth in SEQ ID NOS.:138, 140, 142-144, 146-148 or 150.

49. The method of claim 24, wherein the chimeric nucleic acid molecule comprises:

(a) an mRNA molecule;

(b) a DNA molecule; or (c) a DNA or RNA molecule contained in a vector and operably linked to an expression control sequence.

50. The method of claim 49, wherein the vector of subpart (c) comprises a plasmid vector or a viral vector.

51. The method of claim 50, wherein the vector comprises a viral vector selected from a rhabdoviral, adenoviral, herpesviral, poxviral, or retroviral vector.

52. The method of claim 24, wherein the chimeric nucleic acid molecule is formulated as a composition comprising a therapeutically acceptable carrier or excipient.

53. The method of claim 24, comprising contacting the chimeric nucleic acid molecule with an immune cell ex vivo before administration, and administering to the human subject a population of immune cells containing the chimeric nucleic acid molecule.

* * * * *

SEQUENCE LISTING

```
<160> NUMBER OF SEQ ID NOS: 210

<210> SEQ ID NO 1
<211> LENGTH: 400
<212> TYPE: DNA
<213> ORGANISM: Artificial Sequence
<220> FEATURE:
<223> OTHER INFORMATION: Exemplary Multiplex Translation Initiation
      (MTI) sequence

<400> SEQUENCE: 1

gggtggagat gtagaagatg tgacgccgcg gcccggcggg tgccagatta gcggacgcgg     60

tgcccgcggt tgcaacggga tcccgggcgc tgcagcttgg gaggcggctc tccccaggcg    120

gcgtccgcgg agacacccat ccgtgaaccc caggtcccgg gccgccggct cgccgcgcac    180

caggggccgg cggacagaag agcggccgag cggctcgagg ctgggggacc gcgggcgcgg    240

ccgcgcgctg ccgggcggga ggctgggggg ccggggccgg ggccgtgccc cggagcgggt    300

cggaggccgg ggccggggcc gggggacggc ggctccccgc gcggctccag cggctcgggg    360

atcccggccg ggccccgcag ggaccatggc agccgggagc                          400


<210> SEQ ID NO 2
<211> LENGTH: 513
<212> TYPE: DNA
<213> ORGANISM: Artificial Sequence
<220> FEATURE:
<223> OTHER INFORMATION: Exemplary MTI sequence

<400> SEQUENCE: 2

gccccagaaa acccgagcga gtagggggcg gcgcgcagga gggaggagaa ctgggggcgc     60

gggaggctgg tgggtgtggg gggtggagat gtagaagatg tgacgccgcg gcccggcggg    120

tgccagatta gcggacgcgg tgcccgcggt tgcaacggga tcccgggcgc tgcagcttgg    180

gaggcggctc tccccaggcg gcgtccgcgg agacacccat ccgtgaaccc caggtcccgg    240

gccgccggct cgccgcgcac caggggccgg cggacagaag agcggccgag cggctcgagg    300

ctgggggacc gcgggcgcgg ccgcgcgctg ccgggcggga ggctgggggg ccggggccgg    360

ggccgtgccc cggagcgggt cggaggccgg ggccggggcc gggggacggc ggctccccgc    420
```

gcggctccag cggctcgggg atcccggccg ggccccgcag ggaccatggc agccgggagc 480
atcaccacgc tgcccgcctt gcccgaggat ggc 513

<210> SEQ ID NO 3
<211> LENGTH: 192
<212> TYPE: DNA
<213> ORGANISM: Artificial Sequence
<220> FEATURE:
<223> OTHER INFORMATION: Exemplary MTI sequence

<400> SEQUENCE: 3
agcggctcga ggctggggga ccgcgggcgc ggccgcgcgc tgccgggcgg gaggctgggg 60
ggccggggcc ggggccgtgc cccggagcgg gtcggaggcc ggggccgggg ccgggggacg 120
gcggctcccc gcgcggctcc agcggctcgg ggatcccggc cgggccccgc agggaccatg 180
gcagccggga gc 192

<210> SEQ ID NO 4
<211> LENGTH: 177
<212> TYPE: DNA
<213> ORGANISM: Artificial Sequence
<220> FEATURE:
<223> OTHER INFORMATION: Exemplary Multiplex Translation Initiation
sequence

<400> SEQUENCE: 4
ggggaccgcg ggcgcggccg cgcgctgccg ggcgggaggc tgggggccg gggccggggc 60 cgtgccccgg agcgggtcgg aggccggggc cggggccggg ggacggcggc tccccgcgcg 120
gctccagcgg ctcggggatc ccggccgggc cccgcaggga ccatggcagc cgggagc 177

<210> SEQ ID NO 5
<211> LENGTH: 150
<212> TYPE: DNA
<213> ORGANISM: Artificial Sequence
<220> FEATURE:
<223> OTHER INFORMATION: Exemplary MTI sequence

<400> SEQUENCE: 5
ccgggcggga ggctgggggg ccggggccgg ggccgtgccc cggagcgggt cggaggccgg 60
ggccggggcc gggggacggc ggctccccgc gcggctccag cggctcgggg atcccggccg 120
ggccccgcag ggaccatggc agccgggagc 150

<210> SEQ ID NO 6
<211> LENGTH: 427
<212> TYPE: DNA
<213> ORGANISM: Artificial Sequence
<220> FEATURE:
<223> OTHER INFORMATION: Exemplary MTI sequence with restriction sites
on each end

<400> SEQUENCE: 6
atcgatggtt aacgtttaaa cgggtggaga tgtagaagat gtgacgccgc ggcccggcgg 60
gtgccagatt agcggacgcg gtgcccgcgg ttgcaacggg atcccgggcg ctgcagcttg 120
ggaggcggct ctccccaggc ggcgtccgcg gagacaccca tccgtgaacc ccaggtcccg 180
ggccgccggc tcgccgcgca ccaggggccg gcggacagaa gagcggccga gcggctcgag 240
gctgggggac cgcgggcgcg gccgcgcgct gccgggcggg aggctggggg gccggggccg 300
gggccgtgcc ccggagcggg tcggaggccg gggccggggc cgggggacgg cggctccccg 360

-continued

```
cgcggctcca gcggctcggg gatcccggcc gggccccgca gggaccatgg cagccgggag    420

ctctaga                                                              427


<210> SEQ ID NO 7
<211> LENGTH: 805
<212> TYPE: DNA
<213> ORGANISM: Artificial Sequence
<220> FEATURE:
<223> OTHER INFORMATION: MTI + Small Pox MHC Class I polyantigen array +
      VSV-g epitope tag

<400> SEQUENCE: 7

gggtggagat gtagaagatg tgacgccgcg gcccggcggg tgccagatta gcggacgcgg     60

tgcccgcggt tgcaacggga tcccgggcgc tgcagcttgg gaggcggctc tccccaggcg    120

gcgtccgcgg agacacccat ccgtgaaccc caggtcccgg gccgccggct cgccgcgcac    180

caggggccgg cggacagaag agcggccgag cggctcgagg ctgggggacc gcgggcgcgg    240

ccgcgcgctg ccgggcggga ggctgggggg ccggggccgg ggccgtgccc cggagcgggt    300

cggaggccgg ggccggggcc gggggacggc ggctccccgc gcggctccag cggctcgggg    360

atcccggccg ggccccgcag ggaccatggc agccgggagc tctagagagg tgaacaccat    420

cctgatggac aacaagggcc tgggcgtgag actggccacc ggcggcggcg gcagcggcgg    480

cggcggcagc aagagcctga ccatcctgga cgacaacctg tacaaggtgt acaacggcat    540

cggcggcggc ggcagcggcg gcggcggcag cagaaccgac gacggcctgc tggacagact    600

gtacgacctg accagatacg ccggcggcgg cggcagcggc ggcggcggca gccccctgac    660

caagggcatc ctgggcgtgt tcaccctgac cgtgcccagc ggcggcggcg gcagcggcgg    720

cggcggcagc aagatcgtga acagcctgag caacctggac ttcagactgt acaccgacat    780

cgagatgaac agactgggca agtga                                          805


<210> SEQ ID NO 8
<211> LENGTH: 56
<212> TYPE: PRT
<213> ORGANISM: Artificial Sequence
<220> FEATURE:
<223> OTHER INFORMATION: MTI peptide from first CUG to AUG for Class II
      peptides with bFGF peptide insert

<400> SEQUENCE: 8

Leu Gly Asp Arg Gly Arg Gly Arg Ala Leu Pro Gly Gly Arg Leu Gly
 1               5                  10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Met
    50                  55


<210> SEQ ID NO 9
<211> LENGTH: 50
<212> TYPE: PRT
<213> ORGANISM: Artificial Sequence
<220> FEATURE:
<223> OTHER INFORMATION: MTI peptide from first CUG to AUG for Class II
      peptides with first nuclear localization site removed (delta 17-
      22) and bFGF peptide insert

<400> SEQUENCE: 9

Leu Gly Asp Arg Gly Arg Gly Arg Ala Leu Pro Gly Gly Arg Leu Gly
```

-continued

```
 1               5                   10                  15

Ala Pro Glu Arg Val Gly Gly Arg Gly Arg Gly Arg Gly Thr Ala Ala
            20                  25                  30

Pro Arg Ala Ala Pro Ala Ala Arg Gly Ser Arg Pro Gly Pro Ala Gly
        35                  40                  45

Thr Met
    50


<210> SEQ ID NO 10
<211> LENGTH: 50
<212> TYPE: PRT
<213> ORGANISM: Artificial Sequence
<220> FEATURE:
<223> OTHER INFORMATION: MTI peptide from first CUG to AUG for Class II
      peptides with second nuclear localization site removed (delta 29-
      34) and bFGF peptide insert

<400> SEQUENCE: 10

Leu Gly Asp Arg Gly Arg Gly Arg Ala Leu Pro Gly Gly Arg Leu Gly
 1               5                   10                  15

Gly Arg Gly Arg Gly Arg Ala Pro Glu Arg Val Gly Gly Thr Ala Ala
            20                  25                  30

Pro Arg Ala Ala Pro Ala Ala Arg Gly Ser Arg Pro Gly Pro Ala Gly
        35                  40                  45

Thr Met
    50


<210> SEQ ID NO 11
<211> LENGTH: 44
<212> TYPE: PRT
<213> ORGANISM: Artificial Sequence
<220> FEATURE:
<223> OTHER INFORMATION: MTI peptide from first CUG to AUG for Class II
      peptides with both nuclear localization sites removed (delta 17-
      22/29-34) and bFGF peptide insert

<400> SEQUENCE: 11

Leu Gly Asp Arg Gly Arg Gly Arg Ala Leu Pro Gly Gly Arg Leu Gly
 1               5                   10                  15

Ala Pro Glu Arg Val Gly Gly Thr Ala Ala Pro Arg Ala Ala Pro Ala
            20                  25                  30

Ala Arg Gly Ser Arg Pro Gly Pro Ala Gly Thr Met
        35                  40


<210> SEQ ID NO 12
<211> LENGTH: 56
<212> TYPE: PRT
<213> ORGANISM: Artificial Sequence
<220> FEATURE:
<223> OTHER INFORMATION: MTI peptide from first CUG to AUG for Class II
      peptides with both nuclear localization sites mutated (R(18, 20,
      22, 30, 32, 34)H) and bFGF peptide insert

<400> SEQUENCE: 12

Leu Gly Asp Arg Gly Arg Gly Arg Ala Leu Pro Gly Gly Arg Leu Gly
 1               5                   10                  15

Gly His Gly His Gly His Ala Pro Glu Arg Val Gly Gly His Gly His
            20                  25                  30

Gly His Gly Thr Ala Ala Pro Arg Ala Ala Pro Ala Ala Arg Gly Ser
        35                  40                  45

Arg Pro Gly Pro Ala Gly Thr Met
    50                  55
```

<210> SEQ ID NO 13
<211> LENGTH: 11
<212> TYPE: PRT
<213> ORGANISM: Artificial Sequence
<220> FEATURE:
<223> OTHER INFORMATION: VSV-G epitope tag

<400> SEQUENCE: 13

Tyr Thr Asp Ile Glu Met Asn Arg Leu Gly Lys
1 5 10

<210> SEQ ID NO 14
<211> LENGTH: 14
<212> TYPE: PRT
<213> ORGANISM: Artificial Sequence
<220> FEATURE:
<223> OTHER INFORMATION: V5 epitope tag

<400> SEQUENCE: 14

Gly Lys Pro Ile Pro Asn Pro Leu Leu Gly Leu Asp Ser Thr
1 5 10

<210> SEQ ID NO 15
<211> LENGTH: 6
<212> TYPE: PRT
<213> ORGANISM: Artificial Sequence
<220> FEATURE:
<223> OTHER INFORMATION: AU5 epitope tag

<400> SEQUENCE: 15

Thr Asp Phe Tyr Leu Lys
1 5

<210> SEQ ID NO 16
<211> LENGTH: 1225
<212> TYPE: PRT
<213> ORGANISM: Artificial Sequence
<220> FEATURE:
<223> OTHER INFORMATION: Potential Her2neu MHC peptides

<400> SEQUENCE: 16

Met Lys Leu Arg Leu Pro Ala Ser Pro Glu Thr His Leu Asp Met Leu
1 5 10 15

Arg His Leu Tyr Gln Gly Cys Gln Val Val Gln Gly Asn Leu Glu Leu
20 25 30

Thr Tyr Leu Pro Thr Asn Ala Ser Leu Ser Phe Leu Gln Asp Ile Gln
35 40 45

Glu Val Gln Gly Tyr Val Leu Ile Ala His Asn Gln Val Arg Gln Val
50 55 60

Pro Leu Gln Arg Leu Arg Ile Val Arg Gly Thr Gln Leu Phe Glu Asp
65 70 75 80

Asn Tyr Ala Leu Ala Val Leu Asp Asn Gly Asp Pro Leu Asn Asn Thr
85 90 95

Thr Pro Val Thr Gly Ala Ser Pro Gly Gly Leu Arg Glu Leu Gln Leu
100 105 110

Arg Ser Leu Thr Glu Ile Leu Lys Gly Gly Val Leu Ile Gln Arg Asn
115 120 125

Pro Gln Leu Cys Tyr Gln Asp Thr Ile Leu Trp Lys Asp Ile Phe His
130 135 140

Lys Asn Asn Gln Leu Ala Leu Thr Leu Ile Asp Thr Asn Arg Ser Arg
145 150 155 160

-continued

```
Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575
```

```
Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
    610                 615                 620

Ile Ser Ala Val Val Gly Ile Leu Leu Val Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
```

```
        995                 1000                1005

Ala Gly Gly Met Val His His Arg His Arg Ser Ser Ser Thr Arg Ser
    1010                1015                1020

Gly Gly Gly Asp Leu Thr Leu Gly Leu Glu Pro Ser Glu Glu Glu Ala
1025                1030                1035                1040

Pro Arg Ser Pro Leu Ala Pro Ser Glu Gly Ala Gly Ser Asp Val Phe
                1045                1050                1055

Asp Gly Asp Leu Gly Met Gly Ala Ala Lys Gly Leu Gln Ser Leu Pro
            1060                1065                1070

Thr His Asp Pro Ser Pro Leu Gln Arg Tyr Ser Glu Asp Pro Thr Val
        1075                1080                1085

Pro Leu Pro Ser Glu Thr Asp Gly Tyr Val Ala Pro Leu Thr Cys Ser
    1090                1095                1100

Pro Gln Pro Glu Tyr Val Asn Gln Pro Asp Val Arg Pro Gln Pro Pro
1105                1110                1115                1120

Ser Pro Arg Glu Gly Pro Leu Pro Ala Ala Arg Pro Ala Gly Ala Thr
                1125                1130                1135

Leu Glu Arg Pro Lys Thr Leu Ser Pro Gly Lys Asn Gly Val Val Lys
            1140                1145                1150

Asp Val Phe Ala Phe Gly Gly Ala Val Glu Asn Pro Glu Tyr Leu Thr
        1155                1160                1165

Pro Gln Gly Gly Ala Ala Pro Gln Pro His Pro Pro Pro Ala Phe Ser
    1170                1175                1180

Pro Ala Phe Asp Asn Leu Tyr Tyr Trp Asp Gln Asp Pro Pro Glu Arg
1185                1190                1195                1200

Gly Ala Pro Pro Ser Thr Phe Lys Gly Thr Pro Thr Ala Glu Asn Pro
                1205                1210                1215

Glu Tyr Leu Gly Leu Asp Val Pro Val
            1220                1225
```

<210> SEQ ID NO 17
<211> LENGTH: 180
<212> TYPE: PRT
<213> ORGANISM: Artificial Sequence
<220> FEATURE:
<223> OTHER INFORMATION: Potential NY-ESO1 MHC peptide

<400> SEQUENCE: 17

```
Met Gln Ala Glu Gly Arg Gly Thr Gly Gly Ser Thr Gly Asp Ala Asp
 1               5                  10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
```

```
   130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180


<210> SEQ ID NO 18
<211> LENGTH: 19
<212> TYPE: PRT
<213> ORGANISM: Artificial Sequence
<220> FEATURE:
<223> OTHER INFORMATION: MTI peptide for Class II recognized by specific
      antibody

<400> SEQUENCE: 18

Thr Ala Ala Pro Arg Ala Ala Pro Ala Ala Arg Gly Ser Arg Pro Gly
 1               5                  10                  15

Pro Ala Gly


<210> SEQ ID NO 19
<211> LENGTH: 15
<212> TYPE: PRT
<213> ORGANISM: Artificial Sequence
<220> FEATURE:
<223> OTHER INFORMATION: Potential Her2neu MHC peptide

<400> SEQUENCE: 19

Asn Leu Glu Leu Thr Tyr Leu Pro Thr Asn Ala Ser Leu Ser Phe
 1               5                  10                  15


<210> SEQ ID NO 20
<211> LENGTH: 15
<212> TYPE: PRT
<213> ORGANISM: Artificial Sequence
<220> FEATURE:
<223> OTHER INFORMATION: Potential Her2neu MHC peptide

<400> SEQUENCE: 20

His Asn Gln Val Arg Gln Val Pro Leu Gln Arg Leu Arg Ile Val
 1               5                  10                  15


<210> SEQ ID NO 21
<211> LENGTH: 15
<212> TYPE: PRT
<213> ORGANISM: Artificial Sequence
<220> FEATURE:
<223> OTHER INFORMATION: Potential Her2neu MHC peptide

<400> SEQUENCE: 21

Leu Ser Val Phe Gln Asn Leu Gln Val Ile Arg Gly Arg Ile Leu
 1               5                  10                  15


<210> SEQ ID NO 22
<211> LENGTH: 18
<212> TYPE: PRT
<213> ORGANISM: Artificial Sequence
<220> FEATURE:
<223> OTHER INFORMATION: Potential Her2neu MHC peptide

<400> SEQUENCE: 22

Val Val Gly Ile Leu Leu Val Val Val Leu Gly Val Val Phe Gly Ile
 1               5                  10                  15
```

-continued

Leu Ile

<210> SEQ ID NO 23
<211> LENGTH: 15
<212> TYPE: PRT
<213> ORGANISM: Artificial Sequence
<220> FEATURE:
<223> OTHER INFORMATION: Potential Her2neu MHC peptide

<400> SEQUENCE: 23

Pro Ile Lys Trp Met Ala Leu Glu Ser Ile Leu Arg Arg Arg Phe
1 5 10 15

<210> SEQ ID NO 24
<211> LENGTH: 9
<212> TYPE: PRT
<213> ORGANISM: Artificial Sequence
<220> FEATURE:
<223> OTHER INFORMATION: Positive Peptides From HLA-A2 Mice Virion coat protein

<400> SEQUENCE: 24

Val Leu Ser Leu Glu Leu Pro Glu Val
1 5

<210> SEQ ID NO 25
<211> LENGTH: 9
<212> TYPE: PRT
<213> ORGANISM: Artificial Sequence
<220> FEATURE:
<223> OTHER INFORMATION: Positive Peptides From HLA-A2 Mice Hypothetical Protein

<400> SEQUENCE: 25

Lys Ile Asp Tyr Tyr Ile Pro Tyr Val
1 5

<210> SEQ ID NO 26
<211> LENGTH: 9
<212> TYPE: PRT
<213> ORGANISM: Artificial Sequence
<220> FEATURE:
<223> OTHER INFORMATION: Positive Peptides From HLA-A2 Mice Unknown Function

<400> SEQUENCE: 26

Ser Leu Ser Asn Leu Asp Phe Arg Leu
1 5

<210> SEQ ID NO 27
<211> LENGTH: 10
<212> TYPE: PRT
<213> ORGANISM: Artificial Sequence
<220> FEATURE:
<223> OTHER INFORMATION: Positive Peptides From HLA-A2 Mice Apoptosis Inhibitor

<400> SEQUENCE: 27

Ile Leu Met Asp Asn Lys Gly Leu Gly Val
1 5 10

<210> SEQ ID NO 28
<211> LENGTH: 9
<212> TYPE: PRT
<213> ORGANISM: Artificial Sequence
<220> FEATURE:
<223> OTHER INFORMATION: Positive Peptides From HLA-A2 Mice Viral Morphogenesis

<400> SEQUENCE: 28

Ile Leu Asp Asp Asn Leu Tyr Lys Val
1 5

<210> SEQ ID NO 29
<211> LENGTH: 10
<212> TYPE: PRT
<213> ORGANISM: Artificial Sequence
<220> FEATURE:
<223> OTHER INFORMATION: Positive Peptides From HLA-A2 Mice Poly(A) Polymerase

<400> SEQUENCE: 29

Lys Leu Leu Leu Gly Glu Leu Phe Phe Leu
1 5 10

<210> SEQ ID NO 30
<211> LENGTH: 9
<212> TYPE: PRT
<213> ORGANISM: Artificial Sequence
<220> FEATURE:
<223> OTHER INFORMATION: Positive Peptides From HLA-A2 Mice Unknown Function

<400> SEQUENCE: 30

Gly Leu Leu Asp Arg Leu Tyr Asp Leu
1 5

<210> SEQ ID NO 31
<211> LENGTH: 13
<212> TYPE: PRT
<213> ORGANISM: Artificial Sequence
<220> FEATURE:
<223> OTHER INFORMATION: HBV Core antigen

<400> SEQUENCE: 31

Thr Pro Pro Ala Tyr Arg Pro Pro Asn Ala Pro Ile Leu
1 5 10

<210> SEQ ID NO 32
<211> LENGTH: 15
<212> TYPE: PRT
<213> ORGANISM: Artificial Sequence
<220> FEATURE:
<223> OTHER INFORMATION: Peptide epitope

<400> SEQUENCE: 32

Asn Leu Glu Leu Thr Tyr Leu Pro Thr Asn Ala Ser Leu Ser Phe
1 5 10 15

<210> SEQ ID NO 33
<211> LENGTH: 15
<212> TYPE: PRT
<213> ORGANISM: Artificial Sequence
<220> FEATURE:
<223> OTHER INFORMATION: Peptide epitope

<400> SEQUENCE: 33

His Asn Gln Val Arg Gln Val Pro Leu Gln Arg Leu Arg Ile Val
1 5 10 15

<210> SEQ ID NO 34
<211> LENGTH: 15
<212> TYPE: PRT
<213> ORGANISM: Artificial Sequence
<220> FEATURE:

<223> OTHER INFORMATION: Peptide epitope

<400> SEQUENCE: 34

Leu Ser Val Phe Gln Asn Leu Gln Val Ile Arg Gly Arg Ile Leu
1 5 10 15

<210> SEQ ID NO 35
<211> LENGTH: 15
<212> TYPE: PRT
<213> ORGANISM: Artificial Sequence
<220> FEATURE:
<223> OTHER INFORMATION: Peptide epitope

<400> SEQUENCE: 35

Pro Ile Lys Trp Met Ala Leu Glu Ser Ile Leu Arg Arg Arg Phe
1 5 10 15

<210> SEQ ID NO 36
<211> LENGTH: 10
<212> TYPE: PRT
<213> ORGANISM: Artificial Sequence
<220> FEATURE:
<223> OTHER INFORMATION: Exemplary Peptide epitope

<400> SEQUENCE: 36

Ser Leu Ala Phe Leu Pro Glu Ser Phe Asp
1 5 10

<210> SEQ ID NO 37
<211> LENGTH: 17
<212> TYPE: PRT
<213> ORGANISM: Artificial Sequence
<220> FEATURE:
<223> OTHER INFORMATION: HLA Class II folate receptor alpha antigenic T-cell peptide

<400> SEQUENCE: 37

Arg Thr Glu Leu Leu Asn Val Cys Met Asn Ala Lys His His Lys Glu
1 5 10 15

Lys

<210> SEQ ID NO 38
<211> LENGTH: 15
<212> TYPE: PRT
<213> ORGANISM: Artificial Sequence
<220> FEATURE:
<223> OTHER INFORMATION: HLA Class II folate receptor alpha antigenic T-cell peptide

<400> SEQUENCE: 38

Gln Cys Arg Pro Trp Arg Lys Asn Ala Cys Cys Ser Thr Asn Thr
1 5 10 15

<210> SEQ ID NO 39
<211> LENGTH: 18
<212> TYPE: PRT
<213> ORGANISM: Artificial Sequence
<220> FEATURE:
<223> OTHER INFORMATION: HLA Class II folate receptor alpha antigenic T-cell peptide

<400> SEQUENCE: 39

Lys Asp Val Ser Tyr Leu Tyr Arg Phe Asn Trp Asn His Cys Gly Glu
1 5 10 15

Met Ala

<210> SEQ ID NO 40
<211> LENGTH: 17
<212> TYPE: PRT
<213> ORGANISM: Artificial Sequence
<220> FEATURE:
<223> OTHER INFORMATION: HLA Class II folate receptor alpha antigenic T-cell peptide

<400> SEQUENCE: 40

Leu Gly Pro Trp Ile Gln Gln Val Asp Gln Ser Trp Arg Lys Glu Arg
1 5 10 15

Val

<210> SEQ ID NO 41
<211> LENGTH: 18
<212> TYPE: PRT
<213> ORGANISM: Artificial Sequence
<220> FEATURE:
<223> OTHER INFORMATION: HLA Class II folate receptor alpha antigenic T-cell peptide

<400> SEQUENCE: 41

Pro Trp Ala Ala Trp Pro Pro Leu Leu Ser Leu Ala Leu Met Leu Leu
1 5 10 15

Trp Leu

<210> SEQ ID NO 42
<211> LENGTH: 16
<212> TYPE: PRT
<213> ORGANISM: Artificial Sequence
<220> FEATURE:
<223> OTHER INFORMATION: VSVG signal sequence

<400> SEQUENCE: 42

Lys Cys Leu Leu Tyr Leu Ala Phe Leu Phe Ile Gly Val Asn Cys Lys
1 5 10 15

<210> SEQ ID NO 43
<211> LENGTH: 48
<212> TYPE: DNA
<213> ORGANISM: Artificial Sequence
<220> FEATURE:
<223> OTHER INFORMATION: VSVG signal sequence

<400> SEQUENCE: 43
aagtgcctgc tgtacctggc cttcctgttc atcggcgtga actgcaag 48

<210> SEQ ID NO 44
<211> LENGTH: 12
<212> TYPE: PRT
<213> ORGANISM: Artificial Sequence
<220> FEATURE:
<223> OTHER INFORMATION: Dendritic Cell Targeting Sequence

<400> SEQUENCE: 44

Phe Tyr Pro Ser Tyr His Ser Thr Pro Gln Arg Pro
1 5 10

<210> SEQ ID NO 45
<211> LENGTH: 36
<212> TYPE: DNA
<213> ORGANISM: Artificial Sequence
<220> FEATURE:
<223> OTHER INFORMATION: Dendritic Cell Targeting Sequence

<400> SEQUENCE: 45
ttctacccca gctaccacag caccccccag agaccc 36

<210> SEQ ID NO 46
<211> LENGTH: 174
<212> TYPE: PRT
<213> ORGANISM: Artificial Sequence
<220> FEATURE:
<223> OTHER INFORMATION: VSVG secretion signal

<400> SEQUENCE: 46

Phe Thr Ile Leu Phe Pro His Asn Gln Lys Gly Asn Trp Lys Asn Val
1 5 10 15

Pro Ser Asn Tyr His Tyr Cys Pro Ser Ser Ser Asp Leu Asn Trp His
20 25 30

Asn Asp Leu Ile Gly Thr Ala Ile Gln Val Lys Met Pro Lys Ser His
35 40 45

Lys Ala Ile Gln Ala Asp Gly Trp Met Cys His Ala Ser Lys Trp Val
50 55 60

Thr Thr Cys Asp Phe Arg Trp Tyr Gly Pro Lys Tyr Ile Thr Gln Ser
65 70 75 80

Ile Arg Ser Phe Thr Pro Ser Val Glu Gln Cys Lys Glu Ser Ile Glu
85 90 95

Gln Thr Lys Gln Gly Thr Trp Leu Asn Pro Gly Phe Pro Pro Gln Ser
100 105 110

Cys Gly Tyr Ala Thr Val Thr Asp Ala Glu Ala Val Ile Val Gln Val
115 120 125

Thr Pro His His Val Leu Val Asp Glu Tyr Thr Gly Glu Trp Val Asp
130 135 140

Ser Gln Phe Ile Asn Gly Lys Cys Ser Asn Tyr Ile Cys Pro Thr Val
145 150 155 160

His Asn Ser Thr Thr Trp His Ser Asp Tyr Lys Val Lys Gly
165 170

<210> SEQ ID NO 47
<211> LENGTH: 522
<212> TYPE: DNA
<213> ORGANISM: Artificial Sequence
<220> FEATURE:
<223> OTHER INFORMATION: VSVG secretion signal

<400> SEQUENCE: 47
ttcaccatac tttttccaca caaccaaaaa ggaaactgga aaaatgttcc ttctaattac 60
cattattgcc cgtcaagctc agatttaaat tggcataatg acttaatagg cacagccata 120
caagtcaaaa tgcccaagag tcacaaggct attcaagcag acggttggat gtgtcatgct 180
tccaaatggg tcactacttg tgatttccgc tggtatggac cgaagtatat aacacagtcc 240
atccgatcct tcactccatc tgtagaacaa tgcaaggaaa gcattgaaca aacgaaacaa 300
ggaacttggc tgaatccagg cttccctcct caaagttgtg gatatgcaac tgtgacggat 360
gccgaagcag tgattgtcca ggtgactcct caccatgtgc tggttgatga atacacagga 420
gaatgggttg attcacagtt catcaacgga aaatgcagca attacatatg ccccactgtc 480
cataactcta caacctggca ttctgactat aaggtcaaag gg 522

<210> SEQ ID NO 48
<211> LENGTH: 456
<212> TYPE: DNA
<213> ORGANISM: Artificial Sequence
<220> FEATURE:
<223> OTHER INFORMATION: VSVG alternate trafficking signal

<400> SEQUENCE: 48

```
cttccaatct ctccagtgga tctcagctat cttgctccta aaaacccagg aaccggtcct     60

gctttcacca taatcaatgg taccctaaaa tactttgaga ccagatacat cagagtcgat    120

attgctgctc caatcctctc aagaatggtc ggaatgatca gtggaactac cacagaaagg    180

gaactgtggg atgactgggc accatatgaa gacgtggaaa ttggacccaa tggagttctg    240

aggaccagtt caggatataa gtttccttta tacatgattg gacatggtat gttggactcc    300

gatcttcatc ttagctcaaa ggctcaggtg ttcgaacatc ctcacattca agacgctgct    360

tcgcaacttc ctgatgatga gagtttattt tttggtgata ctgggctatc caaaaatcca    420

atcgagcttg tagaaggttg gttcagtagt tggaaa                              456
```

<210> SEQ ID NO 49
<211> LENGTH: 145
<212> TYPE: PRT
<213> ORGANISM: Artificial Sequence
<220> FEATURE:
<223> OTHER INFORMATION: Folate receptor alpha PAA - Class II with
      embedded Class I two amino acid extensions

<400> SEQUENCE: 49

```
Trp Ala Arg Thr Glu Leu Leu Asn Val Cys Met Asn Ala Lys His His
 1               5                  10                  15

Lys Glu Lys Pro Gly Gly Gly Gly Gly Ser Gly Gly Gly Gly Ser His
            20                  25                  30

Glu Gln Cys Arg Pro Trp Arg Lys Asn Ala Cys Cys Ser Thr Asn Thr
        35                  40                  45

Ser Gln Gly Gly Gly Gly Ser Gly Gly Gly Gly Ser Ala His Lys Asp
    50                  55                  60

Val Ser Tyr Leu Tyr Arg Phe Asn Trp Asn His Cys Gly Glu Met Ala
65                  70                  75                  80

Pro Ala Gly Gly Gly Gly Ser Gly Gly Gly Gly Ser Pro Asn Leu Gly
                85                  90                  95

Pro Trp Ile Gln Gln Val Asp Gln Ser Trp Arg Lys Glu Arg Val Leu
            100                 105                 110

Asn Gly Gly Gly Gly Ser Gly Gly Gly Gly Ser Ala Gly Pro Trp Ala
        115                 120                 125

Ala Trp Pro Phe Leu Leu Ser Leu Ala Leu Met Leu Leu Trp Leu Leu
    130                 135                 140

Ser
145
```

<210> SEQ ID NO 50
<211> LENGTH: 447
<212> TYPE: DNA
<213> ORGANISM: Artificial Sequence
<220> FEATURE:
<223> OTHER INFORMATION: Folate receptor alpha PAA with XbaI sites

<400> SEQUENCE: 50

```
tctagatggg ccagaaccga gctgctgaac gtgtgcatga acgccaagca ccacaaggag     60

aagcccggcg gcggcggcgg cagcggcggc ggcggcagcc acgagcagtg cagaccctgg    120

agaaagaacg cctgctgcag caccaacacc agccagggcg gcggcggcag cggcggcggc    180

ggcagcgccc acaaggacgt gagctacctg tacagattca actggaacca ctgcggcgag    240
```

```
atggccccccg ccggcggcgg cggcagcggc ggcggcggca gccccaacct gggcccctgg    300

atccagcagg tggaccagag ctggagaaag gagagagtgc tgaacggcgg cggcggcagc    360

ggcggcggcg gcagcgccgg cccctgggcc gcctggccct tcctgctgag cctggccctg    420

atgctgctgt ggctgctgag ctctaga                                         447
```

<210> SEQ ID NO 51
<211> LENGTH: 435
<212> TYPE: DNA
<213> ORGANISM: Artificial Sequence
<220> FEATURE:
<223> OTHER INFORMATION: Folate receptor alpha PAA with two amino acid extensions

<400> SEQUENCE: 51

```
tgggccagaa ccgagctgct gaacgtgtgc atgaacgcca agcaccacaa ggagaagccc     60

ggcggcggcg gcggcagcgg cggcggcggc agccacgagc agtgcagacc ctggagaaag    120

aacgcctgct gcagcaccaa caccagccag ggcggcggcg gcagcggcgg cggcggcagc    180

gcccacaagg acgtgagcta cctgtacaga ttcaactgga accactgcgg cgagatggcc    240

cccgccggcg gcggcggcag cggcggcggc ggcagcccca acctgggccc ctggatccag    300

caggtggacc agagctggag aaaggagaga gtgctgaacg gcggcggcgg cagcggcggc    360

ggcggcagcg ccggcccctg ggccgcctgg cccttcctgc tgagcctggc cctgatgctg    420

ctgtggctgc tgagc                                                      435
```

<210> SEQ ID NO 52
<211> LENGTH: 1474
<212> TYPE: DNA
<213> ORGANISM: Artificial Sequence
<220> FEATURE:
<223> OTHER INFORMATION: MTI-PAA Folate Receptor Alpha Class II with VSVG secretion trafficking

<400> SEQUENCE: 52

```
gggtggagat gtagaagatg tgacgccgcg gcccggcggg tgccagatta gcggacgcgg     60

tgcccgcggt tgcaacggga tcccgggcgc tgcagcttgg gaggcggctc tccccaggcg    120

gcgtccgcgg agacacccat ccgtgaaccc caggtcccgg gccgccggct cgccgcgcac    180

caggggccgg cggacagaag agcggccgag cggctcgagg ctgggggacc gcgggcgcgg    240

ccgcgcgctg ccgggcggga ggctgggggg ccggggccgg ggccgtgccc cggagcgggt    300

cggaggccgg ggccggggcc gggggacggc ggctccccgc gcggctccag cggctcgggg    360

atcccggccg ggccccgcag ggaccaagtg cctgctgtac ctggccttcc tgttcatcgg    420

cgtgaactgc aagttctacc ccagctacca cagcaccccc cagagaccct tcaccatact    480

ttttccacac aaccaaaaag gaaactggaa aaatgttcct tctaattacc attattgccc    540

gtcaagctca gatttaaatt ggcataatga cttaataggc acagccatac aagtcaaaat    600

gcccaagagt cacaaggcta ttcaagcaga cggttggatg tgtcatgctt ccaaatgggt    660

cactacttgt gatttccgct ggtatggacc gaagtatata acacagtcca tccgatcctt    720

cactccatct gtagaacaat gcaaggaaag cattgaacaa acgaaacaag gaacttggct    780

gaatccaggc ttccctcctc aaagttgtgg atatgcaact gtgacggatg ccgaagcagt    840

gattgtccag gtgactcctc accatgtgct ggttgatgaa tacacaggag aatgggttga    900

ttcacagttc atcaacggaa aatgcagcaa ttacatatgc cccactgtcc ataactctac    960
```

```
aacctggcat tctgactata aggtcaaagg gtctagatgg gccagaaccg agctgctgaa   1020

cgtgtgcatg aacgccaagc accacaagga gaagcccggc ggcggcggcg gcagcggcgg   1080

cggcggcagc cacgagcagt gcagaccctg gagaaagaac gcctgctgca gcaccaacac   1140

cagccagggc ggcggcggca gcggcggcgg cggcagcgcc cacaaggacg tgagctacct   1200

gtacagattc aactggaacc actgcggcga gatggccccc gccggcggcg gcggcagcgg   1260

cggcggcggc agccccaacc tgggcccctg gatccagcag gtggaccaga gctggagaaa   1320

ggagagagtg ctgaacggcg gcggcggcag cggcggcggc ggcagcgccg gcccctgggc   1380

cgcctggccc ttcctgctga gcctggccct gatgctgctg tggctgctga gctctagata   1440

caccgacatc gagatgaaca gactgggcaa gtaa                               1474
```

```
<210> SEQ ID NO 53
<211> LENGTH: 417
<212> TYPE: PRT
<213> ORGANISM: Artificial Sequence
<220> FEATURE:
<223> OTHER INFORMATION: MTI-PAA Folate Receptor Alpha Class II with
      VSVG secretion trafficking

<400> SEQUENCE: 53

Met Gly Asp Arg Gly Arg Gly Arg Ala Leu Pro Gly Gly Arg Leu Gly
 1               5                  10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Lys Cys Leu Leu Tyr Leu Ala Phe Leu
    50                  55                  60

Phe Ile Gly Val Asn Cys Lys Phe Tyr Pro Ser Tyr His Ser Thr Pro
65                  70                  75                  80

Gln Arg Pro Phe Thr Ile Leu Phe Pro His Asn Gln Lys Gly Asn Trp
                85                  90                  95

Lys Asn Val Pro Ser Asn Tyr His Tyr Cys Pro Ser Ser Ser Asp Leu
            100                 105                 110

Asn Trp His Asn Asp Leu Ile Gly Thr Ala Ile Gln Val Lys Met Pro
        115                 120                 125

Lys Ser His Lys Ala Ile Gln Ala Asp Gly Trp Met Cys His Ala Ser
    130                 135                 140

Lys Trp Val Thr Thr Cys Asp Phe Arg Trp Tyr Gly Pro Lys Tyr Ile
145                 150                 155                 160

Thr Gln Ser Ile Arg Ser Phe Thr Pro Ser Val Glu Gln Cys Lys Glu
                165                 170                 175

Ser Ile Glu Gln Thr Lys Gln Gly Thr Trp Leu Asn Pro Gly Phe Pro
            180                 185                 190

Pro Gln Ser Cys Gly Tyr Ala Thr Val Thr Asp Ala Glu Ala Val Ile
        195                 200                 205

Val Gln Val Thr Pro His His Val Leu Val Asp Glu Tyr Thr Gly Glu
    210                 215                 220

Trp Val Asp Ser Gln Phe Ile Asn Gly Lys Cys Ser Asn Tyr Ile Cys
225                 230                 235                 240

Pro Thr Val His Asn Ser Thr Thr Trp His Ser Asp Tyr Lys Val Lys
                245                 250                 255

Gly Ser Arg Trp Ala Arg Thr Glu Leu Leu Asn Val Cys Met Asn Ala
            260                 265                 270
```

```
Lys His His Lys Glu Lys Pro Gly Gly Gly Gly Gly Ser Gly Gly Gly
        275                 280                 285

Gly Ser His Glu Gln Cys Arg Pro Trp Arg Lys Asn Ala Cys Cys Ser
    290                 295                 300

Thr Asn Thr Ser Gln Gly Gly Gly Gly Ser Gly Gly Gly Gly Ser Ala
305                 310                 315                 320

His Lys Asp Val Ser Tyr Leu Tyr Arg Phe Asn Trp Asn His Cys Gly
                325                 330                 335

Glu Met Ala Pro Ala Gly Gly Gly Gly Ser Gly Gly Gly Gly Ser Pro
            340                 345                 350

Asn Leu Gly Pro Trp Ile Gln Gln Val Asp Gln Ser Trp Arg Lys Glu
        355                 360                 365

Arg Val Leu Asn Gly Gly Gly Gly Ser Gly Gly Gly Gly Ser Ala Gly
    370                 375                 380

Pro Trp Ala Ala Trp Pro Phe Leu Leu Ser Leu Ala Leu Met Leu Leu
385                 390                 395                 400

Trp Leu Leu Ser Ser Arg Tyr Thr Asp Ile Glu Met Asn Arg Leu Gly
                405                 410                 415

Lys


<210> SEQ ID NO 54
<211> LENGTH: 408
<212> TYPE: PRT
<213> ORGANISM: Artificial Sequence
<220> FEATURE:
<223> OTHER INFORMATION: MTI-PAA Folate Receptor Alpha Class II with
      VSVG secretion trafficking

<400> SEQUENCE: 54

Leu Pro Gly Gly Arg Leu Gly Gly Arg Gly Arg Gly Arg Ala Pro Glu
 1               5                  10                  15

Arg Val Gly Gly Arg Gly Arg Gly Arg Gly Thr Ala Ala Pro Arg Ala
            20                  25                  30

Ala Pro Ala Ala Arg Gly Ser Arg Pro Gly Pro Ala Gly Thr Lys Cys
        35                  40                  45

Leu Leu Tyr Leu Ala Phe Leu Phe Ile Gly Val Asn Cys Lys Phe Tyr
    50                  55                  60

Pro Ser Tyr His Ser Thr Pro Gln Arg Pro Phe Thr Ile Leu Phe Pro
65                  70                  75                  80

His Asn Gln Lys Gly Asn Trp Lys Asn Val Pro Ser Asn Tyr His Tyr
                85                  90                  95

Cys Pro Ser Ser Ser Asp Leu Asn Trp His Asn Asp Leu Ile Gly Thr
            100                 105                 110

Ala Ile Gln Val Lys Met Pro Lys Ser His Lys Ala Ile Gln Ala Asp
        115                 120                 125

Gly Trp Met Cys His Ala Ser Lys Trp Val Thr Thr Cys Asp Phe Arg
    130                 135                 140

Trp Tyr Gly Pro Lys Tyr Ile Thr Gln Ser Ile Arg Ser Phe Thr Pro
145                 150                 155                 160

Ser Val Glu Gln Cys Lys Glu Ser Ile Glu Gln Thr Lys Gln Gly Thr
                165                 170                 175

Trp Leu Asn Pro Gly Phe Pro Pro Gln Ser Cys Gly Tyr Ala Thr Val
            180                 185                 190

Thr Asp Ala Glu Ala Val Ile Val Gln Val Thr Pro His His Val Leu
        195                 200                 205
```

Val Asp Glu Tyr Thr Gly Glu Trp Val Asp Ser Gln Phe Ile Asn Gly
210 215 220

Lys Cys Ser Asn Tyr Ile Cys Pro Thr Val His Asn Ser Thr Thr Trp
225 230 235 240

His Ser Asp Tyr Lys Val Lys Gly Ser Arg Trp Ala Arg Thr Glu Leu
245 250 255

Leu Asn Val Cys Met Asn Ala Lys His His Lys Glu Lys Pro Gly Gly
260 265 270

Gly Gly Gly Ser Gly Gly Gly Gly Ser His Glu Gln Cys Arg Pro Trp
275 280 285

Arg Lys Asn Ala Cys Cys Ser Thr Asn Thr Ser Gln Gly Gly Gly Gly
290 295 300

Ser Gly Gly Gly Gly Ser Ala His Lys Asp Val Ser Tyr Leu Tyr Arg
305 310 315 320

Phe Asn Trp Asn His Cys Gly Glu Met Ala Pro Ala Gly Gly Gly Gly
325 330 335

Ser Gly Gly Gly Gly Ser Pro Asn Leu Gly Pro Trp Ile Gln Gln Val
340 345 350

Asp Gln Ser Trp Arg Lys Glu Arg Val Leu Asn Gly Gly Gly Gly Ser
355 360 365

Gly Gly Gly Gly Ser Ala Gly Pro Trp Ala Ala Trp Pro Phe Leu Leu
370 375 380

Ser Leu Ala Leu Met Leu Leu Trp Leu Leu Ser Ser Arg Tyr Thr Asp
385 390 395 400

Ile Glu Met Asn Arg Leu Gly Lys
405

<210> SEQ ID NO 55
<211> LENGTH: 403
<212> TYPE: PRT
<213> ORGANISM: Artificial Sequence
<220> FEATURE:
<223> OTHER INFORMATION: MTI-PAA Folate Receptor Alpha Class II with
VSVG secretion trafficking

<400> SEQUENCE: 55

Leu Gly Gly Arg Gly Arg Gly Arg Ala Pro Glu Arg Val Gly Gly Arg
1 5 10 15

Gly Arg Gly Arg Gly Thr Ala Ala Pro Arg Ala Ala Pro Ala Ala Arg
20 25 30

Gly Ser Arg Pro Gly Pro Ala Gly Thr Lys Cys Leu Leu Tyr Leu Ala
35 40 45

Phe Leu Phe Ile Gly Val Asn Cys Lys Phe Tyr Pro Ser Tyr His Ser
50 55 60

Thr Pro Gln Arg Pro Phe Thr Ile Leu Phe Pro His Asn Gln Lys Gly
65 70 75 80

Asn Trp Lys Asn Val Pro Ser Asn Tyr His Tyr Cys Pro Ser Ser Ser
85 90 95

Asp Leu Asn Trp His Asn Asp Leu Ile Gly Thr Ala Ile Gln Val Lys
100 105 110

Met Pro Lys Ser His Lys Ala Ile Gln Ala Asp Gly Trp Met Cys His
115 120 125

Ala Ser Lys Trp Val Thr Thr Cys Asp Phe Arg Trp Tyr Gly Pro Lys
130 135 140

Tyr Ile Thr Gln Ser Ile Arg Ser Phe Thr Pro Ser Val Glu Gln Cys

```
145                 150                 155                 160

Lys Glu Ser Ile Glu Gln Thr Lys Gln Gly Thr Trp Leu Asn Pro Gly
                165                 170                 175

Phe Pro Pro Gln Ser Cys Gly Tyr Ala Thr Val Thr Asp Ala Glu Ala
            180                 185                 190

Val Ile Val Gln Val Thr Pro His His Val Leu Val Asp Glu Tyr Thr
        195                 200                 205

Gly Glu Trp Val Asp Ser Gln Phe Ile Asn Gly Lys Cys Ser Asn Tyr
    210                 215                 220

Ile Cys Pro Thr Val His Asn Ser Thr Thr Trp His Ser Asp Tyr Lys
225                 230                 235                 240

Val Lys Gly Ser Arg Trp Ala Arg Thr Glu Leu Leu Asn Val Cys Met
                245                 250                 255

Asn Ala Lys His His Lys Glu Lys Pro Gly Gly Gly Gly Gly Ser Gly
            260                 265                 270

Gly Gly Gly Ser His Glu Gln Cys Arg Pro Trp Arg Lys Asn Ala Cys
        275                 280                 285

Cys Ser Thr Asn Thr Ser Gln Gly Gly Gly Gly Ser Gly Gly Gly Gly
    290                 295                 300

Ser Ala His Lys Asp Val Ser Tyr Leu Tyr Arg Phe Asn Trp Asn His
305                 310                 315                 320

Cys Gly Glu Met Ala Pro Ala Gly Gly Gly Gly Ser Gly Gly Gly Gly
                325                 330                 335

Ser Pro Asn Leu Gly Pro Trp Ile Gln Gln Val Asp Gln Ser Trp Arg
            340                 345                 350

Lys Glu Arg Val Leu Asn Gly Gly Gly Gly Ser Gly Gly Gly Gly Ser
        355                 360                 365

Ala Gly Pro Trp Ala Ala Trp Pro Phe Leu Leu Ser Leu Ala Leu Met
    370                 375                 380

Leu Leu Trp Leu Leu Ser Ser Arg Tyr Thr Asp Ile Glu Met Asn Arg
385                 390                 395                 400

Leu Gly Lys


<210> SEQ ID NO 56
<211> LENGTH: 201
<212> TYPE: PRT
<213> ORGANISM: Artificial Sequence
<220> FEATURE:
<223> OTHER INFORMATION: VSVG membrane localization signal

<400> SEQUENCE: 56

Leu Pro Ile Ser Pro Val Asp Leu Ser Tyr Leu Ala Pro Lys Asn Pro
 1               5                  10                  15

Gly Thr Gly Pro Val Phe Thr Ile Ile Asn Gly Thr Leu Lys Tyr Phe
            20                  25                  30

Glu Thr Arg Tyr Ile Arg Val Asp Ile Ala Ala Pro Ile Leu Ser Arg
        35                  40                  45

Met Val Gly Met Ile Ser Gly Thr Thr Thr Glu Arg Glu Leu Trp Asp
    50                  55                  60

Asp Trp Ala Pro Tyr Glu Asp Val Glu Ile Gly Pro Asn Gly Val Leu
65                  70                  75                  80

Arg Thr Ser Leu Gly Tyr Lys Phe Pro Leu Tyr Met Ile Gly His Gly
                85                  90                  95

Met Leu Asp Ser Asp Leu His Leu Ser Ser Lys Ala Gln Val Phe Glu
            100                 105                 110
```

```
His Pro His Ile Gln Asp Ala Ala Ser Gln Leu Pro Asp Asp Glu Thr
        115                 120                 125

Leu Phe Phe Gly Asp Thr Gly Leu Ser Lys Asn Pro Ile Glu Phe Val
    130                 135                 140

Glu Gly Trp Phe Ser Ser Trp Lys Ser Ser Ile Ala Ser Phe Phe Phe
145                 150                 155                 160

Ile Ile Gly Leu Ile Ile Gly Leu Phe Leu Val Leu Arg Val Gly Ile
                165                 170                 175

Tyr Leu Cys Ile Lys Leu Lys His Thr Lys Lys Arg Gln Ile Tyr Thr
            180                 185                 190

Asp Ile Glu Met Asn Arg Leu Gly Lys
        195                 200
```

```
<210> SEQ ID NO 57
<211> LENGTH: 606
<212> TYPE: DNA
<213> ORGANISM: Artificial Sequence
<220> FEATURE:
<223> OTHER INFORMATION: VSVG membrane localization signal

<400> SEQUENCE: 57

cttcccatct ctccagtgga tctcagctat cttgctccta aaaacccagg aaccggtcct     60

gtctttacca taatcaatgg taccctaaaa tactttgaga ccagatacat cagagtcgat    120

attgctgctc caatcctctc aagaatggtc ggaatgatca gtggaactac cacagaaagg    180

gaactgtggg atgactgggc tccatatgaa gacgtggaaa ttggacccaa tggagttctg    240

aggaccagtt taggatataa gtttccttta tatatgattg gacatggtat gttggactcc    300

gatcttcatc ttagctcaaa ggctcaggtg tttgaacatc ctcacattca agacgctgct    360

tcgcagcttc ctgatgatga gactttattt tttggtgata ctgggctatc caaaaatcca    420

atcgagtttg tagaaggttg gttcagtagt tggaagagct ctattgcctc tttttcttt    480

atcatagggt taatcattgg actattcttg gttctccgag ttggtattta tctttgcatt    540

aaattaaagc acaccaagaa aagacagatt tatacagaca tagagatgaa ccgacttgga    600

aagtaa                                                               606
```

```
<210> SEQ ID NO 58
<211> LENGTH: 2067
<212> TYPE: DNA
<213> ORGANISM: Artificial Sequence
<220> FEATURE:
<223> OTHER INFORMATION: MTI-PAA Folate Receptor Alpha Class II with
      VSVG membrane localization

<400> SEQUENCE: 58

atcgaggtta acgtttaaac gggtggagat gtagaagatg tgacgccgcg gcccggcggg     60

tgccagatta gcggacgcgg tgcccgcggt tgcaacggga tcccgggcgc tgcagcttgg    120

gaggcggctc tccccaggcg gcgtccgcgg agacacccat ccgtgaaccc caggtcccgg    180

gccgccggct cgccgcgcac caggggccgg cggacagaag agcggccgag cggctcgagg    240

ctgggggacc gcgggcgcgg ccgcgcgctg ccgggcggga ggctgggggg ccggggccgg    300

ggccgtgccc cggagcgggt cggaggccgg ggccggggcc gggggacggc ggctccccgc    360

gcggctccag cggctcgggg atcccggccg ggccccgcag ggaccaagtg ccttttgtac    420

ttagcctttt tattcattgg ggtgaattgc aagttttacc cttcttatca ctctacccca    480

cagcggccta agttcaccat actttttcca cacaaccaaa aaggaaactg gaaaaatgtt    540
```

-continued

```
ccttctaatt accattattg cccgtcaagc tcagatttaa attggcataa tgacttaata    600

ggcacagcca tacaagtcaa aatgcccaag agtcacaagg ctattcaagc agacggttgg    660

atgtgtcatg cttccaaatg ggtcactact tgtgatttcc gctggtatgg accgaagtat    720

ataacacagt ccatccgatc cttcactcca tctgtagaac aatgcaagga aagcattgaa    780

caaacgaaac aaggaacttg gctgaatcca ggcttccctc ctcaaagttg tggatatgca    840

actgtgacgg atgccgaagc agtgattgtc caggtgactc ctcaccatgt gctggttgat    900

gaatacacag gagaatgggt tgattcacag ttcatcaacg gaaaatgcag caattacata    960

tgccccactg tccataactc tacaacctgg cattctgact ataaggtcaa agggtctaga   1020

tgggccagaa ccgagctgct gaacgtgtgc atgaacgcca agcaccacaa ggagaagccc   1080

ggcggcggcg gcggcagcgg cggcggcggc agccacgagc agtgcagacc ctggagaaag   1140

aacgcctgct gcagcaccaa caccagccag ggcggcggcg gcagcggcgg cggcggcagc   1200

gcccacaagg acgtgagcta cctgtacaga ttcaactgga accactgcgg cgagatggcc   1260

cccgccggcg gcggcggcag cggcggcggc ggcagcccca acctgggccc ctggatccag   1320

caggtggacc agagctggag aaaggagaga gtgctgaacg gcggcggcgg cagcggcggc   1380

ggcggcagcg ccggcccctg ggccgcctgg cccttcctgc tgagcctggc cctgatgctg   1440

ctgtggctgc tgagctctag acttcccatc tctccagtgg atctcagcta tcttgctcct   1500

aaaaacccag gaaccggtcc tgtctttacc ataatcaatg gtaccctaaa atactttgag   1560

accagataca tcagagtcga tattgctgct ccaatcctct caagaatggt cggaatgatc   1620

agtggaacta ccacagaaag ggaactgtgg gatgactggg ctccatatga agacgtggaa   1680

attggaccca atggagttct gaggaccagt ttaggatata agtttccttt atatatgatt   1740

ggacatggta tgttggactc cgatcttcat cttagctcaa aggctcaggt gtttgaacat   1800

cctcacattc aagacgctgc ttcgcagctt cctgatgatg agactttatt ttttggtgat   1860

actgggctat ccaaaaatcc aatcgagttt gtagaaggtt ggttcagtag ttggaagagc   1920

tctattgcct ctttttcttt tatcataggg ttaatcattg gactattctt ggttctccga   1980

gttggtattt atctttgcat taaattaaag cacaccaaga aaagacagat ttatacagac   2040

atagagatga accgacttgg aaagtaa                                       2067
```

```
<210> SEQ ID NO 59
<211> LENGTH: 608
<212> TYPE: PRT
<213> ORGANISM: Artificial Sequence
<220> FEATURE:
<223> OTHER INFORMATION: MTI-PAA Folate Receptor Alpha Class II with
      VSVG membrane localization and secretion trafficking

<400> SEQUENCE: 59

Met Gly Asp Arg Gly Arg Gly Arg Ala Leu Pro Gly Gly Arg Leu Gly
1               5                   10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Lys Cys Leu Leu Tyr Leu Ala Phe Leu
    50                  55                  60

Phe Ile Gly Val Asn Cys Lys Phe Tyr Pro Ser Tyr His Ser Thr Pro
65                  70                  75                  80
```

-continued

```
Gln Arg Pro Lys Phe Thr Ile Leu Phe Pro His Asn Gln Lys Gly Asn
                85                  90                  95

Trp Lys Asn Val Pro Ser Asn Tyr His Tyr Cys Pro Ser Ser Ser Asp
            100                 105                 110

Leu Asn Trp His Asn Asp Leu Ile Gly Thr Ala Ile Gln Val Lys Met
        115                 120                 125

Pro Lys Ser His Lys Ala Ile Gln Ala Asp Gly Trp Met Cys His Ala
    130                 135                 140

Ser Lys Trp Val Thr Thr Cys Asp Phe Arg Trp Tyr Gly Pro Lys Tyr
145                 150                 155                 160

Ile Thr Gln Ser Ile Arg Ser Phe Thr Pro Ser Val Glu Gln Cys Lys
                165                 170                 175

Glu Ser Ile Glu Gln Thr Lys Gln Gly Thr Trp Leu Asn Pro Gly Phe
            180                 185                 190

Pro Pro Gln Ser Cys Gly Tyr Ala Thr Val Thr Asp Ala Glu Ala Val
        195                 200                 205

Ile Val Gln Val Thr Pro His His Val Leu Val Asp Glu Tyr Thr Gly
    210                 215                 220

Glu Trp Val Asp Ser Gln Phe Ile Asn Gly Lys Cys Ser Asn Tyr Ile
225                 230                 235                 240

Cys Pro Thr Val His Asn Ser Thr Thr Trp His Ser Asp Tyr Lys Val
                245                 250                 255

Lys Gly Ser Arg Trp Ala Arg Thr Glu Leu Leu Asn Val Cys Met Asn
            260                 265                 270

Ala Lys His His Lys Glu Lys Pro Gly Gly Gly Gly Gly Ser Gly Gly
        275                 280                 285

Gly Gly Ser His Glu Gln Cys Arg Pro Trp Arg Lys Asn Ala Cys Cys
    290                 295                 300

Ser Thr Asn Thr Ser Gln Gly Gly Gly Gly Ser Gly Gly Gly Gly Ser
305                 310                 315                 320

Ala His Lys Asp Val Ser Tyr Leu Tyr Arg Phe Asn Trp Asn His Cys
                325                 330                 335

Gly Glu Met Ala Pro Ala Gly Gly Gly Gly Ser Gly Gly Gly Gly Ser
            340                 345                 350

Pro Asn Leu Gly Pro Trp Ile Gln Gln Val Asp Gln Ser Trp Arg Lys
        355                 360                 365

Glu Arg Val Leu Asn Gly Gly Gly Gly Ser Gly Gly Gly Gly Ser Ala
    370                 375                 380

Gly Pro Trp Ala Ala Trp Pro Phe Leu Leu Ser Leu Ala Leu Met Leu
385                 390                 395                 400

Leu Trp Leu Leu Ser Ser Arg Leu Pro Ile Ser Pro Val Asp Leu Ser
                405                 410                 415

Tyr Leu Ala Pro Lys Asn Pro Gly Thr Gly Pro Val Phe Thr Ile Ile
            420                 425                 430

Asn Gly Thr Leu Lys Tyr Phe Glu Thr Arg Tyr Ile Arg Val Asp Ile
        435                 440                 445

Ala Ala Pro Ile Leu Ser Arg Met Val Gly Met Ile Ser Gly Thr Thr
    450                 455                 460

Thr Glu Arg Glu Leu Trp Asp Asp Trp Ala Pro Tyr Glu Asp Val Glu
465                 470                 475                 480

Ile Gly Pro Asn Gly Val Leu Arg Thr Ser Leu Gly Tyr Lys Phe Pro
                485                 490                 495

Leu Tyr Met Ile Gly His Gly Met Leu Asp Ser Asp Leu His Leu Ser
```

```
            500                 505                 510

Ser Lys Ala Gln Val Phe Glu His Pro His Ile Gln Asp Ala Ala Ser
        515                 520                 525

Gln Leu Pro Asp Asp Glu Thr Leu Phe Phe Gly Asp Thr Gly Leu Ser
    530                 535                 540

Lys Asn Pro Ile Glu Phe Val Glu Gly Trp Phe Ser Ser Trp Lys Ser
545                 550                 555                 560

Ser Ile Ala Ser Phe Phe Phe Ile Ile Gly Leu Ile Ile Gly Leu Phe
                565                 570                 575

Leu Val Leu Arg Val Gly Ile Tyr Leu Cys Ile Lys Leu Lys His Thr
            580                 585                 590

Lys Lys Arg Gln Ile Tyr Thr Asp Ile Glu Met Asn Arg Leu Gly Lys
        595                 600                 605


<210> SEQ ID NO 60
<211> LENGTH: 599
<212> TYPE: PRT
<213> ORGANISM: Artificial Sequence
<220> FEATURE:
<223> OTHER INFORMATION: MTI-PAA Folate Receptor Alpha Class II with
      VSVG membrane localization and secretion trafficking

<400> SEQUENCE: 60

Leu Pro Gly Gly Arg Leu Gly Gly Arg Gly Arg Gly Arg Ala Pro Glu
 1               5                  10                  15

Arg Val Gly Gly Arg Gly Arg Gly Arg Gly Thr Ala Ala Pro Arg Ala
            20                  25                  30

Ala Pro Ala Ala Arg Gly Ser Arg Pro Gly Pro Ala Gly Thr Lys Cys
        35                  40                  45

Leu Leu Tyr Leu Ala Phe Leu Phe Ile Gly Val Asn Cys Lys Phe Tyr
    50                  55                  60

Pro Ser Tyr His Ser Thr Pro Gln Arg Pro Lys Phe Thr Ile Leu Phe
65                  70                  75                  80

Pro His Asn Gln Lys Gly Asn Trp Lys Asn Val Pro Ser Asn Tyr His
                85                  90                  95

Tyr Cys Pro Ser Ser Ser Asp Leu Asn Trp His Asn Asp Leu Ile Gly
            100                 105                 110

Thr Ala Ile Gln Val Lys Met Pro Lys Ser His Lys Ala Ile Gln Ala
        115                 120                 125

Asp Gly Trp Met Cys His Ala Ser Lys Trp Val Thr Thr Cys Asp Phe
    130                 135                 140

Arg Trp Tyr Gly Pro Lys Tyr Ile Thr Gln Ser Ile Arg Ser Phe Thr
145                 150                 155                 160

Pro Ser Val Glu Gln Cys Lys Glu Ser Ile Glu Gln Thr Lys Gln Gly
                165                 170                 175

Thr Trp Leu Asn Pro Gly Phe Pro Pro Gln Ser Cys Gly Tyr Ala Thr
            180                 185                 190

Val Thr Asp Ala Glu Ala Val Ile Val Gln Val Thr Pro His His Val
        195                 200                 205

Leu Val Asp Glu Tyr Thr Gly Glu Trp Val Asp Ser Gln Phe Ile Asn
    210                 215                 220

Gly Lys Cys Ser Asn Tyr Ile Cys Pro Thr Val His Asn Ser Thr Thr
225                 230                 235                 240

Trp His Ser Asp Tyr Lys Val Lys Gly Ser Arg Trp Ala Arg Thr Glu
                245                 250                 255
```

Leu Leu Asn Val Cys Met Asn Ala Lys His His Lys Glu Lys Pro Gly
260 265 270

Gly Gly Gly Gly Ser Gly Gly Gly Gly Ser His Glu Gln Cys Arg Pro
275 280 285

Trp Arg Lys Asn Ala Cys Cys Ser Thr Asn Thr Ser Gln Gly Gly Gly
290 295 300

Gly Ser Gly Gly Gly Gly Ser Ala His Lys Asp Val Ser Tyr Leu Tyr
305 310 315 320

Arg Phe Asn Trp Asn His Cys Gly Glu Met Ala Pro Ala Gly Gly Gly
325 330 335

Gly Ser Gly Gly Gly Gly Ser Pro Asn Leu Gly Pro Trp Ile Gln Gln
340 345 350

Val Asp Gln Ser Trp Arg Lys Glu Arg Val Leu Asn Gly Gly Gly Gly
355 360 365

Ser Gly Gly Gly Gly Ser Ala Gly Pro Trp Ala Ala Trp Pro Phe Leu
370 375 380

Leu Ser Leu Ala Leu Met Leu Leu Trp Leu Leu Ser Ser Arg Leu Pro
385 390 395 400

Ile Ser Pro Val Asp Leu Ser Tyr Leu Ala Pro Lys Asn Pro Gly Thr
405 410 415

Gly Pro Val Phe Thr Ile Ile Asn Gly Thr Leu Lys Tyr Phe Glu Thr
420 425 430

Arg Tyr Ile Arg Val Asp Ile Ala Ala Pro Ile Leu Ser Arg Met Val
435 440 445

Gly Met Ile Ser Gly Thr Thr Thr Glu Arg Glu Leu Trp Asp Asp Trp
450 455 460

Ala Pro Tyr Glu Asp Val Glu Ile Gly Pro Asn Gly Val Leu Arg Thr
465 470 475 480

Ser Leu Gly Tyr Lys Phe Pro Leu Tyr Met Ile Gly His Gly Met Leu
485 490 495

Asp Ser Asp Leu His Leu Ser Ser Lys Ala Gln Val Phe Glu His Pro
500 505 510

His Ile Gln Asp Ala Ala Ser Gln Leu Pro Asp Asp Glu Thr Leu Phe
515 520 525

Phe Gly Asp Thr Gly Leu Ser Lys Asn Pro Ile Glu Phe Val Glu Gly
530 535 540

Trp Phe Ser Ser Trp Lys Ser Ser Ile Ala Ser Phe Phe Phe Ile Ile
545 550 555 560

Gly Leu Ile Ile Gly Leu Phe Leu Val Leu Arg Val Gly Ile Tyr Leu
565 570 575

Cys Ile Lys Leu Lys His Thr Lys Lys Arg Gln Ile Tyr Thr Asp Ile
580 585 590

Glu Met Asn Arg Leu Gly Lys
595

<210> SEQ ID NO 61
<211> LENGTH: 594
<212> TYPE: PRT
<213> ORGANISM: Artificial Sequence
<220> FEATURE:
<223> OTHER INFORMATION: MTI-PAA Folate Receptor Alpha Class II with VSVG membrane localization and secretion trafficking

<400> SEQUENCE: 61

Leu Gly Gly Arg Gly Arg Gly Arg Ala Pro Glu Arg Val Gly Gly Arg
1 5 10 15

-continued

```
Gly Arg Gly Arg Gly Thr Ala Ala Pro Arg Ala Ala Pro Ala Ala Arg
            20                  25                  30

Gly Ser Arg Pro Gly Pro Ala Gly Thr Lys Cys Leu Leu Tyr Leu Ala
        35                  40                  45

Phe Leu Phe Ile Gly Val Asn Cys Lys Phe Tyr Pro Ser Tyr His Ser
    50                  55                  60

Thr Pro Gln Arg Pro Lys Phe Thr Ile Leu Phe Pro His Asn Gln Lys
65                  70                  75                  80

Gly Asn Trp Lys Asn Val Pro Ser Asn Tyr His Tyr Cys Pro Ser Ser
                85                  90                  95

Ser Asp Leu Asn Trp His Asn Asp Leu Ile Gly Thr Ala Ile Gln Val
            100                 105                 110

Lys Met Pro Lys Ser His Lys Ala Ile Gln Ala Asp Gly Trp Met Cys
        115                 120                 125

His Ala Ser Lys Trp Val Thr Thr Cys Asp Phe Arg Trp Tyr Gly Pro
    130                 135                 140

Lys Tyr Ile Thr Gln Ser Ile Arg Ser Phe Thr Pro Ser Val Glu Gln
145                 150                 155                 160

Cys Lys Glu Ser Ile Glu Gln Thr Lys Gln Gly Thr Trp Leu Asn Pro
                165                 170                 175

Gly Phe Pro Pro Gln Ser Cys Gly Tyr Ala Thr Val Thr Asp Ala Glu
            180                 185                 190

Ala Val Ile Val Gln Val Thr Pro His His Val Leu Val Asp Glu Tyr
        195                 200                 205

Thr Gly Glu Trp Val Asp Ser Gln Phe Ile Asn Gly Lys Cys Ser Asn
    210                 215                 220

Tyr Ile Cys Pro Thr Val His Asn Ser Thr Thr Trp His Ser Asp Tyr
225                 230                 235                 240

Lys Val Lys Gly Ser Arg Trp Ala Arg Thr Glu Leu Leu Asn Val Cys
                245                 250                 255

Met Asn Ala Lys His His Lys Glu Lys Pro Gly Gly Gly Gly Gly Ser
            260                 265                 270

Gly Gly Gly Gly Ser His Glu Gln Cys Arg Pro Trp Arg Lys Asn Ala
        275                 280                 285

Cys Cys Ser Thr Asn Thr Ser Gln Gly Gly Gly Gly Ser Gly Gly Gly
    290                 295                 300

Gly Ser Ala His Lys Asp Val Ser Tyr Leu Tyr Arg Phe Asn Trp Asn
305                 310                 315                 320

His Cys Gly Glu Met Ala Pro Ala Gly Gly Gly Gly Ser Gly Gly Gly
                325                 330                 335

Gly Ser Pro Asn Leu Gly Pro Trp Ile Gln Gln Val Asp Gln Ser Trp
            340                 345                 350

Arg Lys Glu Arg Val Leu Asn Gly Gly Gly Gly Ser Gly Gly Gly Gly
        355                 360                 365

Ser Ala Gly Pro Trp Ala Ala Trp Pro Phe Leu Leu Ser Leu Ala Leu
    370                 375                 380

Met Leu Leu Trp Leu Leu Ser Ser Arg Leu Pro Ile Ser Pro Val Asp
385                 390                 395                 400

Leu Ser Tyr Leu Ala Pro Lys Asn Pro Gly Thr Gly Pro Val Phe Thr
                405                 410                 415

Ile Ile Asn Gly Thr Leu Lys Tyr Phe Glu Thr Arg Tyr Ile Arg Val
            420                 425                 430
```

Asp Ile Ala Ala Pro Ile Leu Ser Arg Met Val Gly Met Ile Ser Gly
435 440 445

Thr Thr Thr Glu Arg Glu Leu Trp Asp Asp Trp Ala Pro Tyr Glu Asp
450 455 460

Val Glu Ile Gly Pro Asn Gly Val Leu Arg Thr Ser Leu Gly Tyr Lys
465 470 475 480

Phe Pro Leu Tyr Met Ile Gly His Gly Met Leu Asp Ser Asp Leu His
485 490 495

Leu Ser Ser Lys Ala Gln Val Phe Glu His Pro His Ile Gln Asp Ala
500 505 510

Ala Ser Gln Leu Pro Asp Asp Glu Thr Leu Phe Phe Gly Asp Thr Gly
515 520 525

Leu Ser Lys Asn Pro Ile Glu Phe Val Glu Gly Trp Phe Ser Ser Trp
530 535 540

Lys Ser Ser Ile Ala Ser Phe Phe Phe Ile Ile Gly Leu Ile Ile Gly
545 550 555 560

Leu Phe Leu Val Leu Arg Val Gly Ile Tyr Leu Cys Ile Lys Leu Lys
565 570 575

His Thr Lys Lys Arg Gln Ile Tyr Thr Asp Ile Glu Met Asn Arg Leu
580 585 590

Gly Lys

<210> SEQ ID NO 62
<211> LENGTH: 433
<212> TYPE: PRT
<213> ORGANISM: Artificial Sequence
<220> FEATURE:
<223> OTHER INFORMATION: MTI-PAA Folate Receptor Alpha Class II with VSVG membrane localization

<400> SEQUENCE: 62

Met Gly Asp Arg Gly Arg Gly Arg Ala Leu Pro Gly Gly Arg Leu Gly
1 5 10 15

Gly Arg Gly Arg Gly Arg Ala Pro Glu Arg Val Gly Gly Arg Gly Arg
20 25 30

Gly Arg Gly Thr Ala Ala Pro Arg Ala Ala Pro Ala Ala Arg Gly Ser
35 40 45

Arg Pro Gly Pro Ala Gly Thr Lys Cys Leu Leu Tyr Leu Ala Phe Leu
50 55 60

Phe Ile Gly Val Asn Cys Lys Phe Tyr Pro Ser Tyr His Ser Thr Pro
65 70 75 80

Gln Arg Pro Ser Arg Trp Ala Arg Thr Glu Leu Leu Asn Val Cys Met
85 90 95

Asn Ala Lys His His Lys Glu Lys Pro Gly Gly Gly Gly Gly Ser Gly
100 105 110

Gly Gly Gly Ser His Glu Gln Cys Arg Pro Trp Arg Lys Asn Ala Cys
115 120 125

Cys Ser Thr Asn Thr Ser Gln Gly Gly Gly Gly Ser Gly Gly Gly Gly
130 135 140

Ser Ala His Lys Asp Val Ser Tyr Leu Tyr Arg Phe Asn Trp Asn His
145 150 155 160

Cys Gly Glu Met Ala Pro Ala Gly Gly Gly Gly Ser Gly Gly Gly Gly
165 170 175

Ser Pro Asn Leu Gly Pro Trp Ile Gln Gln Val Asp Gln Ser Trp Arg
180 185 190

```
Lys Glu Arg Val Leu Asn Gly Gly Gly Gly Ser Gly Gly Gly Gly Ser
        195                 200                 205

Ala Gly Pro Trp Ala Ala Trp Pro Phe Leu Leu Ser Leu Ala Leu Met
    210                 215                 220

Leu Leu Trp Leu Leu Ser Ser Arg Leu Pro Ile Ser Pro Val Asp Leu
225                 230                 235                 240

Ser Tyr Leu Ala Pro Lys Asn Pro Gly Thr Gly Pro Val Phe Thr Ile
                245                 250                 255

Ile Asn Gly Thr Leu Lys Tyr Phe Glu Thr Arg Tyr Ile Arg Val Asp
            260                 265                 270

Ile Ala Ala Pro Ile Leu Ser Arg Met Val Gly Met Ile Ser Gly Thr
        275                 280                 285

Thr Thr Glu Arg Glu Leu Trp Asp Asp Trp Ala Pro Tyr Glu Asp Val
    290                 295                 300

Glu Ile Gly Pro Asn Gly Val Leu Arg Thr Ser Leu Gly Tyr Lys Phe
305                 310                 315                 320

Pro Leu Tyr Met Ile Gly His Gly Met Leu Asp Ser Asp Leu His Leu
                325                 330                 335

Ser Ser Lys Ala Gln Val Phe Glu His Pro His Ile Gln Asp Ala Ala
            340                 345                 350

Ser Gln Leu Pro Asp Asp Glu Thr Leu Phe Phe Gly Asp Thr Gly Leu
        355                 360                 365

Ser Lys Asn Pro Ile Glu Phe Val Glu Gly Trp Phe Ser Ser Trp Lys
    370                 375                 380

Ser Ser Ile Ala Ser Phe Phe Phe Ile Ile Gly Leu Ile Ile Gly Leu
385                 390                 395                 400

Phe Leu Val Leu Arg Val Gly Ile Tyr Leu Cys Ile Lys Leu Lys His
                405                 410                 415

Thr Lys Lys Arg Gln Ile Tyr Thr Asp Ile Glu Met Asn Arg Leu Gly
            420                 425                 430

Lys


<210> SEQ ID NO 63
<211> LENGTH: 424
<212> TYPE: PRT
<213> ORGANISM: Artificial Sequence
<220> FEATURE:
<223> OTHER INFORMATION: MTI-PAA Folate Receptor Alpha Class II with
      VSVG membrane localization

<400> SEQUENCE: 63

Leu Pro Gly Gly Arg Leu Gly Gly Arg Gly Arg Gly Arg Ala Pro Glu
 1               5                  10                  15

Arg Val Gly Gly Arg Gly Arg Gly Arg Gly Thr Ala Ala Pro Arg Ala
            20                  25                  30

Ala Pro Ala Ala Arg Gly Ser Arg Pro Gly Pro Ala Gly Thr Lys Cys
        35                  40                  45

Leu Leu Tyr Leu Ala Phe Leu Phe Ile Gly Val Asn Cys Lys Phe Tyr
    50                  55                  60

Pro Ser Tyr His Ser Thr Pro Gln Arg Pro Ser Arg Trp Ala Arg Thr
65                  70                  75                  80

Glu Leu Leu Asn Val Cys Met Asn Ala Lys His His Lys Glu Lys Pro
                85                  90                  95

Gly Gly Gly Gly Gly Ser Gly Gly Gly Gly Ser His Glu Gln Cys Arg
            100                 105                 110
```

```
Pro Trp Arg Lys Asn Ala Cys Cys Ser Thr Asn Thr Ser Gln Gly Gly
        115                 120                 125

Gly Gly Ser Gly Gly Gly Gly Ser Ala His Lys Asp Val Ser Tyr Leu
    130                 135                 140

Tyr Arg Phe Asn Trp Asn His Cys Gly Glu Met Ala Pro Ala Gly Gly
145                 150                 155                 160

Gly Gly Ser Gly Gly Gly Gly Ser Pro Asn Leu Gly Pro Trp Ile Gln
                165                 170                 175

Gln Val Asp Gln Ser Trp Arg Lys Glu Arg Val Leu Asn Gly Gly Gly
            180                 185                 190

Gly Ser Gly Gly Gly Gly Ser Ala Gly Pro Trp Ala Ala Trp Pro Phe
        195                 200                 205

Leu Leu Ser Leu Ala Leu Met Leu Leu Trp Leu Leu Ser Ser Arg Leu
    210                 215                 220

Pro Ile Ser Pro Val Asp Leu Ser Tyr Leu Ala Pro Lys Asn Pro Gly
225                 230                 235                 240

Thr Gly Pro Val Phe Thr Ile Ile Asn Gly Thr Leu Lys Tyr Phe Glu
                245                 250                 255

Thr Arg Tyr Ile Arg Val Asp Ile Ala Ala Pro Ile Leu Ser Arg Met
            260                 265                 270

Val Gly Met Ile Ser Gly Thr Thr Thr Glu Arg Glu Leu Trp Asp Asp
        275                 280                 285

Trp Ala Pro Tyr Glu Asp Val Glu Ile Gly Pro Asn Gly Val Leu Arg
    290                 295                 300

Thr Ser Leu Gly Tyr Lys Phe Pro Leu Tyr Met Ile Gly His Gly Met
305                 310                 315                 320

Leu Asp Ser Asp Leu His Leu Ser Ser Lys Ala Gln Val Phe Glu His
                325                 330                 335

Pro His Ile Gln Asp Ala Ala Ser Gln Leu Pro Asp Asp Glu Thr Leu
            340                 345                 350

Phe Phe Gly Asp Thr Gly Leu Ser Lys Asn Pro Ile Glu Phe Val Glu
        355                 360                 365

Gly Trp Phe Ser Ser Trp Lys Ser Ser Ile Ala Ser Phe Phe Phe Ile
    370                 375                 380

Ile Gly Leu Ile Ile Gly Leu Phe Leu Val Leu Arg Val Gly Ile Tyr
385                 390                 395                 400

Leu Cys Ile Lys Leu Lys His Thr Lys Lys Arg Gln Ile Tyr Thr Asp
                405                 410                 415

Ile Glu Met Asn Arg Leu Gly Lys
            420
```

<210> SEQ ID NO 64
<211> LENGTH: 419
<212> TYPE: PRT
<213> ORGANISM: Artificial Sequence
<220> FEATURE:
<223> OTHER INFORMATION: MTI-PAA Folate Receptor Alpha Class II with VSVG membrane localization

<400> SEQUENCE: 64

```
Leu Gly Gly Arg Gly Arg Gly Arg Ala Pro Glu Arg Val Gly Gly Arg
 1               5                  10                  15

Gly Arg Gly Arg Gly Thr Ala Ala Pro Arg Ala Ala Pro Ala Ala Arg
            20                  25                  30

Gly Ser Arg Pro Gly Pro Ala Gly Thr Lys Cys Leu Leu Tyr Leu Ala
        35                  40                  45
```

```
Phe Leu Phe Ile Gly Val Asn Cys Lys Phe Tyr Pro Ser Tyr His Ser
    50                  55                  60

Thr Pro Gln Arg Pro Ser Arg Trp Ala Arg Thr Glu Leu Leu Asn Val
65                  70                  75                  80

Cys Met Asn Ala Lys His His Lys Glu Lys Pro Gly Gly Gly Gly Gly
                85                  90                  95

Ser Gly Gly Gly Gly Ser His Glu Gln Cys Arg Pro Trp Arg Lys Asn
            100                 105                 110

Ala Cys Cys Ser Thr Asn Thr Ser Gln Gly Gly Gly Gly Ser Gly Gly
        115                 120                 125

Gly Gly Ser Ala His Lys Asp Val Ser Tyr Leu Tyr Arg Phe Asn Trp
    130                 135                 140

Asn His Cys Gly Glu Met Ala Pro Ala Gly Gly Gly Gly Ser Gly Gly
145                 150                 155                 160

Gly Gly Ser Pro Asn Leu Gly Pro Trp Ile Gln Gln Val Asp Gln Ser
                165                 170                 175

Trp Arg Lys Glu Arg Val Leu Asn Gly Gly Gly Gly Ser Gly Gly Gly
            180                 185                 190

Gly Ser Ala Gly Pro Trp Ala Ala Trp Pro Phe Leu Leu Ser Leu Ala
        195                 200                 205

Leu Met Leu Leu Trp Leu Leu Ser Ser Arg Leu Pro Ile Ser Pro Val
    210                 215                 220

Asp Leu Ser Tyr Leu Ala Pro Lys Asn Pro Gly Thr Gly Pro Val Phe
225                 230                 235                 240

Thr Ile Ile Asn Gly Thr Leu Lys Tyr Phe Glu Thr Arg Tyr Ile Arg
                245                 250                 255

Val Asp Ile Ala Ala Pro Ile Leu Ser Arg Met Val Gly Met Ile Ser
            260                 265                 270

Gly Thr Thr Thr Glu Arg Glu Leu Trp Asp Asp Trp Ala Pro Tyr Glu
        275                 280                 285

Asp Val Glu Ile Gly Pro Asn Gly Val Leu Arg Thr Ser Leu Gly Tyr
    290                 295                 300

Lys Phe Pro Leu Tyr Met Ile Gly His Gly Met Leu Asp Ser Asp Leu
305                 310                 315                 320

His Leu Ser Ser Lys Ala Gln Val Phe Glu His Pro His Ile Gln Asp
                325                 330                 335

Ala Ala Ser Gln Leu Pro Asp Asp Glu Thr Leu Phe Phe Gly Asp Thr
            340                 345                 350

Gly Leu Ser Lys Asn Pro Ile Glu Phe Val Glu Gly Trp Phe Ser Ser
        355                 360                 365

Trp Lys Ser Ser Ile Ala Ser Phe Phe Phe Ile Ile Gly Leu Ile Ile
    370                 375                 380

Gly Leu Phe Leu Val Leu Arg Val Gly Ile Tyr Leu Cys Ile Lys Leu
385                 390                 395                 400

Lys His Thr Lys Lys Arg Gln Ile Tyr Thr Asp Ile Glu Met Asn Arg
                405                 410                 415

Leu Gly Lys
```

<210> SEQ ID NO 65
<211> LENGTH: 1147
<212> TYPE: DNA
<213> ORGANISM: Homo sapiens

<400> SEQUENCE: 65

```
tggaggcctg gctggtgctc acatacaata attaactgct gagtggcctt cgcccaatcc     60

caggctccac tcctgggctc cattcccact ccctgcctgt ctcctaggcc actaaaccac    120

agctgtcccc tggaataagg caagggggag tgtagagcag agcagaagcc tgagccagac    180

ggagagccac ctcctctccc agggacagac atggctcagc ggatgacaac acagctgctg    240

ctccttctag tgtgggtggc tgtagtaggg gaggctcaga caaggattgc atgggccagg    300

actgagcttc tcaatgtctg catgaacgcc aagcaccaca aggaaaagcc aggccccgag    360

gacaagttgc atgagcagtg tcgaccctgg aggaagaatg cctgctgttc taccaacacc    420

agccaggaag cccataagga tgtttcctac ctatatagat tcaactggaa ccactgtgga    480

gagatggcac ctgcctgcaa acggcatttc atccaggaca cctgcctcta cgagtgctcc    540

cccaacttgg ggccctggat ccagcaggtg gatcagagct ggcgcaaaga gcgggtactg    600

aacgtgcccc tgtgcaaaga ggactgtgag caatggtggg aagattgtcg cacctcctac    660

acctgcaaga gcaactggca caagggctgg aactggactt cagggtttaa caagtgcgca    720

gtgggagctg cctgccaacc tttccatttc tacttcccca cacccactgt tctgtgcaat    780

gaaatctgga ctcactccta caaggtcagc aactacagcc gagggagtgg ccgctgcatc    840

cagatgtggt tcgacccagc ccagggcaac cccaatgagg aggtggcgag gttctatgct    900

gcagccatga gtggggctgg gccctgggca gcctggcctt tcctgcttag cctggcccta    960

atgctgctgt ggctgctcag ctgacctcct tttaccttct gatacctgga aatccctgcc   1020

ctgttcagcc ccacagctcc caactatttg gttcctgctc catggtcggg cctctgacag   1080

ccactttgaa taaaccagac accgcacatg tgtcttgaga attatttgga aaaaaaaaaa   1140

aaaaaaa                                                             1147
```

```
<210> SEQ ID NO 66
<211> LENGTH: 257
<212> TYPE: PRT
<213> ORGANISM: Homo sapiens

<400> SEQUENCE: 66

Met Ala Gln Arg Met Thr Thr Gln Leu Leu Leu Leu Leu Val Trp Val
 1               5                  10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160
```

-continued

```
Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 67
<211> LENGTH: 182
<212> TYPE: PRT
<213> ORGANISM: Artificial Sequence
<220> FEATURE:
<223> OTHER INFORMATION: Folate Receptor Alpha PAA - Class II embedded class I

<400> SEQUENCE: 67

```
Ile Ala Trp Ala Arg Thr Glu Leu Leu Asn Val Cys Met Asn Ala Lys
 1               5                  10                  15

His His Lys Glu Lys Pro Gly Pro Glu Gly Gly Gly Gly Ser Gly Gly
            20                  25                  30

Gly Gly Ser Gly Gly Gly Gly Ser Lys Leu His Glu Gln Cys Arg Pro
        35                  40                  45

Trp Arg Lys Asn Ala Cys Cys Ser Thr Asn Thr Ser Gln Glu Ala Gly
    50                  55                  60

Gly Gly Gly Ser Gly Gly Gly Gly Ser Gly Gly Gly Gly Ser Gln Glu
65                  70                  75                  80

Ala His Lys Asp Val Ser Tyr Leu Tyr Arg Phe Asn Trp Asn His Cys
                85                  90                  95

Gly Glu Met Ala Pro Ala Cys Lys Gly Gly Gly Gly Ser Gly Gly Gly
            100                 105                 110

Gly Ser Gly Gly Gly Gly Ser Cys Ser Pro Asn Leu Gly Pro Trp Ile
        115                 120                 125

Gln Gln Val Asp Gln Ser Trp Arg Lys Glu Arg Val Leu Asn Val Pro
    130                 135                 140

Gly Gly Gly Gly Ser Gly Gly Gly Gly Ser Gly Gly Gly Gly Ser Gly
145                 150                 155                 160

Ala Gly Pro Trp Ala Ala Trp Pro Phe Leu Leu Ser Leu Ala Leu Met
                165                 170                 175

Leu Leu Trp Leu Leu Ser
            180
```

<210> SEQ ID NO 68
<211> LENGTH: 144
<212> TYPE: PRT
<213> ORGANISM: Artificial Sequence
<220> FEATURE:
<223> OTHER INFORMATION: Folate Receptor Alpha PAA - Class II embedded class I

<400> SEQUENCE: 68

```
Arg Thr Glu Leu Leu Asn Val Cys Met Asn Ala Lys His His Lys Glu
```

```
 1               5                   10                  15

Lys Gly Gly Gly Gly Ser Gly Gly Gly Gly Ser Gly Gly Gly Gly Ser
            20                  25                  30

Gln Cys Arg Pro Trp Arg Lys Asn Ala Cys Cys Ser Thr Asn Thr Gly
        35                  40                  45

Gly Gly Gly Ser Gly Gly Gly Gly Ser Gly Gly Gly Gly Ser Lys Asp
    50                  55                  60

Val Ser Tyr Leu Tyr Arg Phe Asn Trp Asn His Cys Gly Glu Met Ala
65                  70                  75                  80

Gly Gly Gly Gly Ser Gly Gly Gly Gly Ser Gly Gly Gly Gly Ser Leu
                85                  90                  95

Gly Pro Trp Ile Gln Gln Val Asp Gln Ser Trp Arg Lys Glu Arg Val
            100                 105                 110

Gly Gly Gly Gly Ser Gly Gly Gly Gly Ser Gly Gly Gly Gly Pro Trp
        115                 120                 125

Ala Ala Trp Pro Phe Leu Leu Ser Leu Ala Leu Met Leu Leu Trp Leu
    130                 135                 140


<210> SEQ ID NO 69
<211> LENGTH: 25
<212> TYPE: PRT
<213> ORGANISM: Artificial Sequence
<220> FEATURE:
<223> OTHER INFORMATION: Folate Receptor Alpha PAA - Class II embedded
      class I

<400> SEQUENCE: 69

Ile Ala Trp Ala Arg Thr Glu Leu Leu Asn Val Cys Met Asn Ala Lys
 1               5                   10                  15

His His Lys Glu Lys Pro Gly Pro Glu
            20                  25


<210> SEQ ID NO 70
<211> LENGTH: 23
<212> TYPE: PRT
<213> ORGANISM: Artificial Sequence
<220> FEATURE:
<223> OTHER INFORMATION: Folate Receptor Alpha PAA - Class II embedded
      class I

<400> SEQUENCE: 70

Lys Leu His Glu Gln Cys Arg Pro Trp Arg Lys Asn Ala Cys Cys Ser
 1               5                   10                  15

Thr Asn Thr Ser Gln Glu Ala
            20


<210> SEQ ID NO 71
<211> LENGTH: 26
<212> TYPE: PRT
<213> ORGANISM: Artificial Sequence
<220> FEATURE:
<223> OTHER INFORMATION: Folate Receptor Alpha PAA - Class II embedded
      class I

<400> SEQUENCE: 71

Gln Glu Ala His Lys Asp Val Ser Tyr Leu Tyr Arg Phe Asn Trp Asn
 1               5                   10                  15

His Cys Gly Glu Met Ala Pro Ala Cys Lys
            20                  25


<210> SEQ ID NO 72
```

<211> LENGTH: 25
<212> TYPE: PRT
<213> ORGANISM: Artificial Sequence
<220> FEATURE:
<223> OTHER INFORMATION: Folate Receptor Alpha PAA - Class II embedded class I

<400> SEQUENCE: 72

Cys Ser Pro Asn Leu Gly Pro Trp Ile Gln Gln Val Asp Gln Ser Trp
1 5 10 15

Arg Lys Glu Arg Val Leu Asn Val Pro
20 25

<210> SEQ ID NO 73
<211> LENGTH: 24
<212> TYPE: PRT
<213> ORGANISM: Artificial Sequence
<220> FEATURE:
<223> OTHER INFORMATION: Folate Receptor Alpha PAA - Class II embedded class I

<400> SEQUENCE: 73

Ser Gly Ala Gly Pro Trp Ala Ala Trp Pro Phe Leu Leu Ser Leu Ala
1 5 10 15

Leu Met Leu Leu Trp Leu Leu Ser
20

<210> SEQ ID NO 74
<211> LENGTH: 17
<212> TYPE: PRT
<213> ORGANISM: Artificial Sequence
<220> FEATURE:
<223> OTHER INFORMATION: HLA Class II Folate Receptor Alpha

<400> SEQUENCE: 74

Arg Thr Glu Leu Leu Asn Val Cys Met Asn Ala Lys His His Lys Glu
1 5 10 15

Lys

<210> SEQ ID NO 75
<211> LENGTH: 15
<212> TYPE: PRT
<213> ORGANISM: Artificial Sequence
<220> FEATURE:
<223> OTHER INFORMATION: HLA Class II Folate Receptor Alpha

<400> SEQUENCE: 75

Gln Cys Arg Pro Trp Arg Lys Asn Ala Cys Cys Ser Thr Asn Thr
1 5 10 15

<210> SEQ ID NO 76
<211> LENGTH: 18
<212> TYPE: PRT
<213> ORGANISM: Artificial Sequence
<220> FEATURE:
<223> OTHER INFORMATION: HLA Class II Folate Receptor Alpha

<400> SEQUENCE: 76

Lys Asp Val Ser Tyr Leu Tyr Arg Phe Asn Trp Asn His Cys Gly Glu
1 5 10 15

Met Ala

<210> SEQ ID NO 77
<211> LENGTH: 17
<212> TYPE: PRT

<213> ORGANISM: Artificial Sequence
<220> FEATURE:
<223> OTHER INFORMATION: HLA Class II Folate Receptor Alpha

<400> SEQUENCE: 77

Leu Gly Pro Trp Ile Gln Gln Val Asp Gln Ser Trp Arg Lys Glu Arg
1               5                   10                  15

Val

<210> SEQ ID NO 78
<211> LENGTH: 18
<212> TYPE: PRT
<213> ORGANISM: Artificial Sequence
<220> FEATURE:
<223> OTHER INFORMATION: HLA Class II Folate Receptor Alpha

<400> SEQUENCE: 78

Pro Trp Ala Ala Trp Pro Phe Leu Leu Ser Leu Ala Leu Met Leu Leu
1               5                   10                  15

Trp Leu

<210> SEQ ID NO 79
<211> LENGTH: 9
<212> TYPE: PRT
<213> ORGANISM: Artificial Sequence
<220> FEATURE:
<223> OTHER INFORMATION: Embedded HLA Class I peptide folate receptor
alpha

<400> SEQUENCE: 79

Leu Leu Asn Val Cys Met Asn Ala Lys
1               5

<210> SEQ ID NO 80
<211> LENGTH: 9
<212> TYPE: PRT
<213> ORGANISM: Artificial Sequence
<220> FEATURE:
<223> OTHER INFORMATION: Embedded HLA Class I peptide folate receptor
alpha

<400> SEQUENCE: 80

Arg Pro Trp Arg Lys Asn Ala Cys Cys
1               5

<210> SEQ ID NO 81
<211> LENGTH: 9
<212> TYPE: PRT
<213> ORGANISM: Artificial Sequence
<220> FEATURE:
<223> OTHER INFORMATION: Embedded HLA Class I peptide folate receptor
alpha

<400> SEQUENCE: 81

Val Ser Tyr Leu Tyr Arg Phe Asn Trp
1               5

<210> SEQ ID NO 82
<211> LENGTH: 9
<212> TYPE: PRT
<213> ORGANISM: Artificial Sequence
<220> FEATURE:
<223> OTHER INFORMATION: Embedded HLA Class I peptide folate receptor
alpha

<400> SEQUENCE: 82

Gln Gln Val Asp Gln Ser Trp Arg Lys
1 5

<210> SEQ ID NO 83
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 83

Trp Ile Gln Gln Val Asp Gln Ser Trp
1 5

<210> SEQ ID NO 84
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 84

Phe Leu Leu Ser Leu Ala Leu Met Leu
1 5

<210> SEQ ID NO 85
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 85

Ala Ala Trp Pro Phe Leu Leu Ser Leu
1 5

<210> SEQ ID NO 86
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 86

Ser Leu Ala Leu Met Leu Leu Trp Leu
1 5

<210> SEQ ID NO 87
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 87

Leu Leu Ser Leu Ala Leu Met Leu Leu
1 5

<210> SEQ ID NO 88
<211> LENGTH: 9
<212> TYPE: PRT
<213> ORGANISM: Artificial Sequence
<220> FEATURE:

<223> OTHER INFORMATION: Embedded HLA Class I peptide folate receptor alpha

<400> SEQUENCE: 88

Pro Trp Ala Ala Trp Pro Phe Leu Leu
1 5

<210> SEQ ID NO 89
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 89

Trp Pro Phe Leu Leu Ser Leu Ala Leu
1 5

<210> SEQ ID NO 90
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 90

Ala Ala Trp Pro Phe Leu Leu Ser Leu
1 5

<210> SEQ ID NO 91
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 91

Trp Pro Phe Leu Leu Ser Leu Ala Leu
1 5

<210> SEQ ID NO 92
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 92

Phe Leu Leu Ser Leu Ala Leu Met Leu
1 5

<210> SEQ ID NO 93
<211> LENGTH: 9
<212> TYPE: PRT
<213> ORGANISM: Artificial Sequence
<220> FEATURE:
<223> OTHER INFORMATION: Embedded HLA Class I peptide folate receptor alpha

<400> SEQUENCE: 93

Leu Ser Leu Ala Leu Met Leu Leu Trp
1 5

<210> SEQ ID NO 94
<211> LENGTH: 11
<212> TYPE: PRT
<213> ORGANISM: Artificial Sequence
<220> FEATURE:
<223> OTHER INFORMATION: VSVG tag

<400> SEQUENCE: 94

Tyr Thr Asp Ile Glu Met Asn Arg Leu Gly Lys
1 5 10

<210> SEQ ID NO 95
<211> LENGTH: 426
<212> TYPE: DNA
<213> ORGANISM: Artificial Sequence
<220> FEATURE:
<223> OTHER INFORMATION: PolyStart with XbaI site

<400> SEQUENCE: 95
atcgaggtta acgtttaaac gggtggagat gtagaagatg tgacgccgcg gcccggcggg 60
tgccagatta gcggacgcgg tgcccgcggt tgcaacggga tcccgggcgc tgcagcttgg 120
gaggcggctc tccccaggcg gcgtccgcgg agacacccat ccgtgaaccc caggtcccgg 180
gccgccggct cgccgcgcac caggggccgg cggacagaag agcggccgag cggctcgagg 240
ctgggggacc gcgggcgcgg ccgcgcgctg ccgggcggga ggctgggggg ccggggccgg 300
ggccgtgccc cggagcgggt cggaggccgg ggccggggcc gggggacggc ggctccccgc 360
gcggctccag cggctcgggg atcccggccg ggccccgcag ggaccatggc agccgggagc 420
tctaga 426

<210> SEQ ID NO 96
<211> LENGTH: 405
<212> TYPE: DNA
<213> ORGANISM: Artificial Sequence
<220> FEATURE:
<223> OTHER INFORMATION: PolyStart without XbaI site

<400> SEQUENCE: 96
atcgaggtta acgtttaaac gggtggagat gtagaagatg tgacgccgcg gcccggcggg 60
tgccagatta gcggacgcgg tgcccgcggt tgcaacggga tcccgggcgc tgcagcttgg 120
gaggcggctc tccccaggcg gcgtccgcgg agacacccat ccgtgaaccc caggtcccgg 180
gccgccggct cgccgcgcac caggggccgg cggacagaag agcggccgag cggctcgagg 240
ctgggggacc gcgggcgcgg ccgcgcgctg ccgggcggga ggctgggggg ccggggccgg 300
ggccgtgccc cggagcgggt cggaggccgg ggccggggcc gggggacggc ggctccccgc 360
gcggctccag cggctcgggg atcccggccg ggccccgcag ggacc 405

<210> SEQ ID NO 97
<211> LENGTH: 558
<212> TYPE: DNA
<213> ORGANISM: Artificial Sequence
<220> FEATURE:
<223> OTHER INFORMATION: Folate Receptor Alpha PAA

<400> SEQUENCE: 97
tctagaatcg cctgggccag aaccgagctg ctgaacgtgt gcatgaacgc caagcaccac 60
aaggagaagc ccggccccga gggcggcggc ggcagcggcg gcggcggcag cggcggcggc 120
ggcagcaagc tgcacgagca gtgcagaccc tggagaaaga acgcctgctg cagcaccaac 180
accagccagg aggccggcgg cggcggcagc ggcggcggcg gcagcggcgg cggcggcagc 240
caggaggccc acaaggacgt gagctacctg tacagattca actggaacca ctgcggcgag 300
atggcccccg cctgcaaggg cggcggcggc agcggcggcg gcggcagcgg cggcggcggc 360
agctgcagcc ccaacctggg cccctggatc cagcaggtgg accagagctg gagaaaggag 420
agagtgctga acgtgcccgg cggcggcggc agcggcggcg gcggcagcgg cggcggcggc 480
agcggcgccg gcccctgggc cgcctggccc ttcctgctga gcctggccct gatgctgctg 540
tggctgctga gctctaga 558

<210> SEQ ID NO 98
<211> LENGTH: 546
<212> TYPE: DNA
<213> ORGANISM: Artificial Sequence
<220> FEATURE:
<223> OTHER INFORMATION: Folate Receptor Alpha PAA

<400> SEQUENCE: 98
atcgcctggg ccagaaccga gctgctgaac gtgtgcatga acgccaagca ccacaaggag 60
aagcccggcc ccgagggcgg cggcggcagc ggcggcggcg gcagcggcgg cggcggcagc 120
aagctgcacg agcagtgcag accctggaga aagaacgcct gctgcagcac caacaccagc 180
caggaggccg gcggcggcgg cagcggcggc ggcggcagcg gcggcggcgg cagccaggag 240
gcccacaagg acgtgagcta cctgtacaga ttcaactgga accactgcgg cgagatggcc 300
cccgcctgca agggcggcgg cggcagcggc ggcggcggca gcggcggcgg cggcagctgc 360
agccccaacc tgggcccctg gatccagcag gtggaccaga gctggagaaa ggagagagtg 420
ctgaacgtgc ccggcggcgg cggcagcggc ggcggcggca gcggcggcgg cggcagcggc 480
gccggcccct gggccgcctg gcccttcctg ctgagcctgg ccctgatgct gctgtggctg 540
ctgagc 546

<210> SEQ ID NO 99
<211> LENGTH: 33
<212> TYPE: DNA
<213> ORGANISM: Artificial Sequence
<220> FEATURE:
<223> OTHER INFORMATION: VSVG tag

<400> SEQUENCE: 99
tacaccgaca tcgagatgaa cagactgggc aag 33

<210> SEQ ID NO 100
<211> LENGTH: 979
<212> TYPE: DNA
<213> ORGANISM: Artificial Sequence
<220> FEATURE:
<223> OTHER INFORMATION: MTI-Folate Receptor Alpha PAA

<400> SEQUENCE: 100
gggtggagat gtagaagatg tgacgccgcg gcccggcggg tgccagatta gcggacgcgg 60
tgcccgcggt tgcaacggga tcccgggcgc tgcagcttgg gaggcggctc tccccaggcg 120
gcgtccgcgg agacacccat ccgtgaaccc caggtcccgg gccgccggct cgccgcgcac 180
caggggccgg cggacagaag agcggccgag cggctcgagg atgggggacc gcgggcgcgg 240
ccgcgcgctg ccgggcggga ggctgggggg ccggggccgg ggccgtgccc cggagcgggt 300
cggaggccgg ggccggggcc gggggacggc ggctccccgc gcggctccag cggctcgggg 360
atcccggccg ggccccgcag ggacctctag aatcgcctgg gccagaaccg agctgctgaa 420
cgtgtgcatg aacgccaagc accacaagga gaagcccggc cccgagggcg gcggcggcag 480
cggcggcggc ggcagcggcg gcggcggcag caagctgcac gagcagtgca gaccctggag 540
aaagaacgcc tgctgcagca ccaacaccag ccaggaggcc ggcggcggcg gcagcggcgg 600
cggcggcagc ggcggcggcg gcagccagga ggcccacaag gacgtgagct acctgtacag 660
attcaactgg aaccactgcg gcgagatggc ccccgcctgc aagggcggcg gcggcagcgg 720
cggcggcggc agcggcggcg gcggcagctg cagccccaac ctgggcccct ggatccagca 780
ggtggaccag agctggagaa aggagagagt gctgaacgtg cccggcggcg gcggcagcgg 840
cggcggcggc agcggcggcg gcggcagcgg cgccggcccc tgggccgcct ggcccttcct 900
gctgagcctg gccctgatgc tgctgtggct gctgagctct agatacaccg acatcgagat 960
gaacagactg ggcaagtaa 979

<210> SEQ ID NO 101
<211> LENGTH: 1438
<212> TYPE: DNA
<213> ORGANISM: Homo sapiens

<400> SEQUENCE: 101
tgcggcggcg agggaggagg aagaagcgga ggaggcggct cccgcgctcg cagggccgtg 60
ccacctgccc gcccgcccgc tcgctcgctc gcccgccgcg ccgcgctgcc gaccgccagc 120
atgctgccga gagtgggctg ccccgcgctg ccgctgccgc cgccgccgct gctgccgctg 180
ctgccgctgc tgctgctgct actgggcgcg agtggcggcg gcggcggggc gcgcgcggag 240
gtgctgttcc gctgcccgcc ctgcacaccc gagcgcctgg ccgcctgcgg gcccccgccg 300
gttgcgccgc ccgccgcggt ggccgcagtg gccggggcgc ccgcatgcca tgcgcggagc 360
tcgtccggga gccgggctgc ggctgctgct cggtgtgcgc ccggctggag ggcgaggcgt 420
gcggcgtcta cacccccgcgc tgcggccagg ggctgcgctg ctatccccac ccgggctccg 480
agctgcccct gcaggcgctg gtcatgggcg agggcacttg tgagaagcgc cgggacgccg 540
agtatggcgc cagcccggag caggttgcag acaatggcga tgaccactca gaaggaggcc 600
tggtggagaa ccacgtggac agcaccatga acatgttggg cgggggaggc agtgctggcc 660
ggaagcccct caagtcgggt atgaaggagc tggccgtgtt ccgggagaag gtcactgagc 720
agcaccggca gatgggcaag ggtggcaagc atcaccttgg cctggaggag cccaagaagc 780
tgcgaccacc ccctgccagg actccctgcc aacaggaact ggaccaggtc ctggagcgga 840
tctccaccat gcgccttccg gatgagcggg gccctctgga gcacctctac tccctgcaca 900
tccccaactg tgacaagcat ggcctgtaca acctcaaaca gtgcaagatg tctctgaacg 960
ggcagcgtgg ggagtgctgg tgtgtgaacc ccaacaccgg gaagctgatc cagggagccc 1020
ccaccatccg gggggacccc gagtgtcatc tcttctacaa tgagcagcag gaggctcgcg 1080
gggtgcacac ccagcggatg cagtagaccg cagccagccg gtgcctggcg cccctgcccc 1140
ccgcccctct ccaaacaccg gcagaaaacg gagagtgctt gggtggtggg tgctggagga 1200
ttttccagtt ctgacacacg tatttatatt tggaaagaga ccagcaccga gctcggcacc 1260
tccccggcct ctctcttccc agctgcagat gccacacctg ctccttcttg ctttccccgg 1320
gggaggaagg gggttgtggt cggggagctg gggtacaggt ttggggaggg ggaagagaaa 1380
tttttatttt tgaacccctg tgtccctttt gcataagatt aaaggaagga aaagtaaa 1438

<210> SEQ ID NO 102
<211> LENGTH: 328

<212> TYPE: PRT
<213> ORGANISM: Homo sapiens

<400> SEQUENCE: 102

Met Leu Pro Arg Val Gly Cys Pro Ala Leu Pro Leu Pro Pro Pro Pro
1 5 10 15

Leu Leu Pro Leu Leu Pro Leu Leu Leu Leu Leu Leu Gly Ala Ser Gly
20 25 30

Gly Gly Gly Gly Ala Arg Ala Glu Val Leu Phe Arg Cys Pro Pro Cys
35 40 45

Thr Pro Glu Arg Leu Ala Ala Cys Gly Pro Pro Pro Val Ala Pro Pro
50 55 60

Ala Ala Val Ala Ala Val Ala Gly Gly Ala Arg Met Pro Cys Ala Glu
65 70 75 80

Leu Val Arg Glu Pro Gly Cys Gly Cys Cys Ser Val Cys Ala Arg Leu
85 90 95

Glu Gly Glu Ala Cys Gly Val Tyr Thr Pro Arg Cys Gly Gln Gly Leu
100 105 110

Arg Cys Tyr Pro His Pro Gly Ser Glu Leu Pro Leu Gln Ala Leu Val
115 120 125

Met Gly Glu Gly Thr Cys Glu Lys Arg Arg Asp Ala Glu Tyr Gly Ala
130 135 140

Ser Pro Glu Gln Val Ala Asp Asn Gly Asp Asp His Ser Glu Gly Gly
145 150 155 160

Leu Val Glu Asn His Val Asp Ser Thr Met Asn Met Leu Gly Gly Gly
165 170 175

Gly Ser Ala Gly Arg Lys Pro Leu Lys Ser Gly Met Lys Glu Leu Ala
180 185 190

Val Phe Arg Glu Lys Val Thr Glu Gln His Arg Gln Met Gly Lys Gly
195 200 205

Gly Lys His His Leu Gly Leu Glu Glu Pro Lys Lys Leu Arg Pro Pro
210 215 220

Pro Ala Arg Thr Pro Cys Gln Gln Glu Leu Asp Gln Val Leu Glu Arg
225 230 235 240

Ile Ser Thr Met Arg Leu Pro Asp Glu Arg Gly Pro Leu Glu His Leu
245 250 255

Tyr Ser Leu His Ile Pro Asn Cys Asp Lys His Gly Leu Tyr Asn Leu
260 265 270

Lys Gln Cys Lys Met Ser Leu Asn Gly Gln Arg Gly Glu Cys Trp Cys
275 280 285

Val Asn Pro Asn Thr Gly Lys Leu Ile Gln Gly Ala Pro Thr Ile Arg
290 295 300

Gly Asp Pro Glu Cys His Leu Phe Tyr Asn Glu Gln Gln Glu Ala Arg
305 310 315 320

Gly Val His Thr Gln Arg Met Gln
325

<210> SEQ ID NO 103
<211> LENGTH: 15
<212> TYPE: PRT
<213> ORGANISM: Artificial Sequence
<220> FEATURE:
<223> OTHER INFORMATION: Class II IFGFBP-2

<400> SEQUENCE: 103

Leu Leu Pro Leu Leu Pro Leu Leu Leu Leu Leu Leu Gly Ala Ser

-continued 1 5 10 15

<210> SEQ ID NO 104
<211> LENGTH: 15
<212> TYPE: PRT
<213> ORGANISM: Artificial Sequence
<220> FEATURE:
<223> OTHER INFORMATION: Class II IFGFBP-2

<400> SEQUENCE: 104

Pro Leu Leu Leu Leu Leu Leu Gly Ala Ser Gly Gly Gly Gly Gly
1 5 10 15

<210> SEQ ID NO 105
<211> LENGTH: 15
<212> TYPE: PRT
<213> ORGANISM: Artificial Sequence
<220> FEATURE:
<223> OTHER INFORMATION: Class II IFGFBP-2

<400> SEQUENCE: 105

Glu Arg Gly Pro Leu Glu His Leu Tyr Ser Leu His Ile Pro Asn
1 5 10 15

<210> SEQ ID NO 106
<211> LENGTH: 15
<212> TYPE: PRT
<213> ORGANISM: Artificial Sequence
<220> FEATURE:
<223> OTHER INFORMATION: Class II IFGFBP-2

<400> SEQUENCE: 106

Thr Gly Lys Leu Ile Gln Gly Ala Pro Thr Ile Arg Gly Asp Pro
1 5 10 15

<210> SEQ ID NO 107
<211> LENGTH: 9
<212> TYPE: PRT
<213> ORGANISM: Artificial Sequence
<220> FEATURE:
<223> OTHER INFORMATION: Class I IGFBP-2

<400> SEQUENCE: 107

Leu Leu Pro Leu Leu Leu Leu Leu Leu
1 5

<210> SEQ ID NO 108
<211> LENGTH: 9
<212> TYPE: PRT
<213> ORGANISM: Artificial Sequence
<220> FEATURE:
<223> OTHER INFORMATION: Class I IGFBP-2

<400> SEQUENCE: 108

Pro Leu Leu Pro Leu Leu Leu Leu Leu
1 5

<210> SEQ ID NO 109
<211> LENGTH: 9
<212> TYPE: PRT
<213> ORGANISM: Artificial Sequence
<220> FEATURE:
<223> OTHER INFORMATION: Class I IGFBP-2

<400> SEQUENCE: 109

Leu Pro Leu Leu Pro Leu Leu Leu Leu
1 5

<210> SEQ ID NO 110
<211> LENGTH: 9
<212> TYPE: PRT
<213> ORGANISM: Artificial Sequence
<220> FEATURE:
<223> OTHER INFORMATION: Class I IGFBP-2

<400> SEQUENCE: 110

Gly Pro Leu Glu His Leu Tyr Ser Leu
1 5

<210> SEQ ID NO 111
<211> LENGTH: 9
<212> TYPE: PRT
<213> ORGANISM: Artificial Sequence
<220> FEATURE:
<223> OTHER INFORMATION: Class I IGFBP-2

<400> SEQUENCE: 111

Leu Glu His Leu Tyr Ser Leu His Ile
1 5

<210> SEQ ID NO 112
<211> LENGTH: 9
<212> TYPE: PRT
<213> ORGANISM: Artificial Sequence
<220> FEATURE:
<223> OTHER INFORMATION: Class I IGFBP-2

<400> SEQUENCE: 112

Lys Leu Ile Gln Gly Ala Pro Thr Ile
1 5

<210> SEQ ID NO 113
<211> LENGTH: 4664
<212> TYPE: DNA
<213> ORGANISM: Homo sapiens

<400> SEQUENCE: 113
gcttgctccc aatcacagga gaaggaggag gtggaggagg agggctgctt gaggaagtat 60
aagaatgaag ttgtgaagct gagattcccc tccattggga ccggagaaac caggggagcc 120
ccccgggcag ccgcgcgccc cttcccacgg ggccctttac tgcgccgcgc gcccggcccc 180
cacccctcgc agcaccccgc gccccgcgcc ctcccagccg ggtccagccg gagccatggg 240
gccggagccg cagtgagcac catggagctg gcggccttgt gccgctgggg gctcctcctc 300
gccctcttgc cccccggagc cgcgagcacc caagtgtgca ccggcacaga catgaagctg 360
cggctccctg ccagtcccga gacccacctg gacatgctcc gccacctcta ccagggctgc 420
caggtggtgc agggaaacct ggaactcacc tacctgccca ccaatgccag cctgtccttc 480
ctgcaggata tccaggaggt gcagggctac gtgctcatcg ctcacaacca agtgaggcag 540
gtcccactgc agaggctgcg gattgtgcga ggcacccagc tctttgagga caactatgcc 600
ctggccgtgc tagacaatgg agacccgctg aacaatacca cccctgtcac aggggcctcc 660
ccaggaggcc tgcgggagct gcagcttcga agcctcacag agatcttgaa aggaggggtc 720
ttgatccagc ggaaccccca gctctgctac caggacacga ttttgtggaa ggacatcttc 780
cacaagaaca accagctggc tctcacactg atagacacca accgctctcg ggcctgccac 840
ccctgttctc cgatgtgtaa gggctcccgc tgctggggag agagttctga ggattgtcag 900
agcctgacgc gcactgtctg tgccggtggc tgtgcccgct gcaaggggcc actgcccact 960

```
gactgctgcc atgagcagtg tgctgccggc tgcacgggcc ccaagcactc tgactgcctg   1020
gcctgcctcc acttcaacca cagtggcatc tgtgagctgc actgcccagc cctggtcacc   1080
tacaacacag acacgtttga gtccatgccc aatcccgagg gccggtatac attcggcgcc   1140
agctgtgtga ctgcctgtcc ctacaactac ctttctacgg acgtgggatc ctgcaccctc   1200
gtctgccccc tgcacaacca agaggtgaca gcagaggatg gaacacagcg gtgtgagaag   1260
tgcagcaagc cctgtgcccg agtgtgctat ggtctgggca tggagcactt gcgagaggtg   1320
agggcagtta ccagtgccaa tatccaggag tttgctggct gcaagaagat ctttgggagc   1380
ctggcatttc tgccggagag ctttgatggg gacccagcct ccaacactgc cccgctccag   1440
ccagagcagc tccaagtgtt tgagactctg gaagagatca caggttacct atacatctca   1500
gcatggccgg acagcctgcc tgacctcagc gtcttccaga acctgcaagt aatccgggga   1560
cgaattctgc acaatggcgc ctactcgctg accctgcaag ggctgggcat cagctggctg   1620
gggctgcgct cactgaggga actgggcagt ggactggccc tcatccacca taacacccac   1680
ctctgcttcg tgcacacggt gccctgggac cagctctttc ggaacccgca ccaagctctg   1740
ctccacactg ccaaccggcc agaggacgag tgtgtgggcg agggcctggc ctgccaccag   1800
ctgtgcgccc gagggcactg ctggggtcca gggcccaccc agtgtgtcaa ctgcagccag   1860
ttccttcggg gccaggagtg cgtggaggaa tgccgagtac tgcaggggct ccccagggag   1920
tatgtgaatg ccaggcactg tttgccgtgc caccctgagt gtcagcccca gaatggctca   1980
gtgacctgtt ttggaccgga ggctgaccag tgtgtggcct gtgcccacta taaggaccct   2040
cccttctgcg tggcccgctg ccccagcggt gtgaaacctg acctctccta catgcccatc   2100
tggaagtttc cagatgagga gggcgcatgc cagccttgcc ccatcaactg cacccactcc   2160
tgtgtggacc tggatgacaa gggctgcccc gccgagcaga gagccagccc tctgacgtcc   2220
atcatctctg cggtggttgg cattctgctg gtcgtggtct tgggggtggt ctttgggatc   2280
ctcatcaagc gacggcagca gaagatccgg aagtacacga tgcggagact gctgcaggaa   2340
acggagctgg tggagccgct gacacctagc ggagcgatgc ccaaccaggc gcagatgcgg   2400
atcctgaaag agacggagct gaggaaggtg aaggtgcttg gatctggcgc ttttggcaca   2460
gtctacaagg gcatctggat ccctgatggg gagaatgtga aaattccagt ggccatcaaa   2520
gtgttgaggg aaaacacatc ccccaaagcc aacaaagaaa tcttagacga agcatacgtg   2580
atggctggtg tgggctcccc atatgtctcc cgccttctgg gcatctgcct gacatccacg   2640
gtgcagctgg tgacacagct tatgccctat ggctgcctct tagaccatgt ccgggaaaac   2700
cgcggacgcc tgggctccca ggacctgctg aactggtgta tgcagattgc caaggggatg   2760
agctacctgg aggatgtgcg gctcgtacac agggacttgg ccgctcggaa cgtgctggtc   2820
aagagtccca accatgtcaa aattacagac ttcgggctgg ctcggctgct ggacattgac   2880
gagacagagt accatgcaga tgggggcaag gtgcccatca agtggatggc gctggagtcc   2940
attctccgcc ggcggttcac ccaccagagt gatgtgtgga gttatggtgt gactgtgtgg   3000
gagctgatga cttttggggc caaaccttac gatgggatcc cagcccggga gatccctgac   3060
ctgctggaaa agggggagcg gctgccccag cccccccatct gcaccattga tgtctacatg   3120
atcatggtca aatgttggat gattgactct gaatgtcggc caagattccg ggagttggtg   3180
tctgaattct cccgcatggc cagggacccc cagcgctttg tggtcatcca gaatgaggac   3240
ttgggcccag ccagtccctt ggacagcacc ttctaccgct cactgctgga ggacgatgac   3300
```

```
atgggggacc tggtggatgc tgaggagtat ctggtacccc agcagggctt cttctgtcca   3360

gaccctgccc cgggcgctgg gggcatggtc caccacaggc accgcagctc atctaccagg   3420

agtggcggtg gggacctgac actagggctg gagccctctg aagaggaggc ccccaggtct   3480

ccactggcac cctccgaagg ggctggctcc gatgtatttg atggtgacct gggaatgggg   3540

gcagccaagg ggctgcaaag cctccccaca catgacccca gccctctaca gcggtacagt   3600

gaggacccca cagtacccct gccctctgag actgatggct acgttgcccc cctgacctgc   3660

agcccccagc ctgaatatgt gaaccagcca gatgttcggc cccagccccc ttcgccccga   3720

gagggccctc tgcctgctgc ccgacctgct ggtgccactc tggaaaggcc caagactctc   3780

tccccaggga agaatggggt cgtcaaagac gtttttgcct ttgggggtgc cgtggagaac   3840

cccgagtact tgacacccca gggaggagct gcccctcagc cccaccctcc tcctgccttc   3900

agcccagcct tcgacaacct ctattactgg gaccaggacc caccagagcg gggggctcca   3960

cccagcacct tcaaagggac acctacggca gagaacccag agtacctggg tctggacgtg   4020

ccagtgtgaa ccagaaggcc aagtccgcag aagccctgat gtgtcctcag ggagcaggga   4080

aggcctgact tctgctggca tcaagaggtg ggagggccct ccgaccactt ccaggggaac   4140

ctgccatgcc aggaacctgt cctaaggaac cttccttcct gcttgagttc ccagatggct   4200

ggaaggggtc cagcctcgtt ggaagaggaa cagcactggg gagtctttgt ggattctgag   4260

gccctgccca atgagactct agggtccagt ggatgccaca gcccagcttg gccctttcct   4320

tccagatcct gggtactgaa agccttaggg aagctggcct gagaggggaa gcggccctaa   4380

gggagtgtct aagaacaaaa gcgacccatt cagagactgt ccctgaaacc tagtactgcc   4440

ccccatgagg aaggaacagc aatggtgtca gtatccaggc tttgtacaga gtgcttttct   4500

gtttagtttt tacttttttt gttttgtttt tttaaagatg aaataaagac ccagggggag   4560

aatgggtgtt gtatggggag gcaagtgtgg ggggtccttc tccacaccca ctttgtccat   4620

ttgcaaatat attttggaaa acagctaaaa aaaaaaaaaa aaaa                    4664
```

<210> SEQ ID NO 114
<211> LENGTH: 1255
<212> TYPE: PRT
<213> ORGANISM: Homo sapiens

<400> SEQUENCE: 114

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
```

-continued

```
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560
```

-continued

```
Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975
```

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
        1155                1160                1165

Arg Pro Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Pro Ala Phe Ser Pro Ala
                1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250                1255

<210> SEQ ID NO 115
<211> LENGTH: 181
<212> TYPE: PRT
<213> ORGANISM: Artificial Sequence
<220> FEATURE:
<223> OTHER INFORMATION: HER2 - Class II embedded class I (4 plus 1)

<400> SEQUENCE: 115

Val Val Gln Gly Asn Leu Glu Leu Thr Tyr Leu Pro Thr Asn Ala Ser
 1               5                  10                  15

Leu Ser Phe Leu Gln Asp Ile Gly Gly Gly Gly Ser Gly Gly Gly Gly
            20                  25                  30

Ser Gly Gly Gly Gly Ser Val Leu Ile Ala His Asn Gln Val Arg Gln
        35                  40                  45

Val Pro Leu Gln Arg Leu Arg Ile Val Arg Gly Thr Gln Gly Gly Gly
    50                  55                  60

Gly Ser Gly Gly Gly Gly Ser Gly Gly Gly Gly Ser Lys Ile Phe Gly
65                  70                  75                  80

-continued

```
Ser Leu Ala Phe Leu Pro Glu Ser Phe Asp Gly Asp Pro Ala Gly Gly
                85                  90                  95

Gly Gly Ser Gly Gly Gly Gly Ser Gly Gly Gly Gly Ser Ser Leu Pro
            100                 105                 110

Asp Leu Ser Val Phe Gln Asn Leu Gln Val Ile Arg Gly Arg Ile Leu
        115                 120                 125

His Asn Gly Ala Gly Gly Gly Gly Ser Gly Gly Gly Gly Ser Gly Gly
    130                 135                 140

Gly Gly Ser Gly Gly Lys Val Pro Ile Lys Trp Met Ala Leu Glu Ser
145                 150                 155                 160

Ile Leu Arg Arg Arg Phe Thr His Gln Ser Tyr Thr Asp Ile Glu Met
                165                 170                 175

Asn Arg Leu Gly Lys
            180
```

<210> SEQ ID NO 116
<211> LENGTH: 149
<212> TYPE: PRT
<213> ORGANISM: Artificial Sequence
<220> FEATURE:
<223> OTHER INFORMATION: HER2 - Class II embedded class I (4 plus 1) no flanking AA

<400> SEQUENCE: 116

```
Asn Leu Glu Leu Thr Tyr Leu Pro Thr Asn Ala Ser Leu Ser Phe Gly
 1               5                  10                  15

Gly Gly Gly Ser Gly Gly Gly Gly Ser Gly Gly Gly Gly Ser His Asn
            20                  25                  30

Gln Val Arg Gln Val Pro Leu Gln Arg Leu Arg Ile Val Gly Gly Gly
        35                  40                  45

Gly Ser Gly Gly Gly Gly Ser Gly Gly Gly Gly Ser Lys Ile Phe Gly
    50                  55                  60

Ser Leu Ala Phe Leu Pro Glu Ser Phe Asp Gly Asp Pro Ala Gly Gly
65                  70                  75                  80

Gly Gly Ser Gly Gly Gly Gly Ser Gly Gly Gly Gly Ser Leu Ser Val
                85                  90                  95

Phe Gln Asn Leu Gln Val Ile Arg Gly Arg Ile Leu Gly Gly Gly Gly
            100                 105                 110

Ser Gly Gly Gly Gly Ser Gly Gly Gly Gly Ser Pro Ile Lys Trp Met
        115                 120                 125

Ala Leu Glu Ser Ile Leu Arg Arg Arg Phe Tyr Thr Asp Ile Glu Met
    130                 135                 140

Asn Arg Leu Gly Lys
145
```

<210> SEQ ID NO 117
<211> LENGTH: 15
<212> TYPE: PRT
<213> ORGANISM: Artificial Sequence
<220> FEATURE:
<223> OTHER INFORMATION: HLA Class II HER2

<400> SEQUENCE: 117

```
Asn Leu Glu Leu Thr Tyr Leu Pro Thr Asn Ala Ser Leu Ser Phe
 1               5                  10                  15
```

<210> SEQ ID NO 118
<211> LENGTH: 15
<212> TYPE: PRT

<213> ORGANISM: Artificial Sequence
<220> FEATURE:
<223> OTHER INFORMATION: HLA Class II HER2

<400> SEQUENCE: 118

His Asn Gln Val Arg Gln Val Pro Leu Gln Arg Leu Arg Ile Val
1 5 10 15

<210> SEQ ID NO 119
<211> LENGTH: 15
<212> TYPE: PRT
<213> ORGANISM: Artificial Sequence
<220> FEATURE:
<223> OTHER INFORMATION: HLA Class II HER2

<400> SEQUENCE: 119

Leu Ser Val Phe Gln Asn Leu Gln Val Ile Arg Gly Arg Ile Leu
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: HLA Class II HER2

<400> SEQUENCE: 120

Pro Ile Lys Trp Met Ala Leu Glu Ser Ile Leu Arg Arg Arg Phe
1 5 10 15

<210> SEQ ID NO 121
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 121

Thr Tyr Leu Pro Thr Asn Ala Ser Leu
1 5

<210> SEQ ID NO 122
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 122

Leu Pro Thr Asn Ala Ser Leu Ser Phe
1 5

<210> SEQ ID NO 123
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 123

Thr Tyr Leu Pro Thr Asn Ala Ser Leu
1 5

<210> SEQ ID NO 124
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 124

Gln Val Arg Gln Val Pro Leu Gln Arg
1 5

<210> SEQ ID NO 125
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 125

Val Pro Leu Gln Arg Leu Arg Ile Val
1 5

<210> SEQ ID NO 126
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 126

His Asn Gln Val Arg Gln Val Pro Leu
1 5

<210> SEQ ID NO 127
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 127

Val Pro Leu Gln Arg Leu Arg Ile Val
1 5

<210> SEQ ID NO 128
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 128

Arg Gln Val Pro Leu Gln Arg Leu Arg
1 5

<210> SEQ ID NO 129
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 129

His Asn Gln Val Arg Gln Val Pro Leu
1 5

<210> SEQ ID NO 130
<211> LENGTH: 9
<212> TYPE: PRT
<213> ORGANISM: Artificial Sequence
<220> FEATURE:

<223> OTHER INFORMATION: Embedded HLA Class I peptide HER2

<400> SEQUENCE: 130

Ser Val Phe Gln Asn Leu Gln Val Ile
1 5

<210> SEQ ID NO 131
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 131

Leu Gln Val Ile Arg Gly Arg Ile Leu
1 5

<210> SEQ ID NO 132
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 132

Leu Gln Val Ile Arg Gly Arg Ile Leu
1 5

<210> SEQ ID NO 133
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 133

Met Ala Leu Glu Ser Ile Leu Arg Arg
1 5

<210> SEQ ID NO 134
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 134

Lys Trp Met Ala Leu Glu Ser Ile Leu
1 5

<210> SEQ ID NO 135
<211> LENGTH: 9
<212> TYPE: PRT
<213> ORGANISM: Artificial Sequence
<220> FEATURE:
<223> OTHER INFORMATION: Embedded HLA Class I peptide HER2

<400> SEQUENCE: 135

Leu Glu Ser Ile Leu Arg Arg Arg Phe
1 5

<210> SEQ ID NO 136
<211> LENGTH: 555
<212> TYPE: DNA
<213> ORGANISM: Artificial Sequence
<220> FEATURE:
<223> OTHER INFORMATION: HER2 reverse translated

<400> SEQUENCE: 136
tctagagtgg tgcagggcaa cctggagctg acctacctgc ccaccaacgc cagcctgagc 60
ttcctgcagg acatcggcgg cggcggcagc ggcggcggcg gcagcggcgg cggcggcagc 120
gtgctgatcg cccacaacca ggtgagacag gtgcccctgc agagactgag aatcgtgaga 180
ggcacccagg gcggcggcgg cagcggcggc ggcggcagcg gcggcggcgg cagcaagatc 240
ttcggcagcc tggccttcct gcccgagagc ttcgacggcg accccgccgg cggcggcggc 300
agcggcggcg gcggcagcgg cggcggcggc agcagcctgc ccgacctgag cgtgttccag 360
aacctgcagg tgatcagagg cagaatcctg cacaacggcg ccggcggcgg cggcagcggc 420
ggcggcggca gcggcggcgg cggcagcggc ggcaaggtgc ccatcaagtg gatggccctg 480
gagagcatcc tgagaagaag attcacccac cagagctaca ccgacatcga gatgaacaga 540
ctgggcaagt ctaga 555

<210> SEQ ID NO 137
<211> LENGTH: 976
<212> TYPE: DNA
<213> ORGANISM: Artificial Sequence
<220> FEATURE:
<223> OTHER INFORMATION: MTI-HER2 PAA

<400> SEQUENCE: 137
gggtggagat gtagaagatg tgacgccgcg gcccggcggg tgccagatta gcggacgcgg 60
tgcccgcggt tgcaacggga tcccgggcgc tgcagcttgg gaggcggctc tccccaggcg 120
gcgtccgcgg agacacccat ccgtgaaccc caggtcccgg gccgccggct cgccgcgcac 180
caggggccgg cggacagaag agcggccgag cggctcgagg ctgggggacc gcgggcgcgg 240
ccgcgcgctg ccgggcggga ggctgggggg ccggggccgg ggccgtgccc cggagcgggt 300
cggaggccgg ggccggggcc gggggacggc ggctccccgc gcggctccag cggctcgggg 360
atcccggccg ggccccgcag ggacctctag agtggtgcag ggcaacctgg agctgaccta 420
cctgcccacc aacgccagcc tgagcttcct gcaggacatc ggcggcggcg gcagcggcgg 480
cggcggcagc ggcggcggcg gcagcgtgct gatcgcccac aaccaggtga gacaggtgcc 540
cctgcagaga ctgagaatcg tgagaggcac ccagggcggc ggcggcagcg gcggcggcgg 600
cagcggcggc ggcggcagca agatcttcgg cagcctggcc ttcctgcccg agagcttcga 660
cggcgacccc gccggcggcg gcggcagcgg cggcggcggc agcggcggcg gcggcagcag 720
cctgcccgac ctgagcgtgt tccagaacct gcaggtgatc agaggcagaa tcctgcacaa 780
cggcgccggc ggcggcggca gcggcggcgg cggcagcggc ggcggcggca gcggcggcaa 840
ggtgcccatc aagtggatgg ccctggagag catcctgaga agaagattca cccaccagag 900
ctacaccgac atcgagatga acagactggg caagtctaga tacaccgaca tcgagatgaa 960
cagactgggc aagtaa 976

<210> SEQ ID NO 138
<211> LENGTH: 251
<212> TYPE: PRT
<213> ORGANISM: Artificial Sequence
<220> FEATURE:
<223> OTHER INFORMATION: MTI-HER2 PAA

<400> SEQUENCE: 138

Met Gly Asp Arg Gly Arg Gly Arg Ala Leu Pro Gly Gly Arg Leu Gly
1 5 10 15

-continued

```
Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Ser Arg Val Val Gln Gly Asn Leu Glu
    50                  55                  60

Leu Thr Tyr Leu Pro Thr Asn Ala Ser Leu Ser Phe Leu Gln Asp Ile
65                  70                  75                  80

Gly Gly Gly Gly Ser Gly Gly Gly Gly Ser Gly Gly Gly Gly Ser Val
                85                  90                  95

Leu Ile Ala His Asn Gln Val Arg Gln Val Pro Leu Gln Arg Leu Arg
            100                 105                 110

Ile Val Arg Gly Thr Gln Gly Gly Gly Gly Ser Gly Gly Gly Gly Ser
        115                 120                 125

Gly Gly Gly Gly Ser Lys Ile Phe Gly Ser Leu Ala Phe Leu Pro Glu
    130                 135                 140

Ser Phe Asp Gly Asp Pro Ala Gly Gly Gly Gly Ser Gly Gly Gly Gly
145                 150                 155                 160

Ser Gly Gly Gly Gly Ser Ser Leu Pro Asp Leu Ser Val Phe Gln Asn
                165                 170                 175

Leu Gln Val Ile Arg Gly Arg Ile Leu His Asn Gly Ala Gly Gly Gly
            180                 185                 190

Gly Ser Gly Gly Gly Gly Ser Gly Gly Gly Gly Ser Gly Gly Lys Val
        195                 200                 205

Pro Ile Lys Trp Met Ala Leu Glu Ser Ile Leu Arg Arg Arg Phe Thr
    210                 215                 220

His Gln Ser Tyr Thr Asp Ile Glu Met Asn Arg Leu Gly Lys Ser Arg
225                 230                 235                 240

Tyr Thr Asp Ile Glu Met Asn Arg Leu Gly Lys
                245                 250
```

<210> SEQ ID NO 139
<211> LENGTH: 1582
<212> TYPE: DNA
<213> ORGANISM: Artificial Sequence
<220> FEATURE:
<223> OTHER INFORMATION: MTI-HER2 PAA - secreted

<400> SEQUENCE: 139

```
gggtggagat gtagaagatg tgacgccgcg gcccggcggg tgccagatta gcggacgcgg     60

tgcccgcggt tgcaacggga tcccgggcgc tgcagcttgg gaggcggctc tccccaggcg    120

gcgtccgcgg agacacccat ccgtgaaccc caggtcccgg gccgccggct cgccgcgcac    180

caggggccgg cggacagaag agcggccgag cggctcgagg ctgggggacc gcgggcgcgg    240

ccgcgcgctg ccgggcggga ggctgggggg ccggggccgg ggccgtgccc cggagcgggt    300

cggaggccgg ggccggggcc gggggacggc ggctccccgc gcggctccag cggctcgggg    360

atcccggccg ggccccgcag ggaccaagtg cctgctgtac ctggccttcc tgttcatcgg    420

cgtgaactgc aagttctacc ccagctacca cagcaccccc cagagaccct tcaccatact    480

ttttccacac aaccaaaaag gaaactggaa aaatgttcct tctaattacc attattgccc    540

gtcaagctca gatttaaatt ggcataatga cttaataggc acagccatac aagtcaaaat    600

gcccaagagt cacaaggcta ttcaagcaga cggttggatg tgtcatgctt ccaaatgggt    660

cactacttgt gatttccgct ggtatggacc gaagtatata acacagtcca tccgatcctt    720
```

```
cactccatct gtagaacaat gcaaggaaag cattgaacaa acgaaacaag gaacttggct    780

gaatccaggc ttccctcctc aaagttgtgg atatgcaact gtgacggatg ccgaagcagt    840

gattgtccag gtgactcctc accatgtgct ggttgatgaa tacacaggag aatgggttga    900

ttcacagttc atcaacggaa aatgcagcaa ttacatatgc cccactgtcc ataactctac    960

aacctggcat tctgactata aggtcaaagg gtctagagtg gtgcagggca acctggagct   1020

gacctacctg cccaccaacg ccagcctgag cttcctgcag gacatcggcg gcggcggcag   1080

cggcggcggc ggcagcggcg gcggcggcag cgtgctgatc gcccacaacc aggtgagaca   1140

ggtgcccctg cagagactga gaatcgtgag aggcacccag ggcggcggcg gcagcggcgg   1200

cggcggcagc ggcggcggcg gcagcaagat cttcggcagc ctggccttcc tgcccgagag   1260

cttcgacggc gaccccgccg gcggcggcgg cagcggcggc ggcggcagcg gcggcggcgg   1320

cagcagcctg cccgacctga gcgtgttcca gaacctgcag gtgatcagag gcagaatcct   1380

gcacaacggc gccggcggcg gcggcagcgg cggcggcggc agcggcggcg gcggcagcgg   1440

cggcaaggtg cccatcaagt ggatggccct ggagagcatc ctgagaagaa gattcaccca   1500

ccagagctac accgacatcg agatgaacag actgggcaag tctagataca ccgacatcga   1560

gatgaacaga ctgggcaagt aa                                            1582
```

```
<210> SEQ ID NO 140
<211> LENGTH: 453
<212> TYPE: PRT
<213> ORGANISM: Artificial Sequence
<220> FEATURE:
<223> OTHER INFORMATION: MTI-HER2 PAA - secreted

<400> SEQUENCE: 140

Met Gly Asp Arg Gly Arg Gly Arg Ala Leu Pro Gly Gly Arg Leu Gly
1               5                   10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Lys Cys Leu Leu Tyr Leu Ala Phe Leu
    50                  55                  60

Phe Ile Gly Val Asn Cys Lys Phe Tyr Pro Ser Tyr His Ser Thr Pro
65                  70                  75                  80

Gln Arg Pro Phe Thr Ile Leu Phe Pro His Asn Gln Lys Gly Asn Trp
                85                  90                  95

Lys Asn Val Pro Ser Asn Tyr His Tyr Cys Pro Ser Ser Ser Asp Leu
            100                 105                 110

Asn Trp His Asn Asp Leu Ile Gly Thr Ala Ile Gln Val Lys Met Pro
        115                 120                 125

Lys Ser His Lys Ala Ile Gln Ala Asp Gly Trp Met Cys His Ala Ser
    130                 135                 140

Lys Trp Val Thr Thr Cys Asp Phe Arg Trp Tyr Gly Pro Lys Tyr Ile
145                 150                 155                 160

Thr Gln Ser Ile Arg Ser Phe Thr Pro Ser Val Glu Gln Cys Lys Glu
                165                 170                 175

Ser Ile Glu Gln Thr Lys Gln Gly Thr Trp Leu Asn Pro Gly Phe Pro
            180                 185                 190

Pro Gln Ser Cys Gly Tyr Ala Thr Val Thr Asp Ala Glu Ala Val Ile
        195                 200                 205
```

```
Val Gln Val Thr Pro His His Val Leu Val Asp Glu Tyr Thr Gly Glu
    210                 215                 220

Trp Val Asp Ser Gln Phe Ile Asn Gly Lys Cys Ser Asn Tyr Ile Cys
225                 230                 235                 240

Pro Thr Val His Asn Ser Thr Thr Trp His Ser Asp Tyr Lys Val Lys
                245                 250                 255

Gly Ser Arg Val Val Gln Gly Asn Leu Glu Leu Thr Tyr Leu Pro Thr
            260                 265                 270

Asn Ala Ser Leu Ser Phe Leu Gln Asp Ile Gly Gly Gly Gly Ser Gly
        275                 280                 285

Gly Gly Gly Ser Gly Gly Gly Gly Ser Val Leu Ile Ala His Asn Gln
    290                 295                 300

Val Arg Gln Val Pro Leu Gln Arg Leu Arg Ile Val Arg Gly Thr Gln
305                 310                 315                 320

Gly Gly Gly Gly Ser Gly Gly Gly Gly Ser Gly Gly Gly Gly Ser Lys
                325                 330                 335

Ile Phe Gly Ser Leu Ala Phe Leu Pro Glu Ser Phe Asp Gly Asp Pro
            340                 345                 350

Ala Gly Gly Gly Gly Ser Gly Gly Gly Gly Ser Gly Gly Gly Gly Ser
        355                 360                 365

Ser Leu Pro Asp Leu Ser Val Phe Gln Asn Leu Gln Val Ile Arg Gly
    370                 375                 380

Arg Ile Leu His Asn Gly Ala Gly Gly Gly Gly Ser Gly Gly Gly Gly
385                 390                 395                 400

Ser Gly Gly Gly Gly Ser Gly Gly Lys Val Pro Ile Lys Trp Met Ala
                405                 410                 415

Leu Glu Ser Ile Leu Arg Arg Arg Phe Thr His Gln Ser Tyr Thr Asp
            420                 425                 430

Ile Glu Met Asn Arg Leu Gly Lys Ser Arg Tyr Thr Asp Ile Glu Met
        435                 440                 445

Asn Arg Leu Gly Lys
    450
```

<210> SEQ ID NO 141
<211> LENGTH: 1516
<212> TYPE: DNA
<213> ORGANISM: Artificial Sequence
<220> FEATURE:
<223> OTHER INFORMATION: MTI-HER2 PAA - secreted - VSVG variant

<400> SEQUENCE: 141

```
gggtggagat gtagaagatg tgacgccgcg gcccggcggg tgccagatta gcggacgcgg      60

tgcccgcggt tgcaacggga tcccgggcgc tgcagcttgg gaggcggctc tccccaggcg     120

gcgtccgcgg agacacccat ccgtgaaccc caggtcccgg gccgccggct cgccgcgcac     180

caggggccgg cggacagaag agcggccgag cggctcgagg ctgggggacc gcgggcgcgg     240

ccgcgcgctg ccgggcggga ggctgggggg ccggggccgg ggccgtgccc cggagcgggt     300

cggaggccgg ggccggggcc gggggacggc ggctccccgc gcggctccag cggctcgggg     360

atcccggccg ggccccgcag ggaccaagtg cctgctgtac ctggccttcc tgttcatcgg     420

cgtgaactgc aagttctacc ccagctacca cagcaccccc cagagaccct ctagagtggt     480

gcagggcaac ctggagctga cctacctgcc caccaacgcc agcctgagct tcctgcagga     540

catcggcggc ggcggcagcg gcggcggcgg cagcggcggc ggcggcagcg tgctgatcgc     600
```

-continued

```
ccacaaccag gtgagacagg tgcccctgca gagactgaga atcgtgagag gcacccaggg    660

cggcggcggc agcggcggcg gcggcagcgg cggcggcggc agcaagatct tcggcagcct    720

ggccttcctg cccgagagct tcgacggcga ccccgccggc ggcggcggca gcggcggcgg    780

cggcagcggc ggcggcggca gcagcctgcc cgacctgagc gtgttccaga acctgcaggt    840

gatcagaggc agaatcctgc acaacggcgc cggcggcggc ggcagcggcg gcggcggcag    900

cggcggcggc ggcagcggcg gcaaggtgcc catcaagtgg atggccctgg agagcatcct    960

gagaagaaga ttcacccacc agagctacac cgacatcgag atgaacagac tgggcaagtc   1020

tagacttcca atctctccag tggatctcag ctatcttgct cctaaaaacc caggaaccgg   1080

tcctgctttc accataatca atggtaccct aaaatacttt gagaccagat acatcagagt   1140

cgatattgct gctccaatcc tctcaagaat ggtcggaatg atcagtggaa ctaccacaga   1200

aagggaactg tgggatgact gggcaccata tgaagacgtg gaaattggac ccaatggagt   1260

tctgaggacc agttcaggat ataagtttcc tttatacatg attggacatg gtatgttgga   1320

ctccgatctt catcttagct caaaggctca ggtgttcgaa catcctcaca ttcaagacgc   1380

tgcttcgcaa cttcctgatg atgagagttt attttttggt gatactgggc tatccaaaaa   1440

tccaatcgag cttgtagaag gttggttcag tagttggaaa tacaccgaca tcgagatgaa   1500

cagactgggc aagtaa                                                   1516
```

<210> SEQ ID NO 142
<211> LENGTH: 431
<212> TYPE: PRT
<213> ORGANISM: Artificial Sequence
<220> FEATURE:
<223> OTHER INFORMATION: MTI-HER2 PAA - secreted - VSVG variant

<400> SEQUENCE: 142

```
Met Gly Asp Arg Gly Arg Gly Arg Ala Leu Pro Gly Gly Arg Leu Gly
1               5                   10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Lys Cys Leu Leu Tyr Leu Ala Phe Leu
    50                  55                  60

Phe Ile Gly Val Asn Cys Lys Phe Tyr Pro Ser Tyr His Ser Thr Pro
65                  70                  75                  80

Gln Arg Pro Ser Arg Val Val Gln Gly Asn Leu Glu Leu Thr Tyr Leu
                85                  90                  95

Pro Thr Asn Ala Ser Leu Ser Phe Leu Gln Asp Ile Gly Gly Gly Gly
            100                 105                 110

Ser Gly Gly Gly Gly Ser Gly Gly Gly Gly Ser Val Leu Ile Ala His
        115                 120                 125

Asn Gln Val Arg Gln Val Pro Leu Gln Arg Leu Arg Ile Val Arg Gly
    130                 135                 140

Thr Gln Gly Gly Gly Gly Ser Gly Gly Gly Gly Ser Gly Gly Gly Gly
145                 150                 155                 160

Ser Lys Ile Phe Gly Ser Leu Ala Phe Leu Pro Glu Ser Phe Asp Gly
                165                 170                 175

Asp Pro Ala Gly Gly Gly Gly Ser Gly Gly Gly Gly Ser Gly Gly Gly
            180                 185                 190

Gly Ser Ser Leu Pro Asp Leu Ser Val Phe Gln Asn Leu Gln Val Ile
```

```
        195                 200                 205

Arg Gly Arg Ile Leu His Asn Gly Ala Gly Gly Gly Gly Ser Gly Gly
    210                 215                 220

Gly Gly Ser Gly Gly Gly Gly Ser Gly Gly Lys Val Pro Ile Lys Trp
225                 230                 235                 240

Met Ala Leu Glu Ser Ile Leu Arg Arg Arg Phe Thr His Gln Ser Tyr
                245                 250                 255

Thr Asp Ile Glu Met Asn Arg Leu Gly Lys Ser Arg Leu Pro Ile Ser
            260                 265                 270

Pro Val Asp Leu Ser Tyr Leu Ala Pro Lys Asn Pro Gly Thr Gly Pro
        275                 280                 285

Ala Phe Thr Ile Ile Asn Gly Thr Leu Lys Tyr Phe Glu Thr Arg Tyr
    290                 295                 300

Ile Arg Val Asp Ile Ala Ala Pro Ile Leu Ser Arg Met Val Gly Met
305                 310                 315                 320

Ile Ser Gly Thr Thr Thr Glu Arg Glu Leu Trp Asp Asp Trp Ala Pro
                325                 330                 335

Tyr Glu Asp Val Glu Ile Gly Pro Asn Gly Val Leu Arg Thr Ser Ser
            340                 345                 350

Gly Tyr Lys Phe Pro Leu Tyr Met Ile Gly His Gly Met Leu Asp Ser
        355                 360                 365

Asp Leu His Leu Ser Ser Lys Ala Gln Val Phe Glu His Pro His Ile
    370                 375                 380

Gln Asp Ala Ala Ser Gln Leu Pro Asp Asp Glu Ser Leu Phe Phe Gly
385                 390                 395                 400

Asp Thr Gly Leu Ser Lys Asn Pro Ile Glu Leu Val Glu Gly Trp Phe
                405                 410                 415

Ser Ser Trp Lys Tyr Thr Asp Ile Glu Met Asn Arg Leu Gly Lys
            420                 425                 430


<210> SEQ ID NO 143
<211> LENGTH: 422
<212> TYPE: PRT
<213> ORGANISM: Artificial Sequence
<220> FEATURE:
<223> OTHER INFORMATION: MTI-HER2 PAA - secreted - VSVG variant

<400> SEQUENCE: 143

Leu Pro Gly Gly Arg Leu Gly Gly Arg Gly Arg Gly Arg Ala Pro Glu
 1               5                  10                  15

Arg Val Gly Gly Arg Gly Arg Gly Arg Gly Thr Ala Ala Pro Arg Ala
            20                  25                  30

Ala Pro Ala Ala Arg Gly Ser Arg Pro Gly Pro Ala Gly Thr Lys Cys
        35                  40                  45

Leu Leu Tyr Leu Ala Phe Leu Phe Ile Gly Val Asn Cys Lys Phe Tyr
    50                  55                  60

Pro Ser Tyr His Ser Thr Pro Gln Arg Pro Ser Arg Val Val Gln Gly
65                  70                  75                  80

Asn Leu Glu Leu Thr Tyr Leu Pro Thr Asn Ala Ser Leu Ser Phe Leu
                85                  90                  95

Gln Asp Ile Gly Gly Gly Gly Ser Gly Gly Gly Gly Ser Gly Gly Gly
            100                 105                 110

Gly Ser Val Leu Ile Ala His Asn Gln Val Arg Gln Val Pro Leu Gln
        115                 120                 125

Arg Leu Arg Ile Val Arg Gly Thr Gln Gly Gly Gly Gly Ser Gly Gly
```

```
    130                 135                 140

Gly Gly Ser Gly Gly Gly Gly Ser Lys Ile Phe Gly Ser Leu Ala Phe
145                 150                 155                 160

Leu Pro Glu Ser Phe Asp Gly Asp Pro Ala Gly Gly Gly Gly Ser Gly
                165                 170                 175

Gly Gly Gly Ser Gly Gly Gly Gly Ser Ser Leu Pro Asp Leu Ser Val
            180                 185                 190

Phe Gln Asn Leu Gln Val Ile Arg Gly Arg Ile Leu His Asn Gly Ala
        195                 200                 205

Gly Gly Gly Gly Ser Gly Gly Gly Gly Ser Gly Gly Gly Gly Ser Gly
    210                 215                 220

Gly Lys Val Pro Ile Lys Trp Met Ala Leu Glu Ser Ile Leu Arg Arg
225                 230                 235                 240

Arg Phe Thr His Gln Ser Tyr Thr Asp Ile Glu Met Asn Arg Leu Gly
                245                 250                 255

Lys Ser Arg Leu Pro Ile Ser Pro Val Asp Leu Ser Tyr Leu Ala Pro
            260                 265                 270

Lys Asn Pro Gly Thr Gly Pro Ala Phe Thr Ile Ile Asn Gly Thr Leu
        275                 280                 285

Lys Tyr Phe Glu Thr Arg Tyr Ile Arg Val Asp Ile Ala Ala Pro Ile
    290                 295                 300

Leu Ser Arg Met Val Gly Met Ile Ser Gly Thr Thr Thr Glu Arg Glu
305                 310                 315                 320

Leu Trp Asp Asp Trp Ala Pro Tyr Glu Asp Val Glu Ile Gly Pro Asn
                325                 330                 335

Gly Val Leu Arg Thr Ser Ser Gly Tyr Lys Phe Pro Leu Tyr Met Ile
            340                 345                 350

Gly His Gly Met Leu Asp Ser Asp Leu His Leu Ser Ser Lys Ala Gln
        355                 360                 365

Val Phe Glu His Pro His Ile Gln Asp Ala Ala Ser Gln Leu Pro Asp
    370                 375                 380

Asp Glu Ser Leu Phe Phe Gly Asp Thr Gly Leu Ser Lys Asn Pro Ile
385                 390                 395                 400

Glu Leu Val Glu Gly Trp Phe Ser Ser Trp Lys Tyr Thr Asp Ile Glu
                405                 410                 415

Met Asn Arg Leu Gly Lys
            420


<210> SEQ ID NO 144
<211> LENGTH: 417
<212> TYPE: PRT
<213> ORGANISM: Artificial Sequence
<220> FEATURE:
<223> OTHER INFORMATION: MTI-HER2 PAA - secreted - VSVG variant

<400> SEQUENCE: 144

Leu Gly Gly Arg Gly Arg Gly Arg Ala Pro Glu Arg Val Gly Gly Arg
 1               5                  10                  15

Gly Arg Gly Arg Gly Thr Ala Ala Pro Arg Ala Ala Pro Ala Ala Arg
            20                  25                  30

Gly Ser Arg Pro Gly Pro Ala Gly Thr Lys Cys Leu Leu Tyr Leu Ala
        35                  40                  45

Phe Leu Phe Ile Gly Val Asn Cys Lys Phe Tyr Pro Ser Tyr His Ser
    50                  55                  60

Thr Pro Gln Arg Pro Ser Arg Val Val Gln Gly Asn Leu Glu Leu Thr
```

```
65                  70                  75                  80

Tyr Leu Pro Thr Asn Ala Ser Leu Ser Phe Leu Gln Asp Ile Gly Gly
                85                  90                  95

Gly Gly Ser Gly Gly Gly Gly Ser Gly Gly Gly Gly Ser Val Leu Ile
            100                 105                 110

Ala His Asn Gln Val Arg Gln Val Pro Leu Gln Arg Leu Arg Ile Val
        115                 120                 125

Arg Gly Thr Gln Gly Gly Gly Gly Ser Gly Gly Gly Gly Ser Gly Gly
    130                 135                 140

Gly Gly Ser Lys Ile Phe Gly Ser Leu Ala Phe Leu Pro Glu Ser Phe
145                 150                 155                 160

Asp Gly Asp Pro Ala Gly Gly Gly Gly Ser Gly Gly Gly Gly Ser Gly
                165                 170                 175

Gly Gly Gly Ser Ser Leu Pro Asp Leu Ser Val Phe Gln Asn Leu Gln
            180                 185                 190

Val Ile Arg Gly Arg Ile Leu His Asn Gly Ala Gly Gly Gly Gly Ser
        195                 200                 205

Gly Gly Gly Gly Ser Gly Gly Gly Gly Ser Gly Gly Lys Val Pro Ile
    210                 215                 220

Lys Trp Met Ala Leu Glu Ser Ile Leu Arg Arg Arg Phe Thr His Gln
225                 230                 235                 240

Ser Tyr Thr Asp Ile Glu Met Asn Arg Leu Gly Lys Ser Arg Leu Pro
                245                 250                 255

Ile Ser Pro Val Asp Leu Ser Tyr Leu Ala Pro Lys Asn Pro Gly Thr
            260                 265                 270

Gly Pro Ala Phe Thr Ile Ile Asn Gly Thr Leu Lys Tyr Phe Glu Thr
        275                 280                 285

Arg Tyr Ile Arg Val Asp Ile Ala Ala Pro Ile Leu Ser Arg Met Val
    290                 295                 300

Gly Met Ile Ser Gly Thr Thr Thr Glu Arg Glu Leu Trp Asp Asp Trp
305                 310                 315                 320

Ala Pro Tyr Glu Asp Val Glu Ile Gly Pro Asn Gly Val Leu Arg Thr
                325                 330                 335

Ser Ser Gly Tyr Lys Phe Pro Leu Tyr Met Ile Gly His Gly Met Leu
            340                 345                 350

Asp Ser Asp Leu His Leu Ser Ser Lys Ala Gln Val Phe Glu His Pro
        355                 360                 365

His Ile Gln Asp Ala Ala Ser Gln Leu Pro Asp Asp Glu Ser Leu Phe
    370                 375                 380

Phe Gly Asp Thr Gly Leu Ser Lys Asn Pro Ile Glu Leu Val Glu Gly
385                 390                 395                 400

Trp Phe Ser Ser Trp Lys Tyr Thr Asp Ile Glu Met Asn Arg Leu Gly
                405                 410                 415

Lys
```

<210> SEQ ID NO 145
<211> LENGTH: 2155
<212> TYPE: DNA
<213> ORGANISM: Artificial Sequence
<220> FEATURE:
<223> OTHER INFORMATION: MTI-HER2 PAA - membrane anchored

<400> SEQUENCE: 145

```
gggtggagat gtagaagatg tgacgccgcg gcccggcggg tgccagatta gcggacgcgg     60
```

-continued

```
tgcccgcggt tgcaacggga tcccgggcgc tgcagcttgg gaggcggctc tccccaggcg    120
gcgtccgcgg agacacccat ccgtgaaccc caggtcccgg gccgccggct cgccgcgcac    180
caggggccgg cggacagaag agcggccgag cggctcgagg ctgggggacc gcgggcgcgg    240
ccgcgcgctg ccgggcggga ggctgggggg ccggggccgg ggccgtgccc cggagcgggt    300
cggaggccgg ggccggggcc gggggacggc ggctccccgc gcggctccag cggctcgggg    360
atcccggccg ggccccgcag ggaccaagtg cctttgtac ttagcctttt tattcattgg    420
ggtgaattgc aagttttacc cttcttatca ctctacccca cagcggccta agttcaccat    480
actttttcca cacaaccaaa aaggaaactg gaaaaatgtt ccttctaatt accattattg    540
cccgtcaagc tcagatttaa attggcataa tgacttaata ggcacagcca tacaagtcaa    600
aatgcccaag agtcacaagg ctattcaagc agacggttgg atgtgtcatg cttccaaatg    660
ggtcactact tgtgatttcc gctggtatgg accgaagtat ataacacagt ccatccgatc    720
cttcactcca tctgtagaac aatgcaagga aagcattgaa caaacgaaac aaggaacttg    780
gctgaatcca ggcttccctc ctcaaagttg tggatatgca actgtgacgg atgccgaagc    840
agtgattgtc caggtgactc ctcaccatgt gctggttgat gaatacacag gagaatgggt    900
tgattcacag ttcatcaacg gaaaatgcag caattacata tgccccactg tccataactc    960
tacaacctgg cattctgact ataaggtcaa agggtctaga gtggtgcagg gcaacctgga   1020
gctgacctac ctgcccacca acgccagcct gagcttcctg caggacatcg gcggcggcgg   1080
cagcggcggc ggcggcagcg gcggcggcgg cagcgtgctg atcgcccaca accaggtgag   1140
acaggtgccc ctgcagagac tgagaatcgt gagaggcacc cagggcggcg gcggcagcgg   1200
cggcggcggc agcggcggcg gcggcagcaa gatcttcggc agcctggcct tcctgcccga   1260
gagcttcgac ggcgaccccg ccggcggcgg cggcagcggc ggcggcggca gcggcggcgg   1320
cggcagcagc ctgcccgacc tgagcgtgtt ccagaacctg caggtgatca gaggcagaat   1380
cctgcacaac ggcgccggcg gcggcggcag cggcggcggc ggcagcggcg gcggcggcag   1440
cggcggcaag gtgcccatca agtggatggc cctggagagc atcctgagaa gaagattcac   1500
ccaccagagc tacaccgaca tcgagatgaa cagactgggc aagtctagac ttcccatctc   1560
tccagtggat ctcagctatc ttgctcctaa aaacccagga accggtcctg tctttaccat   1620
aatcaatggt accctaaaat actttgagac cagatacatc agagtcgata ttgctgctcc   1680
aatcctctca agaatggtcg gaatgatcag tggaactacc acagaaaggg aactgtggga   1740
tgactgggct ccatatgaag acgtggaaat tggacccaat ggagttctga ggaccagttt   1800
aggatataag tttcctttat atatgattgg acatggtatg ttggactccg atcttcatct   1860
tagctcaaag gctcaggtgt ttgaacatcc tcacattcaa gacgctgctt cgcagcttcc   1920
tgatgatgag actttatttt ttggtgatac tgggctatcc aaaaatccaa tcgagtttgt   1980
agaaggttgg ttcagtagtt ggaagagctc tattgcctct tttttcttta tcatagggtt   2040
aatcattgga ctattcttgg ttctccgagt tggtatttat ctttgcatta aattaaagca   2100
caccaagaaa agacagattt atacagacat agagatgaac cgacttggaa agtaa        2155
```

<210> SEQ ID NO 146
<211> LENGTH: 644
<212> TYPE: PRT
<213> ORGANISM: Artificial Sequence
<220> FEATURE:
<223> OTHER INFORMATION: MTI-HER2 PAA - membrane anchored

<400> SEQUENCE: 146

-continued

```
Met Gly Asp Arg Gly Arg Gly Arg Ala Leu Pro Gly Gly Arg Leu Gly
 1               5                  10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Lys Cys Leu Leu Tyr Leu Ala Phe Leu
    50                  55                  60

Phe Ile Gly Val Asn Cys Lys Phe Tyr Pro Ser Tyr His Ser Thr Pro
65                  70                  75                  80

Gln Arg Pro Lys Phe Thr Ile Leu Phe Pro His Asn Gln Lys Gly Asn
                85                  90                  95

Trp Lys Asn Val Pro Ser Asn Tyr His Tyr Cys Pro Ser Ser Ser Asp
            100                 105                 110

Leu Asn Trp His Asn Asp Leu Ile Gly Thr Ala Ile Gln Val Lys Met
        115                 120                 125

Pro Lys Ser His Lys Ala Ile Gln Ala Asp Gly Trp Met Cys His Ala
    130                 135                 140

Ser Lys Trp Val Thr Thr Cys Asp Phe Arg Trp Tyr Gly Pro Lys Tyr
145                 150                 155                 160

Ile Thr Gln Ser Ile Arg Ser Phe Thr Pro Ser Val Glu Gln Cys Lys
                165                 170                 175

Glu Ser Ile Glu Gln Thr Lys Gln Gly Thr Trp Leu Asn Pro Gly Phe
            180                 185                 190

Pro Pro Gln Ser Cys Gly Tyr Ala Thr Val Thr Asp Ala Glu Ala Val
        195                 200                 205

Ile Val Gln Val Thr Pro His His Val Leu Val Asp Glu Tyr Thr Gly
    210                 215                 220

Glu Trp Val Asp Ser Gln Phe Ile Asn Gly Lys Cys Ser Asn Tyr Ile
225                 230                 235                 240

Cys Pro Thr Val His Asn Ser Thr Thr Trp His Ser Asp Tyr Lys Val
                245                 250                 255

Lys Gly Ser Arg Val Val Gln Gly Asn Leu Glu Leu Thr Tyr Leu Pro
            260                 265                 270

Thr Asn Ala Ser Leu Ser Phe Leu Gln Asp Ile Gly Gly Gly Gly Ser
        275                 280                 285

Gly Gly Gly Gly Ser Gly Gly Gly Gly Ser Val Leu Ile Ala His Asn
    290                 295                 300

Gln Val Arg Gln Val Pro Leu Gln Arg Leu Arg Ile Val Arg Gly Thr
305                 310                 315                 320

Gln Gly Gly Gly Gly Ser Gly Gly Gly Gly Ser Gly Gly Gly Gly Ser
                325                 330                 335

Lys Ile Phe Gly Ser Leu Ala Phe Leu Pro Glu Ser Phe Asp Gly Asp
            340                 345                 350

Pro Ala Gly Gly Gly Gly Ser Gly Gly Gly Gly Ser Gly Gly Gly Gly
        355                 360                 365

Ser Ser Leu Pro Asp Leu Ser Val Phe Gln Asn Leu Gln Val Ile Arg
    370                 375                 380

Gly Arg Ile Leu His Asn Gly Ala Gly Gly Gly Gly Ser Gly Gly Gly
385                 390                 395                 400

Gly Ser Gly Gly Gly Gly Ser Gly Gly Lys Val Pro Ile Lys Trp Met
                405                 410                 415
```

```
Ala Leu Glu Ser Ile Leu Arg Arg Arg Phe Thr His Gln Ser Tyr Thr
            420                 425                 430

Asp Ile Glu Met Asn Arg Leu Gly Lys Ser Arg Leu Pro Ile Ser Pro
        435                 440                 445

Val Asp Leu Ser Tyr Leu Ala Pro Lys Asn Pro Gly Thr Gly Pro Val
    450                 455                 460

Phe Thr Ile Ile Asn Gly Thr Leu Lys Tyr Phe Glu Thr Arg Tyr Ile
465                 470                 475                 480

Arg Val Asp Ile Ala Ala Pro Ile Leu Ser Arg Met Val Gly Met Ile
                485                 490                 495

Ser Gly Thr Thr Thr Glu Arg Glu Leu Trp Asp Asp Trp Ala Pro Tyr
            500                 505                 510

Glu Asp Val Glu Ile Gly Pro Asn Gly Val Leu Arg Thr Ser Leu Gly
        515                 520                 525

Tyr Lys Phe Pro Leu Tyr Met Ile Gly His Gly Met Leu Asp Ser Asp
    530                 535                 540

Leu His Leu Ser Ser Lys Ala Gln Val Phe Glu His Pro His Ile Gln
545                 550                 555                 560

Asp Ala Ala Ser Gln Leu Pro Asp Asp Glu Thr Leu Phe Phe Gly Asp
                565                 570                 575

Thr Gly Leu Ser Lys Asn Pro Ile Glu Phe Val Glu Gly Trp Phe Ser
            580                 585                 590

Ser Trp Lys Ser Ser Ile Ala Ser Phe Phe Phe Ile Ile Gly Leu Ile
        595                 600                 605

Ile Gly Leu Phe Leu Val Leu Arg Val Gly Ile Tyr Leu Cys Ile Lys
    610                 615                 620

Leu Lys His Thr Lys Lys Arg Gln Ile Tyr Thr Asp Ile Glu Met Asn
625                 630                 635                 640

Arg Leu Gly Lys


<210> SEQ ID NO 147
<211> LENGTH: 635
<212> TYPE: PRT
<213> ORGANISM: Artificial Sequence
<220> FEATURE:
<223> OTHER INFORMATION: MTI-HER2 PAA - membrane anchored

<400> SEQUENCE: 147

Leu Pro Gly Gly Arg Leu Gly Gly Arg Gly Arg Gly Arg Ala Pro Glu
 1               5                  10                  15

Arg Val Gly Gly Arg Gly Arg Gly Arg Gly Thr Ala Ala Pro Arg Ala
            20                  25                  30

Ala Pro Ala Ala Arg Gly Ser Arg Pro Gly Pro Ala Gly Thr Lys Cys
        35                  40                  45

Leu Leu Tyr Leu Ala Phe Leu Phe Ile Gly Val Asn Cys Lys Phe Tyr
    50                  55                  60

Pro Ser Tyr His Ser Thr Pro Gln Arg Pro Lys Phe Thr Ile Leu Phe
65                  70                  75                  80

Pro His Asn Gln Lys Gly Asn Trp Lys Asn Val Pro Ser Asn Tyr His
                85                  90                  95

Tyr Cys Pro Ser Ser Ser Asp Leu Asn Trp His Asn Asp Leu Ile Gly
            100                 105                 110

Thr Ala Ile Gln Val Lys Met Pro Lys Ser His Lys Ala Ile Gln Ala
        115                 120                 125

Asp Gly Trp Met Cys His Ala Ser Lys Trp Val Thr Thr Cys Asp Phe
```

```
    130                 135                 140

Arg Trp Tyr Gly Pro Lys Tyr Ile Thr Gln Ser Ile Arg Ser Phe Thr
145                 150                 155                 160

Pro Ser Val Glu Gln Cys Lys Glu Ser Ile Glu Gln Thr Lys Gln Gly
                165                 170                 175

Thr Trp Leu Asn Pro Gly Phe Pro Pro Gln Ser Cys Gly Tyr Ala Thr
            180                 185                 190

Val Thr Asp Ala Glu Ala Val Ile Val Gln Val Thr Pro His His Val
        195                 200                 205

Leu Val Asp Glu Tyr Thr Gly Glu Trp Val Asp Ser Gln Phe Ile Asn
    210                 215                 220

Gly Lys Cys Ser Asn Tyr Ile Cys Pro Thr Val His Asn Ser Thr Thr
225                 230                 235                 240

Trp His Ser Asp Tyr Lys Val Lys Gly Ser Arg Val Val Gln Gly Asn
                245                 250                 255

Leu Glu Leu Thr Tyr Leu Pro Thr Asn Ala Ser Leu Ser Phe Leu Gln
            260                 265                 270

Asp Ile Gly Gly Gly Gly Ser Gly Gly Gly Gly Ser Gly Gly Gly Gly
        275                 280                 285

Ser Val Leu Ile Ala His Asn Gln Val Arg Gln Val Pro Leu Gln Arg
    290                 295                 300

Leu Arg Ile Val Arg Gly Thr Gln Gly Gly Gly Gly Ser Gly Gly Gly
305                 310                 315                 320

Gly Ser Gly Gly Gly Gly Ser Lys Ile Phe Gly Ser Leu Ala Phe Leu
                325                 330                 335

Pro Glu Ser Phe Asp Gly Asp Pro Ala Gly Gly Gly Gly Ser Gly Gly
            340                 345                 350

Gly Gly Ser Gly Gly Gly Gly Ser Ser Leu Pro Asp Leu Ser Val Phe
        355                 360                 365

Gln Asn Leu Gln Val Ile Arg Gly Arg Ile Leu His Asn Gly Ala Gly
    370                 375                 380

Gly Gly Gly Ser Gly Gly Gly Gly Ser Gly Gly Gly Gly Ser Gly Gly
385                 390                 395                 400

Lys Val Pro Ile Lys Trp Met Ala Leu Glu Ser Ile Leu Arg Arg Arg
                405                 410                 415

Phe Thr His Gln Ser Tyr Thr Asp Ile Glu Met Asn Arg Leu Gly Lys
            420                 425                 430

Ser Arg Leu Pro Ile Ser Pro Val Asp Leu Ser Tyr Leu Ala Pro Lys
        435                 440                 445

Asn Pro Gly Thr Gly Pro Val Phe Thr Ile Ile Asn Gly Thr Leu Lys
    450                 455                 460

Tyr Phe Glu Thr Arg Tyr Ile Arg Val Asp Ile Ala Ala Pro Ile Leu
465                 470                 475                 480

Ser Arg Met Val Gly Met Ile Ser Gly Thr Thr Thr Glu Arg Glu Leu
                485                 490                 495

Trp Asp Asp Trp Ala Pro Tyr Glu Asp Val Glu Ile Gly Pro Asn Gly
            500                 505                 510

Val Leu Arg Thr Ser Leu Gly Tyr Lys Phe Pro Leu Tyr Met Ile Gly
        515                 520                 525

His Gly Met Leu Asp Ser Asp Leu His Leu Ser Ser Lys Ala Gln Val
    530                 535                 540

Phe Glu His Pro His Ile Gln Asp Ala Ala Ser Gln Leu Pro Asp Asp
545                 550                 555                 560
```

Glu Thr Leu Phe Phe Gly Asp Thr Gly Leu Ser Lys Asn Pro Ile Glu
565 570 575

Phe Val Glu Gly Trp Phe Ser Ser Trp Lys Ser Ser Ile Ala Ser Phe
580 585 590

Phe Phe Ile Ile Gly Leu Ile Ile Gly Leu Phe Leu Val Leu Arg Val
595 600 605

Gly Ile Tyr Leu Cys Ile Lys Leu Lys His Thr Lys Lys Arg Gln Ile
610 615 620

Tyr Thr Asp Ile Glu Met Asn Arg Leu Gly Lys
625 630 635

<210> SEQ ID NO 148
<211> LENGTH: 630
<212> TYPE: PRT
<213> ORGANISM: Artificial Sequence
<220> FEATURE:
<223> OTHER INFORMATION: MTI-HER2 PAA - membrane anchored

<400> SEQUENCE: 148

Leu Gly Gly Arg Gly Arg Gly Arg Ala Pro Glu Arg Val Gly Gly Arg
1 5 10 15

Gly Arg Gly Arg Gly Thr Ala Ala Pro Arg Ala Ala Pro Ala Ala Arg
20 25 30

Gly Ser Arg Pro Gly Pro Ala Gly Thr Lys Cys Leu Leu Tyr Leu Ala
35 40 45

Phe Leu Phe Ile Gly Val Asn Cys Lys Phe Tyr Pro Ser Tyr His Ser
50 55 60

Thr Pro Gln Arg Pro Lys Phe Thr Ile Leu Phe Pro His Asn Gln Lys
65 70 75 80

Gly Asn Trp Lys Asn Val Pro Ser Asn Tyr His Tyr Cys Pro Ser Ser
85 90 95

Ser Asp Leu Asn Trp His Asn Asp Leu Ile Gly Thr Ala Ile Gln Val
100 105 110

Lys Met Pro Lys Ser His Lys Ala Ile Gln Ala Asp Gly Trp Met Cys
115 120 125

His Ala Ser Lys Trp Val Thr Thr Cys Asp Phe Arg Trp Tyr Gly Pro
130 135 140

Lys Tyr Ile Thr Gln Ser Ile Arg Ser Phe Thr Pro Ser Val Glu Gln
145 150 155 160

Cys Lys Glu Ser Ile Glu Gln Thr Lys Gln Gly Thr Trp Leu Asn Pro
165 170 175

Gly Phe Pro Pro Gln Ser Cys Gly Tyr Ala Thr Val Thr Asp Ala Glu
180 185 190

Ala Val Ile Val Gln Val Thr Pro His His Val Leu Val Asp Glu Tyr
195 200 205

Thr Gly Glu Trp Val Asp Ser Gln Phe Ile Asn Gly Lys Cys Ser Asn
210 215 220

Tyr Ile Cys Pro Thr Val His Asn Ser Thr Thr Trp His Ser Asp Tyr
225 230 235 240

Lys Val Lys Gly Ser Arg Val Val Gln Gly Asn Leu Glu Leu Thr Tyr
245 250 255

Leu Pro Thr Asn Ala Ser Leu Ser Phe Leu Gln Asp Ile Gly Gly Gly
260 265 270

Gly Ser Gly Gly Gly Gly Ser Gly Gly Gly Gly Ser Val Leu Ile Ala
275 280 285

```
His Asn Gln Val Arg Gln Val Pro Leu Gln Arg Leu Arg Ile Val Arg
    290                 295                 300

Gly Thr Gln Gly Gly Gly Gly Ser Gly Gly Gly Gly Ser Gly Gly Gly
305                 310                 315                 320

Gly Ser Lys Ile Phe Gly Ser Leu Ala Phe Leu Pro Glu Ser Phe Asp
                325                 330                 335

Gly Asp Pro Ala Gly Gly Gly Gly Ser Gly Gly Gly Gly Ser Gly Gly
            340                 345                 350

Gly Gly Ser Ser Leu Pro Asp Leu Ser Val Phe Gln Asn Leu Gln Val
        355                 360                 365

Ile Arg Gly Arg Ile Leu His Asn Gly Ala Gly Gly Gly Gly Ser Gly
    370                 375                 380

Gly Gly Gly Ser Gly Gly Gly Gly Ser Gly Gly Lys Val Pro Ile Lys
385                 390                 395                 400

Trp Met Ala Leu Glu Ser Ile Leu Arg Arg Arg Phe Thr His Gln Ser
                405                 410                 415

Tyr Thr Asp Ile Glu Met Asn Arg Leu Gly Lys Ser Arg Leu Pro Ile
            420                 425                 430

Ser Pro Val Asp Leu Ser Tyr Leu Ala Pro Lys Asn Pro Gly Thr Gly
        435                 440                 445

Pro Val Phe Thr Ile Ile Asn Gly Thr Leu Lys Tyr Phe Glu Thr Arg
    450                 455                 460

Tyr Ile Arg Val Asp Ile Ala Ala Pro Ile Leu Ser Arg Met Val Gly
465                 470                 475                 480

Met Ile Ser Gly Thr Thr Thr Glu Arg Glu Leu Trp Asp Asp Trp Ala
                485                 490                 495

Pro Tyr Glu Asp Val Glu Ile Gly Pro Asn Gly Val Leu Arg Thr Ser
            500                 505                 510

Leu Gly Tyr Lys Phe Pro Leu Tyr Met Ile Gly His Gly Met Leu Asp
        515                 520                 525

Ser Asp Leu His Leu Ser Ser Lys Ala Gln Val Phe Glu His Pro His
    530                 535                 540

Ile Gln Asp Ala Ala Ser Gln Leu Pro Asp Asp Glu Thr Leu Phe Phe
545                 550                 555                 560

Gly Asp Thr Gly Leu Ser Lys Asn Pro Ile Glu Phe Val Glu Gly Trp
                565                 570                 575

Phe Ser Ser Trp Lys Ser Ser Ile Ala Ser Phe Phe Phe Ile Ile Gly
            580                 585                 590

Leu Ile Ile Gly Leu Phe Leu Val Leu Arg Val Gly Ile Tyr Leu Cys
        595                 600                 605

Ile Lys Leu Lys His Thr Lys Lys Arg Gln Ile Tyr Thr Asp Ile Glu
    610                 615                 620

Met Asn Arg Leu Gly Lys
625                 630
```

<210> SEQ ID NO 149
<211> LENGTH: 1630
<212> TYPE: DNA
<213> ORGANISM: Artificial Sequence
<220> FEATURE:
<223> OTHER INFORMATION: MTI-HER2 PAA - membrane anchored variant 2

<400> SEQUENCE: 149

```
gggtggagat gtagaagatg tgacgccgcg gcccggcggg tgccagatta gcggacgcgg     60
```

```
tgcccgcggt tgcaacggga tcccgggcgc tgcagcttgg gaggcggctc tccccaggcg    120

gcgtccgcgg agacacccat ccgtgaaccc caggtcccgg gccgccggct cgccgcgcac    180

caggggccgg cggacagaag agcggccgag cggctcgagg ctgggggacc gcgggcgcgg    240

ccgcgcgctg ccgggcggga ggctgggggg ccggggccgg ggccgtgccc cggagcgggt    300

cggaggccgg ggccggggcc gggggacggc ggctccccgc gcggctccag cggctcgggg    360

atcccggccg ggccccgcag ggaccaagtg ccttttgtac ttagcctttt tattcattgg    420

ggtgaattgc aagttttacc cttcttatca ctctacccca cagcggcctt ctagagtggt    480

gcagggcaac ctggagctga cctacctgcc caccaacgcc agcctgagct tcctgcagga    540

catcggcggc ggcggcagcg gcggcggcgg cagcggcggc ggcggcagcg tgctgatcgc    600

ccacaaccag gtgagacagg tgcccctgca gagactgaga atcgtgagag gcacccaggg    660

cggcggcggc agcggcggcg gcggcagcgg cggcggcggc agcaagatct tcggcagcct    720

ggccttcctg cccgagagct tcgacggcga ccccgccggc ggcggcggca gcggcggcgg    780

cggcagcggc ggcggcggca gcagcctgcc cgacctgagc gtgttccaga acctgcaggt    840

gatcagaggc agaatcctgc acaacggcgc cggcggcggc ggcagcggcg gcggcggcag    900

cggcggcggc ggcagcggcg gcaaggtgcc catcaagtgg atggccctgg agagcatcct    960

gagaagaaga ttcacccacc agagctacac cgacatcgag atgaacagac tgggcaagtc   1020

tagacttccc atctctccag tggatctcag ctatcttgct cctaaaaacc caggaaccgg   1080

tcctgtcttt accataatca atggtaccct aaaatacttt gagaccagat acatcagagt   1140

cgatattgct gctccaatcc tctcaagaat ggtcggaatg atcagtggaa ctaccacaga   1200

aagggaactg tgggatgact gggctccata tgaagacgtg gaaattggac ccaatggagt   1260

tctgaggacc agtttaggat ataagtttcc tttatatatg attggacatg gtatgttgga   1320

ctccgatctt catcttagct caaaggctca ggtgtttgaa catcctcaca ttcaagacgc   1380

tgcttcgcag cttcctgatg atgagacttt attttttggt gatactgggc tatccaaaaa   1440

tccaatcgag tttgtagaag gttggttcag tagttggaag agctctattg cctctttttt   1500

ctttatcata gggttaatca ttggactatt cttggttctc cgagttggta tttatctttg   1560

cattaaatta aagcacacca agaaaagaca gatttataca gacatagaga tgaaccgact   1620

tggaaagtaa                                                          1630
```

<210> SEQ ID NO 150
<211> LENGTH: 469
<212> TYPE: PRT
<213> ORGANISM: Artificial Sequence
<220> FEATURE:
<223> OTHER INFORMATION: MTI-HER2 PAA - membrane anchored variant 2

<400> SEQUENCE: 150

```
Met Gly Asp Arg Gly Arg Gly Arg Ala Leu Pro Gly Gly Arg Leu Gly
 1               5                  10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Lys Cys Leu Leu Tyr Leu Ala Phe Leu
    50                  55                  60

Phe Ile Gly Val Asn Cys Lys Phe Tyr Pro Ser Tyr His Ser Thr Pro
65                  70                  75                  80
```

-continued

```
Gln Arg Pro Ser Arg Val Val Gln Gly Asn Leu Glu Leu Thr Tyr Leu
                85                  90                  95

Pro Thr Asn Ala Ser Leu Ser Phe Leu Gln Asp Ile Gly Gly Gly Gly
            100                 105                 110

Ser Gly Gly Gly Gly Ser Gly Gly Gly Gly Ser Val Leu Ile Ala His
        115                 120                 125

Asn Gln Val Arg Gln Val Pro Leu Gln Arg Leu Arg Ile Val Arg Gly
    130                 135                 140

Thr Gln Gly Gly Gly Gly Ser Gly Gly Gly Gly Ser Gly Gly Gly Gly
145                 150                 155                 160

Ser Lys Ile Phe Gly Ser Leu Ala Phe Leu Pro Glu Ser Phe Asp Gly
                165                 170                 175

Asp Pro Ala Gly Gly Gly Gly Ser Gly Gly Gly Gly Ser Gly Gly Gly
            180                 185                 190

Gly Ser Ser Leu Pro Asp Leu Ser Val Phe Gln Asn Leu Gln Val Ile
        195                 200                 205

Arg Gly Arg Ile Leu His Asn Gly Ala Gly Gly Gly Gly Ser Gly Gly
    210                 215                 220

Gly Gly Ser Gly Gly Gly Gly Ser Gly Gly Lys Val Pro Ile Lys Trp
225                 230                 235                 240

Met Ala Leu Glu Ser Ile Leu Arg Arg Arg Phe Thr His Gln Ser Tyr
                245                 250                 255

Thr Asp Ile Glu Met Asn Arg Leu Gly Lys Ser Arg Leu Pro Ile Ser
            260                 265                 270

Pro Val Asp Leu Ser Tyr Leu Ala Pro Lys Asn Pro Gly Thr Gly Pro
        275                 280                 285

Val Phe Thr Ile Ile Asn Gly Thr Leu Lys Tyr Phe Glu Thr Arg Tyr
    290                 295                 300

Ile Arg Val Asp Ile Ala Ala Pro Ile Leu Ser Arg Met Val Gly Met
305                 310                 315                 320

Ile Ser Gly Thr Thr Thr Glu Arg Glu Leu Trp Asp Asp Trp Ala Pro
                325                 330                 335

Tyr Glu Asp Val Glu Ile Gly Pro Asn Gly Val Leu Arg Thr Ser Leu
            340                 345                 350

Gly Tyr Lys Phe Pro Leu Tyr Met Ile Gly His Gly Met Leu Asp Ser
        355                 360                 365

Asp Leu His Leu Ser Ser Lys Ala Gln Val Phe Glu His Pro His Ile
    370                 375                 380

Gln Asp Ala Ala Ser Gln Leu Pro Asp Asp Glu Thr Leu Phe Phe Gly
385                 390                 395                 400

Asp Thr Gly Leu Ser Lys Asn Pro Ile Glu Phe Val Glu Gly Trp Phe
                405                 410                 415

Ser Ser Trp Lys Ser Ser Ile Ala Ser Phe Phe Phe Ile Ile Gly Leu
            420                 425                 430

Ile Ile Gly Leu Phe Leu Val Leu Arg Val Gly Ile Tyr Leu Cys Ile
        435                 440                 445

Lys Leu Lys His Thr Lys Lys Arg Gln Ile Tyr Thr Asp Ile Glu Met
    450                 455                 460

Asn Arg Leu Gly Lys
465
```

<210> SEQ ID NO 151
<211> LENGTH: 4304
<212> TYPE: DNA

<213> ORGANISM: Homo sapiens

<400> SEQUENCE: 151

```
cacacggact acaggggagt tttgttgaag ttgcaaagtc ctggagcctc cagagggctg     60
tcggcgcagt agcagcgagc agcagagtcc gcacgctccg gcgaggggca gaagagcgcg    120
agggagcgcg gggcagcaga agcgagagcc gagcgcggac ccagccagga cccacagccc    180
tccccagctg cccaggaaga gccccagcca tggaacacca gctcctgtgc tgcgaagtgg    240
aaaccatccg ccgcgcgtac cccgatgcca acctcctcaa cgaccgggtg ctgcgggcca    300
tgctgaaggc ggaggagacc tgcgcgccct cggtgtccta cttcaaatgt gtgcagaagg    360
aggtcctgcc gtccatgcgg aagatcgtcg ccacctggat gctggaggtc tgcgaggaac    420
agaagtgcga ggaggaggtc ttcccgctgg ccatgaacta cctggaccgc ttcctgtcgc    480
tggagcccgt gaaaaagagc cgcctgcagc tgctgggggc cacttgcatg ttcgtggcct    540
ctaagatgaa ggagaccatc cccctgacgg ccgagaagct gtgcatctac accgacaact    600
ccatccggcc cgaggagctg ctgcaaatgg agctgctcct ggtgaacaag ctcaagtgga    660
acctggccgc aatgaccccg cacgatttca ttgaacactt cctctccaaa atgccagagg    720
cggaggagaa caaacagatc atccgcaaac acgcgcagac cttcgttgcc ctctgtgcca    780
cagatgtgaa gttcatttcc aatccgccct ccatggtggc agcggggagc gtggtggccg    840
cagtgcaagg cctgaacctg aggagcccca acaacttcct gtcctactac cgcctcacac    900
gcttcctctc cagagtgatc aagtgtgacc cggactgcct ccgggcctgc caggagcaga    960
tcgaagccct gctggagtca agcctgcgcc aggcccagca gaacatggac cccaaggccg   1020
ccgaggagga ggaagaggag gaggaggagg tggacctggc ttgcacaccc accgacgtgc   1080
gggacgtgga catctgaggg cgccaggcag gcgggcgcca ccgccacccg cagcgagggc   1140
ggagccggcc ccaggtgctc ccctgacagt ccctcctctc cggagcattt tgataccaga   1200
agggaaagct tcattctcct tgttgttggt tgtttttttcc tttgctcttt ccccccttcca   1260
tctctgactt aagcaaaaga aaaagattac ccaaaaactg tctttaaaag agagagagag   1320
aaaaaaaaaa tagtatttgc ataaccctga gcggtggggg aggagggttg tgctacagat   1380
gatagaggat tttatacccc aataatcaac tcgtttttat attaatgtac ttgtttctct   1440
gttgtaagaa taggcattaa cacaaaggag gcgtctcggg agaggattag gttccatcct   1500
ttacgtgttt aaaaaaaagc ataaaaacat tttaaaaaca tagaaaaatt cagcaaacca   1560
tttttaaagt agaagagggt tttaggtaga aaaacatatt cttgtgcttt tcctgataaa   1620
gcacagctgt agtggggttc taggcatctc tgtactttgc ttgctcatat gcatgtagtc   1680
actttataag tcattgtatg ttattatatt ccgtaggtag atgtgtaacc tcttcacctt   1740
attcatggct gaagtcacct cttggttaca gtagcgtagc gtgcccgtgt gcatgtcctt   1800
tgcgcctgtg accaccaccc caacaaacca tccagtgaca aaccatccag tggaggtttg   1860
tcgggcacca gccagcgtag cagggtcggg aaaggccacc tgtcccactc ctacgatacg   1920
ctactataaa gagaagacga aatagtgaca taatatattc tatttttata ctcttcctat   1980
ttttgtagtg acctgtttat gagatgctgg ttttctaccc aacggccctg cagccagctc   2040
acgtccaggt tcaacccaca gctacttggt ttgtgttctt cttcatattc taaaaccatt   2100
ccatttccaa gcactttcag tccaataggt gtaggaaata gcgctgtttt tgttgtgtgt   2160
gcagggaggg cagttttcta atggaatggt ttgggaatat ccatgtactt gtttgcaagc   2220
aggactttga ggcaagtgtg ggccactgtg gtggcagtgg aggtggggtg tttgggaggc   2280
```

```
tgcgtgccag tcaagaagaa aaaggtttgc attctcacat tgccaggatg ataagttcct   2340

ttccttttct ttaaagaagt tgaagtttag gaatcctttg gtgccaactg gtgtttgaaa   2400

gtagggacct cagaggttta cctagagaac aggtggtttt taagggttat cttagatgtt   2460

tcacaccgga aggtttttaa acactaaaat atataattta tagttaaggc taaaaagtat   2520

atttattgca gaggatgttc ataaggccag tatgatttat aaatgcaatc tccccttgat   2580

ttaaacacac agatacacac acacacacac acacacacaa accttctgcc tttgatgtta   2640

cagatttaat acagtttatt tttaaagata gatcctttta taggtgagaa aaaaacaatc   2700

tggaagaaaa aaaccacaca aagacattga ttcagcctgt ttggcgtttc ccagagtcat   2760

ctgattggac aggcatgggt gcaaggaaaa ttagggtact caacctaagt tcggttccga   2820

tgaattctta tcccctgccc cttcctttaa aaaacttagt gacaaaatag acaatttgca   2880

catcttggct atgtaattct tgtaattttt atttaggaag tgttgaaggg aggtggcaag   2940

agtgtggagg ctgacgtgtg agggaggaca ggcgggagga ggtgtgagga ggaggctccc   3000

gaggggaagg ggcggtgccc acaccgggga caggccgcag ctccattttc ttattgcgct   3060

gctaccgttg acttccaggc acggtttgga aatattcaca tcgcttctgt gtatctcttt   3120

cacattgttt gctgctattg gaggatcagt tttttgtttt acaatgtcat atactgccat   3180

gtactagttt tagttttctc ttagaacatt gtattacaga tgcctttttt gtagtttttt   3240

tttttttat gtgatcaatt ttgacttaat gtgattactg ctctattcca aaaaggttgc   3300

tgtttcacaa tacctcatgc ttcacttagc catggtggac ccagcgggca ggttctgcct   3360

gctttggcgg gcagacacgc gggcgcgatc ccacacaggc tggcgggggc cggccccgag   3420

gccgcgtgcg tgagaaccgc gccggtgtcc ccagagacca ggctgtgtcc ctcttctctt   3480

ccctgcgcct gtgatgctgg gcacttcatc tgatcggggg cgtagcatca tagtagtttt   3540

tacagctgtg ttattctttg cgtgtagcta tggaagttgc ataattatta ttattattat   3600

tataacaagt gtgtcttacg tgccaccacg gcgttgtacc tgtaggactc tcattcggga   3660

tgattggaat agcttctgga atttgttcaa gttttgggta tgtttaatct gttatgtact   3720

agtgttctgt ttgttattgt tttgttaatt acaccataat gctaatttaa agagactcca   3780

aatctcaatg aagccagctc acagtgctgt gtgccccggt cacctagcaa gctgccgaac   3840

caaaagaatt tgcaccccgc tgcgggccca cgtggttggg gccctgccct ggcagggtca   3900

tcctgtgctc ggaggccatc tcgggcacag gcccaccccg ccccacccct ccagaacacg   3960

gctcacgctt acctcaacca tcctggctgc ggcgtctgtc tgaaccacgc gggggccttg   4020

agggacgctt tgtctgtcgt gatggggcaa gggcacaagt cctggatgtt gtgtgtatcg   4080

agaggccaaa ggctggtggc aagtgcacgg ggcacagcgg agtctgtcct gtgacgcgca   4140

agtctgaggg tctgggcggc gggcggctgg gtctgtgcat ttctggttgc accgcggcgc   4200

ttcccagcac caacatgtaa ccggcatgtt tccagcagaa gacaaaaaga caaacatgaa   4260

agtctagaaa taaaactggt aaaaccccaa aaaaaaaaaa aaaa                    4304
```

<210> SEQ ID NO 152
<211> LENGTH: 295
<212> TYPE: PRT
<213> ORGANISM: Homo sapiens

<400> SEQUENCE: 152

```
Met Glu His Gln Leu Leu Cys Cys Glu Val Glu Thr Ile Arg Arg Ala
 1               5                  10                  15
```

```
Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
        275                 280                 285

Asp Val Arg Asp Val Asp Ile
    290                 295
```

<210> SEQ ID NO 153
<211> LENGTH: 15
<212> TYPE: PRT
<213> ORGANISM: Artificial Sequence
<220> FEATURE:
<223> OTHER INFORMATION: Class II Cyclin D1

<400> SEQUENCE: 153

```
His Gln Leu Leu Cys Cys Glu Val Glu Thr Ile Arg Arg Ala Tyr
 1               5                  10                  15
```

<210> SEQ ID NO 154
<211> LENGTH: 15
<212> TYPE: PRT
<213> ORGANISM: Artificial Sequence
<220> FEATURE:
<223> OTHER INFORMATION: Class II Cyclin D1

<400> SEQUENCE: 154

```
Gln Lys Glu Val Leu Pro Ser Met Arg Lys Ile Val Ala Thr Trp
```

1 5 10 15

<210> SEQ ID NO 155
<211> LENGTH: 15
<212> TYPE: PRT
<213> ORGANISM: Artificial Sequence
<220> FEATURE:
<223> OTHER INFORMATION: Class II Cyclin D1

<400> SEQUENCE: 155

Leu Pro Ser Met Arg Lys Ile Val Ala Thr Trp Met Leu Glu Val
1 5 10 15

<210> SEQ ID NO 156
<211> LENGTH: 14
<212> TYPE: PRT
<213> ORGANISM: Artificial Sequence
<220> FEATURE:
<223> OTHER INFORMATION: Class II Cyclin D1

<400> SEQUENCE: 156

Leu Gln Leu Leu Gly Ala Thr Cys Met Phe Val Ala Ser Lys
1 5 10

<210> SEQ ID NO 157
<211> LENGTH: 12
<212> TYPE: PRT
<213> ORGANISM: Artificial Sequence
<220> FEATURE:
<223> OTHER INFORMATION: Class II Cyclin D1

<400> SEQUENCE: 157

Leu Leu Gln Met Glu Leu Leu Leu Val Asn Lys Leu
1 5 10

<210> SEQ ID NO 158
<211> LENGTH: 15
<212> TYPE: PRT
<213> ORGANISM: Artificial Sequence
<220> FEATURE:
<223> OTHER INFORMATION: Class II Cyclin D1

<400> SEQUENCE: 158

Val Asn Lys Leu Lys Trp Asn Leu Ala Ala Met Thr Pro His Asp
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: Class II Cyclin D1

<400> SEQUENCE: 159

Asn Lys Gln Ile Ile Arg Lys His Ala Gln Thr Phe Val Ala Leu
1 5 10 15

<210> SEQ ID NO 160
<211> LENGTH: 15
<212> TYPE: PRT
<213> ORGANISM: Artificial Sequence
<220> FEATURE:
<223> OTHER INFORMATION: Class II Cyclin D1

<400> SEQUENCE: 160

Pro Pro Ser Met Val Ala Ala Gly Ser Val Val Ala Ala Val Gln
1 5 10 15

<210> SEQ ID NO 161
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 161

Glu Val Glu Thr Ile Arg Arg Ala Tyr
1 5

<210> SEQ ID NO 162
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 162

Leu Leu Cys Cys Glu Val Glu Thr Ile
1 5

<210> SEQ ID NO 163
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 163

Lys Glu Val Leu Pro Ser Met Arg Lys
1 5

<210> SEQ ID NO 164
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 164

Glu Val Leu Pro Ser Met Arg Lys Ile
1 5

<210> SEQ ID NO 165
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 165

Leu Pro Ser Met Arg Lys Ile Val Ala
1 5

<210> SEQ ID NO 166
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 166

Ser Met Arg Lys Ile Val Ala Thr Trp
1 5

<210> SEQ ID NO 167
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 167

Ile Val Ala Thr Trp Met Leu Glu Val
1 5

<210> SEQ ID NO 168
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 168

Leu Pro Ser Met Arg Lys Ile Val Ala
1 5

<210> SEQ ID NO 169
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 169

Arg Lys Ile Val Ala Thr Trp Met Leu
1 5

<210> SEQ ID NO 170
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 170

Met Arg Lys Ile Val Ala Thr Trp Met
1 5

<210> SEQ ID NO 171
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 171

Ser Met Arg Lys Ile Val Ala Thr Trp
1 5

<210> SEQ ID NO 172
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 172

Leu Leu Gly Ala Thr Cys Met Phe Val
1 5

<210> SEQ ID NO 173
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 173

Ala Thr Cys Met Phe Val Ala Ser Lys
1 5

<210> SEQ ID NO 174
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 174

Gln Leu Leu Gly Ala Thr Cys Met Phe
1 5

<210> SEQ ID NO 175
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 175

Leu Gln Leu Leu Gly Ala Thr Cys Met
1 5

<210> SEQ ID NO 176
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 176

Leu Leu Gln Met Glu Leu Leu Leu Val
1 5

<210> SEQ ID NO 177
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 177

Gln Met Glu Leu Leu Leu Val Asn Lys
1 5

<210> SEQ ID NO 178
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 178

Met Glu Leu Leu Leu Val Asn Lys Leu
1 5

<210> SEQ ID NO 179

<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 179

Lys Leu Lys Trp Asn Leu Ala Ala Met
1 5

<210> SEQ ID NO 180
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 180

Lys His Ala Gln Thr Phe Val Ala Leu
1 5

<210> SEQ ID NO 181
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 181

Ile Ile Arg Lys His Ala Gln Thr Phe
1 5

<210> SEQ ID NO 182
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 182

Gln Ile Ile Arg Lys His Ala Gln Thr
1 5

<210> SEQ ID NO 183
<211> LENGTH: 9
<212> TYPE: PRT
<213> ORGANISM: Artificial Sequence
<220> FEATURE:
<223> OTHER INFORMATION: Class I Cyclin D1

<400> SEQUENCE: 183

Ser Met Val Ala Ala Gly Ser Val Val
1 5

<210> SEQ ID NO 184
<211> LENGTH: 3490
<212> TYPE: DNA
<213> ORGANISM: Homo sapiens

<400> SEQUENCE: 184
gaagagactc agggcagagg gaggaaggac agcagaccag acagtcacag cagccttgac 60
aaaacgttcc tggaactcaa gctcttctcc acagaggagg acagagcaga cagcagagac 120
catggagtct ccctcggccc ctccccacag atggtgcatc ccctggcaga ggctcctgct 180
cacagcctca cttctaacct tctggaaccc gcccaccact gccaagctca ctattgaatc 240

-continued

```
cacgccgttc aatgtcgcag aggggaagga ggtgcttcta cttgtccaca atctgcccca    300
gcatcttttt ggctacagct ggtacaaagg tgaaagagtg gatggcaacc gtcaaattat    360
aggatatgta ataggaactc aacaagctac cccagggccc gcatacagtg gtcgagagat    420
aatataccc  aatgcatccc tgctgatcca gaacatcatc cagaatgaca caggattcta    480
caccctacac gtcataaagt cagatcttgt gaatgaagaa gcaactggcc agttccgggt    540
atacccggag ctgcccaagc cctccatctc cagcaacaac tccaaacccg tggaggacaa    600
ggatgctgtg gccttcacct gtgaacctga gactcaggac gcaacctacc tgtggtgggt    660
aaacaatcag agcctcccgg tcagtcccag gctgcagctg tccaatggca acaggaccct    720
cactctattc aatgtcacaa gaaatgacac agcaagctac aaatgtgaaa cccagaaccc    780
agtgagtgcc aggcgcagtg attcagtcat cctgaatgtc ctctatggcc cggatgcccc    840
caccatttcc cctctaaaca catcttacag atcaggggaa aatctgaacc tctcctgcca    900
cgcagcctct aacccacctg cacagtactc ttggtttgtc aatgggactt tccagcaatc    960
cacccaagag ctctttatcc ccaacatcac tgtgaataat agtggatcct atacgtgcca   1020
agcccataac tcagacactg gcctcaatag gaccacagtc acgacgatca cagtctatgc   1080
agagccaccc aaacccttca tcaccagcaa caactccaac cccgtggagg atgaggatgc   1140
tgtagcctta acctgtgaac ctgagattca gaacacaacc tacctgtggt gggtaaataa   1200
tcagagcctc ccggtcagtc ccaggctgca gctgtccaat gacaacagga ccctcactct   1260
actcagtgtc acaaggaatg atgtaggacc ctatgagtgt ggaatccaga acgaattaag   1320
tgttgaccac agcgacccag tcatcctgaa tgtcctctat ggcccagacg accccaccat   1380
ttcccctca  tacacctatt accgtccagg ggtgaacctc agcctctcct gccatgcagc   1440
ctctaaccca cctgcacagt attcttggct gattgatggg aacatccagc aacacacaca   1500
agagctcttt atctccaaca tcactgagaa gaacagcgga ctctatacct gccaggccaa   1560
taactcagcc agtggccaca gcaggactac agtcaagaca atcacagtct ctgcggagct   1620
gcccaagccc tccatctcca gcaacaactc caaacccgtg gaggacaagg atgctgtggc   1680
cttcacctgt gaacctgagg ctcagaacac aacctacctg tggtgggtaa atggtcagag   1740
cctcccagtc agtcccaggc tgcagctgtc caatggcaac aggaccctca ctctattcaa   1800
tgtcacaaga aatgacgcaa gagcctatgt atgtggaatc cagaactcag tgagtgcaaa   1860
ccgcagtgac ccagtcaccc tggatgtcct ctatgggccg gacaccccca tcatttcccc   1920
cccagactcg tcttaccttt cgggagcgaa cctcaacctc tcctgccact cggcctctaa   1980
cccatccccg cagtattctt ggcgtatcaa tgggataccg cagcaacaca cacaagttct   2040
ctttatcgcc aaaatcacgc caaataataa cgggacctat gcctgttttg tctctaactt   2100
ggctactggc cgcaataatt ccatagtcaa gagcatcaca gtctctgcat ctggaacttc   2160
tcctggtctc tcagctgggg ccactgtcgg catcatgatt ggagtgctgg ttggggttgc   2220
tctgatatag cagccctggt gtagtttctt catttcagga agactgcatt tgcaacagct   2280
acagtctaaa attgcttctt taccaaggat atttacagaa aagactctga ccagagatcg   2340
agaccatcct agccaacatc gtgaaacccc atctctacta aaaatacaaa aatgagctgg   2400
gcttggtggc gcacacctgt agtcccagtt actcgggagg ctgaggcagg agaatcgctt   2460
gaacccggga ggtggagatt gcagtgagcc cagatcgcac cactgcactc cagtctggca   2520
acagagcaag actccatctc aaaaagaaaa gaaaagaaga ctctgacctg tactcttgaa   2580
tacaagtttc tgataccact gcactgtctg agaatttcca aaactttaat gaactaactg   2640
```

-continued

```
acagcttcat gaaactgtcc accaagatca agcagagaaa ataattaatt tcatgggact   2700

aaatgaacta atgaggataa tattttcata attttttatt tgaaattttg ctgattcttt   2760

aaatgtcttg tttcccagat ttcaggaaac tttttttctt ttaagctatc cacagcttac   2820

agcaatttga taaaatatac ttttgtgaac aaaaattgag acatttacat tttctcccta   2880

tgtggtcgct ccagacttgg gaaactattc atgaatattt atattgtatg gtaatatagt   2940

tattgcacaa gttcaataaa aatctgctct ttgtatgaca gaatacattt gaaaacattg   3000

gttatattac caagactttg actagaatgt cgtatttgag gatataaacc cataggtaat   3060

aaacccacag gtactacaaa caaagtctga agtcagcctt ggtttggctt cctagtgtca   3120

attaaacttc taaaagttta atctgagatt ccttataaaa acttccagca aagcaacttt   3180

aaaaaagtct gtgtgggccg ggcgcggtgg ctcacgcctg taatcccagc actttgatcc   3240

gccgaggcgg gcggatcacg aggtcaggag atccagacca tcctggctaa cacagtgaaa   3300

ccccgtctct actaaaaata caaaaaaagt tagccgggcg tggtggtggg ggcctgtagt   3360

cccagctact caggaggctg aggcaggaga acggcatgaa cccgggaggc agggcttgca   3420

gtgagccaag atcatgccgc tgcactccag cctgggagac aaagtgagac tccgtcaaaa   3480

aaaaaaaaaa                                                          3490
```

<210> SEQ ID NO 185
<211> LENGTH: 702
<212> TYPE: PRT
<213> ORGANISM: Homo sapiens

<400> SEQUENCE: 185

```
Met Glu Ser Pro Ser Ala Pro Pro His Arg Trp Cys Ile Pro Trp Gln
 1               5                  10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
```

```
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640
```

-continued

```
Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700


<210> SEQ ID NO 186
<211> LENGTH: 15
<212> TYPE: PRT
<213> ORGANISM: Artificial Sequence
<220> FEATURE:
<223> OTHER INFORMATION: Class II CEA

<400> SEQUENCE: 186

Leu Leu Thr Phe Trp Asn Pro Pro Thr Thr Ala Lys Leu Thr Ile
 1               5                   10                  15


<210> SEQ ID NO 187
<211> LENGTH: 15
<212> TYPE: PRT
<213> ORGANISM: Artificial Sequence
<220> FEATURE:
<223> OTHER INFORMATION: Class II CEA

<400> SEQUENCE: 187

Asn Arg Gln Ile Ile Gly Tyr Val Ile Gly Thr Gln Gln Ala Thr
 1               5                   10                  15


<210> SEQ ID NO 188
<211> LENGTH: 15
<212> TYPE: PRT
<213> ORGANISM: Artificial Sequence
<220> FEATURE:
<223> OTHER INFORMATION: Class II CEA

<400> SEQUENCE: 188

Tyr Leu Trp Trp Val Asn Asn Gln Ser Leu Pro Val Ser Pro Arg
 1               5                   10                  15


<210> SEQ ID NO 189
<211> LENGTH: 15
<212> TYPE: PRT
<213> ORGANISM: Artificial Sequence
<220> FEATURE:
<223> OTHER INFORMATION: Class II CEA

<400> SEQUENCE: 189

Ser Tyr Thr Tyr Tyr Arg Pro Gly Val Asn Leu Ser Leu Ser Cys
 1               5                   10                  15


<210> SEQ ID NO 190
<211> LENGTH: 15
<212> TYPE: PRT
<213> ORGANISM: Artificial Sequence
<220> FEATURE:
<223> OTHER INFORMATION: Class II CEA

<400> SEQUENCE: 190

Arg Thr Thr Val Lys Thr Ile Thr Val Ser Ala Glu Leu Pro Lys
 1               5                   10                  15
```

<210> SEQ ID NO 191
<211> LENGTH: 15
<212> TYPE: PRT
<213> ORGANISM: Artificial Sequence
<220> FEATURE:
<223> OTHER INFORMATION: Class II CEA

<400> SEQUENCE: 191

Asn Gly Thr Tyr Ala Cys Phe Val Ser Asn Leu Ala Thr Gly Arg
1 5 10 15

<210> SEQ ID NO 192
<211> LENGTH: 9
<212> TYPE: PRT
<213> ORGANISM: Artificial Sequence
<220> FEATURE:
<223> OTHER INFORMATION: Class I CEA

<400> SEQUENCE: 192

Leu Leu Thr Phe Trp Asn Pro Pro Thr
1 5

<210> SEQ ID NO 193
<211> LENGTH: 9
<212> TYPE: PRT
<213> ORGANISM: Artificial Sequence
<220> FEATURE:
<223> OTHER INFORMATION: Class I CEA

<400> SEQUENCE: 193

Pro Pro Thr Thr Ala Lys Leu Thr Ile
1 5

<210> SEQ ID NO 194
<211> LENGTH: 9
<212> TYPE: PRT
<213> ORGANISM: Artificial Sequence
<220> FEATURE:
<223> OTHER INFORMATION: Class I CEA

<400> SEQUENCE: 194

Tyr Val Ile Gly Thr Gln Gln Ala Thr
1 5

<210> SEQ ID NO 195
<211> LENGTH: 9
<212> TYPE: PRT
<213> ORGANISM: Artificial Sequence
<220> FEATURE:
<223> OTHER INFORMATION: Class I CEA

<400> SEQUENCE: 195

Asn Arg Gln Ile Ile Gly Tyr Val Ile
1 5

<210> SEQ ID NO 196
<211> LENGTH: 9
<212> TYPE: PRT
<213> ORGANISM: Artificial Sequence
<220> FEATURE:
<223> OTHER INFORMATION: Class I CEA

<400> SEQUENCE: 196

Leu Trp Trp Val Asn Asn Gln Ser Leu
1 5

<210> SEQ ID NO 197

<211> LENGTH: 9
<212> TYPE: PRT
<213> ORGANISM: Artificial Sequence
<220> FEATURE:
<223> OTHER INFORMATION: Class I CEA

<400> SEQUENCE: 197

Thr Tyr Tyr Arg Pro Gly Val Asn Leu
1 5

<210> SEQ ID NO 198
<211> LENGTH: 9
<212> TYPE: PRT
<213> ORGANISM: Artificial Sequence
<220> FEATURE:
<223> OTHER INFORMATION: Class I CEA

<400> SEQUENCE: 198

Tyr Arg Pro Gly Val Asn Leu Ser Leu
1 5

<210> SEQ ID NO 199
<211> LENGTH: 9
<212> TYPE: PRT
<213> ORGANISM: Artificial Sequence
<220> FEATURE:
<223> OTHER INFORMATION: Class I CEA

<400> SEQUENCE: 199

Lys Thr Ile Thr Val Ser Ala Glu Leu
1 5

<210> SEQ ID NO 200
<211> LENGTH: 9
<212> TYPE: PRT
<213> ORGANISM: Artificial Sequence
<220> FEATURE:
<223> OTHER INFORMATION: Class I CEA

<400> SEQUENCE: 200

Ile Thr Val Ser Ala Glu Leu Pro Lys
1 5

<210> SEQ ID NO 201
<211> LENGTH: 9
<212> TYPE: PRT
<213> ORGANISM: Artificial Sequence
<220> FEATURE:
<223> OTHER INFORMATION: Class I CEA

<400> SEQUENCE: 201

Phe Val Ser Asn Leu Ala Thr Gly Arg
1 5

<210> SEQ ID NO 202
<211> LENGTH: 9
<212> TYPE: PRT
<213> ORGANISM: Artificial Sequence
<220> FEATURE:
<223> OTHER INFORMATION: Class I CEA

<400> SEQUENCE: 202

Thr Tyr Ala Cys Phe Val Ser Asn Leu
1 5

<210> SEQ ID NO 203
<211> LENGTH: 4

<212> TYPE: PRT
<213> ORGANISM: Artificial Sequence
<220> FEATURE:
<223> OTHER INFORMATION: consensus ubiqutination motif

<400> SEQUENCE: 203

Lys Glu Glu Glu
1

<210> SEQ ID NO 204
<211> LENGTH: 121
<212> TYPE: PRT
<213> ORGANISM: Artificial Sequence
<220> FEATURE:
<223> OTHER INFORMATION: Small pox PAA

<400> SEQUENCE: 204

```
Glu Val Asn Thr Ile Leu Met Asp Asn Lys Gly Leu Gly Val Arg Leu
 1               5                  10                  15

Ala Thr Gly Gly Gly Gly Ser Gly Gly Gly Gly Ser Lys Ser Leu Thr
            20                  25                  30

Ile Leu Asp Asp Asn Leu Tyr Lys Val Tyr Asn Gly Ile Gly Gly Gly
        35                  40                  45

Gly Ser Gly Gly Gly Gly Ser Arg Thr Asp Asp Gly Leu Leu Asp Arg
    50                  55                  60

Leu Tyr Asp Leu Thr Arg Tyr Ala Gly Gly Gly Gly Ser Gly Gly Gly
65                  70                  75                  80

Gly Ser Pro Leu Thr Lys Gly Ile Leu Gly Val Phe Thr Leu Thr Val
                85                  90                  95

Pro Ser Gly Gly Gly Gly Ser Gly Gly Gly Gly Ser Lys Ile Val Asn
            100                 105                 110

Ser Leu Ser Asn Leu Asp Phe Arg Leu
        115                 120
```

<210> SEQ ID NO 205
<211> LENGTH: 194
<212> TYPE: PRT
<213> ORGANISM: Artificial Sequence
<220> FEATURE:
<223> OTHER INFORMATION: Smallpox MTI-PAA + VSV-G epitope tag

<400> SEQUENCE: 205

```
Met Gly Asp Arg Gly Arg Gly Arg Ala Leu Pro Gly Gly Arg Leu Gly
 1               5                  10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Met Ala Ala Gly Ser Ser Arg Glu Val
    50                  55                  60

Asn Thr Ile Leu Met Asp Asn Lys Gly Leu Gly Val Arg Leu Ala Thr
65                  70                  75                  80

Gly Gly Gly Gly Ser Gly Gly Gly Gly Ser Lys Ser Leu Thr Ile Leu
                85                  90                  95

Asp Asp Asn Leu Tyr Lys Val Tyr Asn Gly Ile Gly Gly Gly Gly Ser
            100                 105                 110

Gly Gly Gly Gly Ser Arg Thr Asp Asp Gly Leu Leu Asp Arg Leu Tyr
        115                 120                 125

Asp Leu Thr Arg Tyr Ala Gly Gly Gly Gly Ser Gly Gly Gly Gly Ser
```

130 135 140

Pro Leu Thr Lys Gly Ile Leu Gly Val Phe Thr Leu Thr Val Pro Ser
145 150 155 160

Gly Gly Gly Gly Ser Gly Gly Gly Gly Ser Lys Ile Val Asn Ser Leu
165 170 175

Ser Asn Leu Asp Phe Arg Leu Tyr Thr Asp Ile Glu Met Asn Arg Leu
180 185 190

Gly Lys

<210> SEQ ID NO 206
<211> LENGTH: 2974
<212> TYPE: DNA
<213> ORGANISM: Homo sapiens

<400> SEQUENCE: 206
gtgtgcgtga tggagaaaat tgggcaccag ggctgctccc gagattctca gatctgattt 60
ccacgcttgc taccaaaata gtctgggcag gccacttttg gaagtaggcg ttatctagtg 120
agcaggcggc cgctttcgat ttcgctttcc cctaaatggc tgagcttctc gccagcgcag 180
gatcagcctg ttcctgggac tttccgagag ccccgccctc gttccctccc ccagccgcca 240
gtaggggagg actcggcggt acccggagct tcaggcccca ccggggcgcg gagagtccca 300
ggcccggccg ggaccgggac ggcgtccgag tgccaatggc tagctctagg tgtcccgctc 360
cccgcgggtg ccgctgcctc cccggagctt ctctcgcatg gctggggaca gtactgctac 420
ttctcgccga ctgggtgctg ctccggaccg cgctgccccg catattctcc ctgctggtgc 480
ccaccgcgct gccactgctc cgggtctggg cggtgggcct gagccgctgg gccgtgctct 540
ggctgggggc ctgcggggtc ctcagggcaa cggttggctc caagagcgaa aacgcaggtg 600
cccagggctg gctggctgct ttgaagccat tagctgcggc actgggcttg gccctgccgg 660
gacttgcctt gttccgagag ctgatctcat ggggagcccc cgggtccgcg gatagcacca 720
ggctactgca ctggggaagt caccctaccg ccttcgttgt cagttatgca gcggcactgc 780
ccgcagcagc cctgtggcac aaactcggga gcctctgggt gcccggcggt cagggcggct 840
ctggaaaccc tgtgcgtcgg cttctaggct gcctgggctc ggagacgcgc cgcctctcgc 900
tgttcctggt cctggtggtc ctctcctctc ttggggagat ggccattcca ttctttacgg 960
gccgcctcac tgactggatt ctacaagatg gctcagccga taccttcact cgaaacttaa 1020
ctctcatgtc cattctcacc atagccagtg cagtgctgga gttcgtgggt gacgggatct 1080
ataacaacac catgggccac gtgcacagcc acttgcaggg agaggtgttt ggggctgtcc 1140
tgcgccagga gacggagttt ttccaacaga accagacagg taacatcatg tctcgggtaa 1200
cagaggacac gtccaccctg agtgattctc tgagtgagaa tctgagctta tttctgtggt 1260
acctggtgcg aggcctatgt ctcttgggga tcatgctctg gggatcagtg tccctcacca 1320
tggtcaccct gatcaccctg cctctgcttt tccttctgcc caagaaggtg ggaaaatggt 1380
accagttgct ggaagtgcag gtgcgggaat ctctggcaaa gtccagccag gtggccattg 1440
aggctctgtc ggccatgcct acagttcgaa gctttgccaa cgaggagggc gaagcccaga 1500
agtttaggga aaagctgcaa gaaataaaga cactcaacca gaaggaggct gtggcctatg 1560
cagtcaactc ctggaccact agtatttcag gtatgctgct gaaagtggga atcctctaca 1620
ttggtgggca gctggtgacc agtggggctg taagcagtgg gaaccttgtc acatttgttc 1680
tctaccagat gcagttcacc caggctgtgg aggtactgct ctccatctac cccagagtac 1740

```
agaaggctgt gggctcctca gagaaaatat ttgagtacct ggaccgcacc cctcgctgcc   1800
cacccagtgg tctgttgact cccttacact tggagggcct tgtccagttc caagatgtct   1860
cctttgccta cccaaaccgc ccagatgtct tagtgctaca ggggctgaca ttcaccctac   1920
gccctggcga ggtgacggcg ctggtgggac ccaatgggtc tgggaagagc acagtggctg   1980
ccctgctgca gaatctgtac cagcccaccg ggggacagct gctgttggat gggaagcccc   2040
ttccccaata tgagcaccgc tacctgcaca ggcaggtggc tgcagtggga caagagccac   2100
aggtatttgg aagaagtctt caagaaaata ttgcctatgg cctgacccag aagccaacta   2160
tggaggaaat cacagctgct gcagtaaagt ctggggccca tagtttcatc tctggactcc   2220
ctcagggcta tgacacagag gtagacgagg ctgggagcca gctgtcaggg ggtcagcgac   2280
aggcagtggc gttggcccga gcattgatcc ggaaaccgtg tgtacttatc ctggatgatg   2340
ccaccagtgc cctggatgca aacagccagt tacaggtgga gcagctcctg tacgaaagcc   2400
ctgagcggta ctcccgctca gtgcttctca tcacccagca cctcagcctg gtggagcagg   2460
ctgaccacat cctctttctg gaaggaggcg ctatccggga gggggaaacc caccagcagc   2520
tcatggagaa aaaggggtgc tactgggcca tggtgcaggc tcctgcagat gctccagaat   2580
gaaagccttc tcagacctgc gcactccatc tccctccctt ttcttctctc tgtggtggag   2640
aaccacagct gcagagtagg cagctgcctc caggatgagt tacttgaaat ttgccttgag   2700
tgtgttacct cctttccaag ctcctcgtga taatgcagac ttcctggagt acaaacacag   2760
gatttgtaat tccttactgt aacggagttt agagccaggg ctgatgcttt ggtgtggcca   2820
gcactctgaa actgagaaat gttcagaatg tacggaaaga tgatcagcta ttttcaacat   2880
aactgaaggc atatgctggc ccataaacac cctgtaggtt cttgatattt ataataaaat   2940
tggtgttttg taaaaaaaaa aaaaaaaaaa aaaa                              2974
```

<210> SEQ ID NO 207
<211> LENGTH: 5679
<212> TYPE: DNA
<213> ORGANISM: Homo sapiens

<400> SEQUENCE: 207

```
gcccgccctg gccgagcgta gctggcggac cagagccggt agcgaggttg ggagagacgg     60
agcggacctc agcgctgaag cagaagtccc cggagctgcg gtctccccgc cgcggctgag    120
ccatgcggct ccctgacctg agaccctgga cctccctgct gctggtggac gcggctttac    180
tgtggctgct tcagggccct ctggggactt tgcttcctca agggctgcca ggactatggc    240
tggaggggac cctgcggctg ggagggctgt gggggctgct aaagctaaga gggctgctgg    300
gatttgtggg gacactgctg ctcccgctct gtctggccac ccccctgact gtctccctga    360
gagccctggt cgcgggggcc tcacgtgctc ccccagccag agtcgcttca gccccttgga    420
gctggctgct ggtggggtac ggggctgcgg ggctcagctg gtcactgtgg gctgttctga    480
gccctcctgg agcccaggag aaggagcagg accaggtgaa caacaaagtc ttgatgtgga    540
ggctgctgaa gctctccagg ccggacctgc ctctcctcgt tgccgccttc ttcttccttg    600
tccttgctgt tttgggtgag acattaatcc ctcactattc tggtcgtgtg attgacatcc    660
tgggaggtga ttttgacccc catgcctttg ccagtgccat cttcttcatg tgcctcttct    720
cctttggcag ctcactgtct gcaggctgcc gaggaggctg cttcacctac accatgtctc    780
gaatcaactt gcggatccgg gagcagcttt tctcctccct gctgcgccag gacctcggtt    840
tcttccagga gactaagaca ggggagctga actcacggct gagctcggat accaccctga    900
```

```
tgagtaactg gcttccttta aatgccaatg tgctcttgcg aagcctggtg aaagtggtgg    960
ggctgtatgg cttcatgctc agcatatcgc ctcgactcac cctcctttct ctgctgcaca   1020
tgcccttcac aatagcagcg gagaaggtgt acaacacccg ccatcaggaa gtgcttcggg   1080
agatccagga tgcagtggcc agggcggggc aggtggtgcg ggaagccgtt ggagggctgc   1140
agaccgttcg cagttttggg gccgaggagc atgaagtctg tcgctataaa gaggcccttg   1200
aacaatgtcg gcagctgtat tggcggagag acctggaacg cgccttgtac ctgctcgtaa   1260
ggagggtgct gcacttgggg gtgcagatgc tgatgctgag ctgtgggctg cagcagatgc   1320
aggatgggga gctcacccag ggcagcctgc tttcctttat gatctaccag gagagcgtgg   1380
ggagctatgt gcagaccctg gtatacatat atggggatat gctcagcaac gtgggagctg   1440
cagagaaggt tttctcctac atggaccgac agccaaatct gccttcacct ggcacgcttg   1500
cccccaccac tctgcagggg gttgtgaaat tccaagacgt ctcctttgca tatcccaatc   1560
gccctgacag gcctgtgctc aaggggctga cgtttaccct acgtcctggt gaggtgacgg   1620
cgctggtggg acccaatggg tctgggaaga gcacagtggc tgccctgctg cagaatctgt   1680
accagcccac agggggacag gtgctgctgg atgaaaagcc catctcacag tatgaacact   1740
gctacctgca cagccaggtg gtttcagttg ggcaggagcc tgtgctgttc tccggttctg   1800
tgaggaacaa cattgcttat gggctgcaga gctgcgaaga tgataaggtg atggcggctg   1860
cccaggctgc ccacgcagat gacttcatcc aggaaatgga gcatggaata tacacagatg   1920
taggggagaa gggaagccag ctggctgcgg gacagaaaca acgtctggcc attgcccggg   1980
cccttgtacg agacccgcgg gtcctcatcc tggatgaggc tactagtgcc ctagatgtgc   2040
agtgcgagca ggccctgcag gactggaatt cccgtgggga tcgcacagtg ctggtgattg   2100
ctcacaggct gcaggcagtt cagcgcgccc accagatcct ggtgctccag gagggcaagc   2160
tgcagaagct tgcccagctc caggagggac aggacctcta ttcccgcctg gttcagcagc   2220
ggctgatgga ctgaggcccc agggatactg ggccctcttc tcaggggcgt ctccaggacc   2280
cagagctgtt cctgctttga gtttccctag agctgtgcgg ccagatagct gttcctgagt   2340
tgcaggcacg atggagattt ggacactgtg tgcttttggt ggggtagaga ggtggggtgg   2400
ggtggggtgg gggctgtctg tgtccaggaa acttaattcc ctggtgacta gagctttgcc   2460
tggtgatgag gagtattttg tggcataata catatatttt aaaatatttt ccttcttaca   2520
tgaactgtat acattcatat agaaaattta gacaatataa aaaagtacaa agaagaaaag   2580
taaaagtacc cattgtttca cttcctggag ataaccatag ttgctatttt gctgcctgtc   2640
ccatcagtcg tttatctgtt gtttgagata gaaattaacc aaaaatgaca taaatattca   2700
tgagattgcc ttcctatatc cttccttgtt cctaccagtg tctgctattt tgaagaagct   2760
agggtctgga gggacagaga acagttccct gattaacagt attaatagcg acattggtaa   2820
cagctaccat ttatagagtt ttaatgggag taggagctat gctaagtgtt tttcatgtat   2880
tatcgttttt aatcattatc cccaacccta tgaggttggt tattatcccc attttacaga   2940
tgaggaaact gaagctcaaa gaggctcaat gactttccca aggtggtcgt agtggtggag   3000
ttggagtttg aacacaggcc tgaccctaga gtccacaccc tgacccaatc aattatattg   3060
catcttgggt ccataaaccc taatccataa tcccatcaag aaaagctctg ctgctcttag   3120
ctctaaataa ttcagaatct attctcttct ctccagtccc gttgttatag tcttcactca   3180
tagacttaag atgatcccat caccagagag gtttctctac cattagcttc cctcttccgg   3240
```

-continued

```
ccattcttca caaagtcatt tttctaaatt ctgtgtcaca tacgatgatg gcatttctgg   3300
aaattccttc aggtgctctc aagccctgct gcagagatcc ttttcagagc acacactgtt   3360
ccagcccatc tgtctcaccc tctcctgttg tatccagctc cacgacaaac ttctgccttc   3420
cccaacacct ttgtgccttt gcatatggtg ttttcttgcc cattttctgc tcgactcgcc   3480
cctgattttc aagttcaaga cttaactcag ggttcaggtc ttccaggagg ccttacttat   3540
gtcgtcagtc tggggaactc tccatgtgct tctatcactg tgcggttacc tctttcacag   3600
ccccttttaaa gttctatctt ccctttccca cctttttga ccttccacta gaccatgagc   3660
acctgggcgg aaagccatat atcttattaa gctttatatc tgctacctgg ccgagggcct   3720
aattcatagt ggagaataaa tagtcaattg aataaatgaa taaatatctc caccatcgta   3780
ctaatcttaa tcctccctgc ccactcccac cactgaaaat gcaacattgt acacatcact   3840
ggttgttggg agggacttac cttggaaagt tgctattcta ggaaagagaa accttcatat   3900
tcctggaaac agcaggtagt ttccagtgct ggcaatgaat tccccagaac tgctgttttg   3960
gatttttct tgcctggcag ctgttgggag cagggtgcag tgaggatggg gtgagagtgg   4020
gcagtttctt gtgcagattt gcctttcttt catcctgggg ctgacttgca gctccacacc   4080
catccatctc tcaaatttca cagagggtaa aataggcatt tggagagaaa gaactctggc   4140
ctgattcctt tctctcccac aaatgtcctt tattcataaa acaggaataa taattcctgt   4200
atctcccaac tacatggaag ctgcagccct cacagaagaa gatgatctga gaaattcttt   4260
gatttcctca gtacagttat acccatgcat cataatactt taagcctgga aggcatctta   4320
aaaataatgc aacagtcaaa cctaatttta cagagaaact gacatgaaat cacgcagcta   4380
atcatgataa agctgggtgg aaaacttatc ttgatgggca gtacaggaag atgcagtaga   4440
ccttaagatg tcctgaaagt ttcttatctc aggggaaact cccaggtagg ctttatgtca   4500
gggacacaga aaaatgctcc ctgaaagtca aaatattcgg gctagacaga caaattcctg   4560
taagtgtggt ttgtctggga accacagatg tcactaatcc tggtttgctc cagagttctt   4620
tttgttcact cctacccccc atcaccattt gattgatctc cttaccctgt aatttcccct   4680
tcttgtcgct tacctgcagt atctttccca cccaggcatg ccttattctt tctaaaggaa   4740
agtatgaatg gagaggggaa agcttgggaa actgatagat ttccttggat gccaaaacac   4800
ctccatagcc tgtctgcccg gccctatgtg gaaacagcat tgagtttcaa gtcctttatg   4860
cctccaccca gggatagcca cttgtaatcc acatggcaat tgtgaaacaa gcaggaaatg   4920
cgtaattgtc agaattttgt ggggaaagga ctagggaata aggaaaacaa agatcttcct   4980
tgtgttttag agctgtcagc tagaggagca cctgcttgag tctgatgcca tctaatggtc   5040
ccagaagaaa ctgggtttg aacctagagt tccatggact cttaggaatt agactactac   5100
tactactaag cattcactgg tgcttactat gtgctattgc tgtgccaagt atctgaaacc   5160
tgtcttctta ccttattttt caagataatt ctatgtggca ggtattacta tctcaattct   5220
aagagtgaga aaatggagtt ttagaaacat ttactaactt gcctgggtca catagctaag   5280
gaagaggtgg acttgcccag ctttgcataa aactcctcaa aagagttgcc tatactccct   5340
gactccactt atcttcctac tatcctcttt ttaaaatata ttatttattt atttaaataa   5400
gcaatatatg aatgtggttt gaaattcaaa agacacaaag aagtatacag aggaaagcct   5460
cactctcaat ccttctcaag gtttgctaat tcctcttgca taggcaatcc gttcttccag   5520
ctttgtgttt atctttccag agaagtttac tgtgtattaa gcaaatatgt atatctttat   5580
tcttgctcag tattttcgca aacagcagct gtctaagttc actgttctga actttatttt   5640
```

ttaaattaaa aatatatggc tatgtagtat tctatttta 5679

<210> SEQ ID NO 208
<211> LENGTH: 3417
<212> TYPE: DNA
<213> ORGANISM: Homo sapiens

<400> SEQUENCE: 208
gtcactgagg ccccgccccg tccatcagcc tgtctcaacg cacgccagtc tcagctccga 60
ccttgcagcg gcgcagcgcg ggtgggaggc ggggaggagc agcgggaaga gcggagcgag 120
gaccgcgtcc ggcgcagtct tcaatgagca gcgcggaaac tgcaccccag acccgagcct 180
gctgcgcgcc ccctcccaga gctcacctgg tgccaggtaa caggcctggc ctcgccctgt 240
ggatgatgat ggccttgccc ccgtgagcta caacctggcc ttcagcaccc gcccacctcc 300
aaccagcagg atgcggctgt ggaaggcggt ggtggtgact ttggccttca tgagtgtgga 360
catctgcgtg accacggcca tctatgtctt cagccacctg gaccgcagcc tcctggagga 420
catccgccac ttcaacatct ttgactcggt gctggatctc tgggcagcct gcctgtaccg 480
cagctgcctg ctgctgggag ccaccattgg tgtggccaag aacagtgcgc tggggccccg 540
gcggctgcgg gcctcgtggc tggtcatcac cctcgtgtgc ctcttcgtgg gcatctatgc 600
catggtgaag ctgctgctct tctcagaggt gcgcaggccc atccgggacc cctggttttg 660
ggccctgttc gtgtggacgt acatttcact cggcgcatcc ttcctgctct ggtggctgct 720
gtccaccgtg cggccaggca cccaggccct ggagccaggg gcggccaccg aggctgaggg 780
cttccctggg agcggccggc caccgcccga gcaggcgtct ggggccacgc tgcagaagct 840
gctctcctac accaagcccg acgtggcctt cctcgtggcc gcctccttct tcctcatcgt 900
ggcagctctg ggagagacct tcctgcccta ctacacgggc cgcgccattg atggcatcgt 960
catccagaaa agcatggatc agttcagcac ggctgtcgtc atcgtgtgcc tgctggccat 1020
tggcagctca tttgccgcag gtattcgggg cggcattttt accctcatat ttgccagact 1080
gaacattcgc cttcgaaact gtctcttccg ctcactggtg tcccaggaga caagcttctt 1140
tgatgagaac cgcacagggg acctcatctc ccgcctgacc tcggacacca ccatggtcag 1200
cgacctggtc tcccagaaca tcaatgtctt cctgcggaac acagtcaagg tcacgggcgt 1260
ggtggtcttc atgttcagcc tctcatggca gctctccttg gtcaccttca tgggcttccc 1320
catcatcatg atggtgtcca acatctacgg caagtactac aagaggctct ccaaagaggt 1380
ccagaatgcc ctggccagag cgagcaacac ggcggaggag accatcagtg ccatgaagac 1440
tgtccggagc ttcgccaatg aggaggagga ggcagaggtg tacctgcgga agctgcagca 1500
ggtgtacaag ctgaacagga aggaggcagc tgcctacatg tactacgtct ggggcagcgg 1560
gtccgtgggc tccgtctaca gtggcctgat gcagggagtg gggctgctg agaaggtgtt 1620 cgagttcatc gaccggcagc cgaccatggt gcacgatggc agcttggccc ccgaccacct 1680
ggagggccgg gtggactttg agaatgtgac cttcacctac cgcactcggc cccacaccca 1740
ggtcctgcag aatgtctcct tcagcctgtc ccccggcaag gtgacggccc tggtggggcc 1800
ctcgggcagt gggaagagct cctgtgtcaa catcctggag aacttctacc ccctggaggg 1860
gggccgggtg ctgctggacg gcaagcccat cagcgcctac gaccacaagt acttgcaccg 1920
tgtgatctcc ctggtgagcc aggagcccgt gctgttcgcc cgctccatca cggataacat 1980
ctcctacggc ctgcccactg tgcctttcga gatggtggtg gaggccgcac agaaggccaa 2040

-continued

```
tgcccacggc ttcatcatgg aactccagga cggctacagc acagagacag gggagaaggg   2100
cgcccagctg tcaggtggcc agaagcagcg ggtggccatg gcccgggctc tggtgcggaa   2160
ccccccagtc ctcatcctgg atgaagccac cagcgctttg gatgccgaga gcgagtatct   2220
gatccagcag gccatccatg gcaacctgca gaagcacacg gtactcatca tcgcgcaccg   2280
gctgagcacc gtggagcacg cgcacctcat tgtggtgctg gacaagggcc gcgtagtgca   2340
gcagggcacc caccagcagc tgctggccca gggcggcctc tacgccaagc tggtgcagcg   2400
gcagatgctg gggcttcagc ccgccgcaga cttcacagct ggccacaacg agcctgtagc   2460
caacggcagt cacaaggcct gatggggggc ccctgcttct cccggtgggg cagaggaccc   2520
ggtgcctgcc tggcagatgt gcccacggag gcccccagct gccctccgag cccaggcctg   2580
cagcactgaa agacgacctg ccatgtccca tggatcaccg cttcctgcat cttgcccctg   2640
gtccctgccc cattcccagg gcactcctta cccctgctgc cctgagccaa cgccttcacg   2700
gacctcccta gcctcctaag caaaggtaga gctgcctttt taaacctagg tcttaccagg   2760
gtttttactg tttggtttga ggcaccccag tcaactccta gatttcaaaa acctttttct   2820
aattgggagt aatggcgggc actttcacca agatgttcta gaaacttctg agccaggagt   2880
gaatggccct tccttagtag cctgggggat gtccagagac taggcctctc ccctttaccc   2940
ctccagagaa ggggcttccc tgtcccggag ggagacacgg ggaacgggat tttccgtctc   3000
tccctcttgc cagctctgtg agtctggcca gggcgggtag ggagcgtgga gggcatctgt   3060
ctgccatcgc ccgctgccaa tctaagccag tctcactgtg aaccacacga aacctcaact   3120
gggggagtga ggggctggcc aggtctggag gggcctcagg ggtgccccca gcccggcacc   3180
cagcgctttc gcccctcgtc cacccacccc tggctggcag cctccctccc cacacccgcc   3240
cctgtgctct gctgtctgga ggccacgtgg atgttcatga gatgcattct cttctgtctt   3300
tggtggatgg gatggtggca aagcccagga tctggctttg ccagaggttg caacatgttg   3360
agagaacccg gtcaataaag tgtactacct cttacccota aaaaaaaaaa aaaaaaa      3417
```

<210> SEQ ID NO 209
<211> LENGTH: 2475
<212> TYPE: DNA
<213> ORGANISM: Artificial Sequence
<220> FEATURE:
<223> OTHER INFORMATION: Tap1 sequence with optimized Kosak and NH2 tag

<400> SEQUENCE: 209

```
gccaccatgg gcaagcccat ccccaacccc ctgctgggcc tggacagcac cgctgagctt     60
ctcgccagcg caggatcagc ctgttcctgg gactttccga gagccccgcc ctcgttccct    120
cccccagccg ccagtagggg aggactcggc ggtacccgga gcttcaggcc ccaccggggc    180
gcggagagtc ccaggcccgg ccgggaccgg gacggcgtcc gagtgccaat ggctagctct    240
aggtgtcccg ctccccgcgg gtgccgctgc ctccccggag cttctctcgc atggctgggg    300
acagtactgc tacttctcgc cgactgggtg ctgctccgga ccgcgctgcc ccgcatattc    360
tccctgctgg tgcccaccgc gctgccactg ctccgggtct gggcggtggg cctgagccgc    420
tgggccgtgc tctggctggg ggcctgcggg gtcctcaggg caacggttgg ctccaagagc    480
gaaaacgcag gtgcccaggg ctggctggct gctttgaagc cattagctgc ggcactgggc    540
ttggccctgc cgggacttgc cttgttccga gagctgatct catggggagc cccccgggtcc   600
gcggatagca ccaggctact gcactgggga agtcacccta ccgccttcgt tgtcagttat    660
gcagcggcac tgcccgcagc agccctgtgg cacaaactcg ggagcctctg ggtgcccggc    720
```

ggtcagggcg gctctggaaa ccctgtgcgt cggcttctag gctgcctggg ctcggagacg 780
cgccgcctct cgctgttcct ggtcctggtg gtcctctcct ctcttgggga gatggccatt 840
ccattcttta cgggccgcct cactgactgg attctacaag atggctcagc cgataccttc 900
actcgaaact taactctcat gtccattctc accatagcca gtgcagtgct ggagttcgtg 960
ggtgacggga tctataacaa caccatgggc cacgtgcaca gccacttgca gggagaggtg 1020
tttggggctg tcctgcgcca ggagacggag tttttccaac agaaccagac aggtaacatc 1080
atgtctcggg taacagagga cacgtccacc ctgagtgatt ctctgagtga gaatctgagc 1140
ttatttctgt ggtacctggt gcgaggccta tgtctcttgg ggatcatgct ctggggatca 1200
gtgtccctca ccatggtcac cctgatcacc ctgcctctgc ttttccttct gcccaagaag 1260
gtgggaaaat ggtaccagtt gctggaagtg caggtgcggg aatctctggc aaagtccagc 1320
caggtggcca ttgaggctct gtcggccatg cctacagttc gaagctttgc caacgaggag 1380
ggcgaagccc agaagtttag ggaaaagctg caagaaataa agacactcaa ccagaaggag 1440
gctgtggcct atgcagtcaa ctcctggacc actagtattt caggtatgct gctgaaagtg 1500
ggaatcctct acattggtgg gcagctggtg accagtgggg ctgtaagcag tgggaacctt 1560
gtcacatttg ttctctacca gatgcagttc acccaggctg tggaggtact gctctccatc 1620
taccccagag tacagaaggc tgtgggctcc tcagagaaaa tatttgagta cctggaccgc 1680
acccctcgct gcccacccag tggtctgttg actcccttac acttggaggg ccttgtccag 1740
ttccaagatg tctcctttgc ctacccaaac cgcccagatg tcttagtgct acaggggctg 1800
acattcaccc tacgccctgg cgaggtgacg gcgctggtgg gacccaatgg gtctgggaag 1860
agcacagtgg ctgccctgct gcagaatctg taccagccca ccgggggaca gctgctgttg 1920
gatgggaagc ccttcccca atatgagcac cgctacctgc acaggcaggt ggctgcagtg 1980
ggacaagagc cacaggtatt tggaagaagt cttcaagaaa atattgccta tggcctgacc 2040
cagaagccaa ctatggagga aatcacagct gctgcagtaa agtctggggc ccatagtttc 2100
atctctggac tccctcaggg ctatgacaca gaggtagacg aggctgggag ccagctgtca 2160
gggggtcagc gacaggcagt ggcgttggcc cgagcattga tccggaaacc gtgtgtactt 2220
atcctggatg atgccaccag tgccctggat gcaaacagcc agttacaggt ggagcagctc 2280
ctgtacgaaa gccctgagcg gtactcccgc tcagtgcttc tcatcaccca gcacctcagc 2340
ctggtggagc aggctgacca catcctcttt ctggaaggag gcgctatccg ggagggggga 2400
acccaccagc agctcatgga gaaaaagggg tgctactggg ccatggtgca ggctcctgca 2460
gatgctccag aatga 2475

<210> SEQ ID NO 210
<211> LENGTH: 2136
<212> TYPE: DNA
<213> ORGANISM: Artificial Sequence
<220> FEATURE:
<223> OTHER INFORMATION: hTap2 with NH2 tag and optimized Kosak

<400> SEQUENCE: 210
gccaccatga ccgacttcta cctgaagcgg ctccctgacc tgagaccctg gacctccctg 60
ctgctggtgg acgcggcttt actgtggctg cttcagggcc ctctggggac tttgcttcct 120
caagggctgc caggactatg gctggagggg accctgcggc tgggagggct gtgggggctg 180
ctaaagctaa gagggctgct gggatttgtg gggacactgc tgctcccgct ctgtctggcc 240

-continued acccccctga ctgtctccct gagagccctg gtcgcggggg cctcacgtgc tcccccagcc 300
agagtcgctt cagccccttg gagctggctg ctggtggggt acggggctgc ggggctcagc 360
tggtcactgt gggctgttct gagccctcct ggagcccagg agaaggagca ggaccaggtg 420
aacaacaaag tcttgatgtg gaggctgctg aagctctcca ggccggacct gcctctcctc 480
gttgccgcct tcttcttcct tgtccttgct gttttgggtg agacattaat ccctcactat 540
tctggtcgtg tgattgacat cctgggaggt gattttgacc cccatgcctt tgccagtgcc 600
atcttcttca tgtgcctctt ctcctttggc agctcactgt ctgcaggctg ccgaggaggc 660
tgcttcacct acaccatgtc tcgaatcaac ttgcggatcc gggagcagct tttctcctcc 720
ctgctgcgcc aggacctcgg tttcttccag gagactaaga caggggagct gaactcacgg 780
ctgagctcgg ataccaccct gatgagtaac tggcttcctt taaatgccaa tgtgctcttg 840
cgaagcctgg tgaaagtggt ggggctgtat ggcttcatgc tcagcatatc gcctcgactc 900
accctccttt ctctgctgca catgcccttc acaatagcag cggagaaggt gtacaacacc 960
cgccatcagg aagtgcttcg ggagatccag gatgcagtgg ccagggcggg gcaggtggtg 1020
cgggaagccg ttggagggct gcagaccgtt cgcagttttg gggccgagga gcatgaagtc 1080
tgtcgctata aagaggccct tgaacaatgt cggcagctgt attggcggag agacctggaa 1140
cgcgccttgt acctgctcgt aaggagggtg ctgcacttgg gggtgcagat gctgatgctg 1200
agctgtgggc tgcagcagat gcaggatggg gagctcaccc agggcagcct gctttccttt 1260
atgatctacc aggagagcgt ggggagctat gtgcagaccc tggtatacat atatggggat 1320
atgctcagca acgtgggagc tgcagagaag gttttctcct acatggaccg acagccaaat 1380
ctgccttcac ctggcacgct tgcccccacc actctgcagg gggttgtgaa attccaagac 1440
gtctcctttg catatcccaa tcgccctgac aggcctgtgc tcaaggggct gacgtttacc 1500
ctacgtcctg gtgaggtgac ggcgctggtg ggacccaatg ggtctgggaa gagcacagtg 1560
gctgccctgc tgcagaatct gtaccagccc acagggggac aggtgctgct ggatgaaaag 1620
cccatctcac agtatgaaca ctgctacctg cacagccagg tggtttcagt tgggcaggag 1680
cctgtgctgt tctccggttc tgtgaggaac aacattgctt atgggctgca gagctgcgaa 1740
gatgataagg tgatggcggc tgcccaggct gcccacgcag atgacttcat ccaggaaatg 1800
gagcatggaa tatacacaga tgtaggggag aagggaagcc agctggctgc gggacagaaa 1860
caacgtctgg ccattgcccg ggcccttgta cgagacccgc gggtcctcat cctggatgag 1920
gctactagtg ccctagatgt gcagtgcgag caggccctgc aggactggaa ttcccgtggg 1980
gatcgcacag tgctggtgat tgctcacagg ctgcaggcag ttcagcgcgc ccaccagatc 2040
ctggtgctcc aggagggcaa gctgcagaag cttgcccagc tccaggaggg acaggacctc 2100
tattcccgcc tggttcagca gcggctgatg gactga 2136